US011384075B2

(12) United States Patent
Guo et al.

(10) Patent No.: US 11,384,075 B2
(45) Date of Patent: Jul. 12, 2022

(54) QUINOLINONE COMPOUNDS

(71) Applicant: Janssen Pharmaceutica NV, Beerse (BE)

(72) Inventors: Haibing Guo, Shanghai (CN); Zhao-Kui Wan, Lexington, MA (US); Luoheng Qin, Shanghai (CN); Qian Liu, Shanghai (CN); Wing Shun Cheung, Shanghai (CN)

(73) Assignee: Janssen Pharmaceutica NV, Beerse (BE)

( * ) Notice: Subject to any disclaimer, the term of this patent is extended or adjusted under 35 U.S.C. 154(b) by 0 days.

(21) Appl. No.: 16/623,011

(22) PCT Filed: Jun. 26, 2018

(86) PCT No.: PCT/CN2018/092830
§ 371 (c)(1),
(2) Date: Dec. 16, 2019

(87) PCT Pub. No.: WO2019/001419
PCT Pub. Date: Jan. 3, 2019

(65) Prior Publication Data
US 2021/0139470 A1 May 13, 2021

(30) Foreign Application Priority Data

Jun. 27, 2017 (WO) ................ PCT/CN2017/090267

(51) Int. Cl.
| | |
|---|---|
| *C07D 413/14* | (2006.01) |
| *C07D 401/14* | (2006.01) |
| *C07D 405/14* | (2006.01) |
| *C07D 417/14* | (2006.01) |
| *C07D 498/08* | (2006.01) |

(52) U.S. Cl.
CPC ......... *C07D 413/14* (2013.01); *C07D 401/14* (2013.01); *C07D 405/14* (2013.01); *C07D 417/14* (2013.01); *C07D 498/08* (2013.01)

(58) Field of Classification Search
CPC .. C07D 413/14; C07D 498/08; C07D 401/14; C07D 405/14; C07D 417/14
USPC ...................................................... 514/230.5
See application file for complete search history.

(56) References Cited

U.S. PATENT DOCUMENTS

| | | | |
|---|---|---|---|
| 4,666,828 A | 5/1987 | Gusella | |
| 4,683,202 A | 7/1987 | Mullis | |
| 4,801,531 A | 1/1989 | Frossard | |
| 5,192,659 A | 3/1993 | Simons | |
| 5,272,057 A | 12/1993 | Smulson et al. | |
| 5,882,864 A | 3/1999 | An et al. | |
| 6,218,529 B1 | 4/2001 | An et al. | |
| 2002/0107392 A1 | 8/2002 | Renhowe et al. | |
| 2003/0028018 A1 | 2/2003 | Renhowe et al. | |
| 2004/0092535 A1 | 5/2004 | Barsanti et al. | |
| 2005/0136065 A1 | 6/2005 | Valiante | |
| 2005/0137399 A1 | 6/2005 | Cai et al. | |
| 2005/0209247 A1 | 9/2005 | Cai et al. | |

FOREIGN PATENT DOCUMENTS

| | | |
|---|---|---|
| CN | 1692112 A | 11/2005 |
| CN | 1960731 A | 5/2007 |
| RU | 2294326 C2 | 2/2007 |
| RU | 2425041 C2 | 7/2011 |
| WO | 2002/022598 A1 | 3/2002 |
| WO | 03/87095 A1 | 10/2003 |
| WO | 2004/018419 A2 | 3/2004 |
| WO | 2004/043389 A2 | 5/2004 |
| WO | 2004/087153 A2 | 10/2004 |
| WO | 2005/046589 A2 | 5/2005 |
| WO | 2005/047244 A2 | 5/2005 |
| WO | 2005/082340 A2 | 9/2005 |

OTHER PUBLICATIONS

International Search Report relating to PCT Patent Application No. PCT/CN2018/092830, filed on Jun. 26, 2018, dated Sep. 18, 2018.
Written Opinion of the International Searching Authority relation to PCT Patent Application no. PCT/CN2018/092830, dated Sep. 18, 2018.
Angerer, Lynne M. et al. "Demonstration of Tissue-Specific Gene Expression by in Situ Hybridization", Methods in Enzymology, vol. 152, 1987, pp. 649-661.
Bartlett, J.M.S., "Fluorescence In Situ Hybridization: Technical Overview," Molecular Diagnosis of Cancer, Second Edition, Mar. 2004, pp. 77-87.
Berg, S. et al., "Pharmaceutical Salts" Journ. of Pharm. Sciences, 1977, 66:1-19, & Handbook of Pharmaceutical Salts, Properties, Selection & Use, Stahl and Wermuth, Eds., Wiley-VCH and VHCA, Zurich.
Cahn, R.S., et al., "Specification of Molecular Chirality", Angew. Chem. Internat. Edit., (1966), vol. 5, No. 4, pp. 385-415.
Deprimo, Samuel E. et al. "Expression profiling of blood samples from an SU5416 Phase III metastatic colorectal cancer clinical trial: a novel strategy for biomarker identification", BMC Cancer, vol. 3, 2003; pp. 1-12.
Knights, Victoria et al. "De-regulated FGF receptors as therapeutic targets in cancer", Pharmacology & Therapeutics, 2010; vol. 125(1), pp. 105-117.
Korc, M. et al. "The Role of Fibroblast Growth Factors in Tumor Growth", Current Cancer Drug Targets, vol. 9(5), 2009, pp. 639-651.

(Continued)

*Primary Examiner* — Kahsay Habte
(74) *Attorney, Agent, or Firm* — BakerHostetler

(57) ABSTRACT

The invention relates to new quinolinone compounds, to pharmaceutical compositions comprising said compounds, to processes for the preparation of said compounds and to the use of said compounds as FGFR (fibroblast growth factor receptor) inhibitors and to their use in the treatment of diseases, e.g. cancer.

23 Claims, No Drawings

(56) References Cited

OTHER PUBLICATIONS

March, J., "Advanced organic chemistry: reactions, mechanisms, and structure," A Wiley Interscience publication, 4th Edition, 1992, pp. 109-114; pp. 131-133.
Orre, Maxine and Rogers, Peter A.W. "VEGF, VEGFR-1, VEGFR-2, Microvessel Density and Endothelial Cell Proliferation in Tumours of the Ovary", Int. J. Cancer (Pred. Oncol), vol. 84(2), 1999, pp. 101-108.

QUINOLINONE COMPOUNDS

CROSS-REFERENCE TO RELATED APPLICATIONS

This application is a U.S. national stage of PCT Application No. PCT/CN2018/092830, filed on Jun. 26, 2018, which claims the benefit of priority of Chinese Patent Application No. PCT/CN2017/090267, filed on Jun. 27, 2017, both of which are incorporated by reference herein, in their entireties and for all purposes.

FIELD OF THE INVENTION

The invention relates to new quinolinone compounds, to pharmaceutical compositions comprising said compounds, to processes for the preparation of said compounds and to the use of said compounds as FGFR (fibroblast growth factor receptor) inhibitors and to their use in the treatment of diseases, e.g. cancer.

BACKGROUND OF THE INVENTION

The fibroblast growth factor (FGF) signaling pathways have been demonstrated to play critical roles in processes ranging from embryogenesis and wound healing and have also shown strong links to several hallmarks of cancer. Genetic alterations in FGFR family members are associated with tumor growth, metastasis, angiogenesis and survival. A variety of FGFR inhibitors are in clinic trials and have shown clinic response in patients with FGFR aberrations. However, it has been reported that mutations affecting aminoacids in FGFR, e.g. FGFR1, 2 or 3, may cause resistance to FGFR inhibitors or decrease sensitivity to FGFR inhibitors. The development of secondary FGFR kinase domain mutations upon treatment with FGFR inhibitors are an important mechanism of acquired resistance to FGFR inhibition. Equivalent FGFR point mutations exist also de novo in cancers. Gatekeeper mutations have been reported as one of the major mechanism leading to resistance to tyrosine kinase inhibitors. Gatekeeper mutations include FGFR3 V555L/V555M, FGFR1 V561M, FGFR2 V564F/V564I/V564M and FGFR4 V550L. FGFR resistant mutations have been reported in clinic trials and in vitro cellular systems. Therefore new (second generation) FGFR inhibitors are needed for more durable activity in cancers harboring alterations in the FGFR signaling pathway to overcome clinical acquired resistance to first generation FGFR inhibitor therapy. Second generation FGFR inhibitors are needed to overcome the reduced activity observed for first generation FGFR inhibitors against FGFRs harboring the above gatekeeper mutations and hence maintain FGFR inhibiting activity.

It was found that the compounds of the invention show activity against mutated FGFRs, in particular against FGFRs harboring gatekeeper mutations or against mutated FGFR1 or mutated FGFR2 or mutated FGFR3, in particular against FGFR3 V555L, FGFR3 V555M, FGFR1 V561M and FGFR2 V564I, particularly against FGFR3 V555L and FGFR3 V555M.

WO2002/022598, WO2003/087095, WO2004/018419, WO2004/043389, WO2005/046589 each disclose a series of quinolinone derivatives.

DESCRIPTION OF THE INVENTION

The invention provides compounds of formula (I):

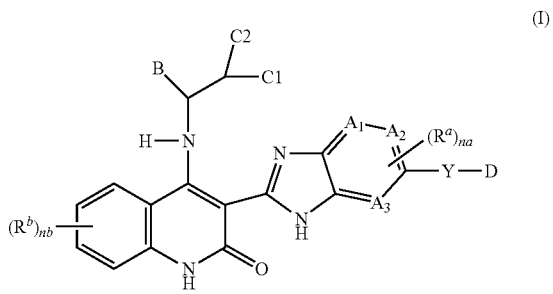

including any tautomeric and stereochemically isomeric form thereof, wherein
$A_1$, $A_2$ and $A_3$ each independently represent a carbon atom or a nitrogen atom;
C1 is hydrogen or $C_{1-4}$alkyl;
C2 is hydrogen, $C_{1-4}$alkyl, hydroxyl o $C_{1-4}$alkoxy;
or C1 and C2 are taken together to form a $C_{3-6}$cycloalkyl together with the carbon atom to which they are attached;
Y is a direct bond, —O—, C(═O), NR$^y$, S(═O)$_2$, or $C_{1-4}$alkyl;
R$^y$ is hydrogen or $C_{1-4}$alkyl;
each R$^a$ independently is hydrogen, $C_{1-6}$alkyl, halo$C_{1-6}$alkyl, halo, $C_{1-6}$alkoxy, carboxyl, $C_{1-6}$alkyloxycarbonyl, $C_{2-6}$alkenyl, $C_{2-6}$alkynyl, cyano, cyano$C_{1-6}$alkyl, hydroxy-$C_{1-6}$alkyl, —C(═O)—NH$_2$, —C(═O)—NH($C_{1-4}$alkyl), —C(═O)—N($C_{1-4}$alkyl)$_2$, or a 3 to 6 membered monocyclic saturated heterocyclyl containing at least one heteroatom selected from N, O or S;
na is an integer equal to 1 or 2;
each R$^b$ independently is hydrogen, $C_{1-6}$alkyl, halo$C_{1-6}$alkyl, halo, $C_{1-6}$alkoxy, $C_{1-6}$alkyloxycarbonyl, $C_{2-6}$alkenyl, $C_{2-6}$alkynyl, cyano, cyano$C_{1-6}$alkyl, hydroxy$C_{1-6}$alkyl, —C(═O)—NH$_2$, —C(═O)—NH($C_{1-4}$alkyl), —C(═O)—N($C_{1-4}$alkyl)$_2$, $C_{3-6}$cycloalkyl, phenyl, a 3 to 6 membered monocyclic heterocyclyl containing at least one heteroatom selected from N, O or S, or $C_{1-6}$alkyl substituted with $C_{3-6}$cycloalkyl or with phenyl or with a 3 to 6 membered monocyclic heterocyclyl containing at least one heteroatom selected from N, O or S;
nb is an integer equal to 1 or 2;
D is a 3 to 12 membered heterocyclyl containing at least one heteroatom selected from N, O or S, wherein said heterocyclyl is optionally being substituted with 1 to 5 R$^c$ substituents; each R$^c$ independently is oxo, halo, $C_{1-6}$alkyl, $C_{1-6}$alkyloxy, hydroxy$C_{1-6}$alkyl, halo$C_{1-6}$alkyl, halo$C_{1-6}$alkyloxy, carboxyl, HOOC—$C_{1-6}$alkyl-, $C_{1-6}$alkyl substituted with —C(═O)—O—$C_{1-6}$alkyl, $C_{1-6}$alkyl-O—C(═O)—, cyano, cyano$C_{1-6}$alkyl, $C_{1-6}$alkyl-C(═O)—, —SO$_2$—$C_{1-6}$alkyl, $C_{3-6}$cycloalkyl, phenyl, a 3 to 6 membered monocyclic saturated heterocyclyl containing at least one heteroatom selected from N, O or S, or a 5 or 6 membered monocyclic aromatic heterocyclyl containing at least one heteroatom selected from N, O or S;
B is a 3 to 12 membered carbocyclyl or a 3 to 12 membered heterocyclyl containing at least one heteroatom selected from N, O or S, wherein said carbocyclyl and heterocyclyl are each optionally being substituted with 1 to 5 R substituents;

each R independently is $C_{1-6}$alkyl, cyano, halo, $C_{1-6}$alkoxy, halo$C_{1-6}$alkoxy, hydroxyl, hydroxy$C_{1-6}$alkyl, halo$C_{1-6}$alkyl, oxo, —$SO_2$—$NH_2$, —$SO_2$—NH($C_{1-4}$alkyl), —$SO_2$—N($C_{1-4}$alkyl)$_2$, —NH—C(=O)—$C_{2-6}$alkenyl, —C(=O)—$C_{1-6}$alkyl, —C(=O)—$C_{2-6}$alkenyl, $C_{1-6}$alkyl-O—C(=O)—, $C_{3-6}$cycloalkyl, phenyl, or a 3 to 6 membered monocyclic heterocyclyl containing at least one heteroatom selected from N, O or S;

or the pharmaceutically acceptable salts thereof or the solvates thereof.

The invention also provides compounds of formula (I):

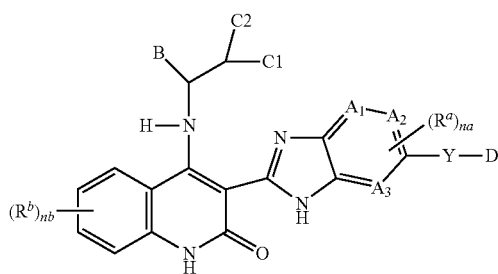

(I)

including any tautomeric and stereochemically isomeric form thereof, wherein $A_1$, $A_2$ and $A_3$ each independently represent a carbon atom or a nitrogen atom;

C1 is hydrogen or $C_{1-4}$alkyl;

C2 is hydrogen or $C_{1-4}$alkyl or hydroxyl;

or C1 and C2 are taken together to form a $C_{3-6}$cycloalkyl together with the carbon atom to which they are attached;

Y is a direct bond, —O—, C(=O), NR$^y$, S(=O)$_2$, or $C_{1-4}$alkyl;

R$^y$ is hydrogen or $C_{1-4}$alkyl;

each R$^a$ independently is hydrogen, $C_{1-6}$alkyl, halo$C_{1-6}$alkyl, halo, $C_{1-6}$alkoxy, carboxyl, $C_{1-6}$alkyloxycarbonyl, $C_{2-6}$alkenyl, $C_{2-6}$alkynyl, cyano, cyano$C_{1-6}$alkyl, hydroxy$C_{1-6}$alkyl, —C(=O)—$NH_2$, —C(=O)—NH($C_{1-4}$alkyl), —C(=O)—N($C_{1-4}$alkyl)$_2$, or a 3 to 6 membered monocyclic saturated heterocyclyl containing at least one heteroatom selected from N, O or S;

na is an integer equal to 1 or 2;

each R$^b$ independently is hydrogen, $C_{1-6}$alkyl, halo$C_{1-6}$alkyl, halo, $C_{1-6}$alkoxy, $C_{1-6}$alkyloxycarbonyl, $C_{2-6}$alkenyl, $C_{2-6}$alkynyl, cyano, cyano$C_{1-6}$alkyl, hydroxy$C_{1-6}$alkyl, —C(=O)—$NH_2$, —C(=O)—NH($C_{1-4}$alkyl), —C(=O)—N($C_{1-4}$alkyl)$_2$, $C_{3-6}$cycloalkyl, phenyl, a 3 to 6 membered monocyclic heterocyclyl containing at least one heteroatom selected from N, O or S, or $C_{1-6}$alkyl substituted with $C_{3-6}$cycloalkyl or with phenyl or with a 3 to 6 membered monocyclic heterocyclyl containing at least one heteroatom selected from N, O or S;

nb is an integer equal to 1 or 2;

D is a 3 to 12 membered heterocyclyl containing at least one heteroatom selected from N, O or S, wherein said heterocyclyl is optionally being substituted with 1 to 5 R$^c$ substituents; each R$^c$ independently is oxo, $C_{1-6}$alkyl, hydroxy$C_{1-6}$alkyl, halo$C_{1-6}$alkyl, halo$C_{1-6}$alkyloxy, carboxyl, HOOC—$C_{1-6}$alkyl-, $C_{1-6}$alkyl substituted with —C(=O)—O—$C_{1-6}$alkyl, $C_{1-6}$alkyl-O—C(=O)—, cyano, cyano$C_{1-6}$alkyl, $C_{1-6}$alkyl-C(=O)—, —$SO_2$—$C_{1-6}$alkyl, $C_{3-6}$cycloalkyl, phenyl, a 3 to 6 membered monocyclic saturated heterocyclyl containing at least one heteroatom selected from N, O or S, or a 5 or 6 membered monocyclic aromatic heterocyclyl containing at least one heteroatom selected from N, O or S;

B is a 3 to 12 membered carbocyclyl or a 3 to 12 membered heterocyclyl containing at least one heteroatom selected from N, O or S, wherein said carbocyclyl and heterocyclyl are each optionally being substituted with 1 to 5 R substituents;

each R independently is $C_{1-6}$alkyl, cyano, halo, $C_{1-6}$alkoxy, halo$C_{1-6}$alkoxy, hydroxyl, hydroxy$C_{1-6}$alkyl, halo$C_{1-6}$alkyl, oxo, —$SO_2$—$NH_2$, —$SO_2$—NH($C_{1-4}$alkyl), —$SO_2$—N($C_{1-4}$alkyl)$_2$, —NH—C(=O)—$C_{2-6}$alkenyl, —C(=O)—$C_{1-6}$alkyl, —C(=O)—$C_{2-6}$alkenyl, $C_{1-6}$alkyl-O—C(=O)—, $C_{3-6}$cycloalkyl, phenyl, or a 3 to 6 membered monocyclic heterocyclyl containing at least one heteroatom selected from N, O or S;

or the pharmaceutically acceptable salts thereof or the solvates thereof.

In another aspect, provided is a method for the prophylaxis or treatment of a disease state or condition mediated by a FGFR kinase, which method comprises administering to a subject in need thereof a compound of formula (I) as defined herein, or a pharmaceutically acceptable salt thereof or a solvate thereof.

In a further aspect, provided is a compound of formula (I) as defined herein or a pharmaceutically acceptable salt thereof or a solvate thereof for use in the prophylaxis or treatment of a disease state or condition mediated by a FGFR kinase.

In a still further aspect, provided is use of a compound of formula (I) as defined herein or a pharmaceutically acceptable salt thereof or a solvate thereof for the manufacture of a medicament for the prophylaxis or treatment of a disease state or condition mediated by a FGFR kinase.

In another aspect, provided is a method for the prophylaxis or treatment of cancer, which method comprises administering to a subject in need thereof a compound of formula (I) as defined herein, or a pharmaceutically acceptable salt thereof or a solvate thereof. In particular, the cancer is a cancer mediated by a FGFR kinase.

In a further aspect, provided is a compound of formula (I) as defined herein or a pharmaceutically acceptable salt thereof or a solvate thereof for use in the prophylaxis or treatment of cancer. In particular, the cancer is a cancer mediated by a FGFR kinase.

In still a further aspect, provided is use of a compound of formula (I) as defined herein or a pharmaceutically acceptable salt thereof or a solvate thereof for the manufacture of a medicament for the prophylaxis or treatment of cancer. In particular, the cancer is a cancer mediated by a FGFR kinase.

DETAILED DESCRIPTION OF THE INVENTION

Unless the context indicates otherwise, references to formula (I) in all sections of this document (including the uses, methods and other aspects of the invention) include references to all other sub-formula (e.g. (I-a), (I-A), (I-A-a), (I-B), (I-B-a), (I-C), (I-C-a), (I-D), (I-D-a)), sub-groups, preferences, embodiments and examples as defined herein.

The prefix "$C_{x-y}$" (where x and y are integers) as used herein refers to the number of carbon atoms in a given group. Thus, a $C_{1-6}$alkyl group contains from 1 to 6 carbon atoms, a $C_{3-6}$cycloalkyl group contains from 3 to 6 carbon atoms, a $C_{1-4}$alkoxy group contains from 1 to 4 carbon atoms, and so on.

The term 'halo' or 'halogen' as used herein refers to a fluorine, chlorine, bromine or iodine atom.

The term '$C_{1-4}$alkyl', or '$C_{1-6}$alkyl' as used herein as a group or part of a group refers to a linear or branched saturated hydrocarbon group containing from 1 to 4 or 1 to 6 carbon atoms. Examples of such groups include methyl, ethyl, n-propyl, isopropyl, n-butyl, isobutyl, sec-butyl, tert-butyl, n-pentyl, isopentyl, neopentyl or hexyl and the like.

The term '$C_{2-4}$alkenyl' or '$C_{2-6}$alkenyl' as used herein as a group or part of a group refers to a linear or branched hydrocarbon group containing from 2 to 4 or 2 to 6 carbon atoms and containing a carbon carbon double bond.

The term '$C_{2-4}$alkynyl' or '$C_{2-6}$alkynyl' as used herein as a group or part of a group refers to a linear or branched hydrocarbon group having from 2 to 4 or 2 to 6 carbon atoms and containing a carbon carbon triple bond.

The term '$C_{1-4}$alkoxy' or '$C_{1-6}$alkoxy' as used herein as a group or part of a group refers to an —O—$C_{1-4}$alkyl group or an —O—$C_{1-6}$alkyl group wherein $C_{1-4}$alkyl and $C_{1-6}$alkyl are as defined herein. Examples of such groups include methoxy, ethoxy, propoxy, butoxy, and the like.

The term '$C_{3-6}$cycloalkyl' as used herein refers to a saturated monocyclic hydrocarbon ring of 3 to 6 carbon atoms. Examples of such groups include cyclopropyl, cyclobutyl, cyclopentyl, or cyclohexyl.

The term 'hydroxy$C_{1-4}$alkyl' or 'hydroxy$C_{1-6}$alkyl' as used herein as a group or part of a group refers to a $C_{1-4}$alkyl or $C_{1-6}$alkyl group as defined herein wherein one or more than one hydrogen atom is replaced with a hydroxyl group. The terms 'hydroxy$C_{1-4}$alkyl' or 'hydroxy$C_{1-6}$alkyl' therefore include monohydroxy$C_{1-4}$alkyl, monohydroxy$C_{1-6}$alkyl and also polyhydroxy$C_{1-4}$alkyl and polyhydroxy $C_{1-6}$alkyl. There may be one, two, three or more hydrogen atoms replaced with a hydroxyl group, so the hydroxy$C_{1-4}$alkyl or hydroxy$C_{1-6}$alkyl may have one, two, three or more hydroxyl groups. Examples of such groups include hydroxymethyl, hydroxyethyl, hydroxypropyl and the like.

The term 'halo$C_{1-4}$alkyl' or 'halo$C_{1-6}$alkyl' as used herein as a group or part of a group refers to a $C_{1-4}$alkyl or $C_{1-6}$alkyl group as defined herein wherein one or more than one hydrogen atom is replaced with a halogen. The term 'halo$C_{1-4}$alkyl' or 'halo$C_{1-6}$alkyl' therefore include monohalo$C_{1-4}$alkyl, monohalo$C_{1-6}$alkyl and also polyhalo$C_{1-4}$alkyl and polyhalo$C_{1-6}$alkyl. There may be one, two, three or more hydrogen atoms replaced with a halogen, so the halo$C_{1-4}$alkyl or halo$C_{1-6}$alkyl may have one, two, three or more halogens. Examples of such groups include fluoroethyl, fluoromethyl, trifluoromethyl or trifluoroethyl and the like.

The term 'halo$C_{1-4}$alkoxy' or 'halo$C_{1-6}$alkoxy' as used herein as a group or part of a group refers to a —O—$C_{1-4}$alkyl group or a —O—$C_{1-6}$ alkyl group as defined herein wherein one or more than one hydrogen atom is replaced with a halogen. The terms 'halo$C_{1-4}$alkoxy' or 'halo$C_{1-6}$alkoxy' therefore include monohalo$C_{1-4}$alkoxy, monohalo$C_{1-6}$alkoxy and also polyhalo$C_{1-4}$alkoxy and polyhalo$C_{1-6}$alkoxy. There may be one, two, three or more hydrogen atoms replaced with a halogen, so the halo$C_{1-4}$alkoxy or halo$C_{1-6}$alkoxy may have one, two, three or more halogens. Examples of such groups include fluoroethyloxy, difluoromethoxy or trifluoromethoxy and the like.

The term cyano$C_{1-4}$alkyl or cyano$C_{1-6}$alkyl as used herein refers to a $C_{1-4}$alkyl or $C_{1-6}$alkyl group as defined herein which is substituted with one or two cyano groups, in particular with one cyano group.

The term "heterocyclyl" as used herein shall, unless the context indicates otherwise, include both aromatic and non-aromatic ring systems. Thus, for example, the term "heterocyclyl" includes within its scope aromatic, non-aromatic, unsaturated, partially saturated and fully saturated heterocyclyl ring systems. In general, unless the context indicates otherwise, such ring systems may be monocyclic or bicyclic or bridged and may contain, for example, 3 to 12 ring members, or 4 to 10 ring members, or more usually 5 to 10 ring members. Reference to 4 to 7 ring members include 4, 5, 6 or 7 atoms in the ring, reference to 3 to 6 ring members include 3, 4, 5, or 6 atoms in the ring and reference to 4 to 6 ring members include 4, 5, or 6 atoms in the ring. Examples of monocyclic heterocyclyl ring systems are ring systems containing 3, 4, 5, 6, 7 or 8 ring members, more usually 3 to 7, and preferably 4, 5, 6 or 7 ring members, more preferably 5 or 6 ring members. Examples of bicyclic heterocyclyl ring systems are those containing 8, 9, 10, 11 or 12 ring members, and more usually 9 or 10 ring members. The heterocyclyl ring systems contain at least one heteroatom typically selected from nitrogen, oxygen or sulphur, in particular contain up to 5, up to 4, up to 3, up to 2, or a single heteroatom. Where reference is made herein to a heterocyclyl ring system, the heterocyclyl ring can, unless the context indicates otherwise, be optionally substituted (i.e. unsubstituted or substituted) by one or more substituents as discussed herein.

The heterocyclyl ring systems can be heteroaryl ring systems having from 5 to 12 ring members, more usually from 5 to 10 ring members. The term "heteroaryl" is used herein to denote a heterocyclyl ring system having aromatic character. The term "heteroaryl" embraces polycyclic (e.g. bicyclic) ring systems wherein one or more rings are non-aromatic, provided that at least one ring is aromatic. In such polycyclic systems, the ring system may be attached to the remainder of the compound by an aromatic ring or by a non-aromatic ring.

Examples of heteroaryl groups are monocyclic and bicyclic groups containing from five to twelve ring members, and more usually from five to ten ring members. The heteroaryl group can be, for example, a five membered or six membered monocyclic ring or a bicyclic structure formed from fused five and six membered rings or two fused six membered rings, or two fused five membered rings. The heteroaryl ring system may contain up to about five heteroatoms typically selected from nitrogen, oxygen and sulphur. Typically the heteroaryl ring will contain up to 4 heteroatoms, more typically up to 3 heteroatoms, more usually up to 2, for example a single heteroatom. In one embodiment, the heteroaryl ring contains at least one ring nitrogen atom. The nitrogen atoms in the heteroaryl rings can be basic, as in the case of an imidazole or pyridine, or essentially non-basic as in the case of an indole or pyrrole nitrogen. In general the number of basic nitrogen atoms present in the heteroaryl group, including any amino group substituents of the ring, will be less than five.

Examples of five membered heteroaryl groups include but are not limited to pyrrolyl, furanyl, thienyl, imidazolyl, oxazolyl, oxadiazolyl, oxatriazole, isoxazolyl, thiazolyl, thiadiazolyl, isothiazolyl, pyrazolyl, triazolyl and tetrazolyl groups. In particular, examples of five membered heteroaryl groups include but are not limited to pyrrolyl, furanyl, thienyl, imidazolyl, oxazolyl, oxadiazolyl, isoxazolyl, thiazolyl, thiadiazolyl, isothiazolyl, pyrazolyl and triazolyl groups Examples of six membered heteroaryl groups include but are not limited to pyridyl, pyrazinyl, pyridazinyl, pyrimidinyl and triazinyl.

A bicyclic heteroaryl group may be, for example, a group selected from:

a) a benzene ring fused to a 5- or 6-membered ring containing 1, 2 or 3 ring heteroatoms;
b) a pyridine ring fused to a 5- or 6-membered ring containing 0, 1, 2 or 3 ring heteroatoms;
c) a pyrimidine ring fused to a 5- or 6-membered ring containing 0, 1 or 2 ring heteroatoms;
d) a pyrrole ring fused to a 5- or 6-membered ring containing 0, 1, 2 or 3 ring heteroatoms;
e) a pyrazole ring fused to a 5- or 6-membered ring containing 0, 1 or 2 ring heteroatoms; f) an imidazole ring fused to a 5- or 6-membered ring containing 0, 1 or 2 ring heteroatoms;
g) an oxazole ring fused to a 5- or 6-membered ring containing 0, 1 or 2 ring heteroatoms;
h) an isoxazole ring fused to a 5- or 6-membered ring containing 0, 1 or 2 ring heteroatoms;
i) a thiazole ring fused to a 5- or 6-membered ring containing 0, 1 or 2 ring heteroatoms;
j) an isothiazole ring fused to a 5- or 6-membered ring containing 0, 1 or 2 ring heteroatoms;
k) a thiophene ring fused to a 5- or 6-membered ring containing 0, 1, 2 or 3 ring heteroatoms;
l) a furan ring fused to a 5- or 6-membered ring containing 0, 1, 2 or 3 ring heteroatoms;
m) a cyclohexyl ring fused to a 5- or 6-membered aromatic ring containing 1, 2 or 3 ring heteroatoms; and
n) a cyclopentyl ring fused to a 5- or 6-membered aromatic ring containing 1, 2 or 3 ring heteroatoms.

Particular examples of bicyclic heteroaryl groups containing a five membered ring fused to another five membered ring include but are not limited to imidazothiazolyl (e.g. imidazo[2,1-b]thiazole) and imidazoimidazolyl (e.g. imidazo[1,2-a]imidazole).

Particular examples of bicyclic heteroaryl groups containing a six membered ring fused to a five membered ring include but are not limited to benzofuranyl, benzothiophenyl, benzimidazolyl, benzoxazolyl, isobenzoxazolyl, benzisoxazolyl, benzthiazolyl, benzisothiazolyl, isobenzofuranyl, indolyl, isoindolyl, indolizinyl, indolinyl, isoindolinyl, purinyl, indazolyl, pyrazolopyrimidinyl (e.g. pyrazolo[1,5-a]pyrimidine), triazolopyrimidinyl (e.g. [1,2,4]triazolo[1,5-a]pyrimidine), benzodioxolyl, imidazopyrazinyl, imidazopyridazinyl, imidazopyridinyl and pyrazolopyridinyl (e.g. pyrazolo[1,5-a]pyridine) groups.

Particular examples of bicyclic heteroaryl groups containing a six membered ring fused to a five membered ring include but are not limited to benzofuranyl, benzothiophenyl, benzimidazolyl, benzoxazolyl, benzisoxazolyl, benzthiazolyl, benzisothiazolyl, indolyl, isoindolyl, indolizinyl, indolinyl, isoindolinyl, indazolyl, pyrazolopyrimidinyl (e.g. pyrazolo[1,5-a]pyrimidine), triazolopyrimidinyl (e.g. [1,2,4]triazolo[1,5-a]pyrimidine), imidazopyrazinyl, imidazopyridazinyl, imidazopyridinyl and pyrazolopyridinyl (e.g. pyrazolo[1,5-a]pyridine) groups.

Particular examples of bicyclic heteroaryl groups containing a six membered ring fused to a five membered ring include but are not limited to benzofuranyl, benzothiophenyl, benzimidazolyl, benzthiazolyl, indolyl, isoindolyl, indolizinyl, indolinyl groups.

Particular examples of bicyclic heteroaryl groups containing two fused six membered rings include but are not limited to quinolizinyl, quinolinyl, isoquinolinyl, cinnolinyl, chromanyl, isochromanyl, thiochromanyl, benzopyranyl, benzodioxanyl, benzoxazinyl, pyridopyridinyl, quinoxalinyl, quinazolinyl, phthalazinyl, naphthyridinyl and pteridinyl groups.

Particular examples of bicyclic heteroaryl groups containing two fused six membered rings include but are not limited to quinolizinyl, quinolinyl, isoquinolinyl, benzopyranyl, benzodioxanyl, benzoxazinyl, pyridopyridinyl, quinoxalinyl, quinazolinyl, phthalazinyl, naphthyridinyl and pteridinyl groups.

Particular examples of bicyclic heteroaryl groups containing two fused six membered rings include but are not limited to quinolizinyl, quinolinyl, isoquinolinyl, quinoxalinyl, quinazolinyl, phthalazinyl, naphthyridinyl and pteridinyl groups.

Examples of polycyclic heteroaryl groups containing an aromatic ring and a non-aromatic ring include, tetrahydroisoquinolinyl, tetrahydroquinolinyl, dihydrobenzothienyl, dihydrobenzofuranyl, 2,3-dihydro-benzo[1,4]dioxinyl, benzo[1,3]dioxolyl, 4,5,6,7-tetrahydrobenzofuranyl, tetrahydrotriazolopyrazinyl (e.g. 5,6,7,8-tetrahydro-[1,2,4]triazolo[4,3-a]pyrazinyl), and indolinyl.

A nitrogen-containing heteroaryl ring must contain at least one ring nitrogen atom. Each ring may, in addition, contain up to about four other heteroatoms typically selected from nitrogen, sulphur and oxygen. Typically the heteroaryl ring will contain up to 3 heteroatoms, for example 1, 2 or 3, more usually up to 2 nitrogens, for example a single nitrogen. The nitrogen atoms in the heteroaryl rings can be basic, as in the case of an imidazole or pyridine, or essentially non-basic as in the case of an indole or pyrrole nitrogen. In general the number of basic nitrogen atoms present in the heteroaryl group, including any amino group substituents of the ring, will be less than five.

Examples of nitrogen-containing heteroaryl groups include, but are not limited to, pyridyl, pyrrolyl, imidazolyl, oxazolyl, oxadiazolyl, thiadiazolyl, oxatriazolyl, isoxazolyl, thiazolyl, isothiazolyl, pyrazolyl, pyrazinyl, pyrimidinyl, pyridazinyl, triazinyl, triazolyl (e.g., 1,2,3-triazolyl, 1,2,4-triazolyl), tetrazolyl, quinolinyl, isoquinolinyl, benzimidazolyl, benzoxazolyl, benzisoxazolyl, benzthiazolyl and benzisothiazole, indolyl, 3H-indolyl, isoindolyl, indolizinyl, isoindolinyl, purinyl, indazolyl, quinolizinyl, benzoxazinyl, pyridopyridinyl, quinoxalinyl, quinazolinyl, cinnolinyl, phthalazinyl, naphthyridinyl and pteridinyl.

Examples of nitrogen-containing polycyclic heteroaryl groups containing an aromatic ring and a non-aromatic ring include tetrahydroisoquinolinyl, tetrahydroquinolinyl, and indolinyl.

The term "non-aromatic group" embraces, unless the context indicates otherwise, unsaturated ring systems without aromatic character, partially saturated and fully saturated heterocyclyl ring systems. The terms "unsaturated" and "partially saturated" refer to rings wherein the ring structure(s) contains atoms sharing more than one valence bond i.e. the ring contains at least one multiple bond e.g. a C═C, C≡C or N═C bond. The term "fully saturated" refers to rings where there are no multiple bonds between ring atoms. Saturated heterocyclyl groups include piperidine, morpholine, thiomorpholine, piperazine. Partially saturated heterocyclyl groups include pyrazolines, for example 2-pyrazoline and 3-pyrazoline.

Examples of non-aromatic heterocyclyl groups are groups having from 3 to 12 ring members, more usually 5 to 10 ring members. Such groups can be monocyclic or bicyclic, for example, and typically have from 1 to 5 heteroatom ring members (more usually 1, 2, 3 or 4 heteroatom ring members), usually selected from nitrogen, oxygen and sulphur. The heterocyclyl groups can contain, for example, cyclic ether moieties (e.g. as in tetrahydrofuran and dioxane), cyclic thioether moieties (e.g. as in tetrahydrothiophene and dithiane), cyclic amine moieties (e.g. as in pyrrolidine), and combinations thereof (e.g. thiomorpholine).

Particular examples include morpholinyl, thiomorpholinyl, piperidinyl (e.g. 1-piperidinyl, 2-piperidinyl, 3-piperidinyl and 4-piperidinyl), pyrrolidinyl (e.g. 1-pyrrolidinyl, 2-pyrrolidinyl and 3-pyrrolidinyl), azetidinyl, pyranyl (2H-pyranyl or 4H-pyranyl), dihydrothiophenyl, dihydropyranyl, dihydrofuranyl, dihydrothiazolyl, tetrahydrofuranyl, tetrahydrothiophenyl, dioxanyl, dioxolanyl, tetrahydropyranyl, imidazolinyl, oxazolinyl, oxazolidinyl, oxetanyl, thiazolinyl, 2-pyrazolinyl, pyrazolidinyl and piperazinyl. In general, preferred non-aromatic heterocyclyl groups include saturated groups such as piperidinyl, pyrrolidinyl, azetidinyl, morpholinyl and piperazinyl.

Particular examples include morpholinyl, thiomorpholinyl, piperidinyl (e.g. 1-piperidinyl, 2-piperidinyl, 3-piperidinyl and 4-piperidinyl), pyrrolidinyl (e.g. 1-pyrrolidinyl, 2-pyrrolidinyl and 3-pyrrolidinyl), pyranyl (2H-pyranyl or 4H-pyranyl), dihydrothiophenyl, dihydropyranyl, dihydrofuranyl, dihydrothiazolyl, tetrahydrofuranyl, tetrahydrothiophenyl, dioxanyl, tetrahydropyranyl, imidazolinyl, oxazolinyl, oxazolidinyl, 2-pyrazolinyl, pyrazolidinyl and piperazinyl. In general, preferred non-aromatic heterocyclyl groups include saturated groups such as piperidinyl, pyrrolidinyl, azetidinyl, morpholinyl and piperazinyl.

In a nitrogen-containing non-aromatic heterocyclyl ring the ring must contain at least one ring nitrogen atom.

Particular examples of nitrogen-containing non-aromatic heterocyclyl groups include aziridinyl, morpholinyl, thiomorpholinyl, piperidinyl (e.g. 1-piperidinyl, 2-piperidinyl, 3-piperidinyl and 4-piperidinyl), pyrrolidinyl (e.g. 1-pyrrolidinyl, 2-pyrrolidinyl and 3-pyrrolidinyl), dihydrothiazolyl, imidazolinyl, oxazolinyl, thiazolinyl, 2-pyrazolinyl, 3-pyrazolinyl, pyrazolidinyl and piperazinyl.

Particular examples of 3 to 6 membered monocyclic saturated heterocyclyls include morpholinyl, thiomorpholinyl, dioxanyl, piperidinyl (e.g. 1-piperidinyl, 2-piperidinyl, 3-piperidinyl and 4-piperidinyl), piperazinyl, pyrrolidinyl (e.g. 1-pyrrolidinyl, 2-pyrrolidinyl and 3-pyrrolidinyl), imidazolidinyl, pyrazolidinyl, oxazolidinyl, isoxazolidinyl, thiazolidinyl, isothiazolidinyl, dioxolanyl, dithiolanyl, tetrahydrofuranyl, tetrahydrothiophenyl, tetrahydropyranyl (e.g. 4-tetrahydro pyranyl), dithianyl, trioxanyl, trithianyl, aziridinyl, oxiranyl, thiiranyl, diaziridinyl, dioxarinyl, oxetanyl, azetidinyl, thietanyl, dioxetanyl ring systems.

Particular examples of 3 to 6 membered monocyclic saturated heterocyclyls include morpholinyl, thiomorpholinyl, dioxanyl, piperidinyl (e.g. 1-piperidinyl, 2-piperidinyl, 3-piperidinyl and 4-piperidinyl), piperazinyl, pyrrolidinyl (e.g. 1-pyrrolidinyl, 2-pyrrolidinyl and 3-pyrrolidinyl), imidazolidinyl, pyrazolidinyl, oxazolidinyl, isoxazolidinyl, thiazolidinyl, isothiazolidinyl, dioxolanyl, tetrahydrofuranyl, tetrahydrothiophenyl, tetrahydropyranyl (e.g. 4-tetrahydro pyranyl), oxiranyl, azetidinyl ring systems.

Particular examples of 3 to 6 membered monocyclic saturated heterocyclyls include morpholinyl, thiomorpholinyl, dioxanyl, piperidinyl (e.g. 1-piperidinyl, 2-piperidinyl, 3-piperidinyl and 4-piperidinyl), piperazinyl, pyrrolidinyl (e.g. 1-pyrrolidinyl, 2-pyrrolidinyl and 3-pyrrolidinyl), imidazolidinyl, pyrazolidinyl, dioxolanyl, tetrahydrofuranyl, tetrahydrothiophenyl, tetrahydropyranyl (e.g. 4-tetrahydro pyranyl) ring systems.

Particular examples of 3 to 6 membered monocyclic heterocyclyls include morpholinyl, thiomorpholinyl, piperidinyl (e.g. 1-piperidinyl, 2-piperidinyl, 3-piperidinyl and 4-piperidinyl), pyrrolidinyl (e.g. 1-pyrrolidinyl, 2-pyrrolidinyl and 3-pyrrolidinyl), imidazolidinyl, pyrazolidinyl, oxazolidinyl, isoxazolidinyl, thiazolidinyl, isothiazolidinyl, dioxolanyl, dithiolanyl, piperazinyl, tetrahydrofuranyl, tetrahydrothiophenyl, dioxanyl, tetrahydropyranyl (e.g. 4-tetrahydro pyranyl), dithianyl, trioxanyl, trithianyl, aziridinyl, oxiranyl, thiiranyl, diaziridinyl, dioxarinyl, oxetanyl, azetidinyl, thietanyl, dioxetanyl, azirinyl, azetyl, 1,2-dithietyl, pyrrolyl, furanyl, thiophenyl, imidazolyl, pyrazolyl, oxazolyl, thiazolyl, isothiazolyl, triazolyl, oxadiazolyl, thiadiazolyl, dithiazolyl, pyridinyl, pyranyl, thiopyranyl, pyrimidinyl, thiazinyl, oxazinyl, triazinyl ring systems.

Particular examples of 3 to 6 membered monocyclic heterocyclyls include morpholinyl, thiomorpholinyl, piperidinyl (e.g. 1-piperidinyl, 2-piperidinyl, 3-piperidinyl and 4-piperidinyl), pyrrolidinyl (e.g. 1-pyrrolidinyl, 2-pyrrolidinyl and 3-pyrrolidinyl), imidazolidinyl, pyrazolidinyl, oxazolidinyl, isoxazolidinyl, thiazolidinyl, isothiazolidinyl, dioxolanyl, dithiolanyl, piperazinyl, tetrahydrofuranyl, tetrahydrothiophenyl, dioxanyl, tetrahydropyranyl (e.g. 4-tetrahydro pyranyl), oxiranyl, oxetanyl, azetidinyl, pyrrolyl, furanyl, thiophenyl, imidazolyl, pyrazolyl, oxazolyl, thiazolyl, isothiazolyl, triazolyl, oxadiazolyl, thiadiazolyl, dithiazolyl, pyridinyl, pyranyl, thiopyranyl, pyrimidinyl, thiazinyl, oxazinyl, triazinyl ring systems.

Particular examples of 3 to 12 membered heterocycles include morpholinyl, thiomorpholinyl, piperidinyl (e.g. 1-piperidinyl, 2-piperidinyl, 3-piperidinyl and 4-piperidinyl), pyrrolidinyl (e.g. 1-pyrrolidinyl, 2-pyrrolidinyl and 3-pyrrolidinyl), imidazolidinyl, pyrazolidinyl, oxazolidinyl, isoxazolidinyl, thiazolidinyl, isothiazolidinyl, dioxolanyl, dithiolanyl, piperazinyl, tetrahydrofuranyl, tetrahydrothiophenyl, dioxanyl, tetrahydropyranyl (e.g. 4-tetrahydropyranyl), dithianyl, trioxanyl, trithianyl, aziridinyl, oxiranyl, thiiranyl, diaziridinyl, dioxarinyl, oxetanyl, azetidinyl, thietanyl, dioxetanyl, azirinyl, azetyl, 1,2-dithietyl, pyrrolyl, furanyl, thiophenyl, imidazolyl, pyrazolyl, oxazolyl, thiazolyl, isothiazolyl, triazolyl, oxadiazolyl, thiadiazolyl, dithiazolyl, pyridinyl, pyranyl, thiopyranyl, pyrimidinyl, thiazinyl, oxazinyl, triazinyl, azepanyl, oxepanyl, thiepanyl, 1,2-diazepanyl, 1,4-diazepanyl, diazepinyl, thiazepinyl, azocanyl, azocinyl, imidazothiazolyl (e.g. imidazo[2,1-b]thiazolyl), imidazoimidazolyl (e.g. imidazo[1,2-a]imidazolyl), benzofuranyl, benzothiophenyl, benzimidazolyl, benzoxazolyl, isobenzoxazolyl, benzisoxazolyl, benzthiazolyl, benzisothiazolyl, isobenzofuranyl, indolyl, isoindolyl, indolizinyl, indolinyl, isoindolinyl, purinyl, indazolyl, pyrazolopyrimidinyl (e.g. pyrazolo[1,5-a]pyrimidinyl), triazolopyrimidinyl (e.g. [1,2,4]triazolo[1,5-a]pyrimidinyl), benzodioxolyl, imidazopyridinyl and pyrazolopyridinyl (e.g. pyrazolo[1,5-a]pyridinyl), quinolinyl, isoquinolinyl, chromanyl, thiochromanyl, isochromanyl, benzodioxanyl, quinolizinyl, benzoxazinyl, pyridopyridinyl, quinoxalinyl, quinazolinyl, cinnolinyl, phthalazinyl, naphthyridinyl, pteridinyl, tetrahydroisoquinolinyl, tetrahydroquinolinyl, dihydrobenzthienyl, dihydrobenzfuranyl, 2,3-dihydro-benzo[1,4]dioxinyl, benzo[1,3]dioxolyl, 4,5,6,7-tetrahydrobenzofuranyl, tetrahydrotriazolopyrazinyl (e.g. 5,6,7,8-tetrahydro-[1,2,4]triazolo[4,3-a]pyrazinyl), 8-oxa-3-azabicyclo[3.2.1]octanyl, 2-oxa-5-azabicyclo[2.2.1]heptanyl, 3-oxa-8-azabicyclo[3.2.1]octanyl, 3,6-diazabicyclo[3.1.1]heptanyl ring systems.

Particular examples of 3 to 12 membered heterocycles include morpholinyl, thiomorpholinyl, piperidinyl (e.g. 1-piperidinyl, 2-piperidinyl, 3-piperidinyl and 4-piperidinyl), pyrrolidinyl (e.g. 1-pyrrolidinyl, 2-pyrrolidinyl and 3-pyrrolidinyl), imidazolidinyl, pyrazolidinyl, oxazolidinyl, isoxazolidinyl, thiazolidinyl, isothiazolidinyl, dioxolanyl, piperazinyl, tetrahydrofuranyl, tetrahydrothiophenyl, dioxanyl, tetrahydropyranyl (e.g. 4-tetrahydropyranyl), oxiranyl, oxetanyl, azetidinyl, pyrrolyl, furanyl, thiophenyl, imidazolyl, pyrazolyl, oxazolyl, thiazolyl, isothiazolyl, triazolyl, oxadiazolyl, thiadiazolyl, dithiazolyl, pyridinyl, pyranyl, thiopyranyl, pyrimidinyl, thiazinyl, oxazinyl, triazinyl, imidazothiazolyl (e.g. imidazo[2,1-b]thiazolyl), imidazoimidazolyl (e.g. imidazo[1,2-a]imidazolyl), benzofuranyl, benzothiophenyl, benzimidazolyl, benzoxazolyl, isobenzoxazolyl, benzisoxazolyl, benzthiazolyl, benzisothiazolyl, isobenzofuranyl, indolyl, isoindolyl, indolizinyl, indolinyl, isoindolinyl, indazolyl, pyrazolopyrimidinyl (e.g. pyrazolo[1,5-a]pyrimidinyl), triazolopyrimidinyl (e.g. [1,2,4]triazolo[1,5-a]pyrimidinyl), benzodioxolyl, imidazopyridinyl and pyrazolopyridinyl (e.g. pyrazolo[1,5-a]pyridinyl), quinolinyl, isoquinolinyl, benzodioxanyl, quinolizinyl, benzoxazinyl, pyridopyridinyl, quinoxalinyl, quinazolinyl, cinnolinyl, phthalazinyl, naphthyridinyl, pteridinyl, tetrahydroisoquinolinyl, tetrahydroquinolinyl, dihydrobenzthienyl, dihydrobenzfuranyl, 2,3-dihydro-benzo[1,4]dioxinyl, benzo[1,3]dioxolyl, 4,5,6,7-tetrahydrobenzofuranyl, tetrahydrotriazolopyrazinyl (e.g. 5,6,7,8-tetrahydro-[1,2,4]triazolo[4,3-a]pyrazinyl) ring systems.

Particular examples of 5 to 6 membered aromatic heterocycles include but are not limited to pyrrolyl, furanyl, thiophenyl, imidazolyl, furazanyl, oxazolyl, oxadiazolyl, oxatriazolyl, isoxazolyl, thiazolyl, thiadiazolyl, isothiazolyl, pyrazolyl, triazolyl, tetrazolyl, pyridinyl, pyrazinyl, pyridazinyl, pyrimidinyl and triazinyl ring systems.

The heterocyclyl and carbocyclyl rings representing the B or D or $D_3$ substituent include bridged ring systems such as for example bridged cycloalkanes, such as for example norbornane (1,4-endo-methylene-cyclohexane), adamantane, oxa-adamantane; bridged morpholine rings such as for example 8-oxa-3-azabicyclo[3.2.1]octane, 2-oxa-5-azabicyclo[2.2.1]heptane, 3-oxa-8-azabicyclo[3.2.1]octane; bridged piperazine rings such as for example 3,6-diazabicyclo[3.1.1]heptane; bridged piperidine rings such as for example 1,4-ethylenepiperidine. For an explanation of the distinction between fused and bridged ring systems, see *Advanced Organic Chemistry*, by Jerry March, 4$^{th}$ Edition, Wiley Interscience, pages 131-133, 1992.

The term "carbocyclyl" as used herein shall, unless the context indicates otherwise, include both aromatic and non-aromatic carbon ring systems. Thus, for example, the term "carbocyclyl" includes within its scope aromatic, non-aromatic, unsaturated, partially saturated and fully saturated carbocyclic ring systems. In general, unless the context indicates otherwise, such ring systems may be monocyclic or bicyclic or bridged and may contain, for example, 3 to 12 ring members, or 4 to 10 ring members, or more usually 5 to 10 ring members. Reference to 4 to 7 ring members include 4, 5, 6 or 7 atoms in the ring and reference to 4 to 6 ring members include 4, 5, or 6 atoms in the ring. Examples of monocyclic carbocyclyl ring systems are ring systems containing 3, 4, 5, 6, 7 and 8 ring members, more usually 3 to 7, and preferably 4, 5, 6 or 7 ring members, more preferably 5 or 6 ring members. Examples of bicyclic carbocyclyl ring systems are those containing 8, 9, 10, 11 and 12 ring members, and more usually 9 or 10 ring members. Where reference is made herein to a carbocyclyl ring system, the carbocyclyl ring can, unless the context indicates otherwise, be optionally substituted (i.e. unsubstituted or substituted) by one or more substituents as discussed herein.

The carbocyclyl ring systems can be aryl ring systems. The term 'aryl' as used herein refers to carbocyclyl aromatic groups and embraces polycyclic (e.g. bicyclic) ring systems wherein one or more rings are non-aromatic, provided that at least one ring is aromatic. In such polycyclic systems, the ring system may be attached to the remainder of the compound by an aromatic ring or by a non-aromatic ring. The term 'aryl' includes phenyl, naphthyl, indenyl, and tetrahydronaphthyl groups.

Particular examples of 3 to 12 membered carbocycles include cyclopropyl, cyclobutyl, cyclopentyl, cyclyhexyl, cycloheptyl, cyclooctyl, phenyl naphthyl, indenyl, tetrahydronaphthyl, azulenyl, norbornane (1,4-endo-methylene-cyclohexane), adamantane ring systems.

Lines (such as '-' in $—(R^a)_{na}$) drawn into ring systems indicate that the bond may be attached to any of the suitable and available ring atoms.

In an embodiment wherein two or more heteroatoms are involved, these heteroatoms may be the same or part or all of the two or more heteroatoms may be different.

The term "optional" or "optionally" means the event described subsequent thereto may or may not happen. This term encompasses the cases that the event may or may not happen.

As used herein, the expression "one or more" refers to at least one, for example one, two, three, four, five or more, whenever possible and depending on the context.

In the compounds of formula (I) the carbon atom indicated with a "*" in the below formula is a chiral center. The present invention provides compounds of formula (I) wherein said chiral center represents a specific stereochemistry (S or R), in particular compounds of formula (I) wherein said chiral center has S-stereochemistry.

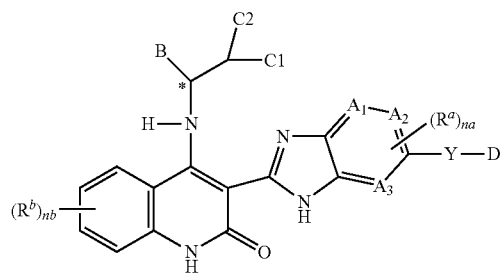

Thus, the present invention provides compounds of formula (I-a)

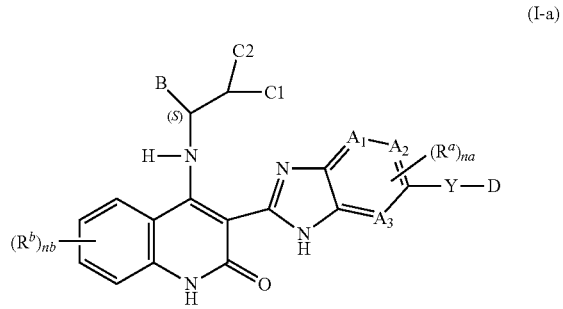

(I-a)

including any tautomeric and stereochemically isomeric form thereof, wherein $A_1$, $A_2$ and $A_3$ each independently represent a carbon atom or a nitrogen atom;

C1 is hydrogen or $C_{1-4}$alkyl;

C2 is hydrogen or $C_{1-4}$alkyl or hydroxyl;

or C1 and C2 are taken together to form a $C_{3-6}$cycloalkyl together with the carbon atom to which they are attached;

Y is a direct bond, —O—, C(=O), $NR^y$, S(=O)$_2$, or $C_{1-4}$alkyl;

$R^y$ is hydrogen or $C_{1-4}$alkyl;

each $R^a$ independently is hydrogen, $C_{1-6}$alkyl, halo$C_{1-6}$alkyl, halo, $C_{1-6}$alkoxy, carboxyl, $C_{1-6}$alkyloxycarbonyl, $C_{2-6}$alkenyl, $C_{2-6}$alkynyl, cyano, cyano$C_{1-6}$alkyl, hydroxy$C_{1-6}$alkyl, —C(=O)—NH$_2$, —C(=O)—NH($C_{1-4}$alkyl), —C(=O)—N($C_{1-4}$alkyl)$_2$, or a 3 to 6 membered monocyclic saturated heterocyclyl containing at least one heteroatom selected from N, O or S;

na is an integer equal to 1 or 2;

each $R^b$ independently is hydrogen, $C_{1-6}$alkyl, halo$C_{1-6}$alkyl, halo, $C_{1-6}$alkoxy, $C_{1-6}$alkyloxycarbonyl, $C_{2-6}$alkenyl, $C_{2-6}$alkynyl, cyano, cyano$C_{1-6}$alkyl, hydroxy$C_{1-6}$alkyl, —C(=O)—NH$_2$, —C(=O)—NH($C_{1-4}$alkyl), —C(=O)—N($C_{1-4}$alkyl)$_2$, $C_{3-6}$cycloalkyl, phenyl, a 3 to 6 membered monocyclic heterocyclyl containing at least one heteroatom selected from N, O or S, or $C_{1-6}$alkyl substituted with $C_{3-6}$cycloalkyl or with phenyl or with a 3 to 6 membered monocyclic heterocyclyl containing at least one heteroatom selected from N, O or S;

nb is an integer equal to 1 or 2;

D is a 3 to 12 membered heterocyclyl containing at least one heteroatom selected from N, O or S, wherein said heterocyclyl is optionally being substituted with 1 to 5 $R^c$ substituents; each $R^c$ independently is oxo, $C_{1-6}$alkyl, hydroxy$C_{1-6}$alkyl, halo$C_{1-6}$alkyl, halo$C_{1-6}$alkyloxy, carboxyl, HOOC—$C_{1-6}$alkyl-, $C_{1-6}$alkyl substituted with —C(=O)—O—$C_{1-6}$alkyl, $C_{1-6}$alkyl-O—C(=O)—, cyano, cyano$C_{1-6}$alkyl, $C_{1-6}$alkyl-C(=O)—, —SO$_2$—$C_{1-6}$alkyl, $C_{3-6}$cycloalkyl, phenyl, a 3 to 6 membered monocyclic saturated heterocyclyl containing at least one heteroatom selected from N, O or S, or a 5 or 6 membered monocyclic aromatic heterocyclyl containing at least one heteroatom selected from N, O or S;

B is a 3 to 12 membered carbocyclyl or a 3 to 12 membered heterocyclyl containing at least one heteroatom selected from N, O or S, wherein said carbocyclyl and heterocyclyl are each optionally being substituted with 1 to 5 R substituents;

each R independently is $C_{1-6}$alkyl, cyano, halo, $C_{1-6}$alkoxy, halo$C_{1-6}$alkoxy, hydroxyl, hydroxy$C_{1-6}$alkyl, halo$C_{1-6}$alkyl, oxo, —SO$_2$—NH$_2$, —SO$_2$—NH($C_{1-4}$alkyl), —SO$_2$—N($C_{1-4}$alkyl)$_2$, —NH—C(=O)—$C_{2-6}$alkenyl, —C(=O)—$C_{1-6}$alkyl, —C(=O)—$C_{2-6}$alkenyl, $C_{1-6}$alkyl-O—C(=O)—, $C_{3-6}$cycloalkyl, phenyl, or a 3 to 6 membered monocyclic heterocyclyl containing at least one heteroatom selected from N, O or S;

or the pharmaceutically acceptable salts thereof or the solvates thereof.

The present invention provides compounds of formula (I-A)

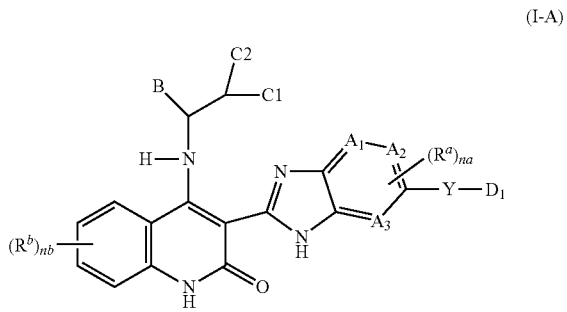

(I-A)

including any tautomeric and stereochemically isomeric form thereof, wherein $A_1$, $A_2$ and $A_3$ each independently represent a carbon atom or a nitrogen atom;

C1 is hydrogen or $C_{1-4}$alkyl;

C2 is hydrogen or $C_{1-4}$alkyl or hydroxyl;

or C1 and C2 are taken together to form a $C_{3-6}$cycloalkyl together with the carbon atom to which they are attached;

Y is a direct bond, —O—, C(=O), $NR^y$, S(=O)$_2$, or $C_{1-4}$alkyl;

R is hydrogen or $C_{1-4}$alkyl;

each $R^a$ independently is hydrogen, $C_{1-6}$alkyl, halo$C_{1-6}$alkyl, halo, $C_{1-6}$alkoxy, carboxyl, $C_{1-6}$alkyloxycarbonyl, $C_{2-6}$alkenyl, $C_{2-6}$alkynyl, cyano, cyano$C_{1-6}$alkyl, hydroxy$C_{1-6}$alkyl, —C(=O)—NH$_2$, —C(=O)—NH($C_{1-4}$alkyl), —C(=O)—N($C_{1-4}$alkyl)$_2$, or a 3 to 6 membered monocyclic saturated heterocyclyl containing at least one heteroatom selected from N, O or S;

na is an integer equal to 1 or 2;

each $R^b$ independently is hydrogen, $C_{1-6}$alkyl, halo$C_{1-6}$alkyl, halo, $C_{1-6}$alkoxy, $C_{1-6}$alkyloxycarbonyl, $C_{2-6}$alkenyl, $C_{2-6}$alkynyl, cyano, cyano$C_{1-6}$alkyl, hydroxy$C_{1-6}$alkyl, —C(=O)—NH$_2$, —C(=O)—NH($C_{1-4}$alkyl), —C(=O)—N($C_{1-4}$alkyl)$_2$, $C_{3-6}$cycloalkyl, phenyl, a 3 to 6 membered monocyclic heterocyclyl containing at least one heteroatom selected from N, O or S, or $C_{1-6}$alkyl substituted with $C_{3-6}$cycloalkyl or with phenyl or with a 3 to 6 membered monocyclic heterocyclyl containing at least one heteroatom selected from N, O or S;

nb is an integer equal to 1 or 2;

$D_1$ is piperazin-1-yl, wherein said piperazin-1-yl is optionally being substituted with 1 to 5 $R^c$ substituents;

each $R^c$ independently is oxo, $C_{1-6}$alkyl, hydroxy$C_{1-6}$alkyl, halo$C_{1-6}$alkyl, halo$C_{1-6}$alkyloxy, carboxyl, HOOC—$C_{1-6}$alkyl-, $C_{1-6}$alkyl substituted with —C(=O)—O—$C_{1-6}$alkyl, $C_{1-6}$alkyl-O—C(=O)—, cyano, cyano$C_{1-6}$alkyl, $C_{1-6}$alkyl-C(=O)—, —SO$_2$—$C_{1-6}$alkyl, $C_{3-6}$cycloalkyl, phenyl, a 3 to 6 membered monocyclic saturated heterocyclyl containing at least one heteroatom selected from N, O or S, or a 5 or 6 membered monocyclic aromatic heterocyclyl containing at least one heteroatom selected from N, O or S;

B is a 3 to 12 membered carbocyclyl or a 3 to 12 membered heterocyclyl containing at least one heteroatom selected from N, O or S, wherein said carbocyclyl and heterocyclyl are each optionally being substituted with 1 to 5 R substituents;

each R independently is $C_{1-6}$alkyl, cyano, halo, $C_{1-6}$alkoxy, halo$C_{1-6}$alkoxy, hydroxyl, hydroxy$C_{1-6}$alkyl, halo$C_{1-6}$alkyl, oxo, —SO$_2$—NH$_2$, —SO$_2$—NH($C_{1-4}$alkyl), —SO$_2$—N($C_{1-4}$alkyl)$_2$, —NH—C(=O)—$C_{2-6}$alkenyl, —C(=O)—$C_{1-6}$alkyl, —C(=O)—$C_{2-6}$alkenyl, $C_{1-6}$alkyl-O—C(=O)—, $C_{3-6}$cycloalkyl, phenyl, or a 3 to 6 membered monocyclic heterocyclyl containing at least one heteroatom selected from N, O or S;

or the pharmaceutically acceptable salts thereof or the solvates thereof.

The present invention provides compounds of formula (I-A) as defined hereinabove having an S stereocenter as in the following formula (I-A-a):

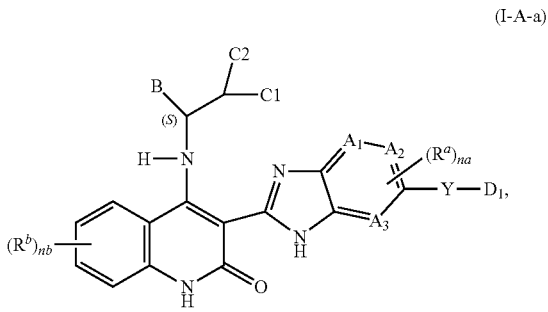

(I-A-a)

including any tautomeric and stereochemically isomeric form thereof, wherein the substituents are as defined above for the compounds of formula (I-A);

or the pharmaceutically acceptable salts thereof or the solvates thereof.

The present invention provides compounds of formula (I-B)

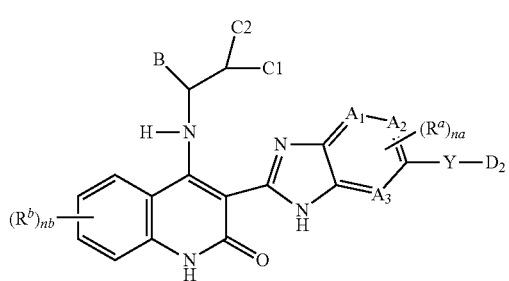

(I-B)

including any tautomeric and stereochemically isomeric form thereof, wherein $A_1$, $A_2$ and $A_3$ each independently represent a carbon atom or a nitrogen atom;

C1 is hydrogen or $C_{1-4}$alkyl;

C2 is hydrogen or $C_{1-4}$alkyl or hydroxyl;

or C1 and C2 are taken together to form a $C_{3-6}$cycloalkyl together with the carbon atom to which they are attached;

Y is a direct bond, —O—, C(=O), NR$^y$, S(=O)$_2$, or $C_{1-4}$alkyl;

R$^y$ is hydrogen or $C_{1-4}$alkyl;

each R$^a$ independently is hydrogen, $C_{1-6}$alkyl, halo$C_{1-6}$alkyl, halo, $C_{1-6}$alkoxy, carboxyl, $C_{1-6}$alkyloxycarbonyl, $C_{2-6}$alkenyl, $C_{2-6}$alkynyl, cyano, cyano$C_{1-6}$alkyl, hydroxy$C_{1-6}$alkyl, —C(=O)—NH$_2$, —C(=O)—NH($C_{1-4}$alkyl), —C(=O)—N($C_{1-4}$alkyl)$_2$, or a 3 to 6 membered monocyclic saturated heterocyclyl containing at least one heteroatom selected from N, O or S;

na is an integer equal to 1 or 2;

each R$^b$ independently is hydrogen, $C_{1-6}$alkyl, halo$C_{1-6}$alkyl, halo, $C_{1-6}$alkoxy, $C_{1-6}$alkyloxycarbonyl, $C_{2-6}$alkenyl, $C_{2-6}$alkynyl, cyano, cyano$C_{1-6}$alkyl, hydroxy$C_{1-6}$alkyl, —C(=O)—NH$_2$, —C(=O)—NH($C_{1-4}$alkyl), —C(=O)—N($C_{1-4}$alkyl)$_2$, $C_{3-6}$cycloalkyl, phenyl, a 3 to 6 membered monocyclic heterocyclyl containing at least one heteroatom selected from N, O or S, or $C_{1-6}$alkyl substituted with $C_{3-6}$cycloalkyl or with phenyl or with a 3 to 6 membered monocyclic heterocyclyl containing at least one heteroatom selected from N, O or S;

nb is an integer equal to 1 or 2;

D$_2$ is morpholin-1-yl, wherein said morpholin-1-yl is optionally being substituted with 1 to 5 R$^c$ substituents;

each R$^c$ independently is oxo, $C_{1-6}$alkyl, hydroxy$C_{1-6}$alkyl, halo$C_{1-6}$alkyl, halo$C_{1-6}$alkyloxy, carboxyl, HOOC—$C_{1-6}$alkyl-, $C_{1-6}$alkyl substituted with —C(=O)—O—$C_{1-6}$alkyl, $C_{1-6}$alkyl-O—C(=O)—, cyano, cyano$C_{1-6}$alkyl, $C_{1-6}$alkyl-C(=O)—, —SO$_2$—$C_{1-6}$alkyl, $C_{3-6}$cycloalkyl, phenyl, a 3 to 6 membered monocyclic saturated heterocyclyl containing at least one heteroatom selected from N, O or S, or a 5 or 6 membered monocyclic aromatic heterocyclyl containing at least one heteroatom selected from N, O or S;

B is a 3 to 12 membered carbocyclyl or a 3 to 12 membered heterocyclyl containing at least one heteroatom selected from N, O or S, wherein said carbocyclyl and heterocyclyl are each optionally being substituted with 1 to 5 R substituents;

each R independently is $C_{1-6}$alkyl, cyano, halo, $C_{1-6}$alkoxy, halo$C_{1-6}$alkoxy, hydroxyl, hydroxy$C_{1-6}$alkyl, halo$C_{1-6}$alkyl, oxo, —SO$_2$—NH$_2$, —SO$_2$—NH($C_{1-4}$alkyl), —SO$_2$—N($C_{1-4}$alkyl)$_2$, —NH—C(=O)—$C_{2-6}$alkenyl, —C(=O)—$C_{1-6}$alkyl, —C(=O)—$C_{2-6}$alkenyl, $C_{1-6}$alkyl-O—C(=O)—, $C_{3-6}$cycloalkyl, phenyl, or a 3 to 6 membered monocyclic heterocyclyl containing at least one heteroatom selected from N, O or S;

or the pharmaceutically acceptable salts thereof or the solvates thereof.

The present invention provides compounds of formula (I-B) as defined hereinabove having an S stereocenter as in the following formula (I-B-a):

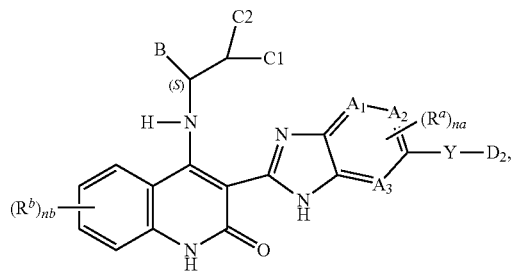

(I-B-a)

including any tautomeric and stereochemically isomeric form thereof, wherein the substituents are as defined above for the compounds of formula (I-B);

or the pharmaceutically acceptable salts thereof or the solvates thereof.

The present invention provides compounds of formula (I-C)

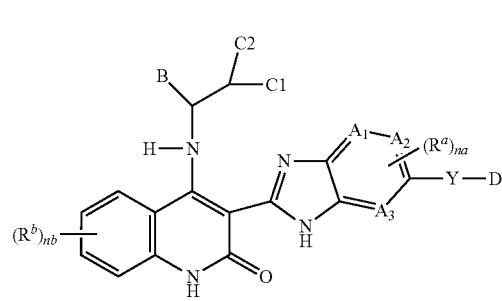

(I-C)

including any tautomeric and stereochemically isomeric form thereof, wherein

A₁, A₂ and A₃ each independently represent a carbon atom or a nitrogen atom;

C1 is hydrogen or $C_{1-4}$alkyl;

C2 is hydrogen or $C_{1-4}$alkyl or hydroxyl;

or C1 and C2 are taken together to form a $C_{3-6}$cycloalkyl together with the carbon atom to which they are attached;

Y is a direct bond, —O—, C(=O), NR$^y$, S(=O)₂, or $C_{1-4}$alkyl;

R$^y$ is hydrogen or $C_{1-4}$alkyl;

each R$^a$ independently is hydrogen, $C_{1-6}$alkyl, halo$C_{1-6}$alkyl, halo, $C_{1-6}$alkoxy, carboxyl, $C_{1-6}$alkyloxycarbonyl, $C_{2-6}$alkenyl, $C_{2-6}$alkynyl, cyano, cyano$C_{1-6}$alkyl, hydroxy$C_{1-6}$alkyl, —C(=O)—NH₂, —C(=O)—NH($C_{1-4}$alkyl), —C(=O)—N($C_{1-4}$alkyl)₂, or a 3 to 6 membered monocyclic saturated heterocyclyl containing at least one heteroatom selected from N, O or S;

na is an integer equal to 1 or 2;

each R$^b$ independently is hydrogen, $C_{1-6}$alkyl, halo$C_{1-6}$alkyl, halo, $C_{1-6}$alkoxy, $C_{1-6}$alkyloxycarbonyl, $C_{2-6}$alkenyl, $C_{2-6}$alkynyl, cyano, cyano$C_{1-6}$alkyl, hydroxy$C_{1-6}$alkyl, —C(=O)—NH₂, —C(=O)—NH($C_{1-4}$alkyl), —C(=O)—N($C_{1-4}$alkyl)₂, $C_{3-6}$cycloalkyl, phenyl, a 3 to 6 membered monocyclic heterocyclyl containing at least one heteroatom selected from N, O or S, or $C_{1-6}$alkyl substituted with $C_{3-6}$cycloalkyl or with phenyl or with a 3 to 6 membered monocyclic heterocyclyl containing at least one heteroatom selected from N, O or S;

nb is an integer equal to 1 or 2;

D₃ is 4, 5, 6, or 7 membered monocyclic heterocyclyl, wherein said heterocyclyl is optionally being substituted with 1 to 5 R$^c$ substituents;

each R$^c$ independently is oxo, $C_{1-6}$alkyl, hydroxy$C_{1-6}$alkyl, halo$C_{1-6}$alkyl, halo$C_{1-6}$alkyloxy, carboxyl, HOOC—$C_{1-6}$alkyl-, $C_{1-6}$alkyl substituted with —C(=O)—O—$C_{1-6}$alkyl, $C_{1-6}$alkyl-O—C(=O)—, cyano, cyano$C_{1-6}$alkyl, $C_{1-6}$alkyl-C(=O)—, —SO₂—$C_{1-6}$alkyl, $C_{3-6}$cycloalkyl, phenyl, a 3 to 6 membered monocyclic saturated heterocyclyl containing at least one heteroatom selected from N, O or S, or a 5 or 6 membered monocyclic aromatic heterocyclyl containing at least one heteroatom selected from N, O or S;

B is a 3 to 12 membered carbocyclyl or a 3 to 12 membered heterocyclyl containing at least one heteroatom selected from N, O or S, wherein said carbocyclyl and heterocyclyl are each optionally being substituted with 1 to 5 R substituents;

each R independently is $C_{1-6}$alkyl, cyano, halo, $C_{1-6}$alkoxy, halo$C_{1-6}$alkoxy, hydroxyl, hydroxy$C_{1-6}$alkyl, halo$C_{1-6}$alkyl, oxo, —SO₂—NH₂, —SO₂—NH($C_{1-4}$alkyl), —SO₂—N($C_{1-4}$alkyl)₂, —NH—C(=O)—$C_{2-6}$alkenyl, —C(=O)—$C_{1-6}$alkyl, —C(=O)—$C_{2-6}$alkenyl, $C_{1-6}$alkyl-O—C(=O)—, $C_{3-6}$cycloalkyl, phenyl, or a 3 to 6 membered monocyclic heterocyclyl containing at least one heteroatom selected from N, O or S;

or the pharmaceutically acceptable salts thereof or the solvates thereof.

The present invention provides compounds of formula (I-C) as defined hereinabove having an S stereocenter as in the following formula (I-C-a):

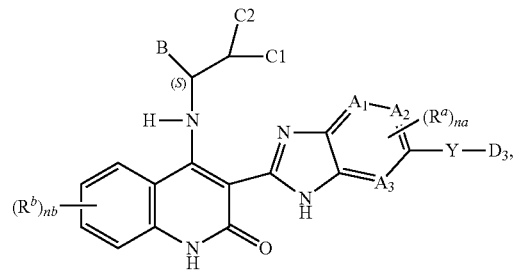

(I-C-a)

including any tautomeric and stereochemically isomeric form thereof, wherein
the substituents are as defined above for the compounds of formula (I-C);
or the pharmaceutically acceptable salts thereof or the solvates thereof.

The invention provides compounds of formula (I-D):

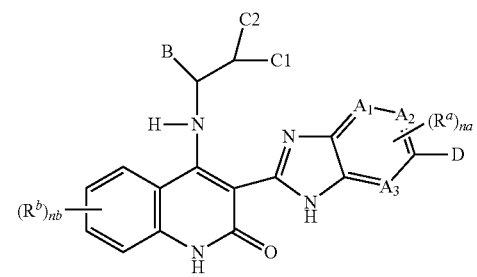

(I-D)

including any tautomeric and stereochemically isomeric form thereof, wherein

A₁, A₂ and A₃ each independently represent a carbon atom or a nitrogen atom;

C1 is hydrogen or $C_{1-4}$alkyl;

C2 is hydrogen or $C_{1-4}$alkyl or hydroxyl;

or C1 and C2 are taken together to form a $C_{3-6}$cycloalkyl together with the carbon atom to which they are attached;

each R$^a$ independently is hydrogen, $C_{1-6}$alkyl, halo$C_{1-6}$alkyl, halo, $C_{1-6}$alkoxy, carboxyl, $C_{1-6}$alkyloxycarbonyl, $C_{2-6}$alkenyl, $C_{2-6}$alkynyl, cyano, cyano$C_{1-6}$alkyl, hydroxy$C_{1-6}$alkyl, —C(=O)—NH₂, —C(=O)—NH($C_{1-4}$alkyl), —C(=O)—N($C_{1-4}$alkyl)₂, or a 3 to 6 membered monocyclic saturated heterocyclyl containing at least one heteroatom selected from N, O or S;

na is an integer equal to 1 or 2;

each R$^b$ independently is hydrogen, $C_{1-6}$alkyl, halo$C_{1-6}$alkyl, halo, $C_{1-6}$alkoxy, $C_{1-6}$alkyloxycarbonyl, $C_{2-6}$alkenyl, $C_{2-6}$alkynyl, cyano, cyano$C_{1-6}$alkyl, hydroxy$C_{1-6}$alkyl, —C(=O)—NH₂, —C(=O)—NH($C_{1-4}$alkyl), —C(=O)—N($C_{1-4}$alkyl)₂, $C_{3-6}$cycloalkyl, phenyl, a 3 to 6 membered monocyclic heterocyclyl containing at least one heteroatom selected from N, O or S, or $C_{1-6}$alkyl substituted with $C_{3-6}$cycloalkyl or with phenyl or with a 3 to 6 membered monocyclic heterocyclyl containing at least one heteroatom selected from N, O or S;

nb is an integer equal to 1 or 2;

D is a 3 to 12 membered heterocyclyl containing at least one heteroatom selected from N, O or S, wherein said heterocyclyl is optionally being substituted with 1 to 5 R$^c$ substituents; each R$^c$ independently is oxo, $C_{1-6}$alkyl, hydroxyC$_{1-6}$alkyl, haloC$_{1-6}$alkyl, haloC$_{1-6}$alkyloxy, carboxyl, HOOC—C$_{1-6}$alkyl-, C$_{1-6}$alkyl substituted with —C(=O)—O—C$_{1-6}$alkyl, C$_{1-6}$alkyl-O—C(=O)—, cyano, cyanoC$_{1-6}$alkyl, C$_{1-6}$alkyl-C(=O)—, —SO$_2$—C$_{1-6}$alkyl, C$_{3-6}$cycloalkyl, phenyl, a 3 to 6 membered monocyclic saturated heterocyclyl containing at least one heteroatom selected from N, O or S, or a 5 or 6 membered monocyclic aromatic heterocyclyl containing at least one heteroatom selected from N, O or S;

B is a 3 to 12 membered carbocyclyl or a 3 to 12 membered heterocyclyl containing at least one heteroatom selected from N, O or S, wherein said carbocyclyl and heterocyclyl are each optionally being substituted with 1 to 5 R substituents;

each R independently is C$_{1-6}$alkyl, cyano, halo, C$_{1-6}$alkoxy, haloC$_{1-6}$alkoxy, hydroxyl, hydroxyC$_{1-6}$alkyl, haloC$_{1-6}$alkyl, oxo, —SO$_2$—NH$_2$, —SO$_2$—NH(C$_{1-4}$alkyl), —SO$_2$—N(C$_{1-4}$alkyl)$_2$, —NH—C(=O)—C$_{2-6}$alkenyl, —C(=O)—C$_{1-6}$alkyl, —C(=O)—C$_{2-6}$alkenyl, C$_{1-6}$alkyl-O—C(=O)—, C$_{3-6}$cycloalkyl, phenyl, or a 3 to 6 membered monocyclic heterocyclyl containing at least one heteroatom selected from N, O or S;

or the pharmaceutically acceptable salts thereof or the solvates thereof.

The present invention provides compounds of formula (I-D) as defined hereinabove having an S stereocenter as in the following formula (I-D-a):

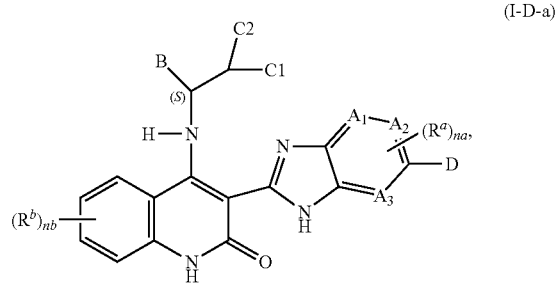

(I-D-a)

including any tautomeric and stereochemically isomeric form thereof, wherein the substituents are as defined above for the compounds of formula (I-D);

or the pharmaceutically acceptable salts thereof or the solvates thereof.

The invention provides compounds of formula (I-a), (I-A), (I-A-a), (I-B), (I-B-a), (I-C), (I-C-a), (I-D) or (I-D-a) as defined above but wherein each R$^c$ independently is oxo, halo, C$_{1-6}$alkyl, C$_{1-6}$alkyloxy, hydroxyC$_{1-6}$alkyl, haloC$_{1-6}$alkyl, haloC$_{1-6}$alkyloxy, carboxyl, HOOC—C$_{1-6}$alkyl-, C$_{1-6}$alkyl substituted with —C(=O)—O—C$_{1-6}$alkyl, C$_{1-6}$alkyl-O—C(=O)—, cyano, cyanoC$_{1-6}$alkyl, C$_{1-6}$alkyl-C(=O)—, —SO$_2$—C$_{1-6}$alkyl, C$_{3-6}$cycloalkyl, phenyl, a 3 to 6 membered monocyclic saturated heterocyclyl containing at least one heteroatom selected from N, O or S, or a 5 or 6 membered monocyclic aromatic heterocyclyl containing at least one heteroatom selected from N, O or S.

In an embodiment, in the compounds of formula (I), (I-a), (I-A), (I-A-a), (I-B), (I-B-a), (I-C), (I-C-a), (I-D) or (I-D-a), A$_1$, A$_2$ and A$_3$ represent a carbon atom.

Thus, the present invention provides compounds of formula (I), (I-a), (I-A), (I-A-a), (I-B), (I-B-a), (I-C), (I-C-a), (I-D) or (I-D-a) wherein

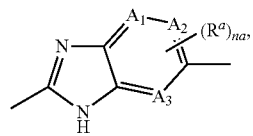

represents

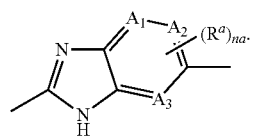

In an embodiment, in the compounds of formula (I), (I-a), (I-A), (I-A-a), (I-B), (I-B-a), (I-C), (I-C-a), (I-D) or (I-D-a), one of A$_1$, A$_2$ and A$_3$ is a nitrogen atom and the remaining A substituents are carbon atoms.

Thus, the present invention provides compounds of formula (I), (I-a), (I-A), (I-A-a), (I-B), (I-B-a), (I-C), (I-C-a), (I-D) or (I-D-a) wherein

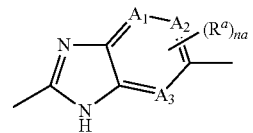

represents

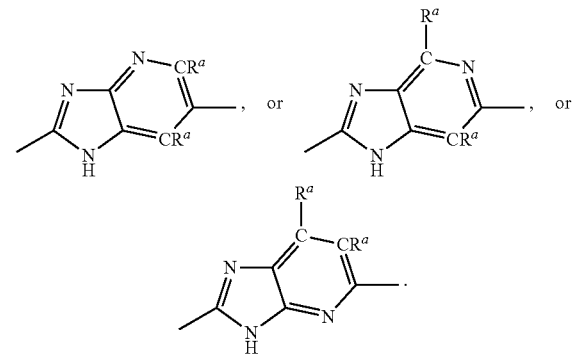

In an embodiment, in the compounds of formula (I), (I-a), (I-A), (I-A-a), (I-B), (I-B-a), (I-C), (I-C-a), (I-D) or (I-D-a), two of A$_1$, A$_2$ and A$_3$ substituents are nitrogen atoms and the remaining A is a carbon atom.

Thus, the present invention provides compounds of formula (I), (I-a), (I-A), (I-A-a), (I-B), (I-B-a), (I-C), (I-C-a), (I-D) or (I-D-a) wherein

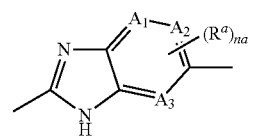

represents

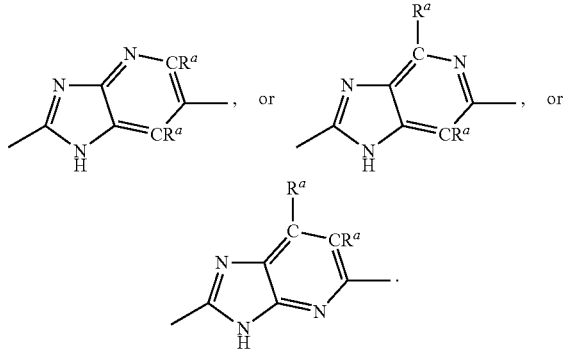

In an embodiment, in the compounds of formula (I), (I-a), (I-A), (I-A-a), (I-B), (I-B-a), (I-C) or (I-C-a), Y is a direct bond.

In an embodiment, in the compounds of formula (I), (I-a), (I-A), (I-A-a), (I-B), (I-B-a), (I-C) or (I-C-a), Y is —O—, C(=O), $NR^y$, $S(=O)_2$, or $C_{1-4}$alkyl.

In an embodiment, in the compounds of formula (I), (I-a), (I-A), (I-A-a), (I-B), (I-B-a), (I-C) or (I-C-a), Y is a direct bond, C(=O), or $NR^y$, e.g. $NCH_3$.

In an embodiment, in the compounds of formula (I), (I-a), (I-A), (I-A-a), (I-B), (I-B-a), (I-C), (I-C-a), (I-D) or (I-D-a), $C_1$ is hydrogen.

In an embodiment, in the compounds of formula (I), (I-a), (I-A), (I-A-a), (I-B), (I-B-a), (I-C), (I-C-a), (I-D) or (I-D-a), $C_2$ is hydrogen.

In an embodiment, in the compounds of formula (I), (I-a), (I-A), (I-A-a), (I-B), (I-B-a), (I-C), (I-C-a), (I-D) or (I-D-a), $C_1$ is hydrogen and $C_2$ is $C_{1-4}$alkyl.

In an embodiment, in the compounds of formula (I), (I-a), (I-A), (I-A-a), (I-B), (I-B-a), (I-C), (I-C-a), (I-D) or (I-D-a), $C_1$ is hydrogen and $C_2$ is hydroxyl.

In an embodiment, in the compounds of formula (I), (I-a), (I-A), (I-A-a), (I-B), (I-B-a), (I-C), (I-C-a), (I-D) or (I-D-a), $C_1$ and $C_2$ are taken together to form $C_{3-6}$cycloalkyl together with the carbon atom to which they are attached.

In an embodiment, in the compounds of formula (I), (I-a), (I-A), (I-A-a), (I-B), (I-B-a), (I-C), (I-C-a), (I-D) or (I-D-a),

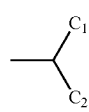

represents —$CH_3$.

In an embodiment, in the compounds of formula (I), (I-a), (I-A), (I-A-a), (I-B), (I-B-a), (I-C), (I-C-a), (I-D) or (I-D-a),

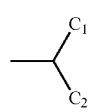

represents —$CH_2(C_{1-4}$alkyl), in particular —$CH_2CH_3$ or —$CH_2CH_2CH_3$.

In an embodiment, in the compounds of formula (I), (I-a), (I-A), (I-A-a), (I-B), (I-B-a), (I-C), (I-C-a), (I-D) or (I-D-a),

represents —$CH(C_{1-4}$alkyl$)_2$, in particular —$CH(CH_3)_2$.

In an embodiment, in the compounds of formula (I), (I-a), (I-A), (I-A-a), (I-B), (I-B-a), (I-C), (I-C-a), (I-D) or (I-D-a),

represents -cyclopropyl.

In an embodiment, in the compounds of formula (I), (I-a), (I-A), (I-A-a), (I-B), (I-B-a), (I-C) or (I-C-a), $R^y$ is hydrogen.

In an embodiment, in the compounds of formula (I), (I-a), (I-A), (I-A-a), (I-B), (I-B-a), (I-C) or (I-C-a), R is $C_{1-4}$alkyl, in particular methyl.

In an embodiment, in the compounds of formula (I), (I-a), (I-A), (I-A-a), (I-B), (I-B-a), (I-C), (I-C-a), (I-D) or (I-D-a), $R^a$ is hydrogen.

In an embodiment, in the compounds of formula (I), (I-a), (I-A), (I-A-a), (I-B), (I-B-a), (I-C), (I-C-a), (I-D) or (I-D-a), one $R^a$ is hydrogen and the other $R^a$ is $C_{1-6}$alkyl, halo$C_{1-6}$alkyl, halo, $C_{1-6}$alkoxy, carboxyl, $C_{1-6}$alkyloxycarbonyl, $C_{2-6}$alkenyl, $C_{2-6}$alkynyl, cyano, cyano$C_{1-6}$alkyl, hydroxy$C_{1-6}$alkyl, —C(=O)—$NH_2$, —C(=O)—NH($C_{1-4}$alkyl), —C(=O)—N($C_{1-4}$alkyl$)_2$, a 3 to 6 membered monocyclic saturated heterocyclyl containing at least one heteroatom selected from N, O or S.

In an embodiment, in the compounds of formula (I), (I-a), (I-A), (I-A-a), (I-B), (I-B-a), (I-C), (I-C-a), (I-D) or (I-D-a), na is an integer equal to 1.

In an embodiment, in the compounds of formula (I), (I-a), (I-A), (I-A-a), (I-B), (I-B-a), (I-C), (I-C-a), (I-D) or (I-D-a), na is an integer equal to 1 and the $R^a$ is hydrogen; $C_{1-6}$alkyl, in particular $C_{1-4}$alkyl, e.g. methyl; halo$C_{1-6}$alkyl, e.g. trifluoromethyl; or halo, e.g. fluoro.

In an embodiment, in the compounds of formula (I), (I-a), (I-A), (I-A-a), (I-B), (I-B-a), (I-C), (I-C-a), (I-D) or (I-D-a), $R^b$ is hydrogen.

In an embodiment, in the compounds of formula (I), (I-a), (I-A), (I-A-a), (I-B), (I-B-a), (I-C), (I-C-a), (I-D) or (I-D-a), $n_b$ is an integer equal to 1 and $R^b$ is $C_{1-6}$alkyl, halo$C_{1-6}$alkyl, halo, $C_{1-6}$alkoxy, $C_{1-6}$alkyloxycarbonyl, $C_{2-6}$alkenyl, $C_{2-6}$alkynyl, cyano, cyano$C_{1-6}$alkyl, hydroxy-$C_{1-6}$alkyl, —C(=O)—$NH_2$, —C(=O)—NH($C_{1-4}$alkyl), —C(=O)—N($C_{1-4}$alkyl$)_2$, $C_{3-6}$cycloalkyl, phenyl, a 3 to 6 membered monocyclic heterocyclyl containing at least one heteroatom selected from N, O or S, or $C_{1-6}$alkyl substituted with $C_{3-6}$cycloalkyl or with phenyl or with a 3 to 6 membered monocyclic heterocyclyl containing at least one heteroatom selected from N, O or S.

In an embodiment, in the compounds of formula (I), (I-a), (I-A), (I-A-a), (I-B), (I-B-a), (I-C), (I-C-a), (I-D) or (I-D-a), $n_b$ is an integer equal to 1 and $R^b$ is $C_{1-6}$alkyl, halo$C_{1-6}$alkyl, halo, $C_{1-6}$alkoxy, $C_{1-6}$alkyloxycarbonyl, $C_{2-6}$alkenyl, $C_{2-6}$alkynyl, cyano, cyano$C_{1-6}$alkyl, hydroxy$C_{1-6}$alkyl, —C(=O)—$NH_2$, —C(=O)—NH($C_{1-4}$alkyl), or —C(=O)—N($C_{1-4}$alkyl$)_2$.

In an embodiment, in the compounds of formula (I), (I-a), (I-A), (I-A-a), (I-B), (I-B-a), (I-C), (I-C-a), (I-D) or (I-D-a), $n_b$ is an integer equal to 1 and $R^b$ is hydrogen or halo, e.g. chloro or fluoro.

In an embodiment, in the compounds of formula (I), (I-a), (I-A), (I-A-a), (I-B), (I-B-a), (I-C), (I-C-a), (I-D) or (I-D-a), $n_b$ is an integer equal to 2.

In an embodiment, in the compounds of formula (I), (I-a), (I-A), (I-A-a), (I-B), (I-B-a), (I-C), (I-C-a), (I-D) or (I-D-a), each $R^b$ independently is hydrogen, $C_{1-6}$alkyl, halo$C_{1-6}$alkyl, halo, $C_{1-6}$alkoxy, $C_{2-6}$alkenyl, $C_{2-6}$alkynyl, cyano, cyano$C_{1-6}$alkyl, hydroxy$C_{1-6}$alkyl, —C(=O)—NH$_2$, —C(=O)—NH($C_{1-4}$alkyl), —C(=O)—N($C_{1-4}$alkyl)$_2$, $C_{3-6}$cycloalkyl, phenyl, a 3 to 6 membered monocyclic heterocyclyl containing at least one heteroatom selected from N, O or S, or $C_{1-6}$alkyl substituted with $C_{3-6}$cycloalkyl or with phenyl or with a 3 to 6 membered monocyclic heterocyclyl containing at least one heteroatom selected from N, O or S.

In an embodiment, in the compounds of formula (I), (I-a), (I-A), (I-A-a), (I-B), (I-B-a), (I-C), (I-C-a), (I-D) or (I-D-a), each $R^b$ independently is hydrogen, $C_{1-6}$alkyl, halo$C_{1-6}$alkyl, $C_{1-6}$alkoxy, $C_{1-6}$alkyloxycarbonyl, $C_{2-6}$alkenyl, $C_{2-6}$alkynyl, cyano$C_{1-6}$alkyl, hydroxy$C_{1-6}$alkyl, —C(=O)—NH$_2$, —C(=O)—NH($C_{1-4}$alkyl), —C(=O)—N($C_{1-4}$alkyl)$_2$, $C_{3-6}$cycloalkyl, phenyl, a 3 to 6 membered monocyclic heterocyclyl containing at least one heteroatom selected from N, O or S, or $C_{1-6}$alkyl substituted with $C_{3-6}$cycloalkyl or with phenyl or with a 3 to 6 membered monocyclic heterocyclyl containing at least one heteroatom selected from N, O or S.

In an embodiment, in the compounds of formula (I), (I-a), (I-A), (I-A-a), (I-B), (I-B-a), (I-C), (I-C-a), (I-D) or (I-D-a), D, $D_1$, $D_2$ or $D_3$ is unsubstituted.

In an embodiment, in the compounds of formula (I), (I-a), (I-A), (I-A-a), (I-B), (I-B-a), (I-C), (I-C-a), (I-D) or (I-D-a), D, $D_1$, $D_2$ or $D_3$ is substituted with 1, 2, 3 or 4 $R_c$ substituents In an embodiment, in the compounds of formula (I), (I-a), (I-A), (I-A-a), (I-B), (I-B-a), (I-C), (I-C-a), (I-D) or (I-D-a), D, $D_1$, $D_2$ or $D_3$ is substituted with 2 $R_c$ substituents.

In an embodiment, in the compounds of formula (I), (I-a), (I-A), (I-A-a), (I-B), (I-B-a), (I-C), (I-C-a), (I-D) or (I-D-a), D, D1, D2 or D3 is substituted with 1 or 2 $R_c$ substituents.

In an embodiment, in the compounds of formula (I), (I-a), (I-A), (I-A-a), (I-B), (I-B-a), (I-C), (I-C-a), (I-D) or (I-D-a), D, D1, D2 or D3 is substituted with 1 or 2 Re substituents and each Re is independently selected from oxo; $C_{1-6}$alkyl, in particular $C_{1-4}$alkyl, e.g. methyl; halo$C_{1-6}$alkyl; halo$C_{1-6}$alkyloxy, e.g. trifluoromethoxy; HOOC—$C_{1-6}$alkyl-, e.g. —CH$_2$—COOH; carboxyl; $C_{1-6}$alkyl substituted with —C(=O)—O—$C_{1-6}$alkyl, e.g. —CH$_2$—C(=O)—O—CH$_2$—CH$_3$; $C_{1-6}$alkyl-O—C(=O)—, e.g. —C(=O)—O—CH$_3$.

In an embodiment, in the compounds of formula (I), (I-a), (I-A), (I-A-a), (I-B), (I-B-a), (I-C), (I-C-a), (I-D) or (I-D-a), D, D1, D2 or D3 is substituted with 4 Re substituents and each Re substituent independently represents $C_{1-6}$alkyl, in particular $C_{1-4}$alkyl, e.g. methyl.

In an embodiment, in the compounds of formula (I), (I-a), (I-C), (I-C-a), (I-D) or (I-D-a), D or $D_3$ is abridged heterocyclyl, e.g. 8-oxa-3-azabicyclo[3.2.1]octane.

In an embodiment, in the compounds of formula (I), (I-a), (I-C), (I-C-a), (I-D) or (I-D-a), D or $D_3$ is a bridged heterocyclyl wherein the bridge is —CH$_2$—, —CH$_2$—CH$_2$— or —CH$_2$—CH$_2$—CH$_2$—, in particular —CH$_2$—CH$_2$—, such as for example in 8-oxa-3-azabicyclo[3.2.1]octane.

In an embodiment, in the compounds of formula (I-C) or (I-C-a), $D_3$ is a 4, 5, 6, or 7 membered saturated monocyclic heterocyclyl containing at least one heteroatom selected from N, O or S, wherein said heterocyclyl is optionally being substituted with 1 to 5 $R^c$ substituents, with 1 to 4 $R^c$ substituents, with 1 to 3 $R^c$ substituents, with 1 or 2 $R^c$ substituents or with 1 $R^c$ substituent.

In an embodiment, in the compounds of formula (I-C) or (I-C-a), $D_3$ is a 5 or 6 membered monocyclic heterocyclyl containing at least one heteroatom selected from N, O or S, wherein said heterocyclyl is optionally being substituted with 1 to 5 $R^c$ substituents, in particular a 6 membered saturated monocyclic heterocyclyl containing at least one heteroatom selected from N, O or S, wherein said heterocyclyl is optionally being substituted with 1 to 5 $R^c$ substituents, with 1 to 4 $R^c$ substituents, with 1 to 3 $R^c$ substituents, with 1 or 2 $R^c$ substituents or with 1 $R^c$ substituent.

In an embodiment, in the compounds of formula (I-C) or (I-C-a), $D_3$ is a 5 or 6 membered aromatic monocyclic heterocyclyl containing at least one heteroatom selected from N, O or S, wherein said heterocyclyl is optionally being substituted with 1 to 5 $R^c$ substituents, in particular a 5 membered aromatic monocyclic heterocyclyl containing at least one heteroatom selected from N, O or S, wherein said heterocyclyl is optionally being substituted with 1 to 5 $R^c$ substituents, with 1 to 4 $R^c$ substituents, with 1 to 3 $R^c$ substituents, with 1 or 2 $R^c$ substituents or with 1 $R^c$ substituent, e.g. optionally substituted pyrazole.

In an embodiment, in the compounds of formula (I), (I-a), (I-A), (I-A-a), (I-B), (I-B-a), (I-C), (I-C-a), (I-D) or (I-D-a), each $R^c$ independently is oxo, $C_{1-6}$alkyl, hydroxy$C_{1-6}$alkyl, halo-$C_{1-6}$alkyl, halo$C_{1-6}$alkyloxy, carboxyl, HOOC—$C_{1-6}$alkyl-, cyano, cyano$C_{1-6}$alkyl, $C_{1-6}$alkyl-C(=O)—, —SO$_2$—$C_{1-6}$alkyl, $C_{3-6}$cycloalkyl, phenyl, a 3 to 6 membered monocyclic saturated heterocyclyl containing at least one heteroatom selected from N, O or S, or a 5 or 6 membered monocyclic aromatic heterocyclyl containing at least one heteroatom selected from N, O or S.

In an embodiment, in the compounds of formula (I), (I-a), (I-A), (I-A-a), (I-B), (I-B-a), (I-C), (I-C-a), (I-D) or (I-D-a), B is a 5 or 6 membered carbocyclyl or heterocyclyl containing at least one heteroatom selected from N, O or S, wherein said carbocyclyl and heterocyclyl are each optionally being substituted with 1 to 5, in particular 1 to 4, or 1 to 3, or 1 or 2, or 1 R substituents. In an embodiment, B is unsubstituted.

In an embodiment, in the compounds of formula (I), (I-a), (I-A), (I-A-a), (I-B), (I-B-a), (I-C), (I-C-a), (I-D) or (I-D-a), B is phenyl or a 5 or 6 membered aromatic heterocyclyl containing at least one heteroatom selected from N, O or S, wherein said phenyl and heterocyclyl are each optionally being substituted with 1 to 5, in particular 1 to 4, or 1 to 3, or 1 or 2, or 1 R substituents. In an embodiment, B is unsubstituted.

In an embodiment, in the compounds of formula (I), (I-a), (I-A), (I-A-a), (I-B), (I-B-a), (I-C), (I-C-a), (I-D) or (I-D-a), B is a 3 to 6 membered monocyclic carbocyclyl or heterocyclyl containing at least one heteroatom selected from N, O or S, wherein said carbocyclyl and heterocyclyl are each optionally being substituted with 1 to 5, in particular 1 to 4, or 1 to 3, or 1 or 2, or 1 R substituents. In an embodiment, B is unsubstituted.

In an embodiment, in the compounds of formula (I), (I-a), (I-A), (I-A-a), (I-B), (I-B-a), (I-C), (I-C-a), (I-D) or (I-D-a), B is a 3 to 6 membered monocyclic non-aromatic carbocyclyl or heterocyclyl containing at least one heteroatom selected from N, O or S, wherein said carbocyclyl and heterocyclyl are each optionally being substituted with 1 to 5, in particular 1 to 4, or 1 to 3, or 1 or 2, or 1 R substituents. In an embodiment, B is unsubstituted.

In an embodiment, in the compounds of formula (I), (I-a), (I-A), (I-A-a), (I-B), (I-B-a), (I-C), (I-C-a), (I-D) or (I-D-a), B is a 6 membered aromatic monocyclic heterocyclyl containing at least one heteroatom selected from N, O or S, wherein said heterocyclyl is optionally being substituted with 1 to 4, in particular 1 to 3, or 1 or 2, or 1 R substituents. For example B is optionally substituted pyridyl, pyrimidinyl or pyrazinyl. In an embodiment, B is unsubstituted. In an embodiment, B is substituted with 1 R substituent. In an embodiment, the R substituent is selected from $C_{1-6}$alkyl, $C_{1-6}$alkoxy and $C_{3-6}$cycloalkyl.

In an embodiment, in the compounds of formula (I), (I-a), (I-A), (I-A-a), (I-B), (I-B-a), (I-C), (I-C-a), (I-D) or (I-D-a), B is a 5 membered aromatic monocyclic heterocyclyl containing at least one heteroatom selected from N, O or S, wherein said heterocyclyl is optionally being substituted with 1 to 3, in particular 1 or 2, or 1 R substituents. For example B is optionally substituted pyrazolyl, oxazolyl or thiazolyl. In an embodiment, B is unsubstituted. In an embodiment, B is substituted with 1 R substituent. In an embodiment, the R substituent is selected from $C_{1-6}$alkyl, $C_{1-6}$alkoxy and $C_{3-6}$cycloalkyl.

In an embodiment, in the compounds of formula (I), (I-a), (I-A), (I-A-a), (I-B), (I-B-a), (I-C), (I-C-a), (I-D) or (I-D-a), B is a 9 to 12 membered bicyclic carbocyclyl or heterocyclyl containing at least one heteroatom selected from N, O or S, wherein said carbocyclyl and heterocyclyl are each optionally being substituted with 1 to 5, in particular 1 to 4, or 1 to 3, or 1 or 2, or 1 R substituents. In an embodiment, B is unsubstituted.

In an embodiment, in the compounds of formula (I), (I-a), (I-A), (I-A-a), (I-B), (I-B-a), (I-C), (I-C-a), (I-D) or (I-D-a), B is pyrimidinyl, optionally being substituted with 1 to 3, in particular 1 or 2, or 1 R substituents; in particular B is unsubstituted pyrimidinyl.

In an embodiment, in the compounds of formula (I), (I-a), (I-A), (I-A-a), (I-B), (I-B-a), (I-C), (I-C-a), (I-D) or (I-D-a), each R independently is $C_{1-6}$alkyl, cyano, halo, $C_{1-6}$alkoxy, halo-$C_{1-6}$alkoxy, hydroxyl, hydroxy$C_{1-6}$alkyl, halo$C_{1-6}$alkyl, oxo, —$SO_2$—$NH_2$, —$SO_2$—NH($C_{1-4}$alkyl), —$SO_2$—N($C_{1-4}$alkyl)$_2$, —NH—C(=O)—$C_{2-6}$alkenyl, —C(=O)—$C_{1-6}$alkyl, —C(=O)—$C_{2-6}$alkenyl, or $C_{1-6}$alkyl-O—C(=O)—.

In an embodiment, in the compounds of formula (I), (I-a), (I-A), (I-A-a), (I-B), (I-B-a), (I-C), (I-C-a), (I-D) or (I-D-a), each R independently is $C_{1-6}$alkyl, cyano, halo, $C_{1-6}$alkoxy, halo$C_{1-6}$alkoxy, hydroxyl, hydroxy$C_{1-6}$alkyl, halo$C_{1-6}$alkyl, oxo, —$SO_2$—$NH_2$, —$SO_2$—NH($C_{1-4}$alkyl), —$SO_2$—N($C_{1-4}$alkyl)$_2$, —NH—C(=O)—$C_{2-6}$alkenyl, —C(=O)—$C_{1-6}$alkyl, —C(=O)—$C_{2-6}$alkenyl, $C_{3-6}$cycloalkyl, phenyl, or a 3 to 6 membered monocyclic heterocyclyl containing at least one heteroatom selected from N, O or S.

In an embodiment, in the compounds of formula (I), (I-a), (I-A), (I-A-a), (I-B), (I-B-a), (I-C), (I-C-a), (I-D) or (I-D-a), B is unsubstituted.

In an embodiment, in the compounds of formula (I), (I-a), (I-A), (I-A-a), (I-B), (I-B-a), (I-C), (I-C-a), (I-D) or (I-D-a), B is substituted with 1 to 5 R substituents, in particular 1 to 4 R substituents, or 1 to 3 R substituents, or 1 or 2 R substituents, or 1 R substituent.

In an embodiment, in the compounds of formula (I), (I-a), (I-A), (I-A-a), (I-B), (I-B-a), (I-C), (I-C-a), (I-D) or (I-D-a), one or more, in particular when possible all of the following conditions apply:
each of $A_1$, $A_2$ and $A_3$ is a carbon;
C1 is hydrogen or $C_{1-4}$alkyl, in particular hydrogen, methyl or ethyl;
C2 is hydrogen or $C_{1-4}$alkyl, in particular hydrogen or methyl;
or C1 and C2 are taken together to form a $C_{3-6}$cycloalkyl together with the carbon atom to which they are attached, in particular cyclopropyl;
Y is a direct bond, C(=O) or $NR^y$;
$R^y$ is hydrogen or $C_{1-4}$alkyl, in particular hydrogen or methyl;
each $R^a$ independently is hydrogen, $C_{1-6}$alkyl e.g. methyl, halo$C_{1-6}$alkyl e.g. trifluoromethyl, or halo e.g. fluoro;
$n_a$ is an integer equal to 1;
each $R^b$ independently is hydrogen or halo e.g. fluoro or chloro;
$n_b$ is an integer equal to 1;
D is a 5 or 6 membered monocyclic saturated or aromatic heterocyclyl containing at least one heteroatom selected from N, O or S, wherein said heterocyclyl is optionally being substituted with 1 or 2 $R^c$ substituents; in particular D is piperazinyl, morpholinyl, piperidinyl, tetrahydrofurane or pyrazolyl, wherein said ring systems are optionally being substituted with 1 or 2 $R^c$ substituents;
D is a bridged heterocyclyl containing at least one heteroatom selected from N, O or S, wherein said heterocyclyl is optionally being substituted with 1 or 2 $R^c$ substituents, in particular wherein the bridged heterocyclyl is unsubstituted;
each $R^c$ independently is oxo, $C_{1-6}$alkyl e.g. methyl or isopropyl, halo$C_{1-6}$alkyl, halo$C_{1-6}$alkyloxy, carboxyl, HOOC—$C_{1-6}$alkyl-, $C_{1-6}$alkyl substituted with —C(=O)—O—$C_{1-6}$alkyl, or $C_{1-6}$alkyl-O—C(=O)—;
B is a 5 or 6 membered aromatic monocyclic heterocyclyl containing at least one heteroatom selected from N, O or S, wherein said heterocyclyl is optionally being substituted with 1 R substituent; in particular B is pyridyl, pyrimidinyl, pyrazinyl, pyrazolyl, thiazolyl, oxazolyl;
each R independently is $C_{1-6}$alkyl e.g. methyl or isopropyl, $C_{1-6}$alkoxy e.g. methoxy, or $C_{3-6}$cycloalkyl e.g. cyclopropyl.

In an embodiment, the compound is a compound of formula (I-D) or (I-D-a), wherein one or more, in particular when possible all of the following conditions apply:
each of $A_1$, $A_2$ and $A_3$ is a carbon;
$C_1$ and $C_2$ are hydrogen; or $C_1$ and $C_2$ are $C_{1-4}$alkyl, in particular methyl;
$R^a$ is hydrogen;
$n_a$ is an integer equal to 1;
$R^b$ is hydrogen;
$n_b$ is an integer equal to 1;
D is a 6 membered monocyclic saturated heterocyclyl containing at least one heteroatom selected from N, O or S, wherein said heterocyclyl is optionally being substituted with 1 or 2 $R^c$ substituents; in particular D is piperazinyl, morpholinyl, or piperidinyl, wherein said ring systems are optionally being substituted with 1 or 2 $R^c$ substituents; more in particular wherein D is unsubstituted morpholinyl; morpholinyl substituted with 1 $C_{1-6}$alkyl e.g. methyl; or morpholinyl substituted with 2 $C_{1-6}$alkyls e.g. substituted twice with methyl;
B is a 6 membered aromatic monocyclic heterocyclyl containing at least one heteroatom selected from N, O or S, wherein said heterocyclyl is optionally being substituted with 1 R substituent; in particular B is pyridyl, pyrimidinyl, pyrazinyl optionally substituted with 1 R selected from $C_{1-6}$alkyl e.g. methyl or isopropyl, $C_{1-6}$alkoxy e.g. methoxy, or $C_{3-6}$cycloalkyl e.g. cyclopropyl; more in particular B is unsubstituted pyrimidinyl.

In an embodiment, the compound of the invention is selected from

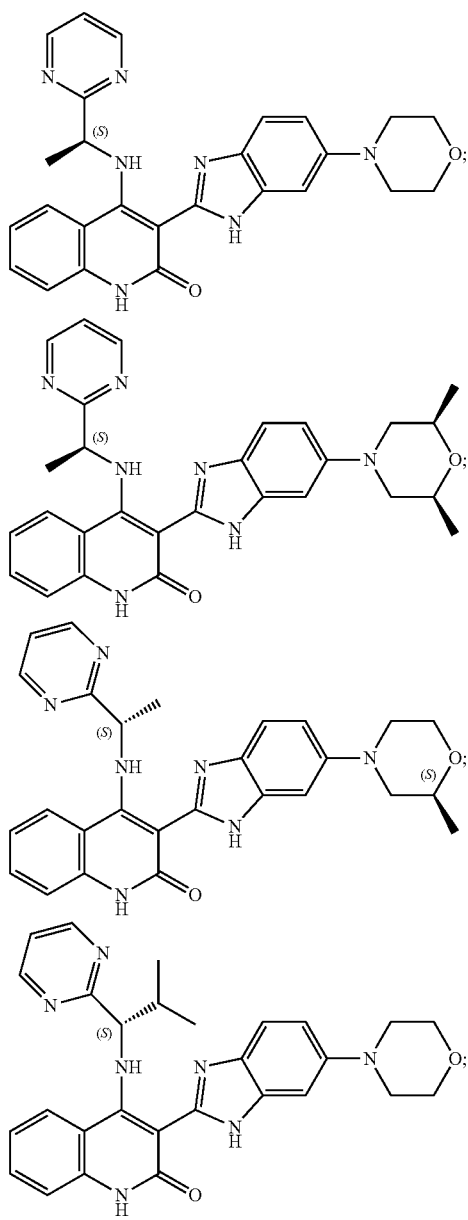

or the pharmaceutically acceptable salts thereof or the solvates thereof.

For the avoidance of doubt, it is to be understood that each general and specific preference, embodiment and example for one substituent may be combined if chemically possible with each general and specific preference, embodiment and example for one or more, preferably, all other substituents as defined herein and that all such embodiments are embraced by this application.

Methods for the Preparation of Compounds of Formula (I)

In this section, as in all other sections of this application unless the context indicates otherwise, references to formula (I) also include all other sub-groups and examples thereof (e.g. (I-a), (I-A), (I-A-a), (I-B), (I-B-a), (I-C), (I-C-a), (I-D) or (I-D-a)) as defined herein.

In general, compounds of formula (I) can be prepared according to the following reaction Scheme 1. In Scheme 1, $W_1$ represents a suitable leaving group, such as for example halo, e.g. chloro. All other variables in Scheme 1 are defined according to the present invention.

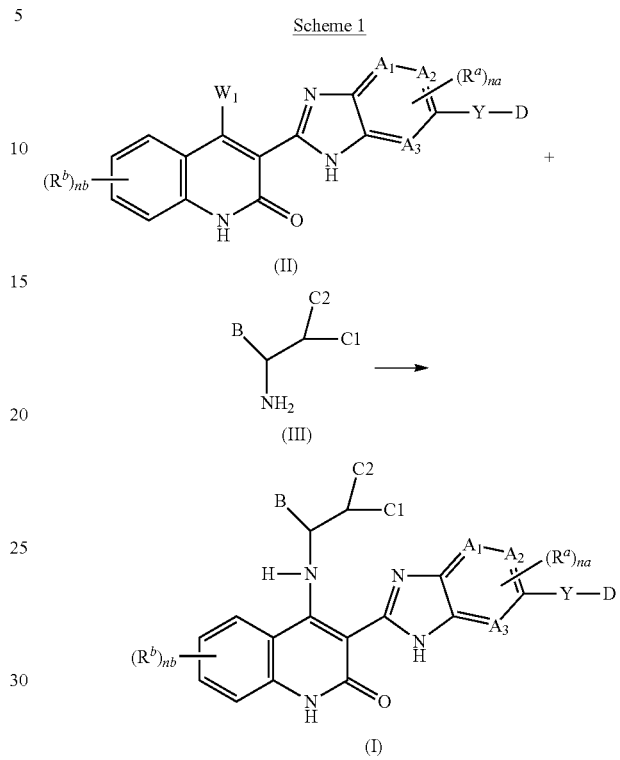

Scheme 1

The reaction of Scheme 1 is performed in the presence of a suitable base, such as for example N,N-diisopropylethylamine, and a suitable solvent, such as for example dimethylformamide.

In Scheme 1, the intermediate of formula (III) can be a specific stereoisomer, e.g. the S enantiomer resulting in a specific stereoisomer, e.g. the S enantiomer, of formula (I), such as shown below in Scheme 1a for the preparation of compounds of formula (I-a).

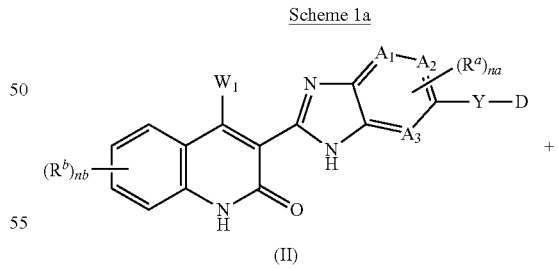

Scheme 1a

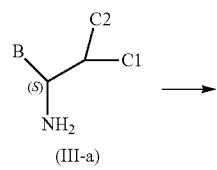

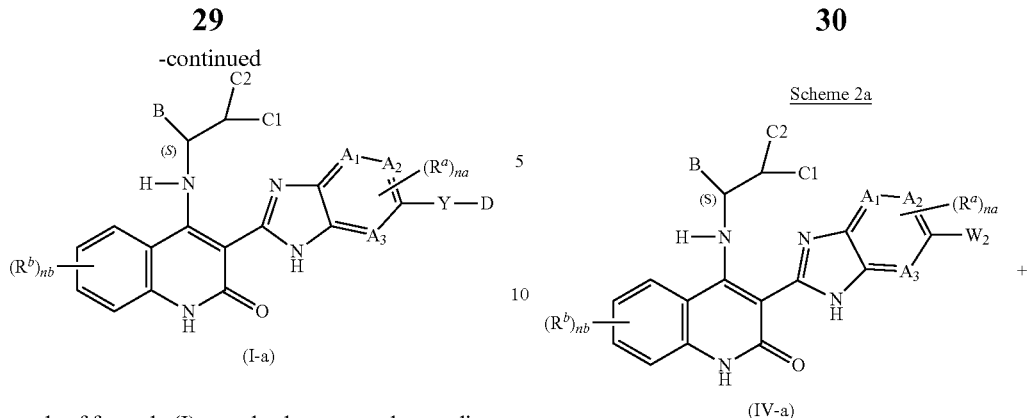

(I-a)

Compounds of formula (I) can also be prepared according to the following reaction Scheme 2. In Scheme 2, $W_2$ represents a suitable leaving group, such as for example halo, e.g. bromo. All other variables in Scheme 2 are defined according to the present invention.

Scheme 2

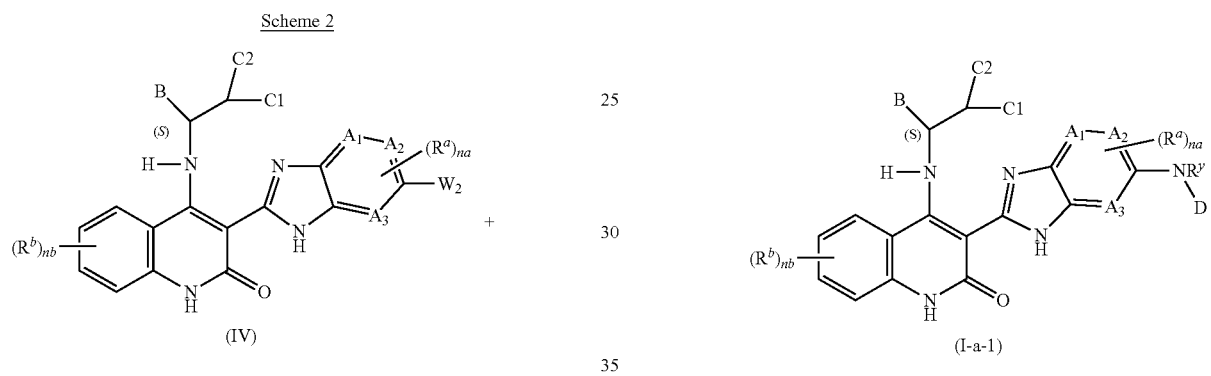

The reaction of Scheme 2 is performed in the presence of a suitable catalyst, such as for example a palladium catalyst, e.g. $Pd_2(dba)_3$, a suitable ligand, such as for example davephos (2-dicyclohexylphosphino-2'-(N,N-dimethylamino) biphenyl), a suitable base, such as for example LiHMDS (lithium bis(trimethylsilyl)amide), and a suitable solvent, such as for example tetrahydrofuran.

In Scheme 2, the intermediate of formula (IV) can be a specific stereoisomer, e.g. the S enantiomer, resulting in a specific stereoisomer, e.g. the S enantiomer, of formula (I), such as shown below in Scheme 2a for the preparation of compounds of formula (I-a-1).

Scheme 2a

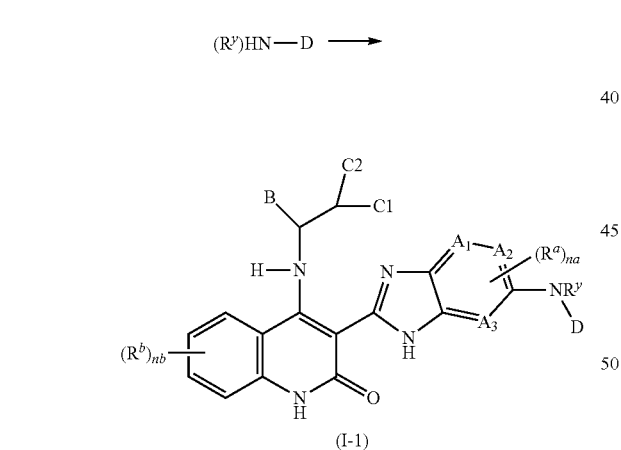

Compounds of formula (I) wherein Y represents a direct bond, said compounds being represented by formula (I-D), can also be prepared according to the following reaction Scheme 3. In Scheme 3, $W_2$ represents a suitable leaving group, such as for example halo, e.g. bromo. All other variables in Scheme 3 are defined according to the present invention.

Scheme 3

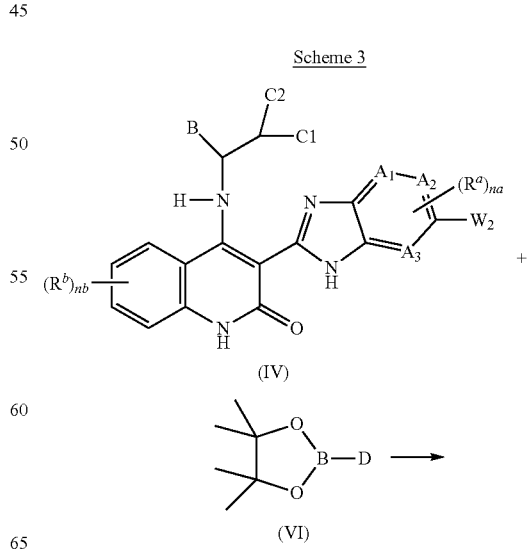

-continued

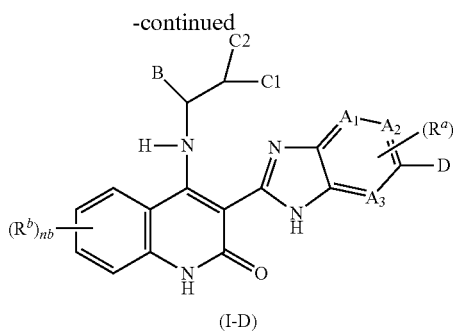

(I-D)

The reaction of Scheme 3 is performed in the presence of a suitable catalyst, such as for example a palladium catalyst, e.g. $Pd_2(dba)_3$, a suitable ligand, such as for example $PCy_3$ (tricyclohexylphosphine), a suitable base, such as for example $K_3PO_4$ (tripotassium phosphate), and a suitable solvent, such as for example dioxane and water.

In Scheme 3, the intermediate of formula (IV) can be a specific stereoisomer, e.g. the S enantiomer, resulting in a specific stereoisomer, e.g. the S enantiomer, of formula (I-D), such as shown below in Scheme 3a for the preparation of compounds of formula (I-D-a).

Scheme 3a

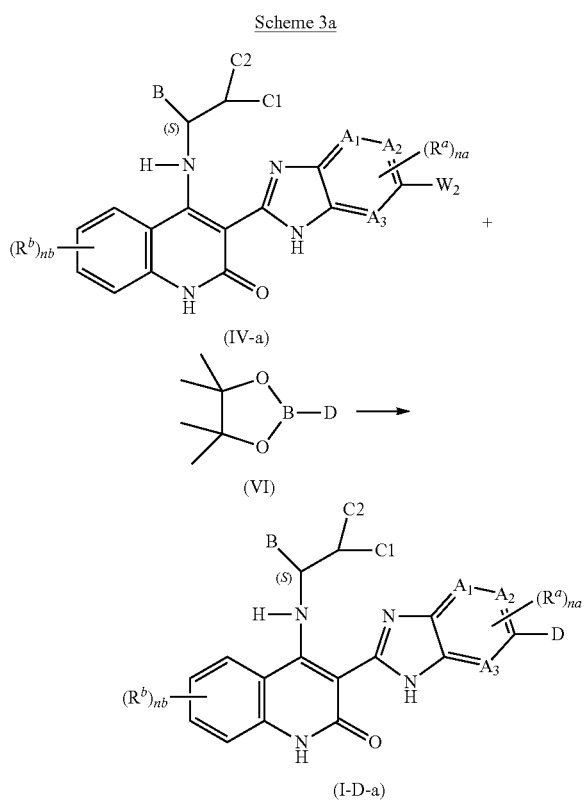

Intermediates of formula (II) can be prepared according to the following reaction Scheme 4. In Scheme 4, $W_1$ represents a suitable leaving group, such as for example halo, e.g. chloro. All other variables in Scheme 4 are defined according to the present invention.

Scheme 4

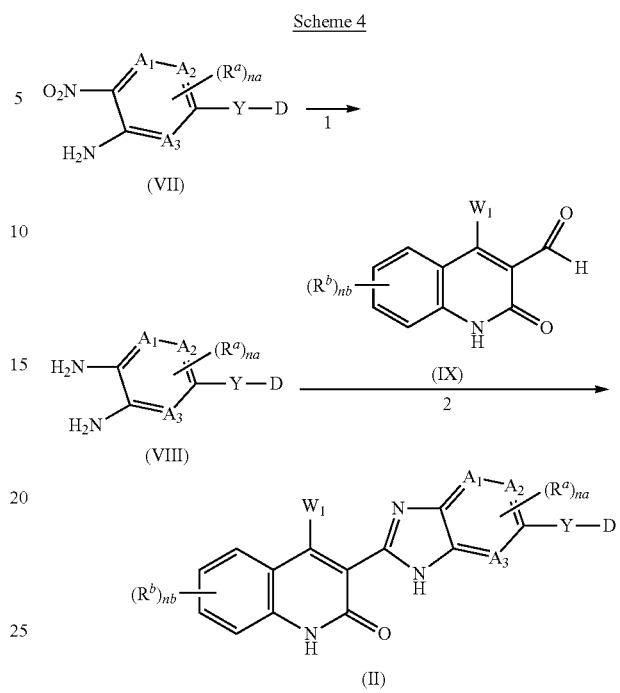

In Scheme 4, the following reaction conditions apply:
1: in the presence of a suitable reducing agent, such as for example $H_2$, a suitable catalyst, such as for example palladium on charcoal, and a suitable solvent, such as for example an alcohol, e.g. ethanol, at a suitable temperature, such as for example room temperature;
2: in the presence of a suitable solvent, such as for example an alcohol, e.g. ethanol, at a suitable temperature, such as for example 80° C.

Intermediates of formula (IV) can be prepared according to the following reaction Scheme 5. In Scheme 5, $W_1$ represents a suitable leaving group, such as for example halo, e.g. chloro, and $W_2$ represents a suitable leaving group, such as for example halo, e.g. bromo. All other variables in Scheme 5 are defined according to the present invention.

Scheme 5

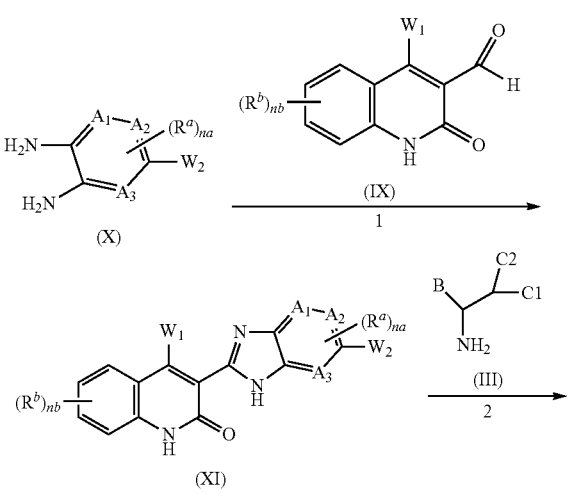

-continued

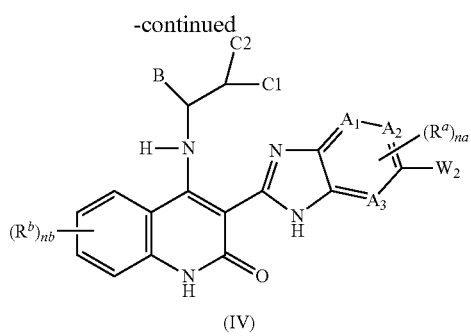

(IV)

In Scheme 5, the following reaction conditions apply:
1: in the presence of a suitable solvent, such as for example an alcohol, e.g. ethanol, at a suitable temperature, such as for example 70° C.;
2: in the presence of a suitable base, such as for example NaHCO$_3$, a suitable solvent, such as for example dimethylformamide, at a suitable temperature, such as for example 80° C.

The compounds of formula (I) may also be converted into each other via art-known reactions or functional group transformations.

For instance, compounds of formula (I) wherein Re represents C$_{1-6}$alkyl substituted with —C(=O)—O—C$_{1-6}$alkyl, or C$_{1-6}$alkyl-O—C(=O)—, can be converted into a compound of formula (I) wherein Re represents HOOC—C1-6alkyl or carboxyl in the presence of lithium hydroxide, and in the presence of a suitable solvent, such as for example tetrahydrofuran or an alcohol, e.g. methanol.

The compounds of the invention as prepared in the processes described herein may be synthesized in the form of mixtures of enantiomers, in particular racemic mixtures of enantiomers, that can be separated from one another following art-known resolution procedures. Racemic compounds of formula (I) containing a basic nitrogen atom may be converted into the corresponding diastereomeric salt forms by reaction with a suitable chiral acid. Said diastereomeric salt forms are subsequently separated, for example, by selective or fractional crystallization and the enantiomers are liberated therefrom by alkali. An alternative manner of separating the enantiomeric forms of the compounds of formula (I), and the pharmaceutically acceptable addition salts and solvates thereof, involves liquid chromatography using a chiral stationary phase e.g. by supercritical fluid chromatography. Said pure stereochemically isomeric forms may also be derived from the corresponding pure stereochemically isomeric forms of the appropriate starting materials, provided that the reaction occurs stereospecifically. Preferably if a specific stereoisomer is desired, said compound would be synthesized by stereospecific methods of preparation. These methods will advantageously employ enantiomerically pure starting materials.

In the preparation of compounds of the present invention, protection of remote functionality (e.g., primary or secondary amine) of intermediates may be necessary. The need for such protection varies depending on the nature of the remote functionality and the conditions of the preparation methods. Suitable amino-protecting groups (NH-PG) include acetyl, trifluoroacetyl, t-butoxycarbonyl (Boc), benzyloxycarbonyl (CBz) and 9-fluorenylmethyleneoxycarbonyl (Fmoc). The need for such protection is readily determined by one skilled in the art. For a general description of protecting groups and their use, see T. W. Greene and P. G. M. Wuts, Protective Groups in Organic Synthesis, 4th ed., Wiley, Hoboken, N.J., 2007.

In all these preparations, the reaction products may be isolated from the reaction medium and, if necessary, further purified according to methodologies generally known in the art such as, for example, extraction, crystallization, trituration and chromatography.

A further aspect of the invention is a process for the preparation of a compound of formula (I) as defined herein, which process comprises:
(i) reacting an intermediate of formula (II)

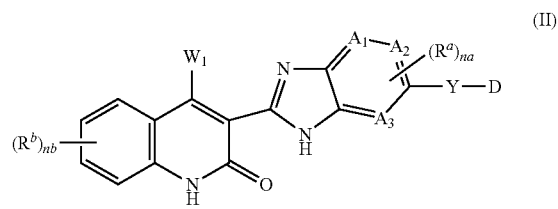

wherein W$_1$ represents a suitable leaving group, such as for example halo, e.g. chloro, with an intermediate of formula (III)

in the presence of a suitable base, such as for example N,N-diisopropylethylamine, and a suitable solvent, such as for example dimethylformamide; or
(ii) reacting an intermediate of formula (IV)

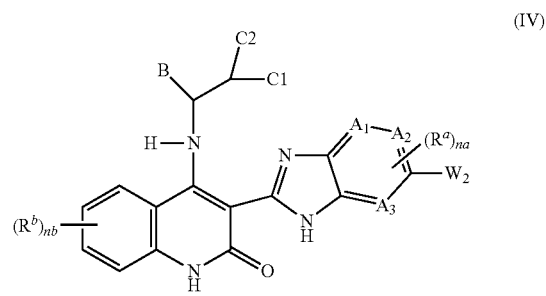

wherein W$_2$ represents a suitable leaving group, such as for example halo, e.g. bromo, with an intermediate of formula (V)

in the presence of a suitable catalyst, such as for example a palladium catalyst, e.g. Pd$_2$(dba)$_3$, a suitable ligand, such as for example davephos (2-dicyclohexylphosphino-2'-(N,N-dimethylamino)biphenyl), a suitable base, such as for example LiHMDS (lithium bis(trimethylsilyl)amide), and a suitable solvent, such as for example tetrahydrofuran; or (iii) reacting an intermediate of formula (IV)

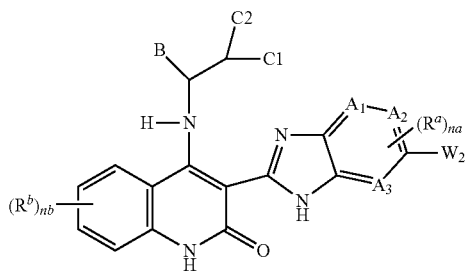

(IV)

wherein W$_2$ represents a suitable leaving group, such as for example halo, e.g. bromo, with an intermediate of formula (VI)

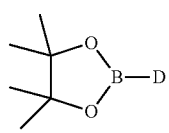

(VI)

in the presence of a suitable catalyst, such as for example a palladium catalyst, e.g. Pd$_2$(dba)$_3$, a suitable ligand, such as for example PCy$_3$ (tricyclohexylphosphine), a suitable base, such as for example K$_3$PO$_4$ (tripotassium phosphate), and a suitable solvent, such as for example dioxane and water;
wherein the variables are as defined herein; and optionally thereafter converting one compound of the formula (I) into another compound of the formula (I).

Pharmaceutically Acceptable Salts, Solvates or Derivatives Thereof

In this section, as in all other sections of this application, unless the context indicates otherwise, references to formula (I) include references to all other sub-groups, preferences, embodiments and examples thereof as defined herein.

Unless otherwise specified, a reference to a particular compound also includes ionic forms, salts, solvates, isomers, tautomers, and isotopes, for example, preferably, the salts or isomers or solvates thereof. Compounds of formula (I) can exist in the form of salts, for example acid addition salts or, in certain cases salts of organic and inorganic bases such as carboxylate, sulphonate and phosphate salts. All such salts are within the scope of this invention, and references to compounds of formula (I) include the salt forms of the compounds.

The salt forms of the compounds of the invention are typically pharmaceutically acceptable salts, and examples of pharmaceutically acceptable salts are discussed in Berge et al. (1977) "Pharmaceutically Acceptable Salts," *J. Pharm. Sci.*, Vol. 66, pp. 1-19. However, salts that are not pharmaceutically acceptable may also be prepared as intermediate forms which may then be converted into pharmaceutically acceptable salts. Such non-pharmaceutically acceptable salts forms, which may be useful, for example, in the purification or separation of the compounds of the invention, also form part of the invention.

The salts of the present invention can be synthesized from the parent compound that contains a basic or acidic moiety by conventional chemical methods such as methods described in *Pharmaceutical Salts: Properties, Selection, and Use*, P. Heinrich Stahl (Editor), Camille G. Wermuth (Editor), ISBN: 3-90639-026-8, Hardcover, 388 pages, August 2002. Generally, such salts can be prepared by reacting the free acid or base forms of these compounds with the appropriate base or acid in water or in an organic solvent, or in a mixture of the two; generally, nonaqueous media such as ether, ethyl acetate, ethanol, isopropanol, or acetonitrile are used. The compounds of the invention may exist as mono- or di-salts depending upon the pKa of the acid from which the salt is formed.

Acid addition salts may be formed with a wide variety of acids, both inorganic and organic. Examples of acid addition salts include salts formed with an acid selected from the group consisting of acetic, 2,2-dichloroacetic, adipic, alginic, ascorbic (e.g. L-ascorbic), L-aspartic, benzenesulphonic, benzoic, 4-acetamidobenzoic, butanoic, (+) camphoric, camphorsulphonic, (+)-(1S)-camphor-10-sulphonic, capric, caproic, caprylic, cinnamic, citric, cyclamic, dodecylsulphuric, ethane-1,2-disulphonic, ethanesulphonic, 2-hydroxyethane-sulphonic, formic, fumaric, galactaric, gentisic, glucoheptonic, D-gluconic, glucuronic (e.g. D-glucuronic), glutamic (e.g. L-glutamic), α-oxoglutaric, glycolic, hippuric, hydrobromic, hydrochloric, hydriodic, isethionic, lactic (e.g. (+)-L-lactic, (±)-DL-lactic), lactobionic, maleic, malic, (−)-L-malic, malonic, (±)-DL-mandelic, methanesulphonic, naphthalenesulphonic (e.g. naphthalene-2-sulphonic), naphthalene-1,5-disulphonic, 1-hydroxy-2-naphthoic, nicotinic, nitric, oleic, orotic, oxalic, palmitic, pamoic, phosphoric, propionic, L-pyroglutamic, pyruvic, salicylic, 4-amino-salicylic, sebacic, stearic, succinic, sulphuric, tannic, (+)-L-tartaric, thiocyanic, toluenesulphonic (e.g. p-toluenesulphonic), undecylenic and valeric acids, as well as acylated amino acids and cation exchange resins.

One particular group of salts consists of salts formed from acetic, hydrochloric, hydriodic, phosphoric, nitric, sulphuric, citric, lactic, succinic, maleic, malic, isethionic, fumaric, benzenesulphonic, toluenesulphonic, methanesulphonic (mesylate), ethanesulphonic, naphthalenesulphonic, valeric, acetic, propanoic, butanoic, malonic, glucuronic and lactobionic acids. Another group of acid addition salts includes salts formed from acetic, adipic, ascorbic, aspartic, citric, DL-Lactic, fumaric, gluconic, glucuronic, hippuric, hydrochloric, glutamic, DL-malic, methanesulphonic, sebacic, stearic, succinic and tartaric acids.

If the compound is anionic, or has a functional group which may be anionic (e.g., —COOH may be —COO$^−$), then a salt may be formed with a suitable cation. Examples of suitable inorganic cations include, but are not limited to, alkali metal ions such as Na$^+$ and K$^+$, alkaline earth metal cations such as Ca$^{2+}$ and Mg$^{2+}$, and other cations such as Al$^{3+}$. Examples of suitable organic cations include, but are not limited to, ammonium ion (i.e., NH$_4$$^+$) and substituted ammonium ions (e.g., NH$_3$R+, NH$_2$R$_2$$^+$, NHR$_3$$^+$, NR$_4$$^+$).

Examples of some suitable substituted ammonium ions are those derived from: ethylamine, diethylamine, dicyclohexylamine, triethylamine, butylamine, ethylenediamine, ethanolamine, diethanolamine, piperazine, benzylamine, phenylbenzylamine, choline, meglumine, and tromethamine, as well as amino acids, such as lysine and arginine. An example of a common quaternary ammonium ion is N(CH$_3$)$_4$$^+$.

Where the compounds of the formula (I) contain an amine function, these may form quaternary ammonium salts, for example by reaction with an alkylating agent according to methods well known to the skilled person. Such quaternary ammonium compounds are within the scope of formula (I).

The compounds of the invention may form solvates, for example with water (i.e., hydrates) or common organic solvents. As used herein, the term "solvate" means a physical association of the compounds of the present invention with one or more solvent molecules, as well as pharmaceutically acceptable addition salts thereof. This physical association involves varying degrees of ionic and covalent bonding, including hydrogen bonding. In certain instances the solvate will be capable of isolation, for example when one or more solvent molecules are incorporated in the crystal lattice of the crystalline solid. The term "solvate" is intended to encompass both solution-phase and isolatable solvates. Non-limiting examples of suitable solvates include compounds of the invention in combination with water (hydrate), isopropanol, ethanol, methanol, DMSO, ethyl acetate, acetic acid or ethanolamine and the like. The compounds of the invention may exert their biological effects whilst they are in solution.

Solvates can be important to the processes for the preparation of a substance (e.g. in relation to their purification, the storage of the substance (e.g. its stability) and the ease of handling of the substance and are often formed as part of the isolation or purification stages of a chemical synthesis. A person skilled in the art can determine by means of standard and long used techniques whether a hydrate or other solvate has formed by the isolation conditions or purification conditions used to prepare a given compound. Examples of such techniques include thermogravimetric analysis (TGA), differential scanning calorimetry (DSC), X-ray crystallography (e.g. single crystal X-ray crystallography or X-ray powder diffraction) and Solid State NMR (SS-NMR, also known as Magic Angle Spinning NMR or MAS-NMR). Such techniques are as much a part of the standard analytical toolkit of the skilled chemist as NMR, IR, HPLC and MS. Alternatively the skilled person can deliberately form a solvate using crystallisation conditions that include an amount of the solvent required for the particular solvate. Thereafter the standard methods described above, can be used to establish whether solvates had formed.

Furthermore, the compounds of the present invention may have one or more polymorph (crystalline) or amorphous forms and these forms as such are intended to be included in the scope of the invention.

Compounds of formula (I) may exist in a number of different geometric isomeric, and tautomeric forms and references to compounds of the formula (I) include all such forms. For the avoidance of doubt, where a compound can exist in one of several geometric isomeric or tautomeric forms and only one is specifically described or shown, all others are nevertheless embraced by formula (I). Examples of tautomeric forms include, for example, keto-, enol-, and enolate-forms, as in, for example, the following tautomeric pairs: keto/enol (illustrated below), imine/enamine, amide/imino alcohol, amidine/enediamines, nitroso/oxime, thioketone/enethiol, and nitro/aci-nitro.

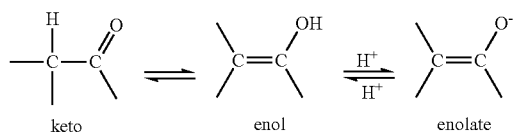

keto          enol          enolate

Such forms in so far as they may exist, are intended to be included within the scope of the present invention. It follows that a single compound may exist in both stereoisomeric and tautomeric form.

Where compounds of formula (I) contain one or more chiral centres, and can exist in the form of two or more optical isomers, references to compounds of formula (I) include all optical isomeric forms thereof (e.g. enantiomers, epimers and diastereoisomers), either as individual optical isomers, or mixtures (e.g. racemic mixtures) of two or more optical isomers, unless the context requires otherwise. When a compound of formula (I) has more than one chiral centre, and one chiral centre is indicated as having an absolute stereoconfiguration, such as in compounds of formula (I-a), (I-A-a), (I-B-a), (I-C-a) or (I-D-a), the other chiral centre(s) include all optical isomeric forms, either as individual optical isomers, or mixtures (e.g. racemic mixtures) of two or more optical isomers, thereof, unless the context requires otherwise. The optical isomers may be characterized and identified by their optical activity (i.e. as + and − isomers depending on the direction in which they rotate plane polarized light, or d and l isomers) or they may be characterized in terms of their absolute stereochemistry using the "R and S" nomenclature developed by Cahn, Ingold and Prelog, see *Advanced Organic Chemistry* by Jerry March, 4$^{th}$ Edition, John Wiley & Sons, New York, 1992, pages 109-114, and see also Cahn, Ingold & Prelog (1966) *Angew. Chem. Int. Ed. Engl.*, 5, 385-415. For instance, resolved enantiomers whose absolute configuration is not known can be designated by (+) or (−) depending on the direction in which they rotate plane polarized light.

Optical isomers can be separated by a number of techniques including chiral chromatography (chromatography on a chiral support) and such techniques are well known to the person skilled in the art. As an alternative to chiral chromatography, optical isomers can be separated by forming diastereoisomeric salts with chiral acids such as (+)-tartaric acid, (−)-pyroglutamic acid, (−)-di-toluoyl-L-tartaric acid, (+)-mandelic acid, (−)-malic acid, and (−)-camphorsulphonic, separating the diastereoisomers by preferential crystallisation, and then dissociating the salts to give the individual enantiomer of the free base.

Where compounds of formula (I) exist as two or more isomeric forms, one isomeric form, e.g. one enantiomer in a pair of enantiomers, may exhibit advantages over the other isomeric form, e.g. over the other enantiomer, for example, in terms of biological activity. Thus, in certain circumstances, it may be desirable to use as a therapeutic agent only one of a pair of enantiomers, or only one of a plurality of diastereoisomers. It was found that compounds wherein the chiral center indicated with * in the following structure

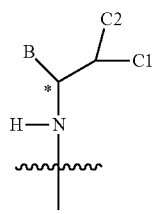

has the S configuration, exhibit higher biological activity than the corresponding R configuration. When a specific stereoisomer is identified, this means that said stereoisomer is substantially free, i.e. associated with less than 50%, preferably less than 20%, more preferably less than 10%, even more preferably less than 5%, in particular less than 2% and most preferably less than 1%, of the other stereoisomers. Thus, when a compound of formula (I) is for instance specified as (S), this means that the compound is substantially free of the (R) isomer; when a compound of formula (I) is for instance specified as F, this means that the compound is substantially free of the Z isomer; when a compound of formula (I) is for instance specified as cis, this means that the compound is substantially free of the trans isomer.

As used herein, any chemical formula with bonds shown only as solid lines and not as solid wedged or hashed wedged bonds, or otherwise not indicated as having a particular configuration (e.g. R, S) around one or more atoms, contemplates each possible stereoisomer, or mixture of two or more stereoisomers.

The terms "stereoisomers", "stereoisomeric forms" or "stereochemically isomeric forms" hereinbefore or hereinafter are used interchangeably.

Enantiomers are stereoisomers that are non-superimposable mirror images of each other. A 1:1 mixture of a pair of enantiomers is a racemate or racemic mixture.

Atropisomers (or atropoisomers) are stereoisomers which have a particular spatial configuration, resulting from a restricted rotation about a single bond, due to large steric hindrance. All atropisomeric forms of the compounds of formula (I) are intended to be included within the scope of the present invention.

Diastereomers (or diastereoisomers) are stereoisomers that are not enantiomers, i.e. they are not related as mirror images. If a compound contains a double bond, the substituents may be in the E or the Z configuration. Substituents on bivalent cyclic (partially) saturated radicals may have either the cis- or trans-configuration; for example if a compound contains a disubstituted cycloalkyl group, the substituents may be in the cis or trans configuration. Therefore, the invention includes enantiomers, atropisomers, diastereomers, racemates, E isomers, Z isomers, cis isomers, trans isomers and mixtures thereof, whenever chemically possible.

The meaning of all those terms, i.e. enantiomers, atropisomers, diastereomers, racemates, E isomers, Z isomers, cis isomers, trans isomers and mixtures thereof are known to the skilled person.

The compounds of the invention include compounds with one or more isotopic substitutions, and a reference to a particular element includes within its scope all isotopes of the element, either naturally occurring or synthetically produced, either with natural abundance or in an isotopically enriched form. For example, a reference to hydrogen includes within its scope $^1H$, $^2H$ (D), and $^3H$ (T). Similarly, references to carbon and oxygen include within their scope respectively $^{12}C$, $^{13}C$ and $^{14}C$ and $^{16}O$ and $^{18}O$. The isotopes may be radioactive or non-radioactive. In one embodiment of the invention, the compounds contain no radioactive isotopes. Such compounds are preferred for therapeutic use. In another embodiment, however, the compound may contain one or more radioisotopes. Compounds containing such radioisotopes may be useful in a diagnostic context. Radiolabeled compounds of formula (I) may comprise a radioactive isotope selected from the group of $^2H$, $^3H$, $^{11}C$, $^{18}F$, $^{122}I$, $^{123}I$, $^{125}I$, $^{131}I$, $^{75}Br$, $^{76}Br$, $^{77}Br$ and $^{82}Br$. Preferably, the radioactive isotope is selected from the group of $^2H$, $^3H$, $^{11}C$ and $^{18}F$. More preferably, the radioactive isotope is $^2H$.

In particular, deuterated compounds are intended to be included within the scope of the present invention.

Pharmacology

Protein Tyrosine Kinases (PTK)

The compounds of the invention described herein inhibit or modulate the activity of certain tyrosine kinases, and thus the compounds will be useful in the treatment or prophylaxis, in particular the treatment, of disease states or conditions mediated by those tyrosine kinases, in particular FGFR.

FGFR

The fibroblast growth factor (FGF) family of protein tyrosine kinase (PTK) receptors regulates a diverse array of physiologic functions including mitogenesis, wound healing, cell differentiation and angiogenesis, and development. Both normal and malignant cell growth as well as proliferation are affected by changes in local concentration of FGFs, extracellular signaling molecules which act as autocrine as well as paracrine factors. Autocrine FGF signaling may be particularly important in the progression of steroid hormone-dependent cancers to a hormone independent state. FGFs and their receptors are expressed at increased levels in several tissues and cell lines and overexpression is believed to contribute to the malignant phenotype. Furthermore, a number of oncogenes are homologues of genes encoding growth factor receptors, and there is a potential for aberrant activation of FGF-dependent signaling in human pancreatic cancer (Knights et al., Pharmacology and Therapeutics 2010 125:1 (105-117); Korc M. et al Current Cancer Drug Targets 2009 9:5 (639-651)).

The two prototypic members are acidic fibroblast growth factor (aFGF or FGF1) and basic fibroblast growth factor (bFGF or FGF2), and to date, at least twenty distinct FGF family members have been identified. The cellular response to FGFs is transmitted via four types of high affinity transmembrane protein tyrosine-kinase fibroblast growth factor receptors (FGFR) numbered 1 to 4 (FGFR1 to FGFR4).

Disruption of the FGFR1 pathway should affect tumor cell proliferation since this kinase is activated in many tumor types in addition to proliferating endothelial cells. The over-expression and activation of FGFR1 in tumor-associated vasculature has suggested a role for these molecules in tumor angiogenesis.

A recent study has shown a link between FGFR1 expression and tumorigenicity in Classic Lobular Carcinomas (CLC). CLCs account for 10-15% of all breast cancers and, in general, lack p53 and Her2 expression whilst retaining expression of the oestrogen receptor. A gene amplification of 8p12-p11.2 was demonstrated in ~50% of CLC cases and this was shown to be linked with an increased expression of FGFR1. Preliminary studies with siRNA directed against FGFR1, or a small molecule inhibitor of the receptor, showed cell lines harbouring this amplification to be particularly sensitive to inhibition of this signaling pathway. Rhabdomyosarcoma (RMS) is the most common pediatric soft tissue sarcoma likely results from abnormal proliferation and differentiation during skeletal myogenesis. FGFR1 is over-expressed in primary rhabdomyosarcoma tumors and is associated with hypomethylation of a 5' CpG island and abnormal expression of the AKT1, NOG, and BMP4 genes.

Fibroblast growth factor receptor 2 has high affinity for the acidic and/or basic fibroblast growth factors, as well as the keratinocyte growth factor ligands. Fibroblast growth factor receptor 2 also propagates the potent osteogenic effects of FGFs during osteoblast growth and differentiation. Mutations in fibroblast growth factor receptor 2, leading to complex functional alterations, were shown to induce abnormal ossification of cranial sutures (craniosynostosis), implying a major role of FGFR signalling in intramembranous bone formation. For example, in Apert (AP) syndrome, characterized by premature cranial suture ossification, most cases are associated with point mutations engendering gain-of-function in fibroblast growth factor receptor 2. In addition, mutation screening in patients with syndromic craniosynostoses indicates that a number of recurrent FGFR2 mutations accounts for severe forms of Pfeiffer syndrome. Particular mutations of FGFR2 include W290C, D321A, Y340C, C342R, C342S, C342W, N549H, K641R in FGFR2.

Several severe abnormalities in human skeletal development, including Apert, Crouzon, Jackson-Weiss, Beare-Stevenson cutis gyrata, and Pfeiffer syndromes are associated with the occurrence of mutations in fibroblast growth factor receptor 2. Most, if not all, cases of Pfeiffer Syndrome (PS) are also caused by de novo mutation of the fibroblast growth factor receptor 2 gene, and it was recently shown that mutations in fibroblast growth factor receptor 2 break one of the cardinal rules governing ligand specificity. Namely, two mutant splice forms of fibroblast growth factor receptor, FGFR2c and FGFR2b, have acquired the ability to bind to and be activated by atypical FGF ligands. This loss of ligand specificity leads to aberrant signaling and suggests that the severe phenotypes of these disease syndromes result from ectopic ligand-dependent activation of fibroblast growth factor receptor 2.

Genetic aberrations of the FGFR3 receptor tyrosine kinase such as chromosomal translocations or point mutations result in ectopically expressed or deregulated, constitutively active, FGFR3 receptors. Such abnormalities are linked to a subset of multiple myelomas and in bladder, hepatocellular, oral squamous cell carcinoma and cervical carcinomas. Accordingly, FGFR3 inhibitors would be useful in the treatment of multiple myeloma, bladder and cervical carcinomas. FGFR3 is also over-expressed in bladder cancer, in particular invasive bladder cancer. FGFR3 is frequently activated by mutation in urothelial carcinoma (UC). Increased expression was associated with mutation (85% of mutant tumors showed high-level expression) but also 42% of tumors with no detectable mutation showed over-expression, including many muscle-invasive tumors.

Over expression of FGFR4 has been linked to poor prognosis in both prostate and thyroid carcinomas. In addition, a germline polymorphism (Gly388 Arg) is associated with increased incidence of lung, breast, colon, liver (HCC) and prostate cancers. In addition, a truncated form of FGFR4 (including the kinase domain) has also been found to be present in 40% of pituitary tumours but not present in normal tissue. FGFR4 overexpression has been observed in liver, colon and lung tumours. FGFR4 has been implicated in colorectal and liver cancer where expression of its ligand FGF19 is frequently elevated.

Fibrotic conditions are a major medical problem resulting from abnormal or excessive deposition of fibrous tissue. This occurs in many diseases, including liver cirrhosis, glomerulonephritis, pulmonary fibrosis, systemic fibrosis, rheumatoid arthritis, as well as the natural process of wound healing. The mechanisms of pathological fibrosis are not fully understood but are thought to result from the actions of various cytokines (including tumor necrosis factor (TNF), fibroblast growth factors (FGF's), platelet derived growth factor (PDGF) and transforming growth factor beta. (TGFβ) involved in the proliferation of fibroblasts and the deposition of extracellular matrix proteins (including collagen and fibronectin). This results in alteration of tissue structure and function and subsequent pathology.

A number of preclinical studies have demonstrated the up-regulation of fibroblast growth factors in preclinical models of lung fibrosis. TGFβ1 and PDGF have been reported to be involved in the fibrogenic process and further published work suggests the elevation of FGF's and consequent increase in fibroblast proliferation, may be in response to elevated TGFβ1. The potential therapeutic benefit of targeting the fibrotic mechanism in conditions such as idiopathic pulmonary fibrosis (IPF) is suggested by the reported clinical effect of the anti-fibrotic agent pirfenidone. Idiopathic pulmonary fibrosis (also referred to as Cryptogenic fibrosing alveolitis) is a progressive condition involving scarring of the lung. Gradually, the air sacs of the lungs become replaced by fibrotic tissue, which becomes thicker, causing an irreversible loss of the tissue's ability to transfer oxygen into the bloodstream. The symptoms of the condition include shortness of breath, chronic dry coughing, fatigue, chest pain and loss of appetite resulting in rapid weight loss. The condition is extremely serious with approximately 50% mortality after 5 years.

As such, the compounds which inhibit FGFR will be useful in providing a means of preventing the growth or inducing apoptosis in tumours, particularly by inhibiting angiogenesis. It is therefore anticipated that the compounds will prove useful in treating or preventing proliferative disorders such as cancers. In particular tumours with activating mutants of receptor tyrosine kinases or upregulation of receptor tyrosine kinases may be particularly sensitive to the inhibitors. Patients with activating mutants of any of the isoforms of the specific RTKs discussed herein may also find treatment with RTK inhibitors particularly beneficial.

As indicated hereinabove, a variety of FGFR inhibitors are in clinic trials and have shown clinic response in patients with FGFR aberrations. However, it has been reported that mutations affecting amino acids in FGFR, e.g. FGFR1, 2 or 3, may cause resistance to FGFR inhibitors or decrease sensitivity to FGFR inhibitors. The development of secondary FGFR kinase domain mutations upon treatment with FGFR inhibitors are an important mechanism of acquired resistance to FGFR inhibition. Equivalent FGFR point mutations exist also de novo in cancers. Gatekeeper mutations have been reported as one of the major mechanism leading to resistance to tyrosine kinase inhibitors. Gatekeeper mutations include FGFR3 V555L/V555M, FGFR1 V561M, FGFR2 V564F/V564I/V564M and FGFR4 V550L. FGFR resistant mutations have been reported in clinic trials and in vitro cellular systems. Therefore new (second generation) FGFR inhibitors are needed to overcome clinical acquired resistance to first generation FGFR inhibitor therapy and to maintain the FGFR inhibiting activity against the primary activating FGFR mutations at the same time.

It was found that the compounds of the invention show activity against wild type FGFRs, in particular FGFR1, 2, 3 or 4, more in particular FGFR3, but also against mutated FGFRs, in particular against FGFRs harboring gatekeeper mutations or against mutated FGFR1 or mutated FGFR2 or mutated FGFR3, in particular against FGFR3 V555L, FGFR3 V555M, FGFR1 V561M and FGFR2 V564I, particularly against FGFR3 V555L and FGFR3 V555M.

Biological Activity and Therapeutic Uses

The compounds of the invention, and subgroups thereof, have fibroblast growth factor receptor (FGFR) inhibiting or modulating activity and will be useful in preventing or treating, in particular treating disease states or conditions described herein. In addition, the compounds of the invention, and subgroups thereof, will be useful in preventing or treating, in particular treating diseases or condition mediated by the kinases. References to the preventing or prophylaxis or treatment of a disease state or condition such as cancer include within their scope alleviating or reducing the incidence of cancer.

As used herein, the term "modulation", as applied to the activity of a kinase, is intended to define a change in the level of biological activity of the protein kinase. Thus, modulation encompasses physiological changes which effect an increase or decrease in the relevant protein kinase activity. In the latter case, the modulation may be described as "inhibition". The modulation may arise directly or indirectly, and may be mediated by any mechanism and at any physiological level, including for example at the level of gene expression (including for example transcription, translation and/or post-translational modification), at the level of expression of genes encoding regulatory elements which act directly or indirectly on the levels of kinase activity. Thus, modulation may imply elevated/suppressed expression or over- or under-expression of a kinase, including gene amplification (i.e. multiple gene copies) and/or increased or decreased expression by a transcriptional effect, as well as hyper- (or hypo-)activity and (de)activation of the protein kinase(s) (including (de)activation) by mutation(s). The terms "modulated", "modulating" and "modulate" are to be interpreted accordingly.

As used herein, the term "mediated", as used e.g. in conjunction with a kinase as described herein (and applied for example to various physiological processes, diseases, states, conditions, therapies, treatments or interventions) is intended to operate limitatively so that the various processes, diseases, states, conditions, treatments and interventions to which the term is applied are those in which the kinase plays a biological role. In cases where the term is applied to a disease state or condition, the biological role played by a kinase may be direct or indirect and may be necessary and/or sufficient for the manifestation of the symptoms of the disease state or condition (or its aetiology or progression). Thus, kinase activity (and in particular aberrant levels of kinase activity, e.g. kinase over-expression) need not necessarily be the proximal cause of the disease state or condition: rather, it is contemplated that the kinase mediated diseases, states or conditions include those having multifactorial aetiologies and complex progressions in which the kinase in question is only partially involved. In cases where the term is applied to treatment, prophylaxis or intervention, the role played by the kinase may be direct or indirect and may be necessary and/or sufficient for the operation of the treatment, prophylaxis or outcome of the intervention. Thus, a disease state or condition mediated by a kinase includes the development of resistance to any particular cancer drug or treatment.

Thus, for example, the compounds of the invention may be useful in alleviating or reducing the incidence of cancer.

More particularly, the compounds of the formulae (I) and sub-groups thereof are inhibitors of FGFRs. For example, compounds of the invention have activity against FGFR1, FGFR2, FGFR3, and/or FGFR4, and in particular against FGFR1, 2 and 3. More in particular compounds of the present invention show activity against wild type FGFRs and/or against mutated FGFRs, in particular FGFRs with point mutations, more in particular against gatekeeper mutations. Gatekeeper mutations include FGFR3 V555L/V555M, FGFR1 V561M, FGFR2 V564F/V564I/V564M and FGFR4 V550L. In particular the compounds of the present invention show activity against gatekeeper mutated FGFR1, FGFR2 and FGFR3, more in particular against FGFR3 V555L, FGFR3 V555M, FGFR1 V561M and FGFR2 V564I, in particular against FGFR3 V555L and FGFR3 V555M.

Diagnosis of tumours with mutations could be performed using techniques known to a person skilled in the art and as described herein such as RT-PCR and FISH.

Examples of cancers which may be treated (or inhibited) include, but are not limited to, a carcinoma, for example a carcinoma of the bladder, breast, colon (e.g. colorectal carcinomas such as colon adenocarcinoma and colon adenoma), kidney, urothelial, uterus, epidermis, liver, lung (for example small cell lung cancer and non-small cell lung carcinomas (e.g. adenocarcinoma and squamous cell carcinoma)), oesophagus, head and neck, gall bladder, ovary, pancreas (e.g. exocrine pancreatic carcinoma), stomach, gastrointestinal (also known as gastric) cancer (e.g. gastrointestinal stromal tumours), cervix, endometrium, thyroid, prostate, or skin (for example squamous cell carcinoma or dermatofibrosarcoma protuberans); pituitary cancer, a hematopoietic tumour of lymphoid lineage, for example leukemia, acute lymphocytic leukemia, chronic lymphocytic leukemia, B-cell lymphoma (e.g. diffuse large B-cell lymphoma), T-cell lymphoma, Hodgkin's lymphoma, non-Hodgkin's lymphoma, hairy cell lymphoma, or Burkett's lymphoma; a hematopoietic tumour of myeloid lineage, for example leukemias, acute and chronic myelogenous leukemias, chronic myelomonocytic leukemia (CMML), myeloproliferative disorder, myeloproliferative syndrome, myelodysplastic syndrome, or promyelocytic leukemia; multiple myeloma; thyroid follicular cancer; hepatocellular cancer, a tumour of mesenchymal origin (e.g. Ewing's sarcoma), for example fibrosarcoma or rhabdomyosarcoma; a tumour of the central or peripheral nervous system, for example astrocytoma, neuroblastoma, glioma (such as glioblastoma multiforme) or schwannoma; melanoma; seminoma; teratocarcinoma; osteosarcoma; xeroderma pigmentosum; keratoctanthoma; thyroid follicular cancer; or Kaposi's sarcoma. In particular, squamous lung cancer, breast cancer, colorectal cancer, glioblastoma, astrocytomas, prostate cancer, small cell lung cancer, melanoma, head and neck cancer, thyroid cancer, uterine cancer, gastric cancer, hepatocellular cancer, cervix cancer, multiple myeloma, bladder cancer, endometrial cancer, urothelial cancer, colon cancer, rhabdomyosarcoma, pituitary gland cancer, cholangiocarcinoma.

Examples of cancers which may be treated (or inhibited) include, but are not limited to, bladder cancer, urothelial cancer, metastatic urothelial cancer, surgically unresectable urothelial cancer, breast cancer, glioblastoma, lung cancer, non small cell lung cancer, squamous cell lung cancer, adenocarcinoma of the lung, pulmonary adenocarcinoma, small cell lung cancer, ovarian cancer, endometrial cancer, cervical cancer, soft tissue sarcoma, head and neck squamous cell carcinoma, gastric cancer, oesophageal cancer, squamous cell carcinoma of the oesophagus, adenocarcinoma of the oesophagus, cholangiocarcinoma, hepatocellular carcinoma.

Certain cancers are resistant to treatment with particular drugs. This can be due to the type of the tumour or can arise due to treatment with the compound. In this regard, references to multiple myeloma includes bortezomib sensitive multiple myeloma or refractory multiple myeloma. Similarly, references to chronic myelogenous leukemia includes imitanib sensitive chronic myelogenous leukemia and refractory chronic myelogenous leukemia. Chronic myelogenous leukemia is also known as chronic myeloid leukemia, chronic granulocytic leukemia or CML. Likewise, acute myelogenous leukemia, is also called acute myeloblastic leukemia, acute granulocytic leukemia, acute nonlymphocytic leukaemia or AML.

The compounds of the invention can also be used in the treatment of hematopoetic diseases of abnormal cell proliferation whether pre-malignant or stable such as myeloproliferative diseases. Myeloproliferative diseases ("MPD"s)

are a group of diseases of the bone marrow in which excess cells are produced. They are related to, and may evolve into, myelodysplastic syndrome. Myeloproliferative diseases include polycythemia vera, essential thrombocythemia and primary myelofibrosis. A further haematological disorder is hypereosinophilic syndrome. T-cell lymphoproliferative diseases include those derived from natural Killer cells.

In addition, the compounds of the invention can be used to treat gastrointestinal (also known as gastric) cancer e.g. gastrointestinal stromal tumours. Gastrointestinal cancer refers to malignant conditions of the gastrointestinal tract, including the esophagus, stomach, liver, biliary system, pancreas, bowels, and anus.

Thus, in the pharmaceutical compositions, uses or methods of this invention for treating a disease or condition comprising abnormal cell growth, the disease or condition comprising abnormal cell growth in one embodiment is a cancer.

Particular subsets of cancers include multiple myeloma, bladder, cervical, prostate, thyroid, lung, breast, and colon cancers.

A further subset of cancers includes multiple myeloma, bladder, hepatocellular, oral squamous cell carcinoma and cervical carcinomas.

The compounds of the invention, having FGFR such as FGFR1 inhibitory activity, may be particularly useful in the treatment or prevention of breast cancer in particular Classic Lobular Carcinomas (CLC) and lung cancer with FGFR1 amplification or FGFR1 mutations.

As the compounds of the invention have FGFR4 activity they will also be useful in the treatment of prostate or pituitary cancers, or they will be useful in the treatment of breast cancer, lung cancer, prostate cancer, liver cancer (HCC) or lung cancer.

In particular the compounds of the invention as FGFR inhibitors, are useful in the treatment of multiple myeloma, myeloproliferative disorders, endometrial cancer, prostate cancer, bladder cancer, lung cancer, ovarian cancer, breast cancer, gastric cancer, colorectal cancer, and oral squamous cell carcinoma.

Further subsets of cancer are multiple myeloma, endometrial cancer, bladder cancer, cervical cancer, prostate cancer, lung cancer, breast cancer, colorectal cancer and thyroid carcinomas. In particular the compounds of the invention are useful in the treatment of multiple myeloma (in particular multiple myeloma with t(4; 14) translocation or overexpressing FGFR3), prostate cancer (hormone refractory prostrate carcinomas), endometrial cancer (in particular endometrial tumours with activating mutations in FGFR2) and breast cancer (in particular lobular breast cancer).

In particular the compounds of the invention are useful in the treatment of cholangiocarcinoma, in particular cholangiocarcinoma with FGFR translocations and mutations, or FGF19 amplifications.

In particular the compounds are useful in the treatment of lobular carcinomas such as CLC (Classic lobular carcinoma).

As the compounds have activity against FGFR3 they will be useful in the treatment of multiple myeloma and bladder cancer.

In particular, the compounds have activity against tumours with FGFR3-TACC3 translocation, in particular bladder or brain tumours with FGFR3-TACC3 translocation.

In particular the compounds are useful for the treatment of t(4; 14) translocation positive multiple myeloma.

In one embodiment the compounds may be useful for the treatment of sarcoma. In one embodiment the compounds may be useful for the treatment of lung cancer, e.g. squamous cell carcinoma.

As the compounds have activity against FGFR2 they will be useful in the treatment of endometrial, ovarian, gastric, hepatocellular, uterine, cervix and colorectal cancers. FGFR2 is also overexpressed in epithelial ovarian cancer, therefore the compounds of the invention may be specifically useful in treating ovarian cancer such as epithelial ovarian cancer.

In one embodiment, the compounds may be useful for the treatment of lung cancer, in particular NSCLC (non small cell lung cancer), squamous cell carcinoma, liver cancer, kidney cancer, breast cancer, colon cancer, colorectal cancer, prostate cancer.

The cancers may be cancers which are sensitive to inhibition of any one or more FGFRs selected from FGFR1, FGFR2, FGFR3, FGFR4, for example, one or more FGFRs selected from FGFR1, FGFR2 or FGFR3.

Whether or not a particular cancer is one which is sensitive to inhibition of FGFR signaling may be determined by means of a cell growth assay as set out below or by a method as set out in the section headed "Methods of Diagnosis".

The compounds of the invention may be particularly useful in the treatment or prevention of cancers of a type associated with or characterized by the presence of elevated levels of FGFR.

The compounds of the invention may be useful in treating other conditions which result from disorders in proliferation such as type II or non-insulin dependent diabetes mellitus, autoimmune diseases, head trauma, stroke, epilepsy, neurodegenerative diseases such as Alzheimer's, motor neurone disease, progressive supranuclear palsy, corticobasal degeneration and Pick's disease for example autoimmune diseases and neurodegenerative diseases.

One sub-group of disease states and conditions that the compounds of the invention may be useful consists of inflammatory diseases, cardiovascular diseases and wound healing.

FGFR is also known to play a role in apoptosis, angiogenesis, proliferation, differentiation and transcription and therefore the compounds of the invention could also be useful in the treatment of the following diseases other than cancer; chronic inflammatory diseases, for example systemic lupus erythematosus, autoimmune mediated glomerulonephritis, rheumatoid arthritis, psoriasis, inflammatory bowel disease, autoimmune diabetes mellitus, Eczema hypersensitivity reactions, asthma, COPD, rhinitis, and upper respiratory tract disease; cardiovascular diseases for example cardiac hypertrophy, restenosis, atherosclerosis; neurodegenerative disorders, for example Alzheimer's disease, AIDS-related dementia, Parkinson's disease, amyotropic lateral sclerosis, retinitis pigmentosa, spinal muscular atropy and cerebellar degeneration; glomerulonephritis; myelodysplastic syndromes, ischemic injury associated myocardial infarctions, stroke and reperfusion injury, arrhythmia, atherosclerosis, toxin-induced or alcohol related liver diseases, haematological diseases, for example, chronic anemia and aplastic anemia; degenerative diseases of the musculoskeletal system, for example, osteoporosis and arthritis, aspirin-sensitive rhinosinusitis, cystic fibrosis, multiple sclerosis, kidney diseases and cancer pain.

In addition, mutations of FGFR2 are associated with several severe abnormalities in human skeletal development and thus the compounds of invention could be useful in the treatment of abnormalities in human skeletal development, including abnormal ossification of cranial sutures (craniosynostosis), Apert (AP) syndrome, Crouzon syndrome, Jackson-Weiss syndrome, Beare-Stevenson cutis gyrate syndrome, and Pfeiffer syndrome.

The compound of the invention, having FGFR such as FGFR2 or FGFR3 inhibitory activity, may be particularly useful in the treatment or prevention of the skeletal diseases. Particular skeletal diseases are achondroplasia or thanatophoric dwarfism (also known as thanatophoric dysplasia).

The compound of the invention, having FGFR such as FGFR1, FGFR2 or FGFR3 inhibitory activity, may be particularly useful in the treatment or prevention in pathologies in which progressive fibrosis is a symptom. Fibrotic conditions in which the compounds of the inventions may be useful in the treatment of include diseases exhibiting abnormal or excessive deposition of fibrous tissue for example in liver cirrhosis, glomerulonephritis, pulmonary fibrosis, systemic fibrosis, rheumatoid arthritis, as well as the natural process of wound healing. In particular, the compounds of the inventions may also be useful in the treatment of lung fibrosis in particular in idiopathic pulmonary fibrosis.

The over-expression and activation of FGFR and VEGFR in tumor-associated vasculature has also suggested a role for compounds of the invention in preventing and disrupting initiation of tumor angiogenesis. In particular the compounds of the invention may be useful in the treatment of cancer, metastasis, leukemia's such as CLL, ocular diseases such as age-related macular degeneration in particular wet form of age-related macular degeneration, ischemic proliferative retinopathies such as retinopathy of prematurity (ROP) and diabetic retinopathy, rheumatoid arthritis and hemangioma.

The activity of the compounds of the invention as inhibitors of FGFR1-4, in particular point mutated FGFR3, such as for example FGFR3 V555L and FGFR3 V555M, can be measured using the assays set forth in the examples below and the level of activity exhibited by a given compound can be defined in terms of the $IC_{50}$ value. Preferred compounds of the present invention are compounds having an $IC_{50}$ value of less than 1 µM, more preferably less than 0.1 µM, less than 0.01 µM, or less than 0.001 µM.

The invention provides compounds that have FGFR inhibiting or modulating activity, and which may be useful in preventing or treating disease states or conditions mediated by FGFR kinases.

In one embodiment, there is provided a compound as defined herein for use in therapy, for use as a medicine. In a further embodiment, there is provided a compound as defined herein for use in the prophylaxis or treatment, in particular in the treatment, of a disease state or condition mediated by a FGFR kinase.

Thus, for example, the compounds of the invention may be useful in alleviating or reducing the incidence of cancer. Therefore, in a further embodiment, there is provided a compound as defined herein for use in the prophylaxis or treatment, in particular the treatment, of cancer. In one embodiment, the compound as defined herein is for use in the prophylaxis or treatment, in particular the treatment, of FGFR-dependent cancer. In one embodiment, the compound as defined herein is for use in the prophylaxis or treatment, in particular the treatment, of cancer mediated by FGFR kinases.

Accordingly, the invention provides inter alia:

A method for the prophylaxis or treatment of a disease state or condition mediated by a FGFR kinase, which method comprises administering to a subject in need thereof a compound of the formula (I) as defined herein.

A method for the prophylaxis or treatment of a disease state or condition as described herein, which method comprises administering to a subject in need thereof a compound of the formula (I) as defined herein.

A method for the prophylaxis or treatment of cancer, which method comprises administering to a subject in need thereof a compound of the formula (I) as defined herein.

A method for alleviating or reducing the incidence of a disease state or condition mediated by a FGFR kinase, which method comprises administering to a subject in need thereof a compound of the formula (I) as defined herein.

A method of inhibiting a FGFR kinase, which method comprises contacting the kinase with a kinase-inhibiting compound of the formula (I) as defined herein.

A method of modulating a cellular process (for example cell division) by inhibiting the activity of a FGFR kinase using a compound of the formula (I) as defined herein.

A compound of formula (I) as defined herein for use as a modulator of a cellular process (for example cell division) by inhibiting the activity of a FGFR kinase.

A compound of formula (I) as defined herein for use in the prophylaxis or treatment of cancer, in particular the treatment of cancer.

A compound of formula (I) as defined herein for use as a modulator (e.g. inhibitor) of FGFR.

Use of a compound of formula (I) as defined herein for the manufacture of a medicament for the prophylaxis or treatment, in particular the treatment, of a disease state or condition mediated by a FGFR kinase, the compound having the formula (I) as defined herein.

Use of a compound of formula (I) as defined herein for the manufacture of a medicament for the prophylaxis or treatment of a disease state or condition as described herein.

Use of a compound of formula (I) as defined herein for the manufacture of a medicament for the prophylaxis or treatment, in particular the treatment, of cancer.

Use of a compound of formula (I) as defined herein for the manufacture of a medicament for modulating (e.g. inhibiting) the activity of FGFR.

Use of a compound of formula (I) as defined herein in the manufacture of a medicament for modulating a cellular process (for example cell division) by inhibiting the activity of a FGFR kinase.

Use of a compound of the formula (I) as defined herein for the manufacture of a medicament for prophylaxis or treatment of a disease or condition characterized by up-regulation of a FGFR kinase (e.g. FGFR1 or FGFR2 or FGFR3 or FGFR4).

Use of a compound of the formula (I) as defined herein for the manufacture of a medicament for the prophylaxis or treatment of a cancer, the cancer being one which is characterized by up-regulation of a FGFR kinase (e.g. FGFR1 or FGFR2 or FGFR3 or FGFR4).

Use of a compound of the formula (I) as defined herein for the manufacture of a medicament for the prophylaxis or treatment of cancer in a patient selected from a sub-population possessing a genetic aberrations of FGFR3 kinase.

Use of a compound of the formula (I) as defined herein for the manufacture of a medicament for the prophylaxis or treatment of cancer in a patient who has been diagnosed as forming part of a sub-population possessing a genetic aberrations of FGFR3 kinase.

A method for the prophylaxis or treatment of a disease or condition characterized by up-regulation of a FGFR kinase (e.g. FGFR1 or FGFR2 or FGFR3 or FGFR4), the method comprising administering a compound of the formula (I) as defined herein.

A method for alleviating or reducing the incidence of a disease or condition characterized by up-regulation of a FGFR kinase (e.g. FGFR1 or FGFR2 or FGFR3 or FGFR4), the method comprising administering a compound of the formula (I) as defined herein.

A method for the prophylaxis or treatment of (or alleviating or reducing the incidence of) cancer in a patient suffering from or suspected of suffering from cancer; which method comprises (i) subjecting a patient to a diagnostic test to determine whether the patient possesses a genetic aberrations of FGFR3 gene; and (ii) where the patient does possess the said variant, thereafter administering to the patient a compound of the formula (I) as defined herein having FGFR3 kinase inhibiting activity.

A method for the prophylaxis or treatment of (or alleviating or reducing the incidence of) a disease state or condition characterized by up-regulation of an FGFR kinase (e.g. FGFR1 or FGFR2 or FGFR3 or FGFR4); which method comprises (i) subjecting a patient to a diagnostic test to detect a marker characteristic of up-regulation of a FGFR kinase (e.g. FGFR1 or FGFR2 or FGFR3 or FGFR4) and (ii) where the diagnostic test is indicative of up-regulation of a FGFR kinase, thereafter administering to the patient a compound of the formula (I) as defined herein having FGFR kinase inhibiting activity.

In one embodiment, the disease mediated by FGFR kinases is a oncology related disease (e.g. cancer). In one embodiment, the disease mediated by FGFR kinases is a non-oncology related disease (e.g. any disease disclosed herein excluding cancer). In one embodiment the disease mediated by FGFR kinases is a condition described herein. In one embodiment the disease mediated by FGFR kinases is a skeletal condition described herein. Particular abnormalities in human skeletal development, include abnormal ossification of cranial sutures (craniosynostosis), Apert (AP) syndrome, Crouzon syndrome, Jackson-Weiss syndrome, Beare-Stevenson cutis gyrate syndrome, Pfeiffer syndrome, achondroplasia and thanatophoric dwarfism (also known as thanatophoric dysplasia).

Mutated Kinases

As indicated hereinabove. drug resistant kinase mutations can arise in patient populations treated with kinase inhibitors. These occur, in part, in the regions of the protein that bind to or interact with the particular inhibitor used in therapy. Such mutations reduce or increase the capacity of the inhibitor to bind to and inhibit the kinase in question. This can occur at any of the amino acid residues which interact with the inhibitor or are important for supporting the binding of said inhibitor to the target. An inhibitor that binds to a target kinase without requiring the interaction with the mutated amino acid residue will likely be unaffected by the mutation and will remain an effective inhibitor of the enzyme.

A study in gastric cancer patient samples showed the presence of two mutations in FGFR2, Ser167Pro in exon IIIa and a splice site mutation 940-2A-G in exon IIIc. These mutations are identical to the germline activating mutations that cause craniosynotosis syndromes and were observed in 13% of primary gastric cancer tissues studied. In addition, activating mutations in FGFR3 were observed in 5% of the patient samples tested and overexpression of FGFRs has been correlated with a poor prognosis in this patient group.

In addition, there are chromosomal translocations or point mutations that have been observed in FGFR which give rise to gain-of-function, over-expressed, or constitutively active biological states.

The compounds of the invention would therefore find particular application in relation to cancers which express a mutated molecular target such as FGFR. Diagnosis of tumours with such mutations could be performed using techniques known to a person skilled in the art and as described herein such as RT-PCR and FISH.

It has been suggested that mutations of a conserved threonine residue at the ATP binding site of FGFR would result in inhibitor resistance. The amino acid valine 561 has been mutated to a methionine in FGFR1 which corresponds to previously reported mutations found in Abl (T315) and EGFR (T766) that have been shown to confer resistance to selective inhibitors. Assay data for FGFR1 V561M showed that this mutation conferred resistance to a tyrosine kinase inhibitor compared to that of the wild type. Other mutations that have been found are gatekeeper mutations FGFR3 V555L/V555M, FGFR1 V561M, FGFR2 V564F/V564I/V564M and FGFR4 V550L. The compounds of the invention are specifically active against gatekeeper mutations, in particular against FGFR3 V555L, FGFR3 V555M, FGFR1 V561M and FGFR2 V564I, particularly against FGFR3 V555L and FGFR3 V555M.

The compounds of the present invention may be useful for the treatment of the adult population. The compounds of the present invention may be useful for the treatment of the pediatric population.

Methods of Diagnosis

Prior to administration of a compound of the formula (I), a patient may be screened to determine whether a disease or condition from which the patient is or may be suffering is one which would be susceptible to treatment with a compound having activity against FGFR, in particular FGFR harboring point mutations, in particular FGFR gatekeeper mutations such as for example FGFR3 V555L, FGFR3 V555M, FGFR1 V561M and FGFR2 V564I, in particular FGFR3 V555L and FGFR3 V555M.

For example, a biological sample taken from a patient may be analysed to determine whether a condition or disease, such as cancer, that the patient is or may be suffering from is one which is characterized by a genetic abnormality or abnormal protein expression which leads to up-regulation of the levels or activity of FGFR or to sensitisation of a pathway to normal FGFR activity, or to upregulation of these growth factor signaling pathways such as growth factor ligand levels or growth factor ligand activity or to upregulation of a biochemical pathway downstream of FGFR activation.

Examples of such abnormalities that result in activation or sensitisation of the FGFR signal include loss of, or inhibition of apoptotic pathways, up-regulation of the receptors or ligands, or presence of mutant variants of the receptors or ligands e.g PTK variants. Tumours with mutants of FGFR1, FGFR2 or FGFR3 or FGFR4 or up-regulation, in particular over-expression of FGFR1, or gain-of-function mutants of FGFR2 or FGFR3 may be particularly sensitive to FGFR inhibitors.

For example, point mutations engendering gain-of-function in FGFR2 have been identified in a number of conditions. In particular activating mutations in FGFR2 have been identified in 10% of endometrial tumours.

In addition, genetic aberrations of the FGFR3 receptor tyrosine kinase such as chromosomal translocations or point mutations resulting in ectopically expressed or deregulated, constitutively active, FGFR3 receptors have been identified and are linked to a subset of multiple myelomas, bladder and cervical carcinomas. A particular mutation T674I of the PDGF receptor has been identified in imatinib-treated patients. In addition, a gene amplification of 8p12-p11.2 was demonstrated in ~50% of lobular breast cancer (CLC) cases and this was shown to be linked with an increased expression of FGFR1. Preliminary studies with siRNA directed against FGFR1, or a small molecule inhibitor of the receptor, showed cell lines harbouring this amplification to be particularly sensitive to inhibition of this signalling pathway.

Alternatively, a biological sample taken from a patient may be analysed for loss of a negative regulator or suppressor of FGFR. In the present context, the term "loss" embraces the deletion of a gene encoding the regulator or suppressor, the truncation of the gene (for example by mutation), the truncation of the transcribed product of the gene, or the inactivation of the transcribed product (e.g. by point mutation) or sequestration by another gene product.

The term up-regulation includes elevated expression or over-expression, including gene amplification (i.e. multiple gene copies) and increased expression by a transcriptional effect, and hyperactivity and activation, including activation by mutations. Thus, the patient may be subjected to a diagnostic test to detect a marker characteristic of up-regulation of FGFR. The term diagnosis includes screening. By marker we include genetic markers including, for example, the measurement of DNA composition to identify mutations of FGFR. The term marker also includes markers which are characteristic of up regulation of FGFR, including enzyme activity, enzyme levels, enzyme state (e.g. phosphorylated or not) and mRNA levels of the aforementioned proteins.

The diagnostic tests and screens are typically conducted on a biological sample selected from tumour biopsy samples, blood samples (isolation and enrichment of shed tumour cells), stool biopsies, sputum, chromosome analysis, pleural fluid, peritoneal fluid, buccal spears, biopsy or urine.

Methods of identification and analysis of mutations and up-regulation of proteins are known to a person skilled in the art. Screening methods could include, but are not limited to, standard methods such as reverse-transcriptase polymerase chain reaction (RT-PCR) or in-situ hybridization such as fluorescence in situ hybridization (FISH).

Identification of an individual carrying a mutation in FGFR may mean that the patient would be particularly suitable for treatment with a FGFR inhibitor. Tumours may preferentially be screened for presence of a FGFR variant prior to treatment. The screening process will typically involve direct sequencing, oligonucleotide microarray analysis, or a mutant specific antibody. In addition, diagnosis of tumours with such mutations could be performed using techniques known to a person skilled in the art and as described herein such as RT-PCR and FISH.

In addition, mutant forms of, for example FGFR, can be identified by direct sequencing of, for example, tumour biopsies using PCR and methods to sequence PCR products directly as hereinbefore described. The skilled artisan will recognize that all such well-known techniques for detection of the over expression, activation or mutations of the aforementioned proteins could be applicable in the present case.

In screening by RT-PCR, the level of mRNA in the tumour is assessed by creating a cDNA copy of the mRNA followed by amplification of the cDNA by PCR. Methods of PCR amplification, the selection of primers, and conditions for amplification, are known to a person skilled in the art. Nucleic acid manipulations and PCR are carried out by standard methods, as described for example in Ausubel, F. M. et al., eds. (2004) Current Protocols in Molecular Biology, John Wiley & Sons Inc., or Innis, M. A. et al., eds. (1990) PCR Protocols: a guide to methods and applications, Academic Press, San Diego. Reactions and manipulations involving nucleic acid techniques are also described in Sambrook et al., (2001), $3^{rd}$ Ed, Molecular Cloning: A Laboratory Manual, Cold Spring Harbor Laboratory Press. Alternatively a commercially available kit for RT-PCR (for example Roche Molecular Biochemicals) may be used, or methodology as set forth in U.S. Pat. Nos. 4,666,828; 4,683,202; 4,801,531; 5,192,659, 5,272,057, 5,882,864, and 6,218,529 and incorporated herein by reference. An example of an in-situ hybridisation technique for assessing mRNA expression would be fluorescence in-situ hybridisation (FISH) (see Angerer (1987) Meth. Enzymol., 152: 649).

Generally, in situ hybridization comprises the following major steps: (1) fixation of tissue to be analyzed; (2) prehybridization treatment of the sample to increase accessibility of target nucleic acid, and to reduce nonspecific binding; (3) hybridization of the mixture of nucleic acids to the nucleic acid in the biological structure or tissue; (4) post-hybridization washes to remove nucleic acid fragments not bound in the hybridization, and (5) detection of the hybridized nucleic acid fragments. The probes used in such applications are typically labelled, for example, with radio-isotopes or fluorescent reporters. Preferred probes are sufficiently long, for example, from about 50, 100, or 200 nucleotides to about 1000 or more nucleotides, to enable specific hybridization with the target nucleic acid(s) under stringent conditions. Standard methods for carrying out FISH are described in Ausubel, F. M. et al., eds. (2004) Current Protocols in Molecular Biology, John Wiley & Sons Inc and Fluorescence In Situ Hybridization: Technical Overview by John M. S. Bartlett in Molecular Diagnosis of Cancer, Methods and Protocols, 2nd ed.; ISBN: 1-59259-760-2; March 2004, pps. 077-088; Series: Methods in Molecular Medicine.

Methods for gene expression profiling are described by (DePrimo et al. (2003), BMC Cancer, 3:3). Briefly, the protocol is as follows: double-stranded cDNA is synthesized from total RNA Using a (dT)24 oligomer for priming first-strand cDNA synthesis, followed by second strand cDNA synthesis with random hexamer primers. The double-stranded cDNA is used as a template for in vitro transcription of cRNA using biotinylated ribonucleotides. cRNA is chemically fragmented according to protocols described by Affymetrix (Santa Clara, Calif., USA), and then hybridized overnight on Human Genome Arrays.

Alternatively, the protein products expressed from the mRNAs may be assayed by immunohistochemistry of tumour samples, solid phase immunoassay with microtitre plates, Western blotting, 2-dimensional SDS-polyacrylamide gel electrophoresis, ELISA, flow cytometry and other methods known in the art for detection of specific proteins. Detection methods would include the use of site specific antibodies. The skilled person will recognize that all such well-known techniques for detection of upregulation of FGFR or detection of FGFR variants or mutants could be applicable in the present case.

Abnormal levels of proteins such as FGFR can be measured using standard enzyme assays, for example, those assays described herein. Activation or overexpression could also be detected in a tissue sample, for example, a tumour tissue. By measuring the tyrosine kinase activity with an assay such as that from Chemicon International. The tyrosine kinase of interest would be immunoprecipitated from the sample lysate and its activity measured.

Alternative methods for the measurement of the over expression or activation of FGFR including the isoforms thereof, include the measurement of microvessel density. This can for example be measured using methods described by Orre and Rogers (Int J Cancer (1999), 84(2) 101-8).

Therefore, all of these techniques could also be used to identify tumours particularly suitable for treatment with the compounds of the invention.

The compounds of the invention are particular useful in treatment of a patient having a mutated FGFR. The G697C mutation in FGFR3 is observed in 62% of oral squamous cell carcinomas and causes constitutive activation of the kinase activity. Activating mutations of FGFR3 have also been identified in bladder carcinoma cases. These mutations were of 6 kinds with varying degrees of prevelence: R248C, S249C, G372C, S373C, Y375C, K652Q. In addition, a Gly388Arg polymorphism in FGFR4 has been found to be associated with increased incidence and aggressiveness of prostate, colon, lung, liver (HCC) and breast cancer. The compounds of the invention are particularly useful in the treatment of a patient having a FGFR3-TACC3 translocation.

Therefore, in a further aspect the invention includes use of a compound according to the invention for the manufacture of a medicament for the treatment or prophylaxis of a disease state or condition in a patient who has been screened and has been determined as suffering from, or being at risk of suffering from, a disease or condition which would be susceptible to treatment with a compound having activity against FGFR.

Particular mutations a patient is screened for include G697C, R248C, S249C, G372C, S373C, Y373C, K652Q mutations in FGFR3 and Gly388Arg polymorphism in FGFR4, in particular FGFR3 R248C, FGFR3 S249C, FGFR3 G370C, or FGFR3 Y373C.

Particular mutations a patient is screened for include in particular FGFR gatekeeper mutations. Gatekeeper mutations include FGFR3 V555L/V555M, FGFR1 V561M, FGFR2 V564F/V564I/V564M and FGFR4 V550L. Particular mutations a patient is screened for include FGFR3 V555L, FGFR3 V555M, FGFR1 V561M and FGFR2 V564I, in particular FGFR3 V555L and FGFR3 V555M.

In another aspect, the invention includes a compound of the invention for use in the prophylaxis or treatment of cancer in a patient selected from a sub-population possessing a variant of the FGFR gene (for example G697C mutation in FGFR3 and Gly388Arg polymorphism in FGFR4).

The compounds of the invention are particular useful in the treatment of a patient having a FGFR fusion or translocation, in particular FGFR3:TACC3 v1; FGFR3:TACC3 v3; FGFR3:TACC3 Intron; FGFR3:BAIAP2L1; FGFR2:AFF3; FGFR2:BICC1; FGFR2:CASP7; FGFR2:CCDCl$_6$; and FGFR2:OFD1. The following abbreviations are used: FGFR (fibroblast growth factor receptor); FGFR3:TACC3 (fusion between genes encoding FGFR3 and transforming acidic coiled-coil containing protein 3); FGFR3:BAIAP2L1 (fusion between genes encoding FGFR3 and brain-specific angiogenesis inhibitor 1-associated protein 2-like protein 1); FGFR2:AFF3 (fusion between genes encoding FGFR2 and AF4/FMR2 family, member 3); FGFR2:BICC1 (fusion between genes encoding FGFR2 and bicaudal C homolog 1); FGFR2: CASP7 (fusion between genes encoding FGFR2 and caspase 7); FGFR2:CCDCl$_6$ (fusion between genes encoding FGFR2 and coiled-coil domain containing 6); FGFR2:OFD1 (fusion between genes encoding FGFR2 and oral-facial-digital syndrome 1).

Pharmaceutical Compositions and Combinations

In view of their useful pharmacological properties, the subject compounds may be formulated into various pharmaceutical forms for administration purposes.

In one embodiment the pharmaceutical composition (e.g. formulation) comprises at least one active compound of the invention together with a pharmaceutically acceptable carrier which may include adjuvants, excipients, diluents, fillers, buffers, stabilisers, preservatives, lubricants, or other materials well known to those skilled in the art and optionally other therapeutic or prophylactic agents.

To prepare the pharmaceutical compositions of this invention, an effective amount of a compound of the present invention, as the active ingredient is combined in intimate admixture with a pharmaceutically acceptable carrier, which carrier may take a wide variety of forms depending on the form of preparation desired for administration. The pharmaceutical compositions can be in any form suitable for oral, parenteral, topical, intranasal, ophthalmic, otic, rectal, intravaginal, or transdermal administration. These pharmaceutical compositions are desirably in unitary dosage form suitable, preferably, for administration orally, rectally, percutaneously, or by parenteral injection. For example, in preparing the compositions in oral dosage form, any of the usual pharmaceutical media may be employed, such as, for example, water, glycols, oils, alcohols and the like in the case of oral liquid preparations such as suspensions, syrups, elixirs and solutions; or solid carriers such as starches, sugars, kaolin, lubricants, binders, disintegrating agents and the like in the case of powders, pills, capsules and tablets.

Because of their ease in administration, tablets and capsules represent the most advantageous oral dosage unit form, in which case solid pharmaceutical carriers are obviously employed. For parenteral compositions, the carrier will usually comprise sterile water, at least in large part, though other ingredients, to aid solubility for example, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. In the compositions suitable for percutaneous administration, the carrier optionally comprises a penetration enhancing agent and/or a suitable wetting agent, optionally combined with suitable additives of any nature in minor proportions, which additives do not cause a significant deleterious effect to the skin. Said additives may facilitate the administration to the skin and/or may be helpful for preparing the desired compositions. These compositions may be administered in various ways, e.g., as a transdermal patch, as a spot-on, as an ointment. It is especially advantageous to formulate the aforementioned pharmaceutical compositions in dosage unit form for ease of administration and uniformity of dosage. Dosage unit form as used herein refers to physically discrete units suitable as unitary dosages, each unit containing a predetermined quantity of active ingredient calculated to produce the desired therapeutic effect in association with the required pharmaceutical carrier. Examples of such dosage unit forms are tablets (including scored or coated tablets), capsules, pills, powder packets, wafers, injectable solutions or suspensions, teaspoonfuls, tablespoonfuls and the like, and segregated multiples thereof.

The compound of the invention is administered in an amount sufficient to exert its anti-tumour activity or to exert its FGFR inhibiting effect.

Those skilled in the art could determine the effective amount from the test results presented hereinafter. In general, it is contemplated that a therapeutically effective amount would be from 0.005 mg/kg to 100 mg/kg body weight, and in particular from 0.005 mg/kg to 10 mg/kg body weight. It may be appropriate to administer the required dose as single, two, three, four or more sub-doses at appropriate intervals throughout the day. Said sub-doses may be formulated as unit dosage forms, for example, containing 0.5 to 500 mg, in particular 1 mg to 500 mg, more in particular 10 mg to 500 mg of active ingredient per unit dosage form.

Depending on the mode of administration, the pharmaceutical composition will preferably comprise from 0.05 to 99% by weight, more preferably from 0.1 to 70% by weight, even more preferably from 0.1 to 50% by weight of the compound of the present invention, and, from 1 to 99.95% by weight, more preferably from 30 to 99.9% by weight, even more preferably from 50 to 99.9% by weight of a pharmaceutically acceptable carrier, all percentages being based on the total weight of the composition.

It has been discovered that some FGFR inhibitors can be used in combination with other anticancer agents. For example, it may be beneficial to combine an inhibitor that induces apoptosis with another agent which acts via a different mechanism to regulate cell growth thus treating two of the characteristic features of cancer development. Examples of such combinations are set out below.

As another aspect of the present invention, a combination of a compound of the present invention with another anticancer agent is envisaged, especially for use as a medicine, more specifically for use in the treatment of cancer or related diseases, in particular a condition or disease mediated by a FGFR kinase.

For the treatment of the above conditions, the compounds of the invention may be advantageously employed in combination with one or more other medicinal agents, more particularly, with other anti-cancer agents or adjuvants in cancer therapy. Examples of anti-cancer agents or adjuvants (supporting agents in the therapy) include but are not limited to:

platinum coordination compounds for example cisplatin optionally combined with amifostine, carboplatin or oxaliplatin;
taxane compounds for example paclitaxel, paclitaxel protein bound particles (Abraxane™) or docetaxel;
topoisomerase I inhibitors such as camptothecin compounds for example irinotecan, SN-38, topotecan, topotecan hcl;
topoisomerase II inhibitors such as anti-tumour epipodophyllotoxins or podophyllotoxin derivatives for example etoposide, etoposide phosphate or teniposide;
anti-tumour *vinca* alkaloids for example vinblastine, vincristine or vinorelbine;
anti-tumour nucleoside derivatives for example 5-fluorouracil, leucovorin, gemcitabine, gemcitabine hcl, capecitabine, cladribine, fludarabine, nelarabine;
alkylating agents such as nitrogen mustard or nitrosourea for example cyclophosphamide, chlorambucil, carmustine, thiotepa, mephalan (melphalan), lomustine, altretamine, busulfan, dacarbazine, estramustine, ifosfamide optionally in combination with mesna, pipobroman, procarbazine, streptozocin, telozolomide, uracil;
anti-tumour anthracycline derivatives for example daunorubicin, doxorubicin optionally in combination with dexrazoxane, doxil, idarubicin, mitoxantrone, epirubicin, epirubicin hcl, valrubicin;
molecules that target the IGF-1 receptor for example picropodophilin;
tetracarcin derivatives for example tetrocarcin A;
glucocorticoids for example prednisone;
antibodies for example trastuzumab (HER2 antibody), rituximab (CD20 antibody), gemtuzumab, gemtuzumab ozogamicin, cetuximab, pertuzumab, bevacizumab, alemtuzumab, eculizumab, ibritumomab tiuxetan, nofetumomab, panitumumab, tositumomab, CNTO 328;
estrogen receptor antagonists or selective estrogen receptor modulators or inhibitors of estrogen synthesis for example tamoxifen, fulvestrant, toremifene, droloxifene, faslodex, raloxifene or letrozole;
aromatase inhibitors such as exemestane, anastrozole, letrazole, testolactone and vorozole;
differentiating agents such as retinoids, vitamin D or retinoic acid and retinoic acid metabolism blocking agents (RAMBA) for example accutane;
DNA methyl transferase inhibitors for example azacytidine or decitabine;
antifolates for example premetrexed disodium;
antibiotics for example antinomycin D, bleomycin, mitomycin C, dactinomycin, carminomycin, daunomycin, levamisole, plicamycin, mithramycin;
antimetabolites for example clofarabine, aminopterin, cytosine arabinoside or methotrexate, azacitidine, cytarabine, floxuridine, pentostatin, thioguanine;
apoptosis inducing agents and antiangiogenic agents such as Bcl-2 inhibitors for example YC 137, BH 312, ABT 737, gossypol, HA 14-1, TW 37 or decanoic acid;
tubuline-binding agents for example combrestatin, colchicines or nocodazole;
kinase inhibitors (e.g. EGFR (epithelial growth factor receptor) inhibitors, MTKI (multi target kinase inhibitors), mTOR inhibitors, cmet inhibitors) for example flavoperidol, imatinib mesylate, erlotinib, gefitinib, dasatinib, lapatinib, lapatinib ditosylate, sorafenib, sunitinib, sunitinib maleate, temsirolimus, 6-{difluoro [6-(1-methyl-1H-pyrazol-4-yl)-[1,2,4]triazolo[4,3-b] pyridazin-3-yl]methyl}quinoline or a pharmaceutically acceptable salt thereof, 6-[difluoro(6-pyridin-4-yl[1,2, 4]triazolo[4,3-b]pyridazin-3-yl)methyl]-quinoline or a pharmaceutically acceptable salt thereof;
farnesyltransferase inhibitors for example tipifarnib;
histone deacetylase (HDAC) inhibitors for example sodium butyrate, suberoylanilide hydroxamide acid (SAHA), depsipeptide (FR 901228), NVP-LAQ824, R306465, JNJ-26481585, trichostatin A, vorinostat;
Inhibitors of the ubiquitin-proteasome pathway for example PS-341, MLN 0.41 or bortezomib;
Yondelis;
Telomerase inhibitors for example telomestatin;
Matrix metalloproteinase inhibitors for example batimastat, marimastat, prinostat or metastat.
Recombinant interleukins for example aldesleukin, denileukin diftitox, interferon alfa 2a, interferon alfa 2b, peginterferon alfa 2b
MAPK inhibitors
Retinoids for example alitretinoin, bexarotene, tretinoin Arsenic trioxide
Asparaginase
Steroids for example dromostanolone propionate, megestrol acetate, nandrolone (decanoate, phenpropionate), dexamethasone
Gonadotropin releasing hormone agonists or antagonists for example abarelix, goserelin acetate, histrelin acetate, leuprolide acetate
Thalidomide, lenalidomide
Mercaptopurine, mitotane, pamidronate, pegademase, pegaspargase, rasburicase
BH3 mimetics for example ABT-737
MEK inhibitors for example PD98059, AZD6244, CI-1040
colony-stimulating factor analogs for example filgrastim, pegfilgrastim, sargramostim; erythropoietin or analogues thereof (e.g. darbepoetin alfa); interleukin 11; oprelvekin; zoledronate, zoledronic acid; fentanyl; bisphosphonate; palifermin.
a steroidal cytochrome P450 17alpha-hydroxylase-17,20-lyase inhibitor (CYP17), e.g. abiraterone, abiraterone acetate
an antibody that blocks the interaction between PD-1 and PD-L1.

In one embodiment, the present invention relates to a combination of a compound of formula (I), a pharmaceutically acceptable salt thereof or a solvate thereof, or any sub-groups and examples thereof, and 6-{difluoro[6-(1-methyl-H-pyrazol-4-yl)[1,2,4]triazolo[4,3-b]-pyridazin-3-yl]methyl}quinoline or a pharmaceutically acceptable salt thereof.

In one embodiment, the present invention relates to a combination of a compound of formula (I), a pharmaceutically acceptable salt thereof or a solvate thereof, or any sub-groups and examples thereof, and 6-[difluoro(6-pyridin-4-yl[1,2,4]triazolo[4,3-b]pyridazin-3-yl)methyl]quinoline or a pharmaceutically acceptable salt thereof.

In one embodiment, the present invention relates to a pharmaceutical composition comprising a compound of formula (I), a pharmaceutically acceptable salt thereof or a solvate thereof, or any sub-groups and examples thereof, and 6-{difluoro[6-(1-methyl-1H-pyrazol-4-yl)[1,2,4]-triazolo[4,3-b]pyridazin-3-yl]methyl}quinoline or a pharmaceutically acceptable salt thereof.

In one embodiment, the present invention relates to a pharmaceutical composition comprising a compound of formula (I), a pharmaceutically acceptable salt thereof or a solvate thereof, or any sub-groups and examples thereof, and 6-[difluoro(6-pyridin-4-yl[1,2,4]triazolo[4,3-b]-pyridazin-3-yl)methyl]quinoline or a pharmaceutically acceptable salt thereof.

The compounds of the present invention also have therapeutic applications in sensitising tumour cells for radiotherapy and chemotherapy.

Hence the compounds of the present invention can be used as "radiosensitizer" and/or "chemosensitizer" or can be given in combination with another "radiosensitizer" and/or "chemosensitizer".

The term "radiosensitizer", as used herein, is defined as a molecule, preferably a low molecular weight molecule, administered to animals in therapeutically effective amounts to increase the sensitivity of the cells to ionizing radiation and/or to promote the treatment of diseases which are treatable with ionizing radiation.

The term "chemosensitizer", as used herein, is defined as a molecule, preferably a low molecular weight molecule, administered to animals in therapeutically effective amounts to increase the sensitivity of cells to chemotherapy and/or promote the treatment of diseases which are treatable with chemotherapeutics.

Several mechanisms for the mode of action of radiosensitizers have been suggested in the literature including: hypoxic cell radiosensitizers (e.g., 2-nitroimidazole compounds, and benzotriazine dioxide compounds) mimicking oxygen or alternatively behave like bioreductive agents under hypoxia; non-hypoxic cell radiosensitizers (e.g., halogenated pyrimidines) can be analogoues of DNA bases and preferentially incorporate into the DNA of cancer cells and thereby promote the radiation-induced breaking of DNA molecules and/or prevent the normal DNA repair mechanisms; and various other potential mechanisms of action have been hypothesized for radiosensitizers in the treatment of disease.

Many cancer treatment protocols currently employ radiosensitizers in conjunction with radiation of x-rays. Examples of x-ray activated radiosensitizers include, but are not limited to, the following: metronidazole, misonidazole, desmethylmisonidazole, pimonidazole, etanidazole, nimorazole, mitomycin C, RSU 1069, SR 4233, E09, RB 6145, nicotinamide, 5-bromodeoxyuridine (BUdR), 5-iododeoxyuridine (IUdR), bromodeoxycytidine, fluorodeoxyuridine (FudR), hydroxyurea, cisplatin, and therapeutically effective analogs and derivatives of the same.

Photodynamic therapy (PDT) of cancers employs visible light as the radiation activator of the sensitizing agent. Examples of photodynamic radiosensitizers include the following, but are not limited to: hematoporphyrin derivatives, Photofrin, benzoporphyrin derivatives, tin etioporphyrin, pheoborbide-a, bacteriochlorophyll-a, naphthalocyanines, phthalocyanines, zinc phthalocyanine, and therapeutically effective analogs and derivatives of the same. Radiosensitizers may be administered in conjunction with a therapeutically effective amount of one or more other compounds, including but not limited to: compounds which promote the incorporation of radiosensitizers to the target cells; compounds which control the flow of therapeutics, nutrients, and/or oxygen to the target cells; chemotherapeutic agents which act on the tumour with or without additional radiation; or other therapeutically effective compounds for treating cancer or other diseases.

Chemosensitizers may be administered in conjunction with a therapeutically effective amount of one or more other compounds, including but not limited to: compounds which promote the incorporation of chemosensitizers to the target cells; compounds which control the flow of therapeutics, nutrients, and/or oxygen to the target cells; chemotherapeutic agents which act on the tumour or other therapeutically effective compounds for treating cancer or other disease. Calcium antagonists, for example verapamil, are found useful in combination with antineoplastic agents to establish chemosensitivity in tumor cells resistant to accepted chemotherapeutic agents and to potentiate the efficacy of such compounds in drug-sensitive malignancies.

In view of their useful pharmacological properties, the components of the combinations according to the invention, i.e. the one or more other medicinal agent and the compound according to the present invention may be formulated into various pharmaceutical forms for administration purposes. The components may be formulated separately in individual pharmaceutical compositions or in a unitary pharmaceutical composition containing all components.

The present invention therefore also relates to a pharmaceutical composition comprising the one or more other medicinal agent and the compound according to the present invention together with a pharmaceutically acceptable carrier.

The present invention further relates to the use of a combination according to the invention in the manufacture of a pharmaceutical composition for inhibiting the growth of tumour cells.

The present invention further relates to a product containing as first active ingredient a compound according to the invention and as further active ingredient one or more anticancer agent, as a combined preparation for simultaneous, separate or sequential use in the treatment of patients suffering from cancer.

The one or more other medicinal agents and the compound according to the present invention may be administered simultaneously (e.g. in separate or unitary compositions) or sequentially in either order. In the latter case, the two or more compounds will be administered within a period and in an amount and manner that is sufficient to ensure that an advantageous or synergistic effect is achieved. It will be appreciated that the preferred method and order of administration and the respective dosage amounts and regimes for each component of the combination will depend on the particular other medicinal agent and compound of the present invention being administered, their route of administration, the particular tumour being treated and the particular host being treated. The optimum method and order of administration and the dosage amounts and regime can be readily determined by those skilled in the art using conventional methods and in view of the information set out herein.

The weight ratio of the compound according to the present invention and the one or more other anticancer agent(s) when given as a combination may be determined by the person skilled in the art. Said ratio and the exact dosage and frequency of administration depends on the particular compound according to the invention and the other anticancer agent(s) used, the particular condition being treated, the severity of the condition being treated, the age, weight, gender, diet, time of administration and general physical condition of the particular patient, the mode of administration as well as other medication the individual may be taking, as is well known to those skilled in the art. Furthermore, it is evident that the effective daily amount may be lowered or increased depending on the response of the treated subject and/or depending on the evaluation of the physician prescribing the compounds of the instant invention. A particular weight ratio for the present compound of formula (I) and another anticancer agent may range from 1/10 to 10/1, more in particular from 1/5 to 5/1, even more in particular from 1/3 to 3/1.

The platinum coordination compound is advantageously administered in a dosage of 1 to 500 mg per square meter (mg/m$^2$) of body surface area, for example 50 to 400 mg/m$^2$, particularly for cisplatin in a dosage of about 75 mg/m$^2$ and for carboplatin in about 300 mg/m$^2$ per course of treatment.

The taxane compound is advantageously administered in a dosage of 50 to 400 mg per square meter (mg/m$^2$) of body surface area, for example 75 to 250 mg/m$^2$, particularly for paclitaxel in a dosage of about 175 to 250 mg/m$^2$ and for docetaxel in about 75 to 150 mg/m$^2$ per course of treatment.

The camptothecin compound is advantageously administered in a dosage of 0.1 to 400 mg per square meter (mg/m$^2$) of body surface area, for example 1 to 300 mg/m$^2$, particularly for irinotecan in a dosage of about 100 to 350 mg/m$^2$ and for topotecan in about 1 to 2 mg/m$^2$ per course of treatment.

The anti-tumour podophyllotoxin derivative is advantageously administered in a dosage of 30 to 300 mg per square meter (mg/m$^2$) of body surface area, for example 50 to 250 mg/m$^2$, particularly for etoposide in a dosage of about 35 to 100 mg/m$^2$ and for teniposide in about 50 to 250 mg/m$^2$ per course of treatment.

The anti-tumour vinca alkaloid is advantageously administered in a dosage of 2 to 30 mg per square meter (mg/m$^2$) of body surface area, particularly for vinblastine in a dosage of about 3 to 12 mg/m$^2$, for vincristine in a dosage of about 1 to 2 mg/m$^2$, and for vinorelbine in dosage of about 10 to 30 mg/m$^2$ per course of treatment.

The anti-tumour nucleoside derivative is advantageously administered in a dosage of 200 to 2500 mg per square meter (mg/m$^2$) of body surface area, for example 700 to 1500 mg/m$^2$, particularly for 5-FU in a dosage of 200 to 500 mg/m$^2$, for gemcitabine in a dosage of about 800 to 1200 mg/m$^2$ and for capecitabine in about 1000 to 2500 mg/m$^2$ per course of treatment.

The alkylating agents such as nitrogen mustard or nitrosourea is advantageously administered in a dosage of 100 to 500 mg per square meter (mg/m$^2$) of body surface area, for example 120 to 200 mg/m$^2$, particularly for cyclophosphamide in a dosage of about 100 to 500 mg/m$^2$, for chlorambucil in a dosage of about 0.1 to 0.2 mg/kg, for carmustine in a dosage of about 150 to 200 mg/m$^2$, and for lomustine in a dosage of about 100 to 150 mg/m$^2$ per course of treatment.

The anti-tumour anthracycline derivative is advantageously administered in a dosage of 10 to 75 mg per square meter (mg/m$^2$) of body surface area, for example 15 to 60 mg/m$^2$, particularly for doxorubicin in a dosage of about 40 to 75 mg/m$^2$, for daunorubicin in a dosage of about 25 to 45 mg/m$^2$, and for idarubicin in a dosage of about 10 to 15 mg/m$^2$ per course of treatment.

The antiestrogen agent is advantageously administered in a dosage of about 1 to 100 mg daily depending on the particular agent and the condition being treated. Tamoxifen is advantageously administered orally in a dosage of 5 to 50 mg, preferably 10 to 20 mg twice a day, continuing the therapy for sufficient time to achieve and maintain a therapeutic effect. Toremifene is advantageously administered orally in a dosage of about 60 mg once a day, continuing the therapy for sufficient time to achieve and maintain a therapeutic effect. Anastrozole is advantageously administered orally in a dosage of about 1 mg once a day. Droloxifene is advantageously administered orally in a dosage of about 20-100 mg once a day. Raloxifene is advantageously administered orally in a dosage of about 60 mg once a day. Exemestane is advantageously administered orally in a dosage of about 25 mg once a day.

Antibodies are advantageously administered in a dosage of about 1 to 5 mg per square meter (mg/m$^2$) of body surface area, or as known in the art, if different. Trastuzumab is advantageously administered in a dosage of 1 to 5 mg per square meter (mg/m$^2$) of body surface area, particularly 2 to 4 mg/m$^2$ per course of treatment.

These dosages may be administered for example once, twice or more per course of treatment, which may be repeated for example every 7, 14, 21 or 28 days.

The compounds of formula (I), the pharmaceutically acceptable addition salts, in particular pharmaceutically acceptable acid addition salts, and stereoisomeric forms thereof can have valuable diagnostic properties in that they can be used for detecting or identifying the formation of a complex between a labelled compound and other molecules, peptides, proteins, enzymes or receptors.

The detecting or identifying methods can use compounds that are labelled with labelling agents such as radioisotopes, enzymes, fluorescent substances, luminous substances, etc. Examples of the radioisotopes include $^{125}I$, $^{131}I$, $^{3}H$ and $^{14}C$. Enzymes are usually made detectable by conjugation of an appropriate substrate which, in turn catalyses a detectable reaction. Examples thereof include, for example, beta-galactosidase, beta-glucosidase, alkaline phosphatase, peroxidase and malate dehydrogenase, preferably horseradish peroxidase. The luminous substances include, for example, luminol, luminol derivatives, luciferin, aequorin and luciferase.

Biological samples can be defined as body tissue or body fluids. Examples of body fluids are cerebrospinal fluid, blood, plasma, serum, urine, sputum, saliva and the like.

EXPERIMENTAL PART

Several methods for preparing the compounds of the invention are illustrated in the following examples. Unless otherwise noted, all starting materials were obtained from commercial suppliers and used without further purification.

When a stereocenter is indicated with 'RS' this means that a mixture of stereoisomers was obtained at the indicated center, unless otherwise indicated. The stereochemical configuration for a stereocenter in some compounds is designated "R" or "S" and/or with a solid wedged or hashed wedged bond indicating the absolute stereoconfiguration is known. For some compounds, the stereochemical configuration at an indicated stereocenter has been designated as "R*" or "S*" with a solid line bond, or a solid wedged or a hashed wedged bond indicating the absolute stereochemistry at the stereocenter is undetermined although it is absolute. So a stereocenter indicated as being S* means it is an absolute stereocenter but it is not determined whether it is S or R.

Example 1

Preparation of Compound 1, Compound 2 and Compound 3

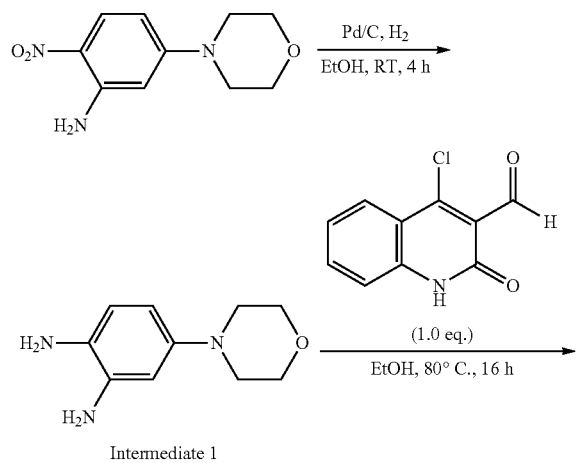

Intermediate 1

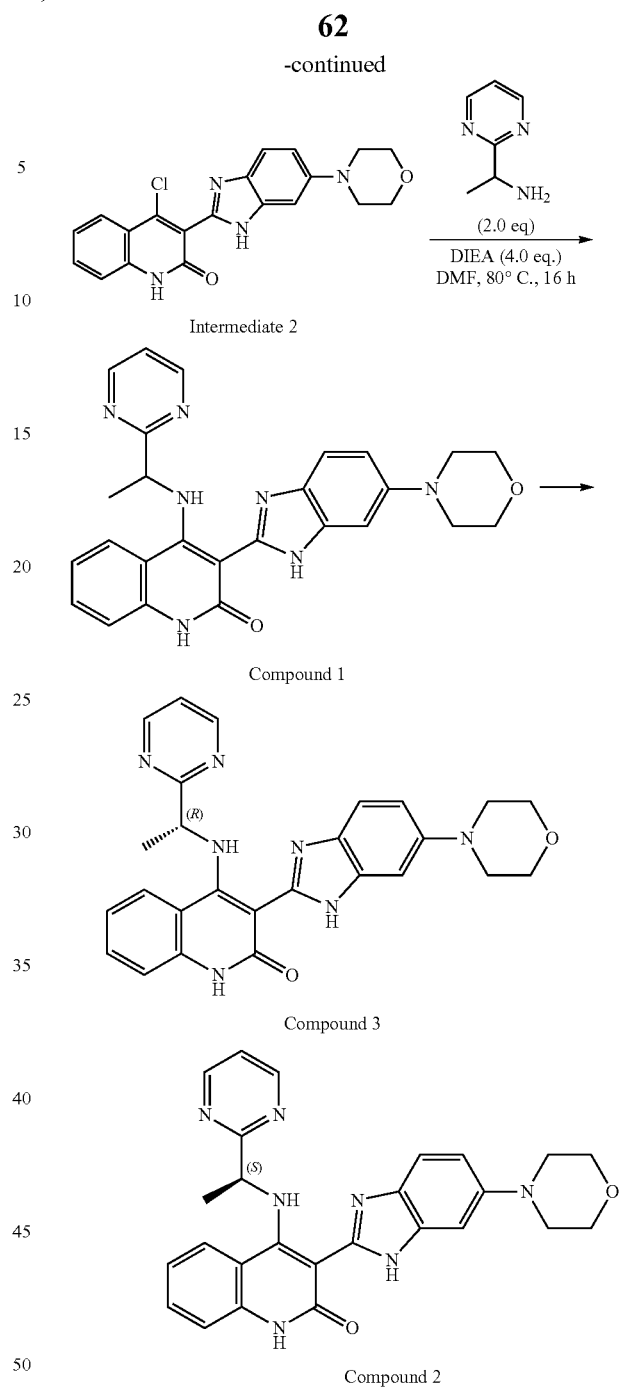

Compound 1

Compound 3

Compound 2 a) Preparation of Intermediate 1

4-morpholinobenzene-1,2-diamine

A mixture of 5-morpholino-2-nitroaniline (1.0 g, 4.48 mmol) and 10% palladium on charcoal by wt (100 mg) in ethanol (50 mL) was stirred at room temperature under balloon pressure of hydrogen gas for 4 hours. The reaction mixture was directly used in the next step without further purification. LC-MS (ESI) General procedure A, method 1: $R_T$=0.33 min, mass calcd. for $C_{10}H_{15}N_3O$ 193.1, m/z found 194.2 $[M+H]^+$.

b) Preparation of Intermediate 2

(4-chloro-3-(6-morpholino-1H-benzo[d]imidazol-2-yl)quinolin-2(1H)-one)

To a mixture of intermediate 1 (4-morpholinobenzene-1,2-diamine) in ethanol (50 mL) was added 4-chloro-2-oxo-1,2-dihydroquinoline-3-carbaldehyde (927 mg, 4.48 mmol) at room temperature. The mixture was stirred at 80° C. under balloon pressure of oxygen gas for 16 hours. After cooling to room temperature, the mixture was filtered through a pad of celite. The filtrate was concentrated under reduced pressure to give a residue which was recrystallized with dichloromethane:petroleum ether to give intermediate 2 (300 mg, 17.6% yield) as dark solids.

LC-MS (ESI) General procedure B, method 1: $R_T$=1.22 min, mass calcd. for $C_{20}H_{17}ClN_4O_2$ 380.1, m/z found 381.0 $[M+H]^+$.

c) Preparation of Compound 1

(3-(6-morpholino-1H-benzo[d]imidazol-2-yl)-4-((1-(pyrimidin-2-yl)ethyl)amino)-quinolin-2(1H)-one), compound 3 (R enantiomer) and compound 2 (S enantiomer)

To a solution of intermediate 2 (4-chloro-3-(6-morpholino-1H-benzo[d]imidazol-2-yl)-quinolin-2(1H)-one) (300 mg, 0.79 mmol) and N,N-diisopropylethylamine (0.50 mL, 3.16 mmol) in N,N-dimethylformamide (2 mL) was added 1-(pyrimidin-2-yl)ethanamine (194 mg, 1.58 mmol). The mixture was stirred at 80° C. for 16 hours. After cooling to room temperature, the reaction mixture was purified by Prep-HPLC (Column: WatersXBridge 30*150 mm 5 um, Flow rate: 20 mL/min, Mobile Phase A: Water (0.1% $NH_3.H_2O$), Mobile Phase B: Acetonitrile, Gradient: 35-55% (% B)). The desired fraction was collected and the volatile was removed under reduced pressure. The water phase was lyophilized to give compound 1 (mixture of stereoisomers) (101 mg, 27.4% yield) as yellow solids. The crude compound was further purified by Prep. SFC (Supercritical Fluid Chromatography) (separation condition: Column: ChiralPak AD-H Daicel chemical Industries, Ltd, 250*30 mm I.D., 5 um; Mobile phase A: Supercritical $CO_2$, Mobile phase B: Ethanol (0.1% $NH_3.H_2O$), A:B=60:40 at 50 mL/min; Column Temp: 38° C.; Nozzle Pressure: 100 Bar; Nozzle Temp: 60° C.; Evaporator Temp: 20° C.; Trimmer Temp: 25° C.; Wavelength: 220 nm) to afford compound 3 (34.26 mg, 33.92% yield, purity >99%) and compound 2 (38.57 mg, 38.19% yield, purity >99%).

Compound 2

((S)-3-(6-morpholino-1H-benzo[d]imidazol-2-yl)-4-((1-(pyrimidin-2-yl)ethyl)amino)-quinolin-2(1H)-one)

LC-MS (ESI) General procedure A, method 1: $R_T$=1.19 min, mass calcd. for $C_{26}H_{25}N_7O_2$ 468.2, m/z found 468.4 $[M+H]^+$.

$^1$H NMR (400 MHz, DMSO-$d_6$) general procedure A: δ 12.85 (d, J=14.9 Hz, 1H), 12.16 (d, J=8.1 Hz, 0.34H), 12.04 (d, J=8.3 Hz, 0.61H), 11.57 (s, 1H), 8.79 (t, J=4.1 Hz, 2H), 8.06 (d, J=8.5 Hz, 1H), 7.59-7.47 (m, 2H), 7.39-7.22 (m, 3H), 7.10 (t, J=7.8 Hz, 1H), 6.97 (t, J=9.5 Hz, 1H), 5.55 (q, 1H), 3.78 (s, 4H), 3.11 (d, J=4.5 Hz, 4H), 1.76 (t, J=7.3 Hz, 3H).

Compound 3

(R)-3-(6-morpholino-1H-benzo[d]imidazol-2-yl)-4-((1-(pyrimidin-2-yl)ethyl)-amino)quinolin-2(1H)-one LC-MS (ESI) General procedure B, method 2: $R_T$=1.19 min, mass calcd. for $C_{26}H_{25}N_7O_2$ 468.2, m/z found 468.4 $[M+H]^+$.

$^1$H NMR (400 MHz, DMSO-$d_6$) General procedure A δ 12.86 (d, J=14.5 Hz, 1H), 12.16 (d, J=8.0 Hz, 0.34H), 12.04 (d, J=8.4 Hz, 0.42H), 11.57 (s, 1H), 8.79 (t, J=4.3 Hz, 2H), 8.06 (d, J=8.6 Hz, 1H), 7.59-7.44 (m, 2H), 7.39-7.21 (m, 3H), 7.11 (t, J=7.6 Hz, 1H), 6.97 (t, J=9.6 Hz, 1H), 5.55 (q, 1H), 3.79 (s, 4H), 3.11 (d, J=2.8 Hz, 4H), 1.76 (t, J=7.3 Hz, 3H).

Other compounds were prepared according to the above procedure. See Table 1.

For instance, compound 8a ((S)-3-(6-(4-methylpiperazin-1-yl)-1H-benzo[d]imidazol-2-yl)-4-((1-(pyridin-2-yl)ethyl)amino)quinolin-2(1H)-one) and compound 8b ((R)-3-(6-(4-methylpiperazin-1-yl)-1H-benzo[d]imidazol-2-yl)-4-((1-(pyridin-2-yl)ethyl)amino)-quinolin-2(1H)-one) was prepared as follows:

To a solution of 4-chloro-3-(6-(4-methylpiperazin-1-yl)-1H-benzo[d]imidazol-2-yl)quinolin-2(1H)-one (600 mg, 1.53 mmol) and N,N-diisopropylethylamine (0.83 mL, 4.59 mmol) in N,N-dimethylformamide (5 mL) was added 1-(pyridin-2-yl)ethanamine (373 mg, 3.06 mmol). The mixture was stirred at 80° C. for 16 hours. After cooling to room temperature, the reaction mixture was purified by Prep-HPLC (Column: WatersXBridge 30*150 mm 5 um, Flow rate: 20 mL/min, Mobile Phase A: Water (0.1% $NH_3.H_2O$), Mobile Phase B: Acetonitrile, Gradient: 35-55% (% B)). The desired fraction was collected and the volatile was removed under reduced pressure. The water phase was lyophilized to give compound 8 (mixture of stereoisomers) (250 mg, 34% yield) as yellow solids. The crude compound was further purified by prep. SFC (separation condition: Column: ChiralCel OJ-H Daicel chemical Industries, Ltd, 250*30 mm I.D., 5 um; Mobile phase A: Supercritical $CO_2$, Mobile phase B: Ethanol (0.1% $NH_3.H_2O$)A:B=70:30 at 50 ml/min, A:B=60:40 at 50 mL/min; Column Temp: 38° C.; Nozzle Pressure: 100 Bar; Nozzle Temp: 60° C.; Evaporator Temp: 20° C.; Trimmer Temp: 25° C.; Wavelength: 220 nm) to afford compound 8a (89 mg, 36% yield, purity >99%) and compound 8b.

Compound 8a

LC-MS (ESI) General procedure A, method 2: $R_T$=0.96 min, mass calcd. for $C_{28}H_{29}N_7O$ 479.24, m/z found 480.5 $[M+H]^+$.

$^1$H NMR (400 MHz, DMSO-$d_6$) General procedure A: δ 12.88 (d, J=15.4 Hz, 1H), 12.23 (dd, J=54.1, 8.1 Hz, 1H), 11.57 (s, 1H), 8.54 (s, 1H), 7.97 (d, J=8.4 Hz, 1H), 7.82-7.71 (m, 1H), 7.61-7.43 (m, 3H), 7.34 (d, J=8.1 Hz, 1H), 7.25 (d, J=7.0 Hz, 2H), 7.08 (dd, J=16.7, 8.9 Hz, 1H), 6.96 (t, J=10.2 Hz, 1H), 5.50 (d, J=6.5 Hz, 1H), 3.20-3.10 (m, 4H), 2.51 (s, 4H), 2.24 (s, 3H), 1.79-1.64 (m, 3H).

For instance compound 30a (S*)-3-(6-morpholino-1H-benzo[d]imidazol-2-yl)-4-((1-(pyrimidin-2-yl)propyl) amino)quinolin-2(1H)-one) and compound 30b (R)-3-(6-morpholino-1H-benzo[d]imidazol-2-yl)-4-((1-(pyrimidin-2-yl)propyl)amino)-quinolin-2(1H)-one) was prepared as follows:

To a solution of 4-chloro-3-(6-morpholino-H-benzo[d]imidazol-2-yl)quinolin-2(1H)-one (260 mg, 0.68 mmol) and N,N-diisopropylethylamine (0.5 mL, 3.03 mmol) in N,N-dimethylethanamide (2 mL) was added 1-(pyrimidin-2-yl)propan-1-amine (230 mg, 1.33 mmol). The mixture was stirred at 100° C. for 2 hours. After cooling to room temperature, the reaction mixture was purified by Prep-HPLC (Column: WatersXBridge 30*150 mm 5 um, Flow rate: 20 mL/min, Mobile Phase A: Water (0.1% TFA), Mobile Phase B: Acetonitrile, Gradient: 35-55% (% B)). The desired fraction was collected and the volatile was removed under reduced pressure. The water phase was lyophilized to give compound 30 (mixture of stereoisomers)(88 mg, 26.9% yield) as brown solids. The crude compound was further purified by prep. SFC (separation condition: Column: ChiralPak AD-H Daicel chemical Industries, Ltd, 250*30 mm I.D., 5 um; Mobile phase A: Supercritical $CO_2$, Mobile phase B: Ethanol (0.1% DEA), A:B=50:50 at 50 mL/min; Column Temp: 38° C.; Nozzle Pressure: 100 Bar; Nozzle Temp: 60° C.; Evaporator Temp: 20° C.; Trimmer Temp: 25° C.; Wavelength: 220 nm) to afford compound 30a as a trifluoroacetic acid salt (13.80 mg, 15.7% yield, purity >99%) and 30b as a trifluoroacetic acid salt.

Compound 30a

LC-MS (ESI) General procedure A, method 2: $R_T$=1.19 min, mass calcd. for $C_{27}H_{27}N_7O_2$ 481.2, m/z found 482.4 $[M+H]^+$.

$^1$H NMR (400 MHz, $CD_3OD$) General procedure A: δ8.74 (d, J=4.9, 2H), 8.02 (d, J=8.8, 1H), 7.60-7.00 (m, 7H), 5.28 (t, J=6.4, 1H), 3.93-3.84 (m, 4H), 3.22-3.12 (m, 4H), 2.26-2.13 (m, 2H), 0.97 (t, J=7.3, 3H).

For instance compound 31a ((S*)-3-(6-morpholino-1H-benzo[d]imidazol-2-yl)-4-((1-(pyrimidin-2-yl)butyl)amino)quinolin-2(1H)-one) and compound 31b ((R*)-3-(6-morpholino-1H-benzo[d]imidazol-2-yl)-4-((1-(pyrimidin-2-yl)butyl)amino)-quinolin-2(1H)-one) was prepared as follows:

To a solution of 4-chloro-3-(6-morpholino-H-benzo[d]imidazol-2-yl)quinolin-2(1H)-one (200 mg, 0.53 mmol) and N,N-diisopropylethylamine (1 mL, 6.06 mmol) in N,N-dimethylethanamide (3 mL) was added 1-(pyrimidin-2-yl)butan-1-amine (240 mg, 1.59 mmol). The mixture was stirred at 100° C. for 4 hours. After cooling to room temperature, the reaction mixture was purified by Prep-HPLC (Column: WatersXBridge 30*150 mm 5 um, Flow rate: 20 mL/min, Mobile Phase A: Water (0.1% $NH_3.H_2O$), Mobile Phase B: Acetonitrile, Gradient: 35-55% (% B)). The desired fraction was collected and the volatile was removed under reduced pressure. The water phase was lyophilized to give compound 31 (mixture of stereoisomers)(50 mg, 19.1% yield) as yellow solids. The crude compound was further purified by prep. SFC (separation condition: Column: ChiralPak AD-H Daicel chemical Industries, Ltd, 250*30 mm I.D., 5 um; Mobile phase A: Supercritical $CO_2$, Mobile phase B: Ethanol (0.1% DEA), A:B=50:50 at 50 mL/min; Column Temp: 38° C.; Nozzle Pressure: 100 Bar; Nozzle Temp: 60° C.; Evaporator Temp: 20° C.; Trimmer Temp: 25° C.; Wavelength: 220 nm) to afford compound 31a (6.83 mg, 13.7% yield, purity >99%) and compound 31b.

Compound 31a

LC-MS (ESI) General procedure A, method 2: $R_T$=1.27 min, mass calcd. for $C_2H_{29}N_7O_2$ 495.2, m/z found 496.4 $[M+H]^+$.

$^1$H NMR (400 MHz, $CD_3OD$) General procedure A: δ 8.74 (d, J=4.8, 2H), 8.01 (d, J=8.2, 1H), 7.61-6.94 (m, 7H), 5.41-5.31 (m, 1H), 3.94-3.82 (m, 4H), 3.23-3.10 (m, 4H), 2.26-2.02 (m, 2H), 1.51-1.35 (m, 2H), 0.87 (t, J=7.3, 3H).

For instance compound 32a (S*)-4-((2-methyl-1-(pyrimidin-2-yl)propyl)amino)-3-(6-morpholino-1H-benzo[d]imidazol-2-yl)quinolin-2(1H)-one) and compound 32b (R*)-4-((2-methyl-1-(pyrimidin-2-yl)propyl)amino)-3-(6-morpholino-1H-benzo[d]imidazol-2-yl)-quinolin-2(1H)-one) was prepared as follows:

To a solution of 4-chloro-3-(6-morpholino-1H-benzo[d]imidazol-2-yl)quinolin-2(1H)-one (200 mg, 0.53 mmol) and N,N-diisopropylethylamine (0.8 mL, 4.85 mmol) in N,N-dimethylethanamide (4 mL) was added 2-methyl-1-(pyrimidin-2-yl)propan-1-amine (240 mg, 1.59 mmol). The mixture was stirred at 100° C. for 3 hours. After cooling to room temperature, the reaction mixture was purified by Prep-HPLC (Column: WatersXBridge 30*150 mm 5 um, Flow rate: 20 mL/min, Mobile Phase A: Water (0.1% $NH_3.H_2O$), Mobile Phase B: Acetonitrile, Gradient: 35-55% (% B)). The desired fraction was collected and the volatile was removed under reduced pressure. The water phase was lyophilized to give compound 32 (mixture of stereoisomers) (30 mg, 11.4% yield) as yellow solids. The crude compound was further purified by prep. SFC (separation condition: Column: ChiralPak IC-H Daicel chemical Industries, Ltd, 250*30 mm I.D., 5 um; Mobile phase A: Supercritical $CO_2$, Mobile phase B: Ethanol (0.1% DEA), A:B=60:40 at 50 mL/min; Column Temp: 38° C.; Nozzle Pressure: 100 Bar; Nozzle Temp: 60° C.; Evaporator Temp: 20° C.; Trimmer Temp: 25° C.; Wavelength: 220 nm) to afford compound 32a (6.34 mg, 21.1% yield, purity >99%) and compound 32b.

Compound 32a

LC-MS (ESI) General procedure A, method 2: $R_T$=1.28 min, mass calcd. for $C_{28}H_{29}N_7O_2$ 495.2, m/z found 496.2 $[M+H]^+$.

$^1$H NMR (400 MHz, $CD_3OD$) General procedure A: δ8.87-8.78 (m, 2H), 8.01-7.91 (m, 1H), 7.62-7.46 (m, 2H), 7.42-7.28 (m, 2H), 7.17 (s, 1H), 7.15-7.00 (m, 2H), 5.22-5.15 (m, 1H), 3.98-3.82 (m, 4H), 3.22-3.12 (m, 4H), 2.64-2.49 (m, 1H), 1.06 (d, J=6.8, 3H), 0.84 (d, J=6.7, 3H).

For instance compound 33a ((S*)-4-((cyclopropyl(pyrimidin-2-yl)methyl)amino)-3-(6-morpholino-1H-benzo[d]imidazol-2-yl)quinolin-2(1H)-one) and compound 33b ((R*)-4-((cyclopropyl(pyrimidin-2-yl)methyl)amino)-3-(6-morpholino-1H-benzo[d]-imidazol-2-yl)quinolin-2(1H)-one) was prepared as follows:

To a solution of 4-chloro-3-(6-morpholino-H-benzo[d]imidazol-2-yl)quinolin-2(1H)-one (200 mg, 0.53 mmol) and N,N-diisopropylethylamine (1.0 mL, 6.06 mmol) in N,N-dimethylethanamide (3 mL) was added cyclopropyl(pyrimidin-2-yl)methanamine (237 mg, 1.59 mmol). The mixture was stirred at 100° C. for 4 hours. After cooling to room temperature, the reaction mixture was purified by Prep-HPLC (Column: WatersXBridge 30*150 mm 5 um, Flow rate: 20 mL/min, Mobile Phase A: Water (0.1% $NH_3.H_2O$), Mobile Phase B: Acetonitrile, Gradient: 35-55% (% B)). The desired fraction was collected and the volatile was removed under reduced pressure. The water phase was lyophilized to give compound 33 (mixture of stereoisomers)(35 mg, 13.4% yield) as yellow solids. The crude compound was further purified by prep. SFC (separation condition: Column: ChiralPak AD-H Daicel chemical Industries, Ltd, 250*30 mm I.D., 5 um; Mobile phase A: Supercritical $CO_2$, Mobile phase B: Ethanol (0.1% DEA), A:B=45:55 at 50 mL/min;

Column Temp: 38° C.; Nozzle Pressure: 100 Bar; Nozzle Temp: 60° C.; Evaporator Temp: 20° C.; Trimmer Temp: 25° C.; Wavelength: 220 nm) to afford compound 33a (9.30 mg, 26.7% yield, purity >99%) and compound 33b.

Compound 33a

LC-MS (ESI) General procedure B, method 2: $R_T$=1.33 min, mass calcd. for $C_{28}H_{27}N_7O_2$ 493.2, m/z found 494.3 $[M+H]^+$.

$^1$H NMR (400 MHz, $CD_3OD$) General procedure A δ8.72 (d, J=4.9, 2H), 8.03 (d, J=8.2, 1H), 7.55 (d, J=8.9, 1H), 7.48 (t, J=7.5, 1H), 7.36-7.27 (m, 2H), 7.21 (s, 1H), 7.12 (t, J=7.6, 1H), 7.05 (dd, J=8.8, 1.9, 1H), 4.80 (d, J=8.0, 1H), 3.99-3.79 (m, 4H), 3.22-3.10 (m, 4H), 1.63-1.50 (m, 1H), 0.70-0.58 (m, 1H), 0.58-0.40 (m, 3H).

Example 1a

Preparation of Compound 17

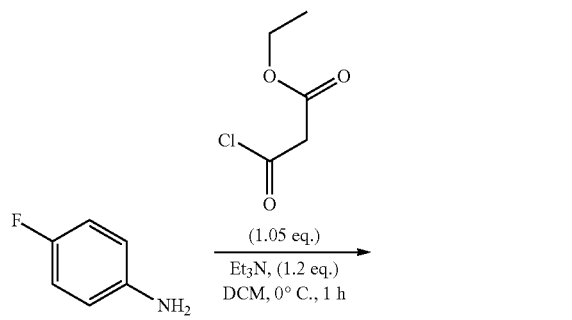

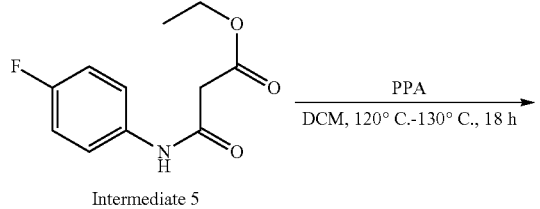

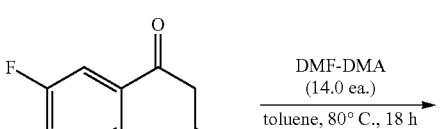

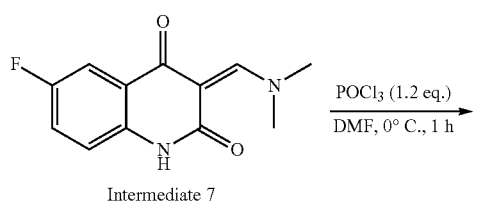

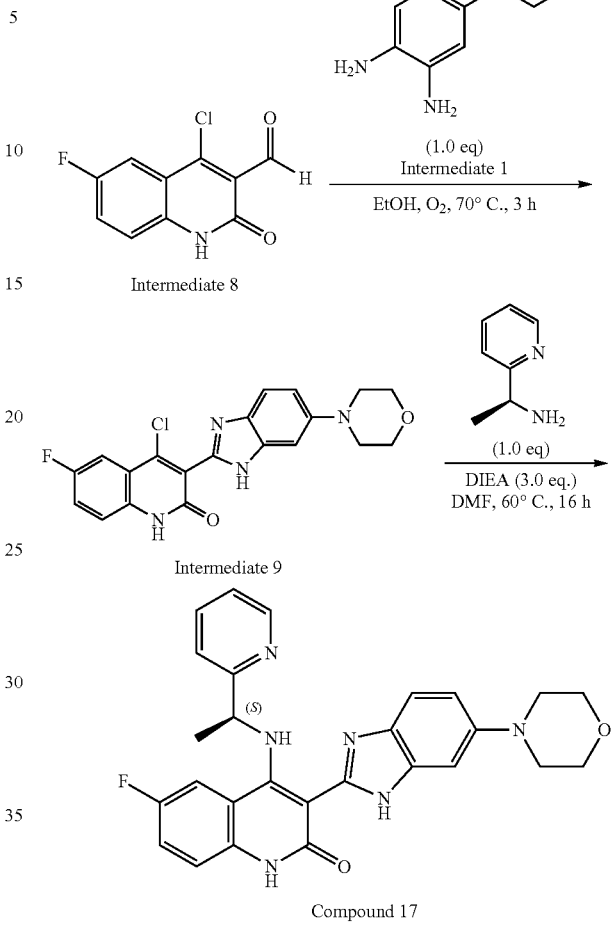

a) Preparation of Intermediate 5

(ethyl 3-(4-fluorophenylamino)-3-oxopropanoate)

To a solution of 4-fluoroaniline (16.65 g, 150 mmol), triethylamine (25.1 mL, 180 mmol) in dichloromethane (500 mL) under argon atmosphere at 0° C. was added dropwise ethyl 3-chloro-3-oxopropanoate (19.7 mL, 158 mmol). The reaction mixture was stirred at this temperature for an hour. The mixture was washed with saturated sodium bicarbonate aqueous solution (200 mL), saturated ammonium chloride aqueous solution (150 mL) and brine (150 mL). The result solution was dried over anhydrous $Na_2SO_4$, filtered and concentrated under reduced pressure to give the crude intermediate 5 (22.5 g, 66.7% yield) as yellow solids. LC-MS (ESI) General procedure B, method 2: $R_T$=0.88 min, mass calcd. for $C_{11}H_{12}FNO_3$ 225.1, m/z found 226.1 $[M+H]^+$.

b) Preparation of Intermediate 6

(6-fluoroquinoline-2,4(1H,3H)-dione)

To a hot polyphosphoric acid solution (120° C.) was added a solution of intermediate 5 (ethyl 3-(4-fluorophenylamino)-3-oxopropanoate) (22.5 g, 100 mmol) in dichloromethane (100 mL) dropwise. The mixture was stirred at 130° C. for 18 hours. After cooling to room temperature, the reaction mixture was added to ice water (200 mL) dropwise while stirring. The solid was precipitated, filtered in vacuum and collected and dissolved into 2.0 M sodium hydroxide aqueous solution (100 mL). The resulting mixture was filtered. The filtration was adjusted to pH=9-10 with concentrated hydrochloric acid aqueous solution. The solid was precipitated, filtered and washed with ether (30 mL×3) and dried in vacuum to give intermediate 6 (8.20 g, 45.8% yield) as yellow solids. LC-MS (ESI) General procedure B, method 2: $R_T$=1.21 min, mass calcd. for $C_9H_6FNO_2$ 179.0, m/z found 180.1 $[M+H]^+$.

c) Preparation of Intermediate 7

((Z)-3-((dimethylamino)methylene)-6-fluoroquinoline-2,4(1H,3H)-dione)

A mixture of intermediate 6 (6-fluoroquinoline-2,4(1H, 3H)-dione) (4.10 g, 22.9 mmol), N,N-dimethylformamide dimethyl acetal (42.4 mL, 32.1 mmol) and toluene (100 mL) was stirred at 80° C. for 18 hours. After cooling to 0° C., the mixture was filtered in vacuum and the filter cake was washed with toluene (10 mL×2), and dried in vacuum to give intermediate 7 (4.40 g, 82.1% yield) as yellow solids. LC-MS (ESI) General procedure B, method 2: $R_T$=0.48 min, mass calcd. for $C_{12}H_{11}FN_2O_2$ 234.1, m/z found 235.1 $[M+H]^+$.

d) Preparation of Intermediate 8

4-chloro-6-fluoro-2-oxo-1,2-dihydroquinoline-3-carbaldehyde)

To a solution of intermediate 7 ((Z)-3-((dimethylamino) methylene)-6-fluoroquinoline-2,4(1H,3H)-dione) (3.47 g, 14.8 mmol) in N,N-dimethylformamide (50 mL) was added phosphoryl trichloride (1.62 mL, 17.7 mmol) dropwise at 0° C. Then the reaction mixture was stirred at 0° C. for 1 hour. The resulting mixture was poured into ice water (100 mL). The solid was precipitated, filtered, washed with ether (20 mL) and dried in vacuum to give intermediate 8 (2.10 g, 63.1% yield) as yellow solids. LC-MS (ESI) General procedure B, method 2: $R_T$=1.07 min, mass calcd. for $C_{10}H_5ClFNO_2$ 225.0, m/z found 226.1 $[M+H]^+$. $^1$H NMR (400 MHz, DMSO-$d_6$) General procedure A: δ12.51 (s, 1H), 10.29 (s, 1H), 7.82-7.79 (m, 1H), 7.68-7.63 (m, 1H), 7.48-7.44 (m, 1H).

e) Preparation of Intermediate 9

(4-chloro-6-fluoro-3-(6-morpholino-1H-benzo[d]imidazol-2-yl)quinolin-2(1H)-one)

To a mixture of intermediate 1 (4-morpholinobenzene-1,2-diamine) (0.84 g, 4.4 mmol) in ethanol (100 mL) was added intermediate 8 (4-chloro-6-fluoro-2-oxo-1,2-dihydroquinoline-3-carbaldehyde) (0.99 g, 4.4 mmol) at room temperature. The mixture was stirred at 70° C. under $O_2$ atmosphere for 3 hours. After cooling to room temperature, the mixture was concentrated, stirred with petroleum ether: ethyl acetate (10:1) and filtered to give intermediate 9 as yellow solid (1.0 g, 57% yield). LC-MS (ESI) General procedure B, method 2: $R_T$=1.06 min, mass calcd. for $C_{20}H_{16}ClFN_4O_2$ 398.0, m/z found 399.1 $[M+H]^+$.

f) Preparation of Compound 17

((S)-6-fluoro-3-(6-morpholino-1H-benzo[d]imidazol-2-yl)-4-((1-(pyridin-2-yl)ethyl)-amino)quinolin-2 (1H)-one)

To a solution of intermediate 9 (4-chloro-6-fluoro-3-(6-morpholino-1H-benzo[d]imidazol-2-yl)quinolin-2(1H)-one) (398 mg, 1.0 mmol) and N,N-diisopropylethylamine (387 mg, 3.0 mmol) in N,N-dimethylformamide (2 mL) was added (S)-1-(pyridin-2-yl)ethanamine (122 mg, 1.0 mmol). The mixture was stirred at 60° C. for 16 hours. After cooling to room temperature, the mixture was purified by Prep-HPLC (Column: WatersXBridge 30*150 mm 5 um, Flow rate: 20 mL/min, Mobile Phase A: Water (0.1% $NH_3.H_2O$), Mobile Phase B: Acetonitrile, Gradient: 35-55% (% B)). The desired fraction was collected and the volatile was removed under reduced pressure. The water phase was lyophilized to give compound 17 (120 mg, 24.8% yield) as yellow solids.

LC-MS (ESI) General procedure B Method 2: $R_T$=1.34 min, mass calcd. for $C_{27}H_{25}FN_6O_2$ 484.2, m/z found 485.1 $[M+H]^+$.

$^1$H NMR (400 MHz, DMSO-$d_6$) general procedure A δ12.92-12.88 (m, 1H), 12.33 (d, J=8.0 Hz, 0.40H), 12.19 (d, J=8.0 Hz, 0.53H), 11.65 (m, 1H), 8.55 (m, 1H), 7.79-7.70 (m, 2H), 7.61-7.34 (m, 4H), 7.28-7.23 (m, 2H), 7.01-6.96 (m, 1H), 5.48-5.44 (m, 1H), 3.78 (m, 4H), 3.11 (m, 4H), 1.73-1.70 (m, 3H).

Example 2

Preparation of Compound 4

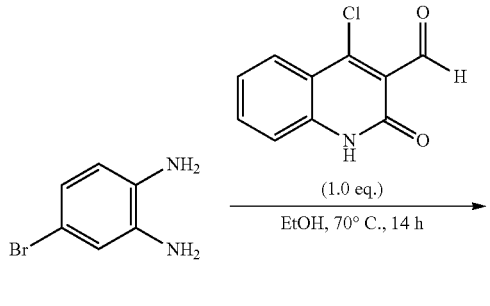

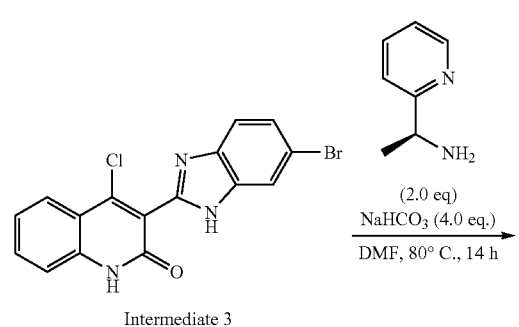

Intermediate 3

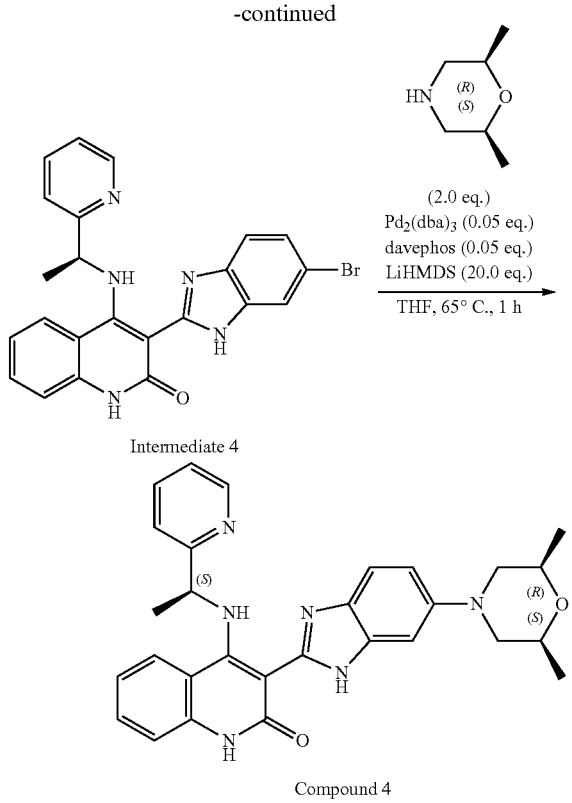

Intermediate 4

Compound 4 a) Preparation of Intermediate 3

3-(6-bromo-1H-benzo[d]imidazol-2-yl)-4-chloroquinolin-2(1H)-one

To a mixture of 4-bromobenzene-1,2-diamine (5.0 g, 26.7 mmol) in ethanol (300 mL) was added 4-chloro-2-oxo-1,2-dihydroquinoline-3-carbaldehyde (5.5 g, 26.7 mmol) at room temperature. The mixture was stirred at 70° C. under balloon pressure of oxygen gas for 14 hours. After cooling to room temperature, the whole was filtered through a pad of celite. The filtrate was concentrated under reduced pressure to give a residue which was recrystallized with dichloromethane:petroleum ether to give intermediate 3 (5.9 g, 59% yield) as yellow solids.

LC-MS (ESI) General procedure A, method 2: $R_T$=1.38 min, mass calcd. for $C_{16}H_9BrClN_3O$ 373.0, m/z found 374.0 $[M+H]^+$.

b) Preparation of Intermediate 4

(S)-3-(6-bromo-1H-benzo[d]imidazol-2-yl)-4-((1-(pyrimidin-2-yl)ethyl)amino)quinolin-2(1H)-one To a solution of intermediate 3 (3-(6-bromo-1H-benzo[d]imidazol-2-yl)-4-chloroquinolin-2(1H)-one) (3.00 g, 8.02 mmol) and sodium hydrogen carbonate (2.70 g, 32.08 mmol) in N,N-dimethylformamide (20 mL) was added (S)-1-(pyridin-2-yl)ethanamine (1.47 g, 12.03 mmol). The mixture was stirred at 80° C. for 14 hours. After cooling to room temperature, the whole was filtered through a pad of celite. The filtrate was concentrated under reduced pressure to give a residue which was recrystallized with dichloromethane and petroleum ether to give intermediate 4 (2.50 mg, 68% yield) as yellow solids.

LC-MS (ESI) General procedure B, method 4: $R_T$=1.26 min, mass calcd. for $C_{23}H_{18}BrN_5O$ 459.7, m/z found 460.1 $[M+H]^+$.

c) Preparation of Compound 4

3-(6-((2S,6R)-2,6-dimethylmorpholino)-1H-benzo[d]imidazol-2-yl)-4-(((S)-1-(pyridin-2-yl)ethyl)amino)quinolin-2(1H)-one To a degassed suspension of intermediate 4 (3-(6-bromo-1H-benzo[d]imidazol-2-yl)-4-((1-(pyrimidin-2-yl)ethyl)amino)quinolin-2(1H)-one) (200 mg, 0.43 mmol), tris(dibenzylideneacetone)dipalladium(0) (20 mg, 0.022 mmol), and 2-dicyclohexyl-phosphino-2'-(N,N-dimethylamino)biphenyl (8 mg, 0.022 mmol) in anhydrous THF (2 mL) was added (2S,6R)-2,6-dimethylmorpholine (100 mg, 0.87 mmol) and 1.0 M lithiumbis(trimethylsilyl)amide in THF (8.8 ml, 8.8 mmol) at room temperature under argon atmosphere. The mixture was stirred at 65° C. for an hour. After cooling to room temperature, the mixture was concentrated under reduced pressure to give a residue which was purified by silica gel chromatography (dichloromethane:methanol=30:1) and then further purified by Prep-HPLC (Column: WatersXBridge 30*150 mm 5 um, Flow rate: 20 mL/min, Mobile Phase A: Water (0.1% $NH_3.H_2O$), Mobile Phase B: Acetonitrile, Gradient: 35-55% (% B)). The desired fraction was collected and the volatile was removed under reduced pressure. The water phase was lyophilized to give compound 4 (7.23 mg, 3.4% yield, purity >99%) as yellow solids.

LC-MS (ESI) General procedure A, method 2: $R_T$=1.36 min, mass calcd. for $C_{29}H_{30}N_6O_2$ 494.6, m/z found 495.4 $[M+H]^+$.

$^1$H NMR (400 MHz, DMSO-$d_6$) General procedure A: δ 12.92 (s, 0.5H), 12.89 (s, 0.5H), 12.30 (s, 0.5H), 12.17 (s, 0.5H), 11.58 (s, 1H), 8.55 (brs, 1H), 8.05-7.88 (m, 1H), 7.77 (brs, 1H), 7.66-7.19 (m, 5H), 7.18-6.87 (m, 2H), 5.50 (brs, 1H), 3.77 (s, 2H), 3.60-3.51 (m, 2H), 2.38-2.19 (m, 2H), 1.73 (s, 3H), 1.19 (s, 6H).

Other compounds were prepared according to the above procedure. See Table 1.

Example 3

Preparation of Compound 5

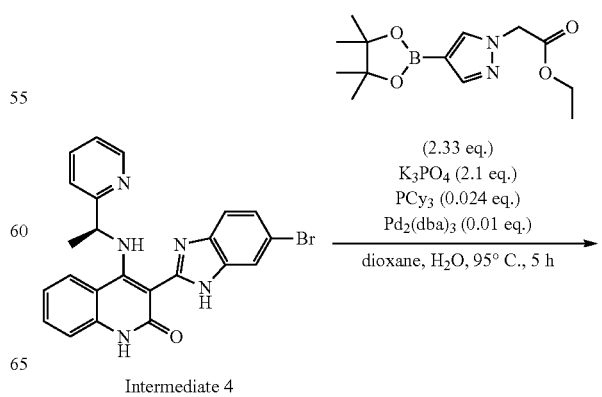

Intermediate 4

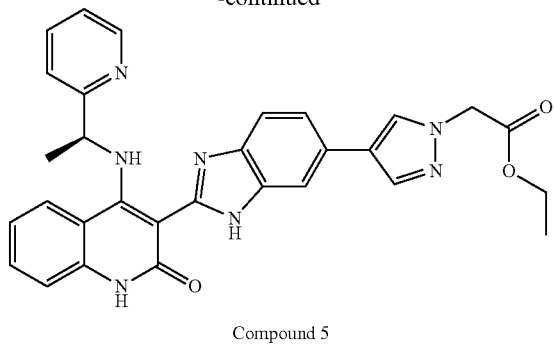

Compound 5 a) Preparation of Compound 5

(S)-ethyl 2-(4-(2-(2-oxo-4-((1-(pyridin-2-yl)ethyl)amino)-1,2-dihydroquinolin-3-yl)-1H-benzo[d]imidazol-6-yl)-1H-pyrazol-1-yl)acetate To a mixture of intermediate 4 ((S)-3-(6-bromo-1H-benzo[d]imidazol-2-yl)-4-((1-(pyridin-2-yl)ethyl)amino)quinolin-2(1H)-one)(420 mg, 0.915 mmol), potassium phosphate (420 mg, 1.98 mmol), tricyclohexyl phosphine (6.15 mg, 0.0220 mmol) in dioxane (10 mL) and water (2 mL) was added tris(dibenzylideneacetone)dipalladium(0) (8.37 mg, 0.00915 mmol). The mixture was stirred at 95° C. for 5 hours under argon atmosphere. The mixture was used in the next step without further purification.

LC-MS (ESI) General procedure B, method 3: $R_T$=1.45 min, mass calcd. for $C_{30}H_{27}N_7O_3$ 533.2, m/z found 534.3 $[M+H]^+$.

Example 4—Conversion

Preparation of Compound 5a

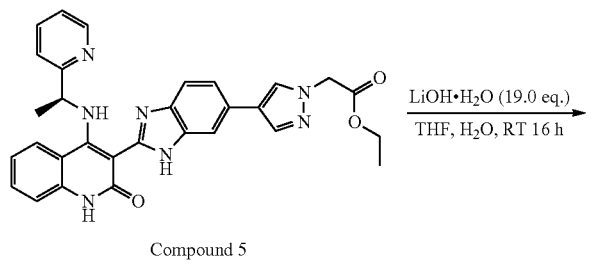

Compound 5

Compound 5a

Preparation of Compound 5a (S)-2-(4-(2-(2-oxo-4-((1-(pyridin-2-yl)ethyl)amino)-1,2-dihydroquinolin-3-yl)-1H-benzo[d]imidazol-6-yl)-1H-pyrazol-1-yl)acetic acid To a mixture of compound 5 ((S)-ethyl 2-(4-(2-(2-oxo-4-((1-(pyridin-2-yl)ethyl)amino)-1,2-dihydroquinolin-3-yl)-1H-benzo[d]imidazol-6-yl)-1H-pyrazol-1-yl)acetate) (crude) in tetrahydrofuran (10 mL) was added Lithium hydroxide monohydrate (820.0 mg, 19.5 mmol) at room temperature. The mixture was stirred at room temperature for 16 hours. The reaction mixture was purified by Prep-HPLC (Column: Inertsil ODS-3 20*250 mm 10 um, Flow rate: 20 mL/min, Mobile Phase A: Water (0.05% TFA), Mobile Phase B: Acetonitrile, Gradient: 25-40% (% B)). The desired fraction was collected and the volatile was removed under reduced pressure. The water phase was lyophilized to give compound 5a (10.32 mg, 2.3% yield, purity 97%) as a trifluoroacetic acid salt (as yellow solids).

LC-MS (ESI) General procedure A, method 3: $R_T$=0.98 min, mass calcd. for $C_{28}H_{23}N_7O_3$ 505.2, m/z found 506.4 $[M+H]^+$.

$^1$H NMR (400 MHz, $CD_3OD$) General procedure A: δ 8.35 (d, J=8.2 Hz, 1H), 8.17 (d, J=7.2 Hz, 2H), 7.99 (s, 1H), 7.81-7.77 (m, 2H), 7.76-7.66 (m, 2H), 7.60 (d, J=8.5 Hz, 1H), 7.42-7.37 (m, 2H), 7.32-7.26 (m, 2H), 5.06 (s, 2H), 4.50 (d, J=6.7 Hz, 1H), 1.58 (d, J=6.6 Hz, 3H).

Other compounds were prepared according to the above procedure. See Table 1.

Example 5—Conversion

Preparation of Compound 6

(S)-1-(2-(2-Oxo-4-((1-(pyridin-2-yl)ethyl)amino)-1,2-dihydroquinolin-3-yl)-H-benzo[d]imidazol-6-yl)piperidine-4-carboxylic acid 0.5formate

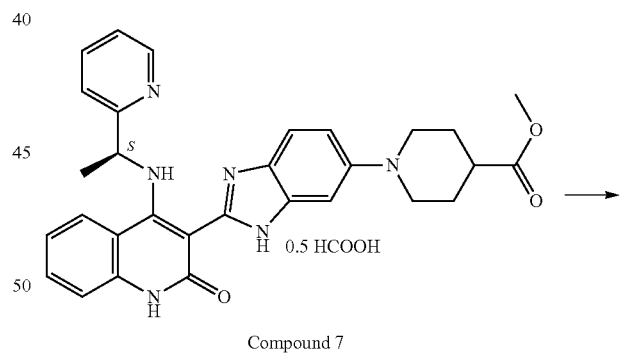

Compound 7

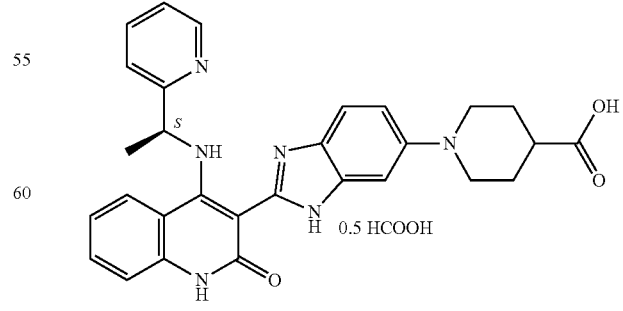

Compound 6

To a solution of compound 7 ((S)-methyl 1-(2-(2-oxo-4-((1-(pyridin-2-yl)ethyl)amino)-1,2-dihydroquinolin-3-yl)-1H-benzo[d]imidazol-6-yl)piperidine-4-carboxylate) (60.0 mg, 0.115 mmol) in MeOH (2 mL) was added 3 M LiOH aqueous solution (1.5 mL). The mixture was stirred at 25° C. for 12 hours. The reaction mixture was concentrated in vacuum to give a residue which was purified by prep. HPLC (Column: Agela Durashell C18 150*25 5 u, Mobile Phase A: water (0.225% water•TFA, Mobile Phase B: acetonitrile, Flow rate: 22 mL/min, gradient condition from 22% B to 52%). The pure fractions were collected and the solvent was evaporated under vacuum. The aqueous layer was lyophilized to give compound 6 as a trifluoroacetic acid salt as yellow solids (18.1 mg, 96.2% purity, 28.5% yield).

LC-MS (ESI) General procedure B-2 method 5: $R_T$=3.822 min, mass calcd. for $C_{29}H_{28}N_6O_3$ 508.22, m/z found 509.0 $[M+H]^+$.

$^1$H NMR (400 MHz, DMSO-d$^6$) General procedure B: δ=12.89 (br. s., 0.4H), 12.85 (br. s., 0.6H), 12.31 (d, J=8.2 Hz, 0.4H), 12.17 (d, J=8.2 Hz, 0.6H), 11.58 (br. s., 1H), 8.54 (d, J=2.9 Hz, 1H), 8.41-8.35 (m, 0.5H), 7.97 (d, J=8.4 Hz, 1H), 7.79-7.71 (m, 1H), 7.56 (d, J=8.6 Hz, 0.4H), 7.52-7.46 (m, 2.6H), 7.34 (d, J=8.6 Hz, 1H), 7.27-7.23 (m, 1.6H), 7.14-7.12 (m, 0.4H), 7.09-7.04 (m, 1H), 7.00-6.93 (m, 1H), 5.55-5.43 (m, 1H), 3.69-3.52 (m, 2H), 2.78-2.71 (m, 2H), 2.53-2.52 (m, 1H), 1.95-1.91 (m, 2H), 1.75-1.69 (m, 5H).

Example 6—Conversion

Preparation of Compound 61

(S*)-methyl 4-(2-(2-oxo-4-(((S)-1-(pyridin-2-yl)ethyl)amino)-1,2-dihydroquinolin-3-yl)-1H-benzo[d]imidazol-6-yl)morpholine-2-carboxylate The compound 59 (40.0 mg, 0.0760 mmol) was separated by Supercritical Fluid Chromatography (separation condition: AD (250 mm×30 mm, 10 um); Mobile phase: A: Supercritical $CO_2$, B: 0.1% $NH_3H_2O$ EtOH, A:B=45:55 at 80 mL/min; Column Temp: 38; Nozzle Pressure: 100 Bar; Nozzle Temp: 60; Evaporator Temp: 20; Trimmer Temp: 25; Wavelength: 220 nm). The pure fraction was collected and the solvent was evaporated under vacuum. The residue was re-suspended in water (10 mL) and the resulting mixture was lyophilized to dryness to give compound 61 (20.0 mg, 96.5% purity, 48.3% yield).

LC-MS (ESI) General procedure B, method 5: $R_T$=3.599 min, mass calcd. for $C_{29}H_{28}N_6O_4$ 524.22, m/z found 525.0 $[M+H]^+$.

$^1$H NMR (400 MHz, DMSO-d$^6$) General procedure B: δ12.95 (br. s., 0.4H), 12.92 (br. s., 0.6H), 12.28 (d, J=8.6 Hz, 0.4H), 12.16 (d, J=7.9 Hz, 0.6H), 11.58 (br. s., 1H), 8.57-8.52 (m, 1H), 7.96 (dd, J=4.5, 8.0 Hz, 1H), 7.79-7.72 (m, 1H), 7.61 (d, J=8.6 Hz, 0.4H), 7.53 (d, J=2.4 Hz, 0.6H), 7.52-7.47 (m, 2H), 7.35 (s, 0.6H), 7.33 (s, 0.4H), 7.31 (d, J=2.2 Hz, 0.6H), 7.28-7.22 (m, 1H), 7.15 (d, J=1.8 Hz, 0.4H), 7.10-7.03 (m, 1H), 6.97 (ddd, J=2.3, 8.8, 11.0 Hz, 1H), 5.56-5.44 (m, 1H), 4.46 (dt, J=3.2, 7.4 Hz, 1H), 4.09-3.99 (m, 1H), 3.82-3.75 (m, 1H), 3.73 (d, J=3.3 Hz, 3H), 3.52-3.42 (m, 1H), 3.24 (d, J=4.2 Hz, 1H), 3.13 (dd, J=7.6, 12.0 Hz, 1H), 2.98 (dt, J=4.3, 8.0 Hz, 1H), 1.75-1.69 (m, 3H).

The following compounds were prepared according to reaction protocols of one of the above Examples using alternative starting materials as appropriate. (In the table 1, Ex. X indicates that the preparation of this compound is described in Example X or is prepared according to Example X).

As understood by a person skilled in the art, compounds synthesised using the protocols as indicated may exist as a solvate e.g. hydrate, and/or contain residual solvent or minor impurities. Compounds isolated as a salt form, may be integer stoichiometric i.e. mono- or di-salts, or of intermediate stoichiometry.

TABLE 1

| Compound Number | Structure | Procedure |
| --- | --- | --- |
| Compound 8 | 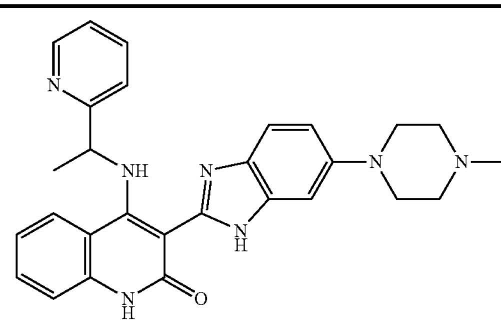 | Ex 1 |
| Compound 8a | 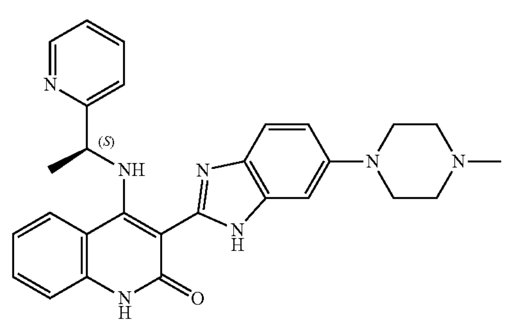 | Ex 1 |

TABLE 1-continued

| Compound Number | Structure | Procedure |
|---|---|---|
| Compound 8b | (structure: 4-[(1R)-1-(pyridin-2-yl)ethylamino]-3-[6-(4-methylpiperazin-1-yl)-1H-benzimidazol-2-yl]quinolin-2(1H)-one) | Ex 1 |
| Compound 9 | (structure: 4-[1-(oxazol-4-yl)ethylamino]-3-[7-fluoro-6-(4-methylpiperazin-1-yl)-1H-benzimidazol-2-yl]quinolin-2(1H)-one) | Ex 1 |
| Compound 9a | (structure: 4-[(1S*)-1-(oxazol-4-yl)ethylamino]-3-[7-fluoro-6-(4-methylpiperazin-1-yl)-1H-benzimidazol-2-yl]quinolin-2(1H)-one) | Ex 1 |
| Compound 9b | (structure: 4-[(1R*)-1-(oxazol-4-yl)ethylamino]-3-[7-fluoro-6-(4-methylpiperazin-1-yl)-1H-benzimidazol-2-yl]quinolin-2(1H)-one) | Ex 1 |
| Compound 10 | (structure: 4-[1-(oxazol-4-yl)ethylamino]-3-[6-(4-methylpiperazin-1-yl)-5-(trifluoromethyl)-1H-benzimidazol-2-yl]quinolin-2(1H)-one) | Ex 1 |

TABLE 1-continued

| Compound Number | Structure | Procedure |
|---|---|---|
| Compound 10b | *(structure)* | Ex 1 |
| Compound 10a | *(structure)* | Ex 1 |
| Compound 11 | *(structure)* | Ex 1 |
| Compound 11b | *(structure)* | Ex 1 |
| Compound 11a | *(structure)* | Ex 1 |

TABLE 1-continued

| Compound Number | Structure | Procedure |
|---|---|---|
| Compound 12 | 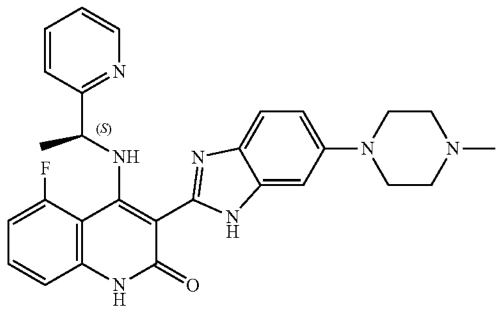 | Ex 1a |
| Compound 13 | 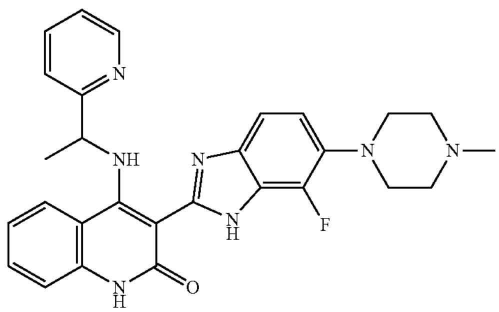 [SMILES: CC(Nc1c(-c2nc3ccc(N4CCN(C)CC4)c(F)c3[nH]2)c(=O)[nH]c2ccccc12)c1ccccn1] | Ex 1 |
| Compound 13b | 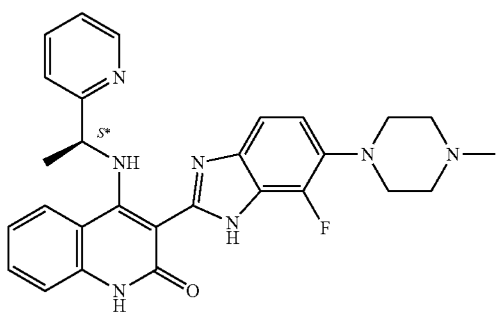 [SMILES: C[C@H](Nc1c(-c2nc3ccc(N4CCN(C)CC4)c(F)c3[nH]2)c(=O)[nH]c2ccccc12)c1ccccn1] | Ex 1 |
| Compound 13a | 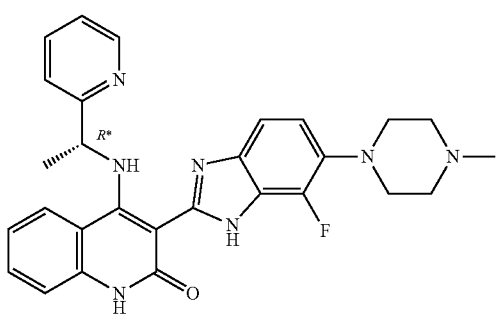 [SMILES: C[C@@H](Nc1c(-c2nc3ccc(N4CCN(C)CC4)c(F)c3[nH]2)c(=O)[nH]c2ccccc12)c1ccccn1] | Ex 1 |
| Compound 14 | 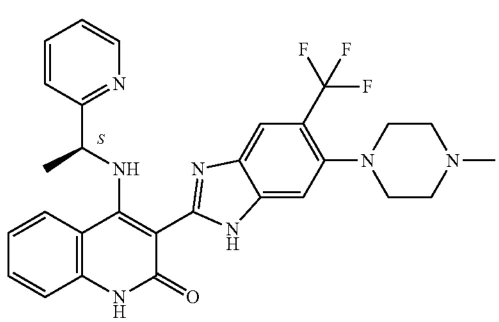 | Ex 1a |

TABLE 1-continued

| Compound Number | Structure | Procedure |
|---|---|---|
| Compound 15 | [Structure: 4-[(1S)-1-(pyridin-2-yl)ethylamino]-3-[6-(4-methyl-3-oxopiperazin-1-yl)-1H-benzimidazol-2-yl]quinolin-2(1H)-one] | Ex 1a |
| Compound 1 | [Structure: 4-[1-(pyrimidin-2-yl)ethylamino]-3-(6-morpholino-1H-benzimidazol-2-yl)quinolin-2(1H)-one] | Ex 1 |
| Compound 2 | [Structure: 4-[(1S)-1-(pyrimidin-2-yl)ethylamino]-3-(6-morpholino-1H-benzimidazol-2-yl)quinolin-2(1H)-one] | Ex 1 |
| Compound 3 | [Structure: 4-[(1R)-1-(pyrimidin-2-yl)ethylamino]-3-(6-morpholino-1H-benzimidazol-2-yl)quinolin-2(1H)-one] | Ex 1 |
| Compound 16 | [Structure: 4-[(1S)-1-(pyridin-2-yl)ethylamino]-3-(6-morpholino-1H-benzimidazol-2-yl)-8-fluoroquinolin-2(1H)-one] | Ex 1a |

TABLE 1-continued

| Compound Number | Structure | Procedure |
|---|---|---|
| Compound 17 | 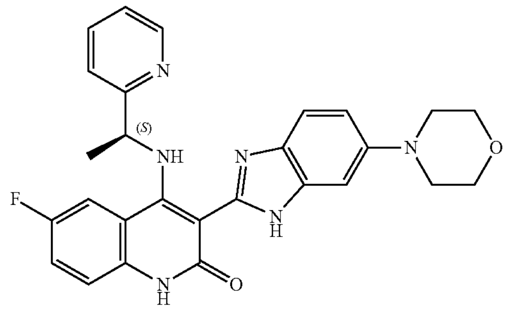 | Ex 1a |
| Compound 18 | 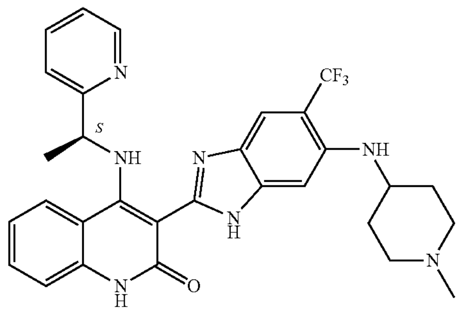 | Ex 1a |
| Compound 19 | 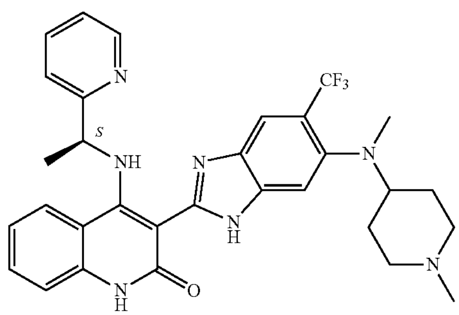 | Ex 1a |
| Compound 20 | 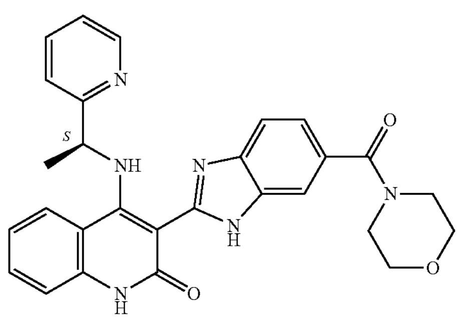 | Ex 1a |
| Compound 5 | 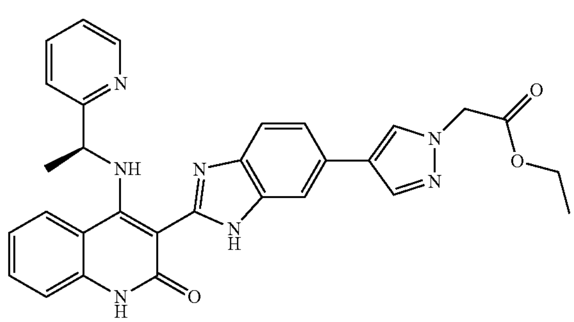 [SMILES: CCOC(=O)Cn1cc(-c2ccc3nc(-c4c(N[C@@H](C)c5ccccn5)c5ccccc5[nH]c4=O)[nH]c3c2)cn1] | Ex 3 |

TABLE 1-continued
| Compound Number | Structure | Procedure |
|---|---|---|
| Compound 5a | 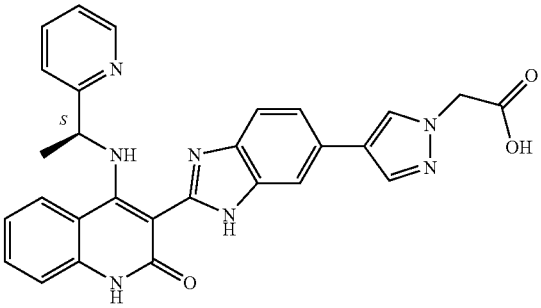 as a trifluoroacetic acid salt | Ex 4 |
| Compound 4 | 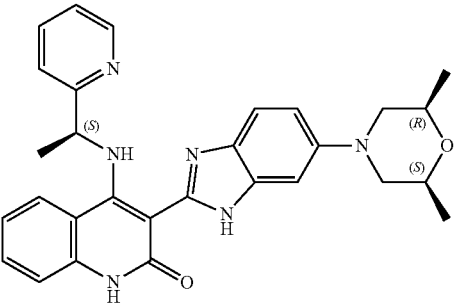 | Ex 2 |
| Compound 21 | 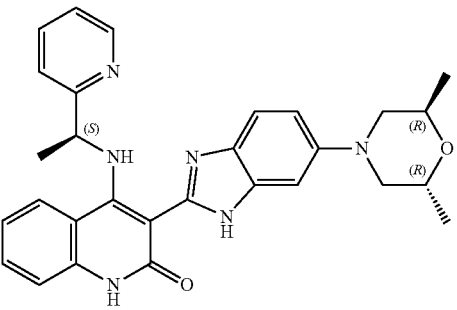 | Ex 2 |
| Compound 22 | 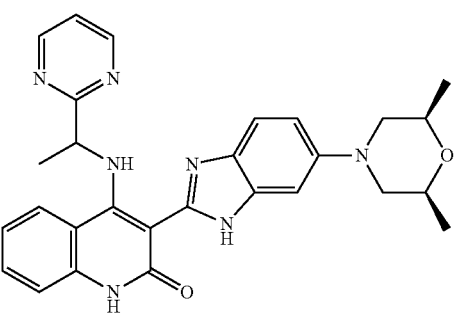 [SMILES: CC(Nc1c(-c2nc3ccc(N4C[C@@H](C)O[C@@H](C)C4)cc3[nH]2)c(=O)[nH]c2ccccc12)c1ncccn1] | Ex 1 |

TABLE 1-continued

| Compound Number | Structure | Procedure |
|---|---|---|
| Compound 22a | 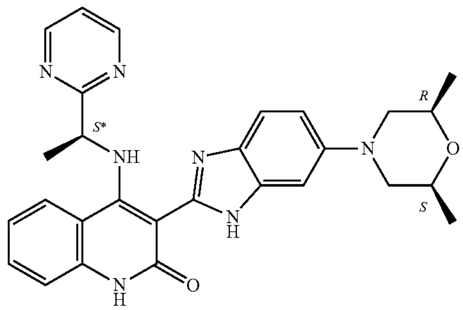 | Ex 1 |
| Compound 22b | 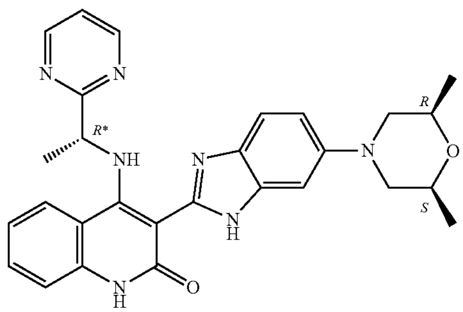 | Ex 1 |
| Compound 23 | 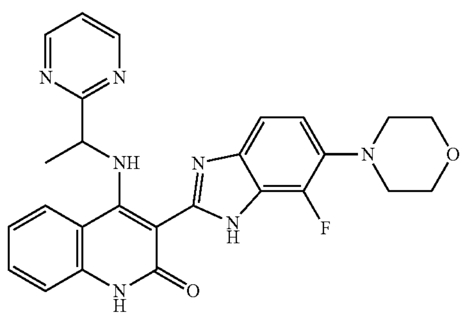 [SMILES: CC(Nc1c(-c2nc3ccc(N4CCOCC4)c(F)c3[nH]2)c(=O)[nH]c2ccccc12)c1ncccn1] | Ex 1 |
| Compound 23a | 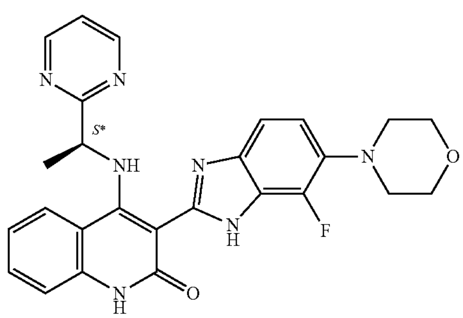 [SMILES: C[C@H](Nc1c(-c2nc3ccc(N4CCOCC4)c(F)c3[nH]2)c(=O)[nH]c2ccccc12)c1ncccn1] | Ex 1 |
| Compound 23b | 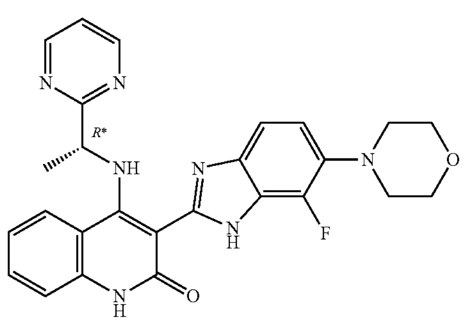 [SMILES: C[C@@H](Nc1c(-c2nc3ccc(N4CCOCC4)c(F)c3[nH]2)c(=O)[nH]c2ccccc12)c1ncccn1] | Ex 1 |

TABLE 1-continued

| Compound Number | Structure | Procedure |
|---|---|---|
| Compound 24 | 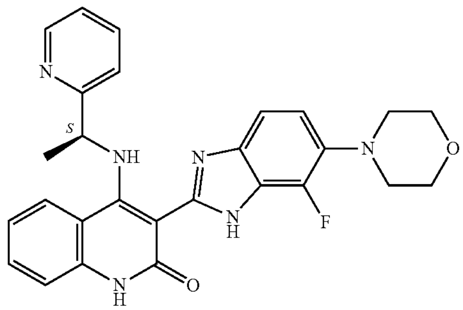 | Ex 1a |
| Compound 25 | 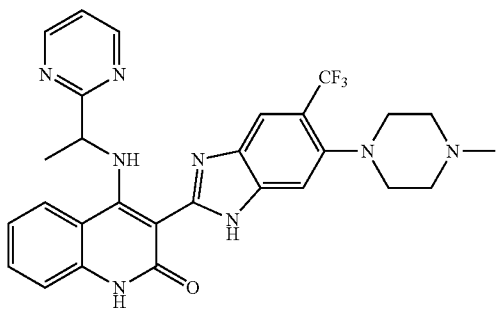 [SMILES: CC(Nc1c(-c2nc3cc(C(F)(F)F)c(N4CCN(C)CC4)cc3[nH]2)c(=O)[nH]c2ccccc12)c1ncccn1] | Ex 1 |
| Compound 25a | 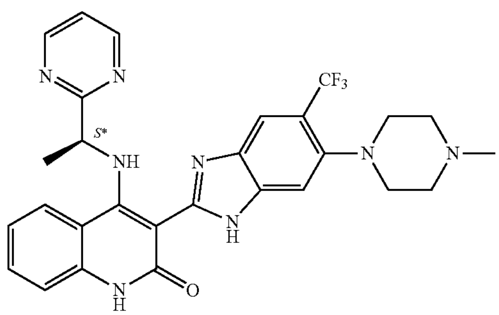 [SMILES: C[C@H](Nc1c(-c2nc3cc(C(F)(F)F)c(N4CCN(C)CC4)cc3[nH]2)c(=O)[nH]c2ccccc12)c1ncccn1] | Ex 1 |
| Compound 25b | 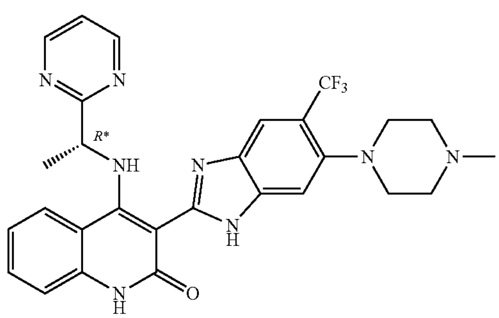 [SMILES: C[C@@H](Nc1c(-c2nc3cc(C(F)(F)F)c(N4CCN(C)CC4)cc3[nH]2)c(=O)[nH]c2ccccc12)c1ncccn1] | Ex 1 |
| Compound 26a | 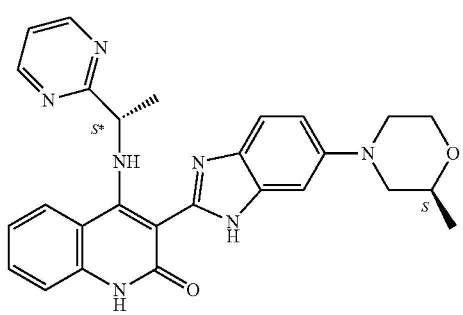 | Ex 2 |

TABLE 1-continued

| Compound Number | Structure | Procedure |
|---|---|---|
| Compound 26b | 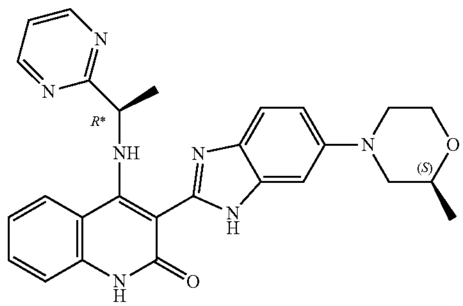 | Ex 2 |
| Compound 27 | 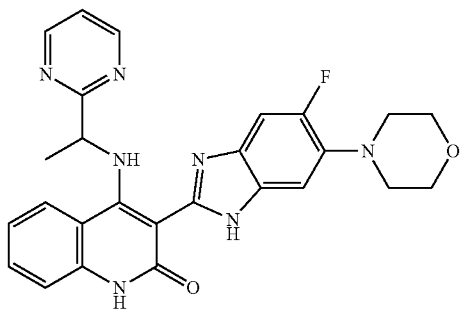 [SMILES: CC(Nc1c(-c2nc3cc(F)c(N4CCOCC4)cc3[nH]2)c(=O)[nH]c2ccccc12)c1ncccn1] | Ex 1 |
| Compound 27a | 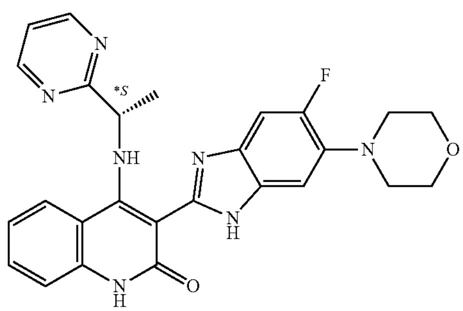 [SMILES: C[C@H](Nc1c(-c2nc3cc(F)c(N4CCOCC4)cc3[nH]2)c(=O)[nH]c2ccccc12)c1ncccn1] | Ex 1 |
| Compound 27b | 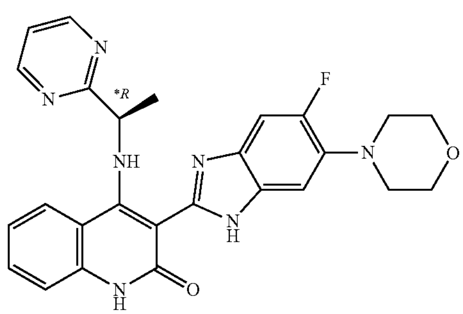 [SMILES: C[C@@H](Nc1c(-c2nc3cc(F)c(N4CCOCC4)cc3[nH]2)c(=O)[nH]c2ccccc12)c1ncccn1] | Ex 1 |
| Compound 28a | 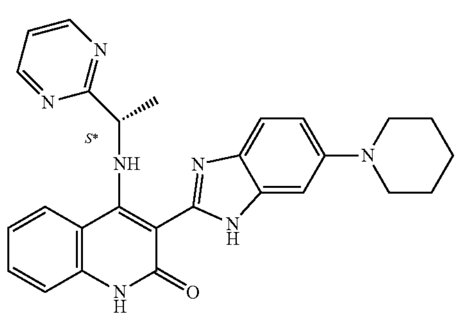 [SMILES: C[C@H](Nc1c(-c2nc3ccc(N4CCCCC4)cc3[nH]2)c(=O)[nH]c2ccccc12)c1ncccn1] | Ex 2 |

TABLE 1-continued

| Compound Number | Structure | Procedure |
|---|---|---|
| Compound 28b | (R*)-4-((1-(pyrimidin-2-yl)ethyl)amino)-3-(6-(piperidin-1-yl)-1H-benzo[d]imidazol-2-yl)quinolin-2(1H)-one | Ex 2 |
| Compound 29 | 4-((1-(pyrimidin-2-yl)ethyl)amino)-3-(6-(tetrahydro-2H-pyran-4-yl)-1H-benzo[d]imidazol-2-yl)quinolin-2(1H)-one | Ex 1 |
| Compound 29a | (S*)-4-((1-(pyrimidin-2-yl)ethyl)amino)-3-(6-(tetrahydro-2H-pyran-4-yl)-1H-benzo[d]imidazol-2-yl)quinolin-2(1H)-one | Ex 1 |
| Compound 29b | (R*)-4-((1-(pyrimidin-2-yl)ethyl)amino)-3-(6-(tetrahydro-2H-pyran-4-yl)-1H-benzo[d]imidazol-2-yl)quinolin-2(1H)-one | Ex 1 |
| Compound 30 | 4-((1-(pyrimidin-2-yl)propyl)amino)-3-(6-morpholino-1H-benzo[d]imidazol-2-yl)quinolin-2(1H)-one | Ex 1 |

TABLE 1-continued
| Compound Number | Structure | Procedure |
|---|---|---|
| Compound 30a | 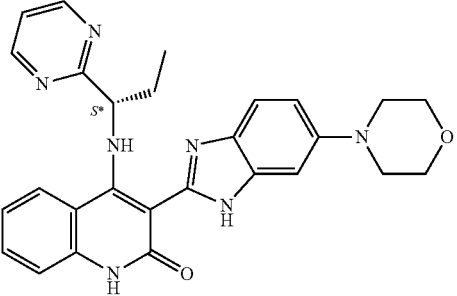 [SMILES: CCC(Nc1c(-c2nc3ccc(N4CCOCC4)cc3[nH]2)c(=O)[nH]c2ccccc12)c1ncccn1] as a trifluoroacetic acid salt | Ex 1 |
| Compound 30b | 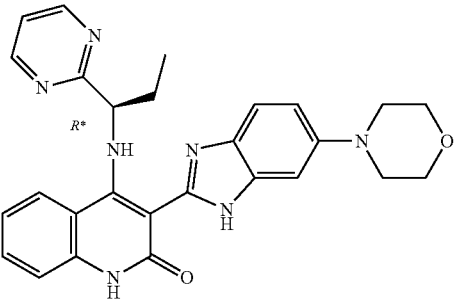 as a trifluoroacetic acid salt | Ex 1 |
| Compound 31 | 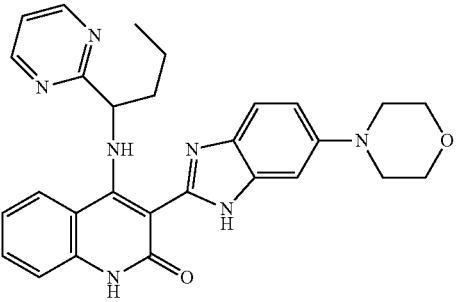 [SMILES: CCCC(Nc1c(-c2nc3ccc(N4CCOCC4)cc3[nH]2)c(=O)[nH]c2ccccc12)c1ncccn1] | Ex 1 |
| Compound 31a | 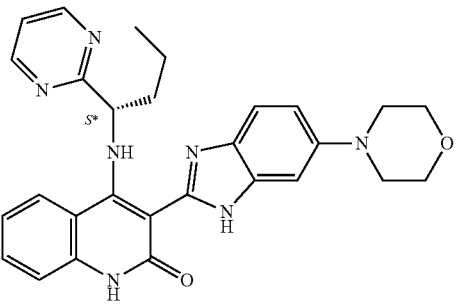 [SMILES: CCC[C@H](Nc1c(-c2nc3ccc(N4CCOCC4)cc3[nH]2)c(=O)[nH]c2ccccc12)c1ncccn1] | Ex 1 |

TABLE 1-continued

| Compound Number | Structure | Procedure |
|---|---|---|
| Compound 31b | (structure) | Ex 1 |
| Compound 32 | (structure) | Ex 1 |
| Compound 32a | (structure) | Ex 1 |
| Compound 32b | (structure) | Ex 1 |
| Compound 33 | (structure) | Ex 1 |

TABLE 1-continued

| Compound Number | Structure | Procedure |
|---|---|---|
| Compound 33a | 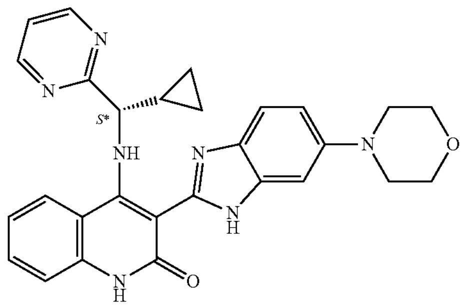 [SMILES: O=c1[nH]c2ccccc2c(N[C@H](c2ncccn2)C2CC2)c1-c1nc2ccc(N3CCOCC3)cc2[nH]1] | Ex 1 |
| Compound 33b | 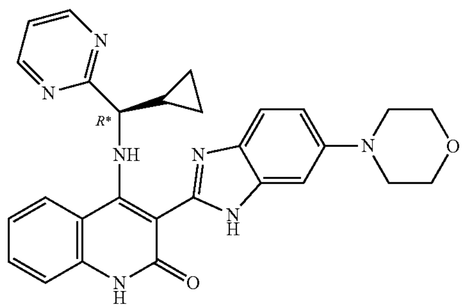 [SMILES: O=c1[nH]c2ccccc2c(N[C@@H](c2ncccn2)C2CC2)c1-c1nc2ccc(N3CCOCC3)cc2[nH]1] | Ex 1 |
| Compound 34 | 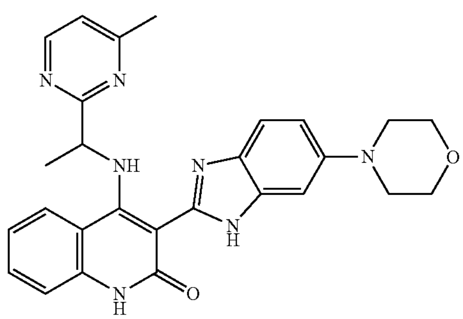 [SMILES: Cc1ccnc(C(C)Nc2c(-c3nc4ccc(N5CCOCC5)cc4[nH]3)c(=O)[nH]c3ccccc23)n1] | Ex 1 |
| Compound 34a | 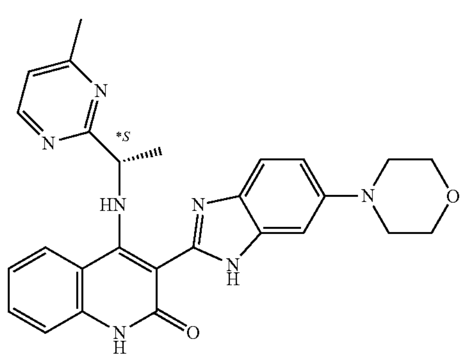 [SMILES: Cc1ccnc([C@H](C)Nc2c(-c3nc4ccc(N5CCOCC5)cc4[nH]3)c(=O)[nH]c3ccccc23)n1] | Ex 1 |

TABLE 1-continued

| Compound Number | Structure | Procedure |
|---|---|---|
| Compound 34b | 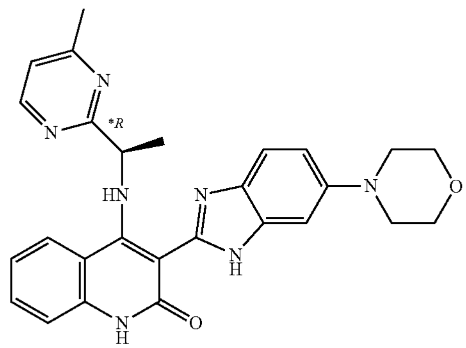 [SMILES: Cc1ccnc([C@@H](C)Nc2c(-c3nc4ccc(N5CCOCC5)cc4[nH]3)c(=O)[nH]c3ccccc23)n1] | Ex 1 |
| Compound 35 | 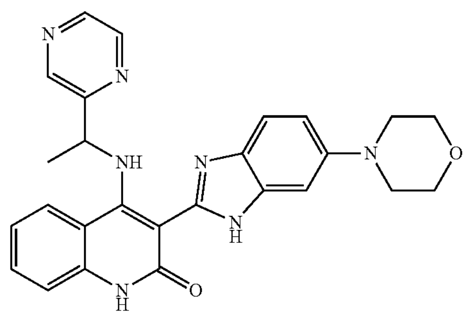 [SMILES: CC(Nc1c(-c2nc3ccc(N4CCOCC4)cc3[nH]2)c(=O)[nH]c2ccccc12)c1cnccn1] | Ex 1 |
| Compound 35b | 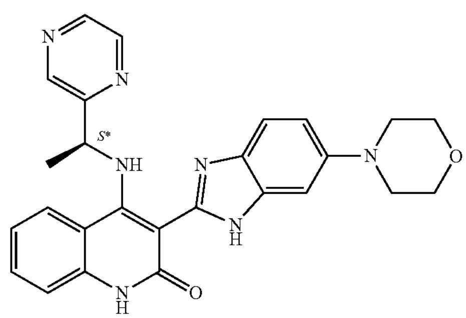 [SMILES: C[C@H](Nc1c(-c2nc3ccc(N4CCOCC4)cc3[nH]2)c(=O)[nH]c2ccccc12)c1cnccn1] | Ex 1 |
| Compound 35a | 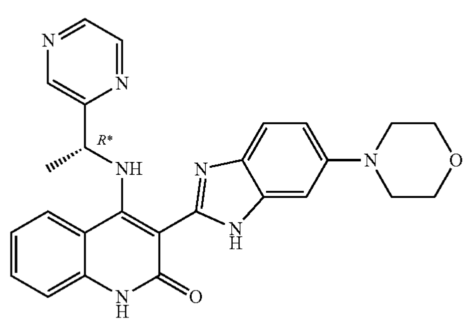 [SMILES: C[C@@H](Nc1c(-c2nc3ccc(N4CCOCC4)cc3[nH]2)c(=O)[nH]c2ccccc12)c1cnccn1] | Ex 1 |

TABLE 1-continued

| Compound Number | Structure | Procedure |
|---|---|---|
| Compound 36 | 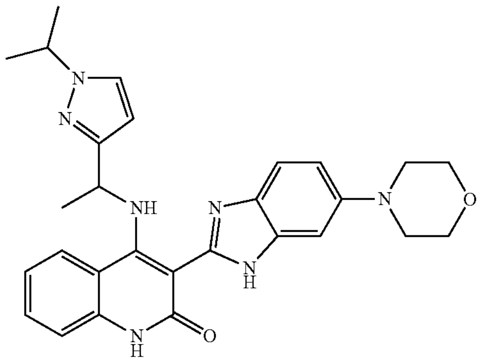 [SMILES: CC(Nc1c(-c2nc3ccc(N4CCOCC4)cc3[nH]2)c(=O)[nH]c2ccccc12)c1ccn(C(C)C)n1] | Ex 1 |
| Compound 36b | 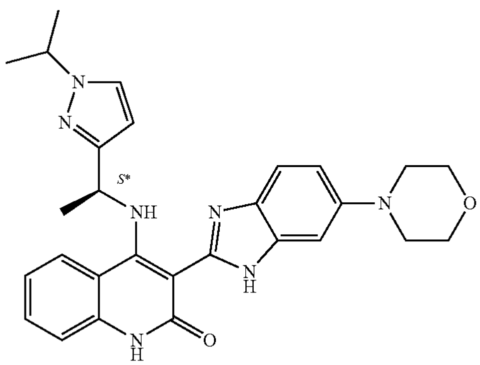 [SMILES: CC(C)n1ccc([C@H](C)Nc2c(-c3nc4ccc(N5CCOCC5)cc4[nH]3)c(=O)[nH]c3ccccc23)n1] | Ex 1 |
| Compound 36a | 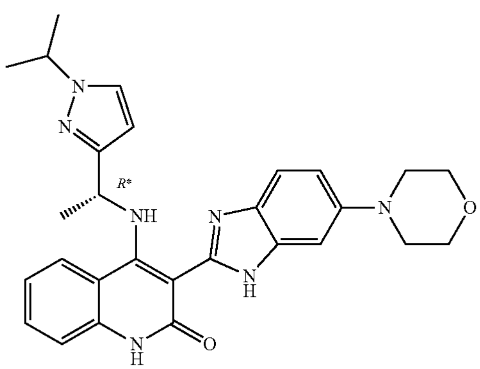 [SMILES: CC(C)n1ccc([C@@H](C)Nc2c(-c3nc4ccc(N5CCOCC5)cc4[nH]3)c(=O)[nH]c3ccccc23)n1] | Ex 1 |
| Compound 37b | 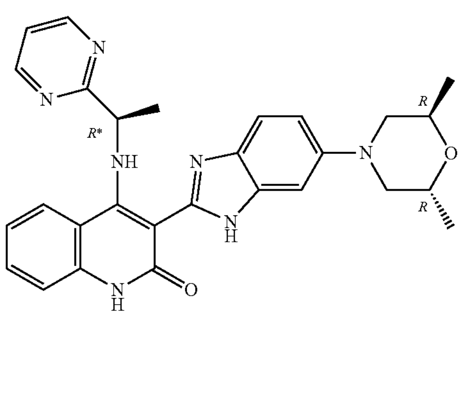 | Ex 2 |

TABLE 1-continued

| Compound Number | Structure | Procedure |
|---|---|---|
| Compound 37a | 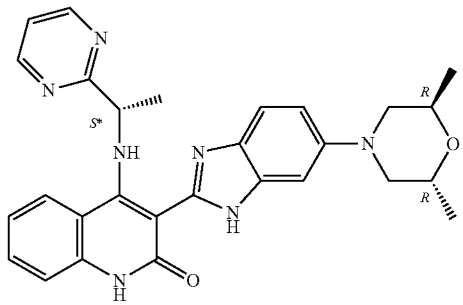 | Ex 2 |
| Compound 39a | 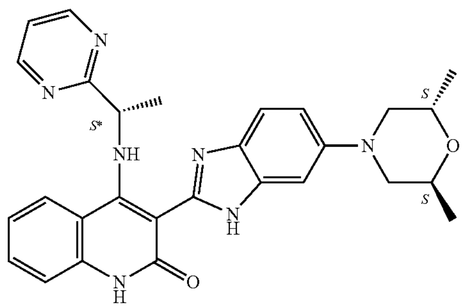 | Ex 2 |
| Compound 40a | 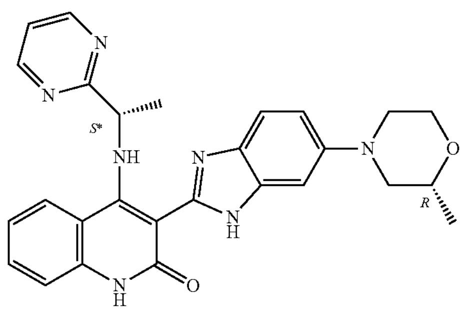 | Ex 2 |
| Compound 40b | 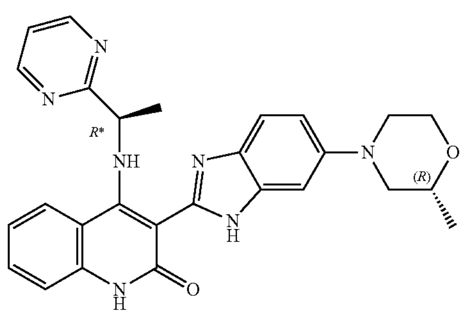 | Ex 2 |
| Compound 41b | 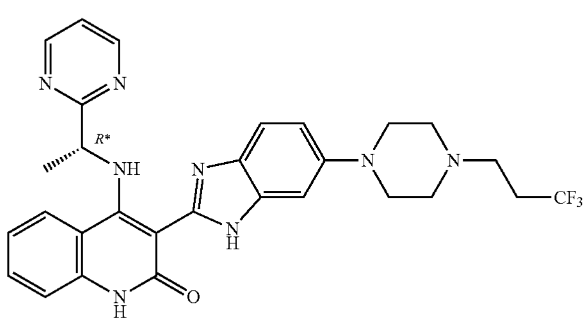 [SMILES: C[C@@H](Nc1c(-c2nc3ccc(N4CCN(CCC(F)(F)F)CC4)cc3[nH]2)c(=O)[nH]c2ccccc12)c1ncccn1] | Ex 2 |

TABLE 1-continued

| Compound Number | Structure | Procedure |
|---|---|---|
| Compound 41a | (structure) | Ex 2 |
| Compound 43a | (structure) | Ex 2 |
| Compound 43b | (structure) | Ex 2 |
| Compound 44a | (structure) | Ex 2 |
| Compound 44b | (structure) | Ex 2 |

TABLE 1-continued

| Compound Number | Structure | Procedure |
|---|---|---|
| Compound 45 | (S*)-4-((1-(pyrimidin-2-yl)ethyl)amino)-3-(6-morpholino-5-(trifluoromethyl)-1H-benzo[d]imidazol-2-yl)quinolin-2(1H)-one | Ex 1 |
| Compound 45a | (R*)-4-((1-(pyrimidin-2-yl)ethyl)amino)-3-(6-morpholino-5-(trifluoromethyl)-1H-benzo[d]imidazol-2-yl)quinolin-2(1H)-one | Ex 1 |
| Compound 46 | (S)-4-((1-(pyrimidin-2-yl)ethyl)amino)-3-(4-methyl-6-morpholino-1H-benzo[d]imidazol-2-yl)quinolin-2(1H)-one | Ex 1a |
| Compound 47 | (S)-4-((1-(pyrimidin-2-yl)ethyl)amino)-3-(7-methyl-6-morpholino-1H-benzo[d]imidazol-2-yl)quinolin-2(1H)-one | Ex 1 |

TABLE 1-continued

| Compound Number | Structure | Procedure |
|---|---|---|
| Compound 48 | 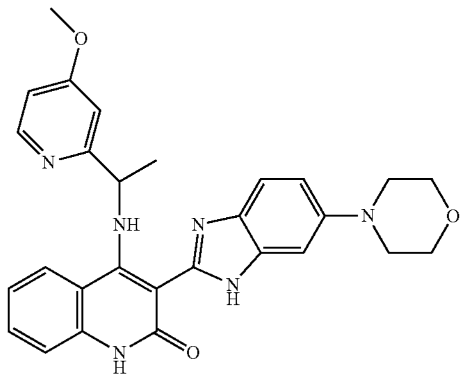 [SMILES: COc1ccnc(C(C)Nc2c(-c3nc4ccc(N5CCOCC5)cc4[nH]3)c(=O)[nH]c3ccccc23)c1] | Ex 1 |
| Compound 48a | 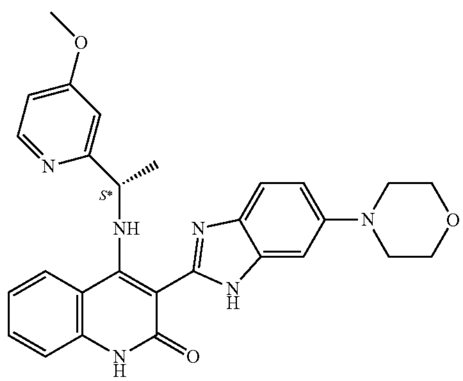 [SMILES: COc1ccnc([C@H](C)Nc2c(-c3nc4ccc(N5CCOCC5)cc4[nH]3)c(=O)[nH]c3ccccc23)c1] | Ex 1 |
| Compound 48b | 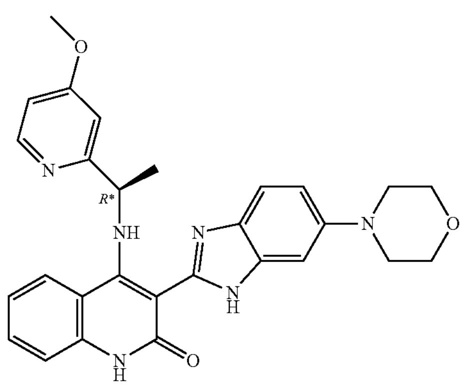 [SMILES: COc1ccnc([C@@H](C)Nc2c(-c3nc4ccc(N5CCOCC5)cc4[nH]3)c(=O)[nH]c3ccccc23)c1] | Ex 1 |
| Compound 49 | 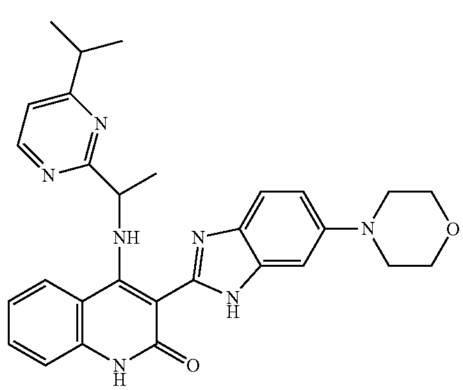 [SMILES: CC(C)c1ccnc(C(C)Nc2c(-c3nc4ccc(N5CCOCC5)cc4[nH]3)c(=O)[nH]c3ccccc23)n1] | Ex 1 |

TABLE 1-continued

| Compound Number | Structure | Procedure |
|---|---|---|
| Compound 49a | (structure: 4-isopropylpyrimidin-2-yl with (S*)-CH(CH₃)-NH- linked to 3-(6-morpholino-1H-benzimidazol-2-yl)-2-oxo-1,2-dihydroquinolin-4-yl) | Ex 1 |
| Compound 49b | (structure: 4-isopropylpyrimidin-2-yl with (R*)-CH(CH₃)-NH- linked to 3-(6-morpholino-1H-benzimidazol-2-yl)-2-oxo-1,2-dihydroquinolin-4-yl) | Ex 1 |
| Compound 50 | (structure: 4-cyclopropylpyrimidin-2-yl with CH(CH₃)-NH- linked to 3-(6-morpholino-1H-benzimidazol-2-yl)-2-oxo-1,2-dihydroquinolin-4-yl) | Ex 1 |
| Compound 50a | (structure: 4-cyclopropylpyrimidin-2-yl with (S*)-CH(CH₃)-NH- linked to 3-(6-morpholino-1H-benzimidazol-2-yl)-2-oxo-1,2-dihydroquinolin-4-yl) | Ex 1 |

TABLE 1-continued

| Compound Number | Structure | Procedure |
|---|---|---|
| Compound 50b | (structure) | Ex 1 |
| Compound 51 | (structure) | Ex 1 |
| Compound 51a | (structure) | Ex 1 |
| Compound 51b | (structure) | Ex 1 |
| Compound 52 | (structure) | Ex 1 |

TABLE 1-continued

| Compound Number | Structure | Procedure |
|---|---|---|
| Compound 52a | 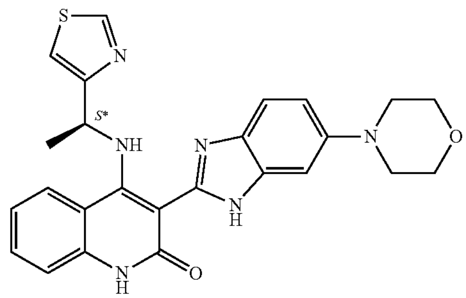 [SMILES: C[C@H](Nc1c(-c2nc3ccc(N4CCOCC4)cc3[nH]2)c(=O)[nH]c2ccccc12)c1cscn1] | Ex 1 |
| Compound 52b | 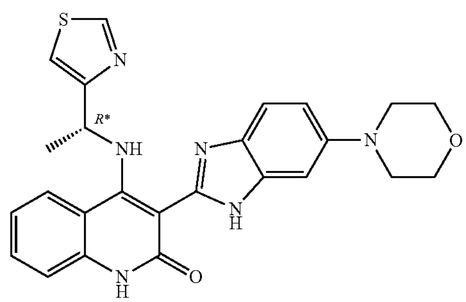 [SMILES: C[C@@H](Nc1c(-c2nc3ccc(N4CCOCC4)cc3[nH]2)c(=O)[nH]c2ccccc12)c1cscn1] | Ex 1 |
| Compound 53 | 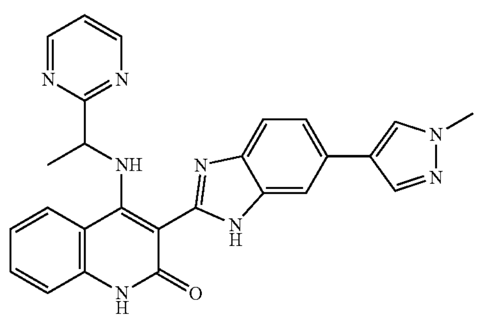 [SMILES: CC(Nc1c(-c2nc3ccc(-c4cnn(C)c4)cc3[nH]2)c(=O)[nH]c2ccccc12)c1ncccn1] | Ex 3 |
| Compound 53b | 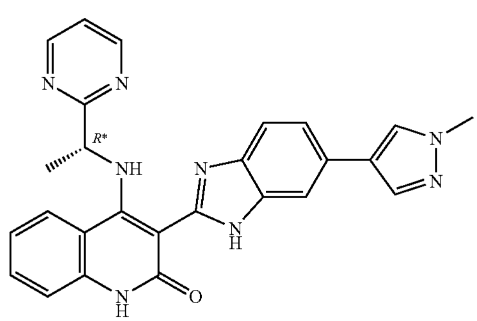 [SMILES: C[C@@H](Nc1c(-c2nc3ccc(-c4cnn(C)c4)cc3[nH]2)c(=O)[nH]c2ccccc12)c1ncccn1] | Ex 3 |
| Compound 53a | 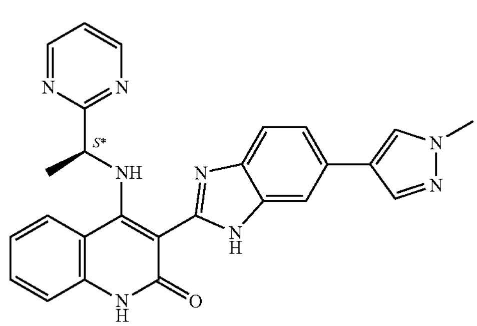 [SMILES: C[C@H](Nc1c(-c2nc3ccc(-c4cnn(C)c4)cc3[nH]2)c(=O)[nH]c2ccccc12)c1ncccn1] | Ex 3 |

TABLE 1-continued

| Compound Number | Structure | Procedure |
|---|---|---|
| Compound 55 | 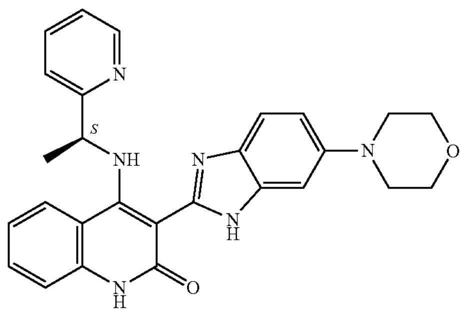 | Ex 1a |
| Compound 56 | 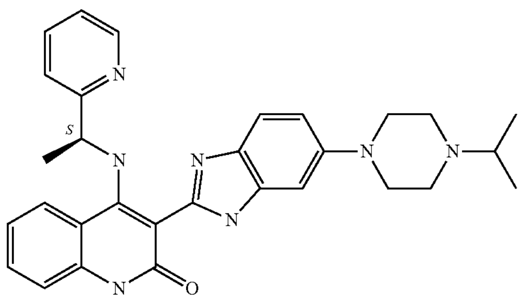 | Ex 1a |
| Compound 7 | 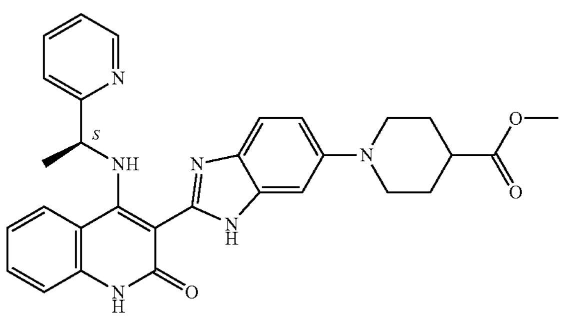 | Ex 1a |
| Compound 6 | as a trifluoroacetic acid salt | Ex 5 |

TABLE 1-continued

| Compound Number | Structure | Procedure |
|---|---|---|
| Compound 57 | 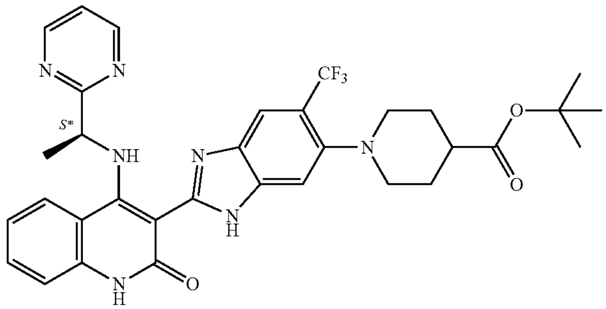 | Ex 1a |
| Compound 58 | 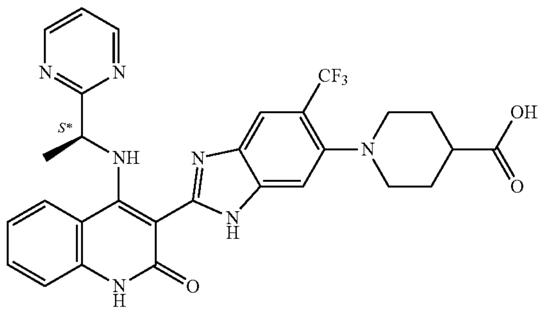 | Ex 5 |
| Compound 59 | 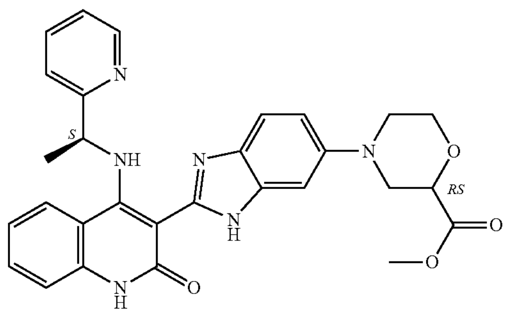 | Ex 1a |
| Compound 60 | 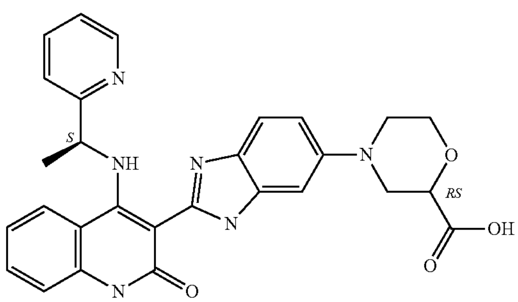 | Ex 5 |
| Compound 61 | 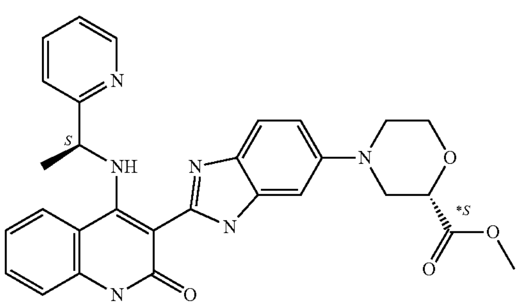 | Ex 6 |

TABLE 1-continued

| Compound Number | Structure | Procedure |
|---|---|---|
| Compound 62 | 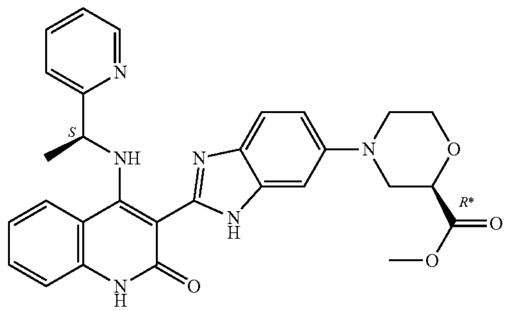 | Ex 6 |
| Compound 63 | 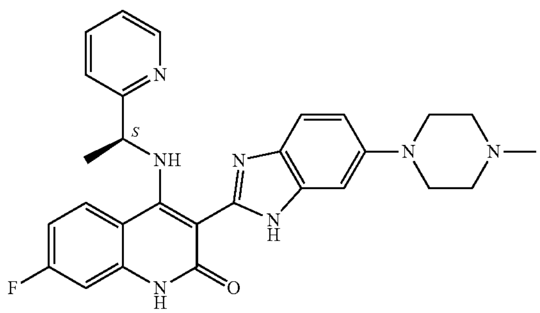 | Ex 1a |
| Compound 64 | 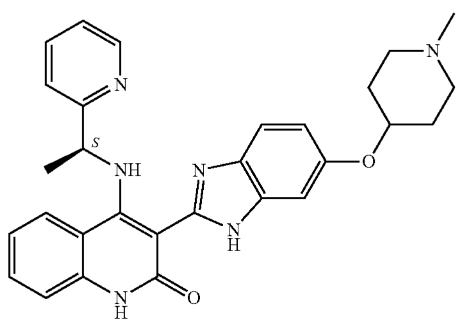 | Ex 1a |
| Compound 65 | 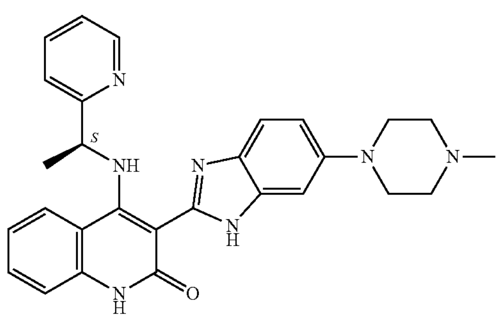 | Ex 1a |
| Compound 38a | 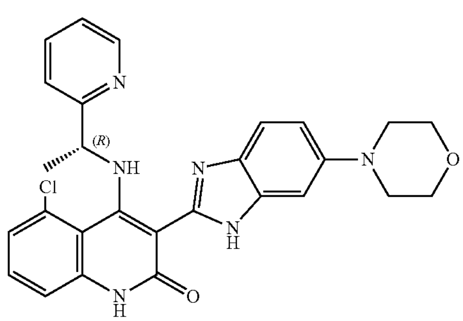 | Ex 2 |

TABLE 1-continued

| Compound Number | Structure | Procedure |
|---|---|---|
| Compound 38b | 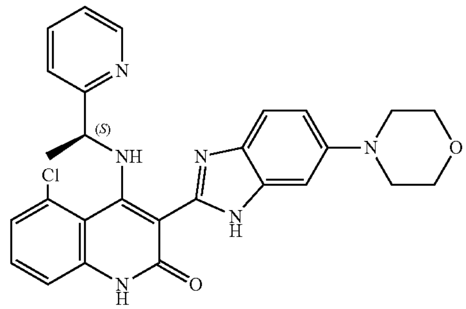 | Ex 2 |
| Compound 42 | 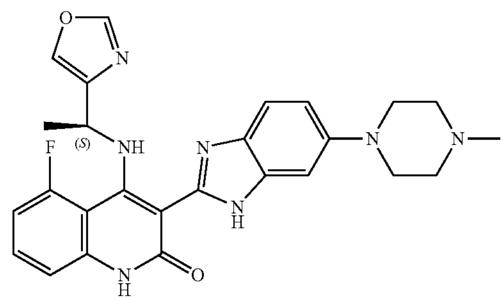 | Ex 1a |

Purification Method, LCMS and NMR for Compounds Prepared According to the Procedures Indicated in Table 1

Compound 9a (S*)-3-(7-fluoro-6-(4-methylpiperazin-1-yl)-1H-benzo[d]imidazol-2-yl)-4-((1-(oxazol-4-yl)ethyl)amino)quinolin-2(1H)-one and compound 9b (R*)-3-(7-fluoro-6-(4-methylpiperazin-1-yl)-1H-benzo[d]imidazol-2-yl)-4-((1-(oxazol-4-yl)ethyl)amino)quinolin-2(1H)-one The reaction mixture was purified by Prep-HPLC (Column: WatersXBridge 30*150 mm 5 um, Flow rate: 20 mL/min, Mobile Phase A: Water (0.1% $NH_3.H_2O$), Mobile Phase B: Acetonitrile, Gradient: 35-55% (% B)). The desired fraction was collected and the volatile was removed under reduced pressure. The water phase was lyophilized to give compound 9 (mixture of stereoisomers) (260 mg, 55% yield) as yellow solids. The crude compound was further purified by prep. SFC (separation condition: Column: ChiralPak AD-H Daicel chemical Industries, Ltd, 250*30 mm I.D., 5 um; Mobile phase A: Supercritical $CO_2$, Mobile phase B: Ethanol (0.1% $NH_3.H_2O$), A:B=60:40 at 50 mL/min; Column Temp: 38° C.; Nozzle Pressure: 100 Bar; Nozzle Temp: 60° C.; Evaporator Temp: 20° C.; Trimmer Temp: 25° C.; Wavelength: 220 nm) to afford the compound 9a (50 mg, 19% yield, purity >99%) and compound 9b.

LC-MS (ESI) General procedure A, method 2: $R_T$=1.12 min, mass calcd. for $C_{26}H_{26}FN_7O_2$ 487.21, m/z found 488.4 $[M+H]^+$.

$^1$H NMR (400 MHz, DMSO-$d_6$) General procedure A: δ 13.06 (s, 1H), 11.76 (d, J=8.4 Hz, 1H), 11.68 (s, 1H), 8.35 (s, 1H), 8.22-8.07 (m, 2H), 7.57 (t, J=7.6 Hz, 1H), 7.40 (m, J=17.7, 8.9 Hz, 2H), 7.19 (t, J=7.6 Hz, 1H), 6.98 (t, J=8.1 Hz, 1H), 5.42-5.30 (m, 1H), 3.35 (s, 4H), 3.03 (s, 4H), 2.24 (s, 3H), 1.65 (d, J=6.4 Hz, 3H).

Compound 10b (S*)-3-(6-(4-methylpiperazin-1-yl)-5-(trifluoromethyl)-1H-benzo[d]imidazol-2-yl)-4-((1-(oxazol-4-yl)ethyl)amino)quinolin-2(1H)-one and Compound 10a (R*)-3-(6-(4-methylpiperazin-1-yl)-5-(trifluoromethyl)-1H-benzo[d]imidazol-2-yl)-4-((1-(oxazol-4-yl)ethyl)amino)quinolin-2(1H)-one The reaction mixture was purified by Prep-HPLC (Column: WatersXBridge 30*150 mm 5 um, Flow rate: 20 mL/min, Mobile Phase A: Water (0.1% $NH_3.H_2O$), Mobile Phase B: Acetonitrile, Gradient: 35-55% (% B)). The desired fraction was collected and the volatile was removed under reduced pressure. The water phase was lyophilized to give the compound 10 (mixture of stereoisomers) (115 mg, 12.4% yield) as yellow solids. The crude compound was further purified by prep. SFC (separation condition: Column: ChiralPak IA Daicel chemical Industries, Ltd, 250*50 mm I.D., 10 um; Mobile phase A: Hexane, Mobile phase B: IPA (0.1% DEA), A:B=70:30 at 60 ml/min; Column Temp: 35° C.; Column Pressure: 2.0 MPa; Evaporator Temp: 35° C.; Wavelength: 254 nm) to afford compound 10b (16.44 mg, 14.30% yield, purity >98%) and compound 10a.

Compound 10b: LC-MS (ESI) General procedure A, method 1: $R_T$=1.29 min, mass calcd. for $C_{27}H_{26}F3N_7O_2$ 537.2, m/z found 538.4 $[M+H]^+$.

$^1$H NMR (400 MHz, $CD_3OD$) General procedure A: δ 8.15 (s, 1H), 8.11 (s, 1H), 7.93 (s, 2H), 7.77 (d, J=17.1 Hz, 1H), 7.56 (t, J=7.5 Hz, 1H), 7.35 (d, J=8.3 Hz, 1H), 7.21 (t, J=7.6 Hz, 1H), 5.38 (q, J=6.4 Hz, 1H), 3.09 (d, J=38.6 Hz, 8H), 2.69 (d, J=14.3 Hz, 3H), 1.76 (d, J=6.6 Hz, 3H).

Compound 11b (R*)-3-(6-(4-methylpiperazin-1-yl)-1H-benzo[d] imidazol-2-yl)-4-((1-(oxazol-4-yl)-ethyl)amino)quinolin-2(1H)-one; and compound 11a (S*)-3-(6-(4-methylpiperazin-1-yl)-1H-benzo[d] imidazol-2-yl)-4-((1-(oxazol-4-yl)-ethyl)amino)quinolin-2(1H)-one The residue was purified by Prep-HPLC (Column: Inertsil ODS-3 20*250 mm 10 um, Flow rate: 20 mL/min, Mobile Phase A: Water (0.05% $NH_3.H_2O$), Mobile Phase B: Acetonitrile, Gradient: 25-40% (% B)). The desired fraction was collected and the volatile was removed under reduced pressure. The water phase was lyophilized to give the compound 11 (mixture of stereoisomers) (140 mg, 16.8% yield) as yellow solids. The isolated material was further purified by prep. SFC (separation condition: ChiralPak AD-H Daicel chemical Industries, Ltd, 250*30 mm I.D., 5 um; Mobile phase A: Supercritical $CO_2$, Mobile phase B: Ethanol (0.1% $NH_3.H_2O$), A:B=60:40 at 50 ml/min; Column Temp: 38° C.; Nozzle Pressure: 100 Bar; Nozzle Temp: 60° C.; Evaporator Temp: 20° C.; Trimmer Temp: 25° C.; Wavelength: 220 nm) to afford compound 11b (47.82 mg, 5.73% yield, ee: >99%) and compound 11a (47.66 mg, 5.71% yield, ee: >99%).

Compound 11b

LC-MS (ESI) General procedure A, method 2: $R_T$=0.97 min, mass calcd. for $C_{26}H_{27}N_7O_2$ 469.2, m/z found 470.5 $[M+H]^+$.

$^1$H NMR (400 MHz, DMSO-$d_6$) General procedure A: δ 12.86-12.81 (m, 1H), 11.77-11.63 (m, 2H), 8.36 (d, J=4.8 Hz, 1H), 8.12-8.07 (m, 2H), 7.57-7.38 (m, 3H), 7.23-6.92 (m, 3H), 5.29 (s, 1H), 3.33 (s, 4H), 3.21 (s, 4H), 2.24 (s, 3H), 1.64 (t, J=6.4 Hz, 3H).

Compound 11a

LC-MS (ESI) General procedure A, method 2: $R_T$=0.97 min, mass calcd. for $C_{26}H_{27}N_7O_2$ 469.2, m/z found 470.5 $[M+H]^+$.

$^1$H NMR (400 MHz, DMSO-$d_6$) General procedure A: δ 12.86-12.82 (m, 1H), 11.77-11.63 (m, 2H), 8.36 (d, J=5.2 Hz, 1H), 8.12-8.07 (m, 2H), 7.57-7.38 (m, 3H), 7.23-6.92 (m, 3H), 5.29 (s, 1H), 3.33 (s, 4H), 3.21 (s, 4H), 2.24 (s, 3H), 1.64 (t, J=6.8 Hz, 3H).

Compound 13b (S*)-3-(7-fluoro-6-(4-methylpiperazin-1-yl)-1H-benzo[d]imidazol-2-yl)-4-((1-(pyridin-2-yl)ethyl) amino)quinolin-2(1H)-one The reaction mixture was purified by Prep-HPLC (Column: WatersXBridge 30*150 mm 5 um, Flow rate: 20 mL/min, Mobile Phase A: Water (0.1% $NH_3.H_2O$), Mobile Phase B: Acetonitrile, Gradient: 35-55% (% B)). The desired fraction was collected and the volatile was removed under reduced pressure. The water phase was lyophilized to give the compound 13 (mixture of stereoisomers) (400 mg, 66% yield) as yellow solids. The crude compound was further purified by prep. SFC (separation condition: Column: ChiralPak AD-H Daicel chemical Industries, Ltd, 250*30 mm I.D., 5 um; Mobile phase A: Supercritical $CO_2$, Mobile phase B: Ethanol (0.1% $NH_3.H_2O$), A:B=60:40 at 50 mL/min; Column Temp: 38° C.; Nozzle Pressure: 100 Bar; Nozzle Temp: 60° C.; Evaporator Temp: 20° C.; Trimmer Temp: 25° C.; Wavelength: 220 nm) to afford compound 13b (80 mg, 20% yield, purity >99%).

LC-MS (ESI) General procedure A, method 2: $R_T$=1.11 min, mass calcd. for $C_2H_{28}FN_7O$ 497.23, m/z found 498.4 $[M+H]^+$.

$^1$H NMR (400 MHz, DMSO-$d_6$+$D_2O$) General procedure A: δ8.52 (d, J=3.9 Hz, 1H), 8.02 (d, J=8.4 Hz, 1H), 7.76 (t, J=7.6 Hz, 1H), 7.57-7.42 (m, 3H), 7.36 (t, J=8.9 Hz, 1H), 7.31-7.24 (m, 1H), 7.10 (t, J=7.9 Hz, 1H), 7.02 (t, J=8.1 Hz, 1H), 5.55 (m, J=6.7 Hz, 1H), 3.68 (s, 4H), 3.05 (s, 4H), 2.25 (s, 3H), 1.72 (d, J=6.3 Hz, 3H).

Compound 14

(S)-3-(6-(4-methylpiperazin-1-yl)-5-(trifluoromethyl)-1H-benzo[d]imidazol-2-yl)-4-((1-(pyridin-2-yl)ethyl)amino)quinolin-2(1H)-one The reaction mixture was purified by Prep-HPLC (Column: WatersXBridge 30*150 mm 5 um, Flow rate: 20 mL/min, Mobile Phase A: Water (0.1% $NH_3.H_2O$), Mobile Phase B: Acetonitrile, Gradient: 35-55% (% B)). The desired fraction was collected and the volatile was removed under reduced pressure. The water phase was lyophilized to give compound 14 (166.33 mg, 14.1% yield, purity >98%) as yellow solids.

LC-MS (ESI) General procedure A, method 1: $R_T$=1.26 min, mass calcd. for $C_{29}H_{28}F_3N_7O$ 547.2, m/z found 548.4 $[M+H]^+$.

$^1$H NMR (400 MHz, $CD_3OD$) General procedure A: δ 8.50 (s, 1H), 8.03-7.86 (m, 2H), 7.80 (s, 1H), 7.75 (s, 1H), 7.58 (s, 1H), 7.50 (t, J=7.6 Hz, 1H), 7.31 (s, 1H), 7.29 (s, 1H), 7.02 (d, J=44.7 Hz, 1H), 5.50 (s, 1H), 3.03 (s, 4H), 2.65 (s, 4H), 2.38 (s, 3H), 1.82 (s, 3H).

Compound 15

(S)-3-(6-(4-methyl-3-oxopiperazin-1-yl)-1H-benzo [d]imidazol-2-yl)-4-((1-(pyridin-2-yl)ethyl)amino) quinolin-2(1H)-one

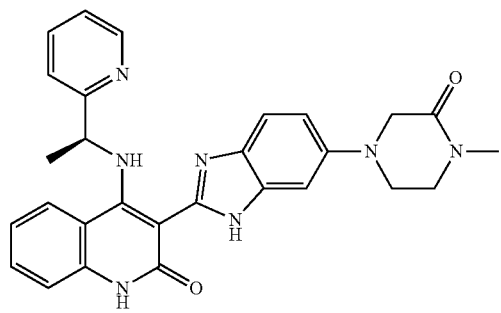

The reaction mixture was purified by Prep-HPLC (Column: WatersXBridge 30*150 mm 5 um, Flow rate: 20 mL/min, Mobile Phase A: Water (0.1% $NH_3.H_2O$), Mobile Phase B: Acetonitrile, Gradient: 35-55% (% B)). The desired fraction was collected and the volatile was removed under reduced pressure. The water phase was lyophilized to give compound 15 (16.64 mg, 14.06% yield) as yellow solids.

LC-MS (ESI) General procedure A, method 2: $R_T$=1.13 min, mass calcd. for $C_{28}H_{27}N_7O_2$ 493.2, m/z found 494.3 [M+H]$^+$.

$^1$H NMR (400 MHz, CD$_3$OD) General procedure A: δ 8.49 (s, 1H), 7.95 (d, J=8.2 Hz, 1H), 7.78-7.75 (m, 1H), 7.58 (t, J=8.3 Hz, 2H), 7.52-7.47 (m, 1H), 7.34-7.24 (m, 2H), 7.18-6.98 (m, 3H), 5.47-5.42 (m, 1H), 3.85 (s, 2H), 3.54 (s, 4H), 3.03 (s, 3H), 1.78 (d, J=6.0 Hz, 3H).

Compound 16

(S)-8-fluoro-3-(6-morpholino-1H-benzo[d]imidazol-2-yl)-4-((1-(pyridin-2-yl)ethyl)-amino)quinolin-2(1H)-one The reaction mixture was purified with Prep-HPLC (Column: WatersXBridge 30*150 mm 5 um, Flow rate: 20 mL/min, Mobile Phase A: Water (0.1% NH$_3$.H$_2$O), Mobile Phase B: Acetonitrile, Gradient: 35-55% (% B)). The desired fraction was collected and the volatile was removed under reduced pressure. The water phase was lyophilized to give compound 16 (25 mg, 10.3% yield) as brown solids.

LC-MS (ESI) General procedure B, method 2: $R_T$=1.44 min, mass calcd. for $C_{27}H_{25}FN_6O_2$ 484.2, m/z found 485.1 [M+H]$^+$.

$^1$H NMR (400 MHz, CD$_3$OD) General procedure A: δ 8.48 (d, J=4.4 Hz, 1H), 7.81-7.77 (m, 2H), 7.58-7.53 (m, 1.5H), 7.52-7.46 (m, 0.5H), 7.36-7.24 (m, 2.5H), 7.16 (s, 0.5H), 7.06 (m, 2H), 5.48-5.38 (m, 1H), 3.96-3.84 (m, 4H), 3.18 (m, 4H), 1.78 (d, J=6.2 Hz, 3H).

Compound 17

(S)-6-fluoro-3-(6-morpholino-1H-benzo[d]imidazol-2-yl)-4-((1-(pyridin-2-yl)ethyl)-amino)quinolin-2(1H)-one The mixture was purified by Prep-HPLC (Column: WatersXBridge 30*150 mm 5 um, Flow rate: 20 mL/min, Mobile Phase A: Water (0.1% NH$_3$.H$_2$O), Mobile Phase B: Acetonitrile, Gradient: 35-55% (% B)). The desired fraction was collected and the volatile was removed under reduced pressure. The water phase was lyophilized to give compound 17 (120 mg, 24.8% yield) as yellow solids.

LC-MS (ESI) General procedure B, method 2: $R_T$=1.34 min, mass calcd. for $C_{27}H_{25}FN_6O_2$ 484.2, m/z found 485.1 [M+H]$^+$.

$^1$H NMR (400 MHz, DMSO-d$_6$) General procedure A: δ12.92-12.88 (m, 1H), 12.33 (d, J=8.0 Hz, 0.40H), 12.19 (d, J=8.0 Hz, 0.53H), 11.65 (m, 1H), 8.55 (m, 1H), 7.79-7.70 (m, 2H), 7.61-7.34 (m, 4H), 7.28-7.23 (m, 2H), 7.01-6.96 (m, 1H), 5.48-5.44 (m, 1H), 3.78 (m, 4H), 3.11 (m, 4H), 1.73-1.70 (m, 3H).

Compound 18

(S)-3-(6-((1-methylpiperidin-4-yl)amino)-5-(trifluoromethyl)-1H-benzo[d]imidazol-2-yl)-4-((1-(pyridin-2-yl)ethyl)amino)quinolin-2(1H)-one The reaction mixture was purified by Prep-HPLC (Column: WatersXBridge 30*150 mm 5 um, Flow rate: 20 mL/min, Mobile Phase A: Water (0.1% NH$_3$.H$_2$O), Mobile Phase B: Acetonitrile, Gradient: 35-55% (% B)). The desired fraction was collected and the volatile was removed under reduced pressure. The water phase was lyophilized to give the crude compound, then purified by Pre-TLC (dichloromethane/methanol=8/1, R$_f$=0.3) to give compound 18 (39.35 mg, 8.4% yield, purity >99%) as yellow solids.

LC-MS (ESI) General procedure B, method 2: $R_T$=1.31 min, mass calcd. for $C_{30}H_{30}F_3N_7O$ 561.2, m/z found 562.2 [M+H]$^+$.

$^1$H NMR (400 MHz, DMSO-d$_6$) General procedure A: δ 13.06 (d, J=16.9 Hz, 1H), 12.18 (d, J=8.1 Hz, 0.5H), 12.06 (d, J=8.0 Hz, 0.5H), 11.62 (d, J=10.1 Hz, 1H), 8.62-8.48 (m, 1H), 2.91-7.68 (m, 3H), 7.59-7.45 (m, 2H), 7.40-7.02 (m, 4H), 5.59-5.46 (m, 1H), 4.52 (d, J=6.3 Hz, 0.5H), 4.32 (d, J=7.0 Hz, 0.5H), 3.84-3.51 (m, 3H), 3.08-2.87 (m, 2H), 2.68 (s, 3H), 2.26-2.10 (m, 2H), 1.94-1.53 (m, 5H).

Compound 19

(S)-3-(6-(methyl(1-methylpiperidin-4-yl)amino)-5-(trifluoromethyl)-1H-benzo[d]-imidazol-2-yl)-4-((1-(pyridin-2-yl)ethyl)amino)quinolin-2(1H)-one The reaction mixture was purified by Prep-HPLC (Column: WatersXBridge 30*150 mm 5 um, Flow rate: 20 mL/min, Mobile Phase A: Water (0.1% NH$_3$.H$_2$O), Mobile Phase B: Acetonitrile, Gradient: 35-55% (% B)). The desired fraction was collected and the volatile was removed under reduced pressure. The water phase was lyophilized to give compound 19 (2.10 mg, 3.7% yield, purity >99%) as yellow solids.

LC-MS (ESI) General procedure A, method 2: $R_T$=1.50 min, mass calcd. for $C_{31}H_{32}F3N_7O$ 575.2, m/z found 576.4 [M+H]$^+$.

$^1$H NMR (400 MHz, CD$_3$OD) General procedure A: δ 8.54-8.47 (m, 1H), 8.01-7.90 (m, 2H), 7.84-7.71 (m, 2H), 7.58 (d, J=7.9 Hz, 1H), 7.55-7.47 (m, 1H), 7.37-7.24 (m, 2H), 7.13-7.05 (m, 1H), 5.55-5.46 (m, 1H), 3.00-2.84 (m, 3H), 2.70 (s, 3H), 2.26 (s, 3H), 2.16-2.01 (m, 2H), 1.96-1.54 (m, 7H).

Compound 20

(S)-3-(6-(morpholine-4-carbonyl)-1H-benzo[d]imidazol-2-yl)-4-((1-(pyridin-2-yl)-ethyl)amino)quinolin-2(1H)-one The reaction mixture was purified by Prep-HPLC (Column: WatersXBridge 30*150 mm 5 um, Flow rate: 20 mL/min, Mobile Phase A: Water (0.1% NH$_3$.H$_2$O), Mobile Phase B: Acetonitrile, Gradient: 35-55% (% B)). The desired fraction was collected and the volatile was removed under reduced pressure. The water phase was lyophilized to give compound 20 (105.21 mg, 24.76% yield, purity >99%) as yellow solids.

LC-MS (ESI) General procedure B, method 1: $R_T$=1.48 min, mass calcd. for $C_2H_{26}N_6O_3$ 494.2, m/z found 495.2 [M+H]$^+$.

$^1$H NMR (400 MHz, DMSO-d$_6$) General procedure A: δ 13.22 (d, J=3.8 Hz, 1H), 12.26 (d, J=7.8 Hz, 1H), 11.60 (s, 1H), 8.55 (s, 1H), 8.00 (d, J=8.5 Hz, 1H), 7.83-7.75 (m, 2H), 7.67 (d, J=11.0 Hz, 1H), 7.51 (d, J=7.3 Hz, 2H), 7.35 (d, J=8.2 Hz, 1H), 7.26 (d, J=7.6 Hz, 2H), 7.08 (t, J=7.5 Hz, 1H), 5.58-5.50 (m, 1H), 3.63 (s, 4H), 3.55 (s, 4H), 1.74 (d, J=4.2 Hz, 3H).

Compound 21

3-(6-((2R,6R)-2,6-dimethylmorpholino)-1H-benzo[d]imidazol-2-yl)-4-(((S)-1-(pyridin-2-yl)ethyl)amino)quinolin-2(1H)-one

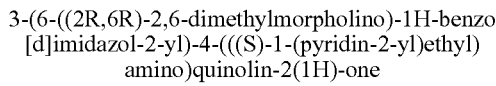

The mixture was concentrated under reduced pressure to give a residue that was purified by silica gel chromatography (dichloromethane:methanol=30:1) and then further purified by Prep-HPLC (Column: WatersXBridge 30*150 mm 5 um, Flow rate: 20 mL/min, Mobile Phase A: Water (0.1% $NH_3.H_2O$), Mobile Phase B: Acetonitrile, Gradient: 35-55% (% B)). The desired fraction was collected and the volatile was removed under reduced pressure. The water phase was lyophilized to give compound 21 (8.11 mg, 3.8% yield, purity >99%) as yellow solids.

LC-MS (ESI) General procedure A, method 2: $R_T$=1.37 min, mass calcd. for $C_{29}H_{30}N_6O_2$ 494.6, m/z found 495.4 [M+H]$^+$.

$^1$H NMR (400 MHz, DMSO-d$_6$) General procedure A: δ 12.91 (s, 0.5H), 12.87 (s, 0.5H), 12.27 (d, J=8.4 Hz, 0.5H), 12.15 (d, J=7.8 Hz, 0.5H), 11.57 (s, 1H), 8.54 (t, J=5.1 Hz, 1H), 7.96 (t, J=7.7 Hz, 1H), 7.76 (dd, J=15.1, 7.6 Hz, 1H), 7.62-7.45 (m, 3H), 7.38-7.20 (m, 3H), 7.16-6.88 (m, 2H), 5.55-5.43 (m, 1H), 4.18-4.01 (m, 2H), 3.16 (d, J=10.8 Hz, 3H), 2.84 (dd, J=11.3, 6.0 Hz, 2H), 1.72 (t, J=7.3 Hz, 3H), 1.25 (d, J=6.1 Hz, 6H).

Compound 22a 3-(6-((2S,6R)-2,6-dimethylmorpholino)-1H-benzo[d]imidazol-2-yl)-4-(((S*)-1-(pyrimidin-2-yl)ethyl)amino)quinolin-2(1H)-one

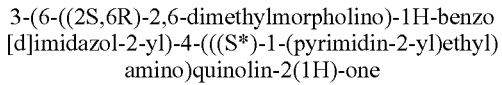

The reaction mixture was purified by Prep-HPLC (Column: WatersXBridge 30*150 mm 5 um, Flow rate: 20 mL/min, Mobile Phase A: Water (0.1% $NH_3.H_2O$), Mobile Phase B: Acetonitrile, Gradient: 35-55% (% B)). The desired fraction was collected and the volatile was removed under reduced pressure. The water phase was lyophilized to give the compound 22 (mixture of stereoisomers) (23 mg, 9.5% yield) as yellow solids. The crude compound was further purified by prep. SFC (separation condition: Column: ChiralPak AD-H Daicel chemical Industries, Ltd, 250*30 mm I.D., 5 um; Mobile phase A: Supercritical $CO_2$, Mobile phase B: Isopropanol (0.1% DEA), A:B=60:40 at 50 mL/min; Column Temp: 38° C.; Nozzle Pressure: 100 Bar; Nozzle Temp: 60° C.; Evaporator Temp: 20° C.; Trimmer Temp: 25° C.; Wavelength: 220 nm) to afford compound 22a (2.17 mg, 9.4% yield, ee: >99%) and compound 22b.

Compound 22a: LC-MS (ESI) General procedure A, method 2: $R_T$=1.16 min, mass calcd. for $C_{28}H_{29}N_7O_2$ 495.2, m/z found 496.4 [M+H]$^+$.

$^1$H NMR (400 MHz, CD$_3$OD) General procedure A: δ 8.67 (d, J=4.9 Hz, 2H), 8.08 (d, J=8.3 Hz, 1H), 7.51 (t, J=7.3 Hz, 2H), 7.35-7.24 (m, 2H), 7.17 (m, 2H), 7.03 (d, J=8.7 Hz, 1H), 5.44 (d, J=6.7 Hz, 1H), 3.86 (s, 2H), 3.51 (d, J=11.4 Hz, 2H), 2.40 (t, J=11.0 Hz, 2H), 1.78 (d, J=6.7 Hz, 3H), 1.25 (d, J=6.2 Hz, 6H).

Compound 23a (S*)-3-(7-fluoro-6-morpholino-1H-benzo[d]imidazol-2-yl)-4-((1-(pyrimidin-2-yl)-ethyl)amino)quinolin-2(1H)-one

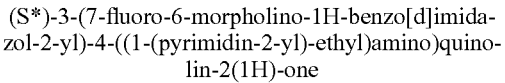

The reaction mixture was purified by Prep-HPLC (Column: WatersXBridge 30*150 mm 5 um, Flow rate: 20 mL/min, Mobile Phase A: Water (0.1% $NH_3.H_2O$), Mobile Phase B: Acetonitrile, Gradient: 35-55% (% B)). The desired fraction was collected and the volatile was removed under reduced pressure. The water phase was lyophilized to give compound 23 (mixture of stereoisomers) (140 mg, 19% yield) as yellow solids. The crude compound was further purified by prep. SFC (separation condition: Column: ChiralPak AD-H Daicel chemical Industries, Ltd, 250*30 mm I.D., 5 um; Mobile phase A: Supercritical $CO_2$, Mobile phase B: Ethanol (0.1% $NH_3.H_2O$), A:B=60:40 at 50 mL/min; Column Temp: 38° C.; Nozzle Pressure: 100 Bar; Nozzle Temp: 60° C.; Evaporator Temp: 20° C.; Trimmer Temp: 25° C.; Wavelength: 220 nm) to afford compound 23a (50 mg, 36% yield, purity >99%) and compound 23b.

Compound 23a: LC-MS (ESI) General procedure A, method 2: $R_T$=1.56 min, mass calcd. for $C_{26}H_{24}FN_7O_2$ 485.2, m/z found 486.4 [M+H]$^+$.

$^1$H NMR (400 MHz, DMSO-d$_6$) General procedure A; δ 13.08 (s, 1H), 12.14 (d, J=7.9 Hz, 1H), 11.59 (s, 1H), 8.77 (d, J=4.9 Hz, 2H), 8.09 (d, J=8.3 Hz, 1H), 7.51 (t, J=7.6 Hz, 1H), 7.45 (d, J=8.5 Hz, 1H), 7.36 (m, 2H), 7.09 (t, J=7.8 Hz, 1H), 7.00 (t, J=8.0 Hz, 1H), 5.65-5.55 (m, 1H), 3.83-3.74 (m, 4H), 3.04 (m, 4H), 1.75 (d, J=6.6 Hz, 3H).

Compound 24

(S)-3-(7-fluoro-6-morpholino-1H-benzo[d]imidazol-2-yl)-4-((1-(pyridin-2-yl)ethyl)-amino)quinolin-2(1H)-one

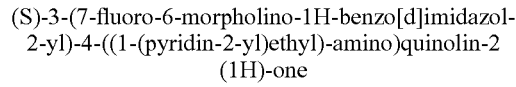

The reaction mixture was purified by Prep-HPLC (Column: WatersXBridge 30*150 mm 5 um, Flow rate: 20 mL/min, Mobile Phase A: Water (0.1% $NH_3.H_2O$), Mobile Phase B: Acetonitrile, Gradient: 35-55% (% B)). The desired fraction was collected and the volatile was removed under reduced pressure. The water phase was lyophilized to give compound 24 (75 mg, 12% yield, purity >99%) as yellow solids.

LC-MS (ESI) General procedure A, method 2: $R_T$=1.45 min, mass calcd. for $C_{27}H_{25}FN_6O_2$, 484.20, m/z found 485.4 [M+H]$^+$.

$^1$H NMR (400 MHz, DMSO-d$_6$) General procedure A: δ 11.63 (s, 1H), 8.50 (d, J=4.9 Hz, 1H), 8.05 (d, J=8.2 Hz, 1H), 7.81 (t, J=7.8 Hz, 1H), 7.60-7.43 (m, 3H), 7.39-7.24 (m, 2H), 7.08 (m, J=16.3, 7.9 Hz, 2H), 5.42 (d, J=5.8 Hz, 1H), 3.78 (s, 4H), 3.05 (s, 4H), 1.69 (d, J=6.6 Hz, 3H).

Compound 25a (S*)-3-(6-(4-methylpiperazin-1-yl)-5-(trifluoromethyl)-1H-benzo[d]imidazol-2-yl)-4-((1-(pyrimidin-2-yl)ethyl)amino)quinolin-2(1H)-one

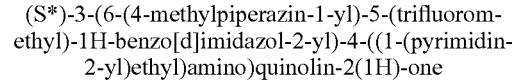

The reaction mixture was purified by Prep-HPLC (Column: WatersXBridge 30*150 mm 5 um, Flow rate: 20 mL/min, Mobile Phase A: Water (0.1% $NH_3.H_2O$), Mobile Phase B: Acetonitrile, Gradient: 35-55% (% B)). The desired fraction was collected and the volatile was removed under reduced pressure. The water phase was lyophilized to give compound 25 (mixture of stereoisomers) (16 mg, 5.2% yield) as brown solids. The crude compound was further purified by prep. SFC (separation condition: Column: ChiralPak AD-H Daicel chemical Industries, Ltd, 250*30 mm I.D., 5 um; Mobile phase A: Supercritical $CO_2$, Mobile phase B: Ethanol (0.1% DEA), A:B=60:40 at 50 mL/min; Column Temp: 38° C.; Nozzle Pressure: 100 Bar; Nozzle Temp: 60° C.; Evaporator Temp: 20° C.; Trimmer Temp: 25°

C.; Wavelength: 220 nm) to afford compound 25a (3.81 mg, 23.8% yield, purity >99%) and compound 25b.

Compound 25a: LC-MS (ESI) General procedure A, method 2: $R_T$=1.30 min, mass calcd. for $C_{28}H_{27}F_3N_8O$ 548.2, m/z found 549.3 [M+H]$^+$.

$^1$H NMR (400 MHz, CD$_3$OD) General procedure A: δ 8.72 (d, J=4.9 Hz, 2H), 8.09 (d, J=8.2 Hz, 1H), 7.98-7.89 (m, 1H), 7.85-7.71 (m, 1H), 7.57-7.48 (m, 1H), 7.37-7.27 (m, 2H), 7.20-7.12 (m, 1H), 5.60-5.52 (m, 1H), 3.20-2.87 (m, 8H), 2.65 (d, J=13.3 Hz, 3H), 1.83 (d, J=6.6 Hz, 3H).

Compound 26a 3-(6-((S)-2-methylmorpholino)-1H-benzo[d]imidazol-2-yl)-4-(((S*)-1-(pyrimidin-2-yl)-ethyl)amino)quinolin-2(1H)-one The mixture was cooled to room temperature and then concentrated under reduced pressure. The residue was purified by silica gel chromatography (dichloromethane:methanol=30:1) and then further purified by Prep-HPLC (Column: WatersXBridge 30*150 mm 5 um, Flow rate: 20 mL/min, Mobile Phase A: Water (0.1% NH$_3$.H$_2$O), Mobile Phase B: Acetonitrile, Gradient: 35-55% (% B)). The desired fraction was collected and the volatile was removed under reduced pressure. The water phase was lyophilized to give compound 26 (mixture of stereoisomers)(45.0 mg, 28.3% yield) as yellow solids. The crude compound was further purified by prep. SFC (separation condition: Column: ChiralCel OZ-H Daicel chemical Industries, Ltd, 250*30 mm I.D., 5 um; Mobile phase A: Supercritical CO$_2$, Mobile phase B: Isopropanol (0.1% DEA), A:B=55:45 at 50 mL/min; Column Temp: 38° C.; Nozzle Pressure: 100 Bar; Nozzle Temp: 60° C.; Evaporator Temp: 20° C.; Trimmer Temp: 25° C.; Wavelength: 220 nm) to compound 26a (12.49 mg, 27.7% yield, purity >99%) and compound 26b.

Compound 26a

LC-MS (ESI) General procedure B, method 2: $R_T$=1.26 min, mass calcd. for $C_{27}H_{27}N_7O_2$ 481.2, m/z found 482.2 [M+H]$^+$.

$^1$H NMR (400 MHz, CD$_3$OD) General procedure A: δ: 8.68 (d, J=4.8 Hz, 2H), 8.09 (d, J=8.4 Hz, 1H), 7.53-7.49 (m, 2H), 7.32 (d, J=8.0 Hz, 1H), 7.28-7.25 (m, 1H), 7.18-7.12 (m, 2H), 7.03 (dd, J=8.4 Hz, 1H), 5.47 (q, J=6.8 Hz, 1H), 7.01-3.98 (m, 1H), 3.86-3.80 (m, 2H), 3.53 (d, J=11.6 Hz, 1H), 3.45 (d, J=12 Hz, 1H), 2.83-2.77 (m, 1H), 2.50-2.45 (m, 1H), 1.79 (d, J=6.8 Hz, 3H), 1.25 (d, J=6.0 Hz, 3H).

Compound 27a (S*)-3-(5-fluoro-6-morpholino-1H-benzo[d]imidazol-2-yl)-4-((1-(pyrimidin-2-yl)-ethyl)amino)quinolin-2(1H)-one The reaction mixture was purified by Prep-HPLC (Column: WatersXBridge 30*150 mm 5 um, Flow rate: 20 mL/min, Mobile Phase A: Water (0.1% NH$_3$.H$_2$O), Mobile Phase B: Acetonitrile, Gradient: 35-55% (% B)). The desired fraction was collected and the volatile was removed under reduced pressure. The water phase was lyophilized to give compound 27 (mixture of stereoisomers) (88 mg, 19.0% yield) as yellow solids. The crude compound was further purified by prep. SFC (separation condition: Column: ChiralPak AD-H Daicel chemical Industries, Ltd, 250*30 mm I.D., 5 um; Mobile phase A: Supercritical CO$_2$, Mobile phase B: Ethanol (0.1% DEA), A:B=60:40 at 50 mL/min; Column Temp: 38° C.; Nozzle Pressure: 100 Bar; Nozzle Temp: 60° C.; Evaporator Temp: 20° C.; Trimmer Temp: 25° C.; Wavelength: 254 nm) to afford compound 27a (15.13 mg, 17.19% yield, purity >99%) and compound 27b.

Compound 27a: LC-MS (ESI) General procedure B, method 2: $R_T$=1.51 min, mass calcd. for $C_{26}H_{24}FN_7O_2$ 485.2, m/z found 486.3 [M+H]$^+$.

$^1$H NMR (400 MHz, DMSO-d$_6$) General procedure A: δ 13.00 (d, J=6.5 Hz, 1H), 12.03 (d, J=7.3 Hz, 0.45H), 11.90 (d, J=6.9 Hz, 0.42H), 11.58 (s, 1H), 8.80-8.77 (m, 2H), 8.05 (s, 1H), 7.53-7.46 (m 1H), 7.45-7.17 (m, 4H), 7.12-7.07 (s, 1H), 5.56-5.51 (m, 1H), 3.78 (s, 4H), 3.00 (s, 4H), 1.74 (t, J=6.9 Hz, 3H).

Compound 28a (S*)-3-(6-(piperidin-1l-yl)-1H-benzo[d]imidazol-2-yl)-4-((1-(pyrimidin-2-yl)ethyl)-amino)quinolin-2(1H)-one The mixture was cooled to room temperature and then concentrated under reduced pressure. The residue was purified by silica gel chromatography (dichloromethane:methanol=40:1) and then further purified by Prep-HPLC (Column: WatersXBridge 30*150 mm 5 um, Flow rate: 20 mL/min, Mobile Phase A: Water (0.1% NH$_3$.H$_2$O), Mobile Phase B: Acetonitrile, Gradient: 35-55% (% B)). The desired fraction was collected and the volatile was removed under reduced pressure. The water phase was lyophilized to give compound 28 (mixture of stereoisomers) (45.0 mg, 32.3% yield) as yellow solids. The crude compound was further purified by prep. SFC (separation condition: Column: ChiralPak AD-H Daicel chemical Industries, Ltd, 250*30 mm I.D., 5 um; Mobile phase A: Supercritical CO$_2$, Mobile phase B: Ethanol (0.1% DEA), A:B=50:50 at 50 mL/min; Column Temp: 38° C.; Nozzle Pressure: 100 Bar; Nozzle Temp: 60° C.; Evaporator Temp: 20° C.; Trimmer Temp: 25° C.; Wavelength: 220 nm) to afford compound 28a (10.53 mg, 23.4% yield, purity >99%) and compound 28b. Compound 28a: LC-MS (ESI) General procedure B, method 2: $R_T$=1.20 min, mass calcd. for $C_{27}H_{27}N_7O$ 465.2, m/z found 466.3 [M+H]$^+$.

$^1$H NMR (400 MHz, CD$_3$OD) General procedure A: δ: 8.67 (d, J=4.8 Hz, 2H), 8.09 (d, J=8.4 Hz, 1H), 7.53-7.49 (m, 2H), 7.33 (d, J=8.0 Hz, 1H), 7.28 (t, J=4.8 Hz, 1H), 7.22-7.15 (m, 2H), 7.06 (dd, J$_{1,2}$=1.6 Hz, J$_{1,3}$=8.8 Hz, 1H), 5.46 (q, J=6.4 Hz, 1H), 3.16 (t, J=5.2 Hz, 4H), 1.82-1.77 (m, 7H), 1.64-1.60 (m, 2H).

Compound 29a (S*)-4-((1-(pyrimidin-2-yl)ethyl)amino)-3-(6-(tetrahydro-2H-pyran-4-yl)-1H-benzo[d]-imidazol-2-yl)quinolin-2(1H)-one The reaction mixture was purified by Prep-HPLC (Column: WatersXBridge 30*150 mm 5 um, Flow rate: 20 mL/min, Mobile Phase A: Water (0.1% NH$_3$.H$_2$O), Mobile Phase B: Acetonitrile, Gradient: 35-55% (% B)). The desired fraction was collected and the volatile was removed under reduced pressure. The water phase was lyophilized to give compound 29 (mixture of stereoisomers) (35 mg, 23.7% yield) as yellow solids. The crude compound was further purified by prep. SFC (separation condition: Column: ChiralPak AD-H Daicel chemical Industries, Ltd, 250*30 mm I.D., 5 um; Mobile phase A: Supercritical CO$_2$, Mobile phase B: Ethanol (0.1% DEA), A:B=50:50 at 50 mL/min;

Column Temp: 38° C.; Nozzle Pressure: 100 Bar; Nozzle Temp: 60° C.; Evaporator Temp: 20° C.; Trimmer Temp: 25° C.; Wavelength: 220 nm) to afford compound 29a (6.17 mg, 17.63% yield, purity >99%) and compound 29b.

Compound 29a: LC-MS (ESI) General procedure A, method 2: $R_T$=1.27 min, mass calcd. for $C_{27}H_{26}N_6O_2$ 466.2, m/z found 467.4 [M+H]$^+$.

$^1$H NMR (400 MHz, DMSO-d$_6$) General procedure A: δ 12.96 (d, J=7.8 Hz, 1H), 12.20 (d, J=8.2 Hz, 0.5H), 12.10 (d, J=8.2 Hz, 0.5H), 11.58 (s, 1H), 8.85-8.71 (m, 2H), 8.07 (dd, J=7.9, 5.0 Hz, 1H), 7.63 (d, J=8.3 Hz, 0.5H), 7.59 (s, 0.5H), 7.55-7.45 (m, 2H), 7.39-7.33 (m, 2H), 7.13-7.08 (m, 2H), 5.60-5.52 (m, 1H), 3.98 (d, J=10.7 Hz, 2H), 3.51-3.33 (m, 2H), 2.93-2.78 (m, 2H), 1.79-1.70 (m, 7H).

Compound 34a (S*)-4-((1-(4-methylpyrimidin-2-yl)ethyl)amino)-3-(6-morpholino-1H-benzo[d]imidazol-2-yl)quinolin-2(1H)-one The reaction mixture was purified by Prep-HPLC (Column: WatersXBridge 30*150 mm 5 um, Flow rate: 20 mL/min, Mobile Phase A: Water (0.1% NH$_3$.H$_2$O), Mobile Phase B: Acetonitrile, Gradient: 35-55% (% B)). The desired fraction was collected and the volatile was removed under reduced pressure. The water phase was lyophilized to give compound 34 (mixture of stereoisomers) (100 mg, 33.0% yield) as yellow solids. The crude compound was further purified by prep. SFC (separation condition: Column: ChiralPak AD-H Daicel chemical Industries, Ltd, 250*30 mm I.D., 5 um; Mobile phase A: Supercritical CO$_2$, Mobile phase B: Ethanol (0.1% DEA), A:B=50:50 at 50 mL/min; Column Temp: 38° C.; Nozzle Pressure: 100 Bar; Nozzle Temp: 60° C.; Evaporator Temp: 20° C.; Trimmer Temp: 25° C.; Wavelength: 220 nm) to afford compound 34a (15.14 mg, 15.1% yield, purity >99%) and compound 34b.

Compound 34a: LC-MS (ESI) General procedure B, method 2: $R_T$=1.16 min, mass calcd. for $C_{27}H_{27}N_7O_2$ 481.2, m/z found 482.2 [M+H]$^+$.

$^1$H NMR (400 MHz, CD$_3$OD) General procedure A: δ 8.45 (d, J=5.1 Hz, 1H), 8.09 (d, J=8.4 Hz, 1H), 7.62-7.42 (m, 2H), 7.37-7.00 (m, 5H), 5.35 (q, J=6.6 Hz, 1H), 3.95-3.81 (m, 4H), 3.21-3.11 (m, 4H), 2.37 (s, 3H), 1.76 (d, J=6.6 Hz, 3H).

Compound 35b (S*)-3-(6-morpholino-1H-benzo[d]imidazol-2-yl)-4-((1-(pyrazin-2-yl)ethyl)amino)-quinolin-2(1H)-one The reaction mixture was purified by Prep-HPLC (Column: WatersXBridge 30*150 mm 5 um, Flow rate: 20 mL/min, Mobile Phase A: Water (0.1% NH$_3$.H$_2$O), Mobile Phase B: Acetonitrile, Gradient: 35-55% (% B)). The desired fraction was collected and the volatile was removed under reduced pressure. The water phase was lyophilized to give compound 35 (mixture of stereoisomers) (178 mg, 24.1% yield) as yellow solids. The crude compound was further purified by prep. SFC (separation condition: Column: ChiralCel OJ-H Daicel chemical Industries, Ltd, 250*30 mm I.D., 5 um; Mobile phase A: Supercritical CO$_2$, Mobile phase B: Ethanol (0.1% DEA) A:B=60:40 at 50 ml/min; Column Temp: 38° C.; Nozzle Pressure: 100 Bar; Nozzle Temp: 60° C.; Evaporator Temp: 20° C.; Trimmer Temp: 25° C.; Wavelength: 220 nm) to afford compound 35b (63.71 mg, 35.8% yield, purity >99%) and compound 35a. Compound 35b: LC-MS (ESI) General procedure A, method 3: $R_T$=1.01 min, mass calcd. for $C_{26}H_{25}N_7O_2$ 467.21, m/z found 468.2 [M+H]$^+$.

$^1$H NMR (400 MHz, CD$_3$OD) General procedure A: δ 8.67 (d, J=4.8 Hz, 1H), 8.46 (d, J=8.3 Hz, 1H), 8.41 (t, J=7.4 Hz, 1H), 8.00 (m, 1H), 7.56-7.49 (m, 2H), 7.32 (s, 1H), 7.19-7.12 (m, 2H), 7.03 (m, 1H), 5.47 (d, J=6.6 Hz, 1H), 3.87 (m, 4H), 3.16 (m, 4H), 1.80 (d, J=6.6 Hz, 3H).

Compound 36b (S*)-4-((1-(1-isopropyl-1H-pyrazol-3-yl)ethyl)amino)-3-(6-morpholino-1H-benzo[d]-imidazol-2-yl)quinolin-2(1H)-one The reaction mixture was purified by Prep-HPLC (Column: WatersXBridge 30*150 mm 5 um, Flow rate: 20 mL/min, Mobile Phase A: Water (0.1% NH$_3$.H$_2$O), Mobile Phase B: Acetonitrile, Gradient: 35-55% (% B)). The desired fraction was collected and the volatile was removed under reduced pressure. The water phase was lyophilized to give compound 36 (mixture of stereoisomers) (110 mg, 13% yield) as yellow solids. The crude compound was further purified by prep. SFC (separation condition: Column: ChiralPak AD-H Daicel chemical Industries, Ltd, 250*25 mm I.D., 10 um; Mobile phase A: Supercritical CO$_2$, Mobile phase B: MeOH (0.1% DEA) A:B=50:50 at 60 ml/min, Column Temp: 25° C.; Nozzle Pressure: 100 Bar; Nozzle Temp: 60° C.; Evaporator Temp: 20° C.; Trimmer Temp: 25° C.; Wavelength: 220 nm) to afford compound 36b (31.35 mg, 28.5% yield, purity >99%) and compound 36a.

Compound 36b: LC-MS (ESI) General procedure B, method 5: $R_T$=1.18 min, mass calcd. for $C_{26}H_{25}N_7O_2$ 497.25, m/z found 498.2 [M+H]$^+$.

$^1$H NMR (400 MHz, DMSO-d$_6$) General procedure A: δ 12.86 (d, J=10.8 Hz, 1H), 11.95 (d, J=8.7 Hz, 0.5H), 11.84 (d, J=8.9 Hz, 0.5), 11.56 (s, 1H), 8.23-8.15 (m, 1H), 7.67-7.61 (m, 1H), 7.60-7.45 (m, 2H), 7.36 (d, J=8.2 Hz, 1H), 7.25 (d, J=1.9 Hz, 0.6H), 7.15 (t, J=7.7 Hz, 1H), 7.10 (d, J=1.5 Hz, 0.4H), 6.97 (td, J=9.1, 1.9 Hz, 1H), 6.22 (dd, J=4.2, 2.3 Hz, 1H), 5.44-5.35 (m, 1H), 4.41 (ddd, J=17.2, 8.9, 4.6 Hz, 1H), 3.78 (s, 4H), 3.11 (d, J=3.9 Hz, 4H), 1.66 (t, J=7.4 Hz, 3H), 1.35 (dd, J=6.4, 2.9 Hz, 6H).

Compound 37b 3-(6-((2R,6R)-2,6-dimethylmorpholino)-1H-benzo[d]imidazol-2-yl)-4-(((R*)-1-(pyrimidin-2-yl)ethyl)amino)quinolin-2(1H)-one and compound 37a 3-(6-((2R,6R)-2,6-dimethylmorpholino)-1H-benzo[d]imidazol-2-yl)-4-(((S*)-1-(pyrimidin-2-yl)ethyl)amino)quinolin-2(1H)-one The reaction mixture was purified by silica gel column chromatography (dichloromethane:methanol=30:1), to give the compound 37 (mixture of stereoisomers) as yellow solid (45 mg, yield 20.9%). The crude compound was further purified by prep. SFC (separation condition: Column: ChiralPak AD-H Daicel chemical Industries, Ltd, 250*25 mm I.D., 10 um; Mobile phase A: Supercritical CO$_2$, Mobile phase B: EtOH/ACN/DEA=85/15/0.2, A:B=50:50 at 60 mL/min; Column Temp: 25° C.; Nozzle Pressure: 100 Bar; Nozzle Temp: 60° C.; Evaporator Temp: 20° C.; Trimmer Temp: 25° C.; Wavelength: 220 nm) to afford compound 37b (17.16 mg, 38.13% yield, purity 96%) and compound 37a (14.79 mg, 32.87% yield, purity 97%).

Compound 37b: LC-MS (ESI) General procedure A, method 2: $R_T$=1.34 min, mass calcd. for $C_{28}H_{29}N_7O_2$ 495.2, m/z found 496.4 [M+H]$^+$.

$^1$H NMR (400 MHz, CD$_3$OD) General procedure B δ 8.67 (d, J=4.9 Hz, 2H), 8.09 (d, J=8.2 Hz, 1H), 7.52 (t, J=7.7 Hz, 2H), 7.35-7.23 (m, 2H), 7.18 (t, J=7.6 Hz, 1H), 7.11 (s, 1H), 7.00 (d, J=8.2 Hz, 1H), 5.38 (d, J=5.9 Hz, 1H), 4.23-4.12 (m, 2H), 3.21 (d, J=11.5 Hz, 2H), 2.90 (dd, J=11.5, 5.8 Hz, 2H), 1.76 (d, J=6.5 Hz, 3H), 1.33 (d, J=6.3 Hz, 6H).

Compound 37a: LC-MS (ESI) General procedure A, method 2: $R_T$=1.34 min, mass calcd. for $C_{28}H_{29}N_7O_2$ 495.2, m/z found 496.4 [M+H]$^+$.

$^1$H NMR (400 MHz, CD$_3$OD) General procedure A: δ 8.66 (d, J=4.9 Hz, 2H), 8.06 (d, J=8.2 Hz, 1H), 7.53-7.45 (m, 2H), 7.33-7.23 (m, 2H), 7.14 (dd, J=17.4, 9.8 Hz, 2H), 6.97 (d, J=8.6 Hz, 1H), 5.49-5.37 (m, 1H), 4.19-4.15 (m, 2H), 3.19 (d, J=9.4 Hz, 2H), 2.88 (dd, J=11.5, 5.8 Hz, 2H), 1.77 (d, J=6.6 Hz, 3H), 1.33 (d, J=6.4 Hz, 6H).

Compound 39a 3-(6-((2S,6S)-2,6-dimethylmorpholino)-1H-benzo[d] imidazol-2-yl)-4-(((S*)-1-(pyrimidin-2-yl)ethyl) amino)quinolin-2(1H)-one The reaction mixture was purified by silica gel column chromatography (dichloromethane:methanol=30:1), to give compound 39 (mixture of stereoisomers) as yellow solid (45 mg, yield 20.9%). The crude compound was further purified by prep. SFC (Separation condition: Column: ChiralCel OZ-H Daicel chemical Industries, Ltd, 250*30 mm I.D., 5 um, Mobile phase A: Supercritical CO$_2$, Mobile phase B: Ethanol (0.1% DEA), A:B=60:40 at 50 ml/min, Column Temp: 38° C., Nozzle Pressure: 100 Bar; Nozzle Temp: 60° C.; Evaporator Temp: 20° C.; Trimmer Temp: 25° C.; Wavelength: 220 nm) to afford compound 39a (8.96 mg, 19.91% yield, purity 99%).

LC-MS (ESI) General procedure A, method 2: $R_T$=1.30 min, mass calcd. for $C_2H_{29}N_7O_2$ 495.2, m/z found 496.3 [M+H]$^+$.

$^1$H NMR (400 MHz, DMSO-d$_6$) General procedure A: δ 12.85 (d, J=17.5 Hz, 1H), 12.09 (dd, J=45.6, 8.2 Hz, 1H), 11.57 (s, 1H), 8.86-8.74 (m, 2H), 8.06 (d, J=8.3 Hz, 1H), 7.57 (d, J=8.7 Hz, 0.6H), 7.49 (dd, J=14.9, 8.2 Hz, 1.4H), 7.41-7.31 (m, 2H), 7.22 (d, J=2.0 Hz, 0.6H), 7.09 (dd, J=15.1, 6.8 Hz, 1H), 6.97-6.92 (m, 1H), 5.55 (d, J=6.8 Hz, 1H), 4.12-4.08 (m, 2H), 3.16 (d, J=11.5 Hz, 2H), 2.88-2.78 (m, 2H), 1.76 (dd, J=9.7, 6.7 Hz, 3H), 1.27-1.24 (m, 6H).

Compound 40a

The reaction mixture was purified by silica gel column chromatography (dichloromethane:methanol=30:1) to give compound 40 (mixture of stereoisomers) as yellow solid (40 mg, yield 25.5%). The crude compound was further purified by prep. SFC (Separation condition: Column: ChiralPak AD-H Daicel chemical Industries, Ltd, 250*30 mm I.D., 5 um, Mobile phase A: Supercritical CO$_2$, Mobile phase B: Ethanol (0.1% DEA) A:B=50:50 at 50 ml/min Column Temp: 38° C. Nozzle Pressure: 100 Bar; Nozzle Temp: 60° C.; Evaporator Temp: 20° C.; Trimmer Temp: 25° C.; Wavelength: 220 nm) to compound 40a (7.17 mg, 17.9% yield, purity >99%) and compound 40b.

Compound 40a

LC-MS (ESI) General procedure A, method 2: $R_T$=1.23 min, mass calcd. for $C_{27}H_{27}N_7O_2$ 481.2, m/z found 482.3 [M+H]$^+$.

$^1$H NMR (400 MHz, CD$_3$OD) General procedure A: δ 8.67 (d, J=4.9 Hz, 2H), 8.08 (d, J=8.3 Hz, 1H), 7.51 (t, J=7.5 Hz, 2H), 7.35-7.23 (m, 2.5H), 7.16 (t, J=7.7 Hz, 1.54H), 7.03 (d, J=8.6 Hz, 1H), 5.44 (d, J=6.7 Hz, 1H), 4.00 (d, J=9.8 Hz, 1H), 3.83 (t, J=10.3 Hz, 2H), 3.48 (dd, J=32.3, 11.4 Hz, 2H), 2.80 (d, J=3.0 Hz, 1H), 2.47 (t, J=10.9 Hz, 1H), 1.78 (d, J=6.7 Hz, 3H), 1.24 (d, J=6.2 Hz, 3H).

Compound 41b (R*)-4-((1-(pyrimidin-2-yl)ethyl)amino)-3-(6-(4-(3, 3,3-trifluoropropyl)piperazin-1-yl)-1H-benzo[d]imidazol-2-yl)quinolin-2(1H)-one and compound 41a (S*)-4-((1-(pyrimidin-2-yl)ethyl)amino)-3-(6-(4-(3, 3,3-trifluoropropyl)piperazin-1-yl)-1H-benzo[d]imidazol-2-yl)quinolin-2(1H)-one The mixture was cooled to room temperature and then concentrated under reduced pressure. The residue was purified by silica gel chromatography (dichloromethane:methanol=50:1) and then further purified by Prep-HPLC (Column: WatersXBridge 30*150 mm 5 um, Flow rate: 20 mL/min, Mobile Phase A: Water (0.1% NH$_3$.H$_2$O), Mobile Phase B: Acetonitrile, Gradient: 35-55% (% B)). The desired fraction was collected and the volatile was removed under reduced pressure. The water phase was lyophilized to give compound 41 (mixture of stereoisomers)(40.0 mg, 21.6% yield) as yellow solids. The crude compound was further purified by prep. SFC (separation condition: Column: ChiralPak AD-H Daicel chemical Industries, Ltd, 250*30 mm I.D., 5 um; Mobile phase A: Supercritical CO$_2$, Mobile phase B: Ethanol (0.1% DEA), A:B=60:40 at 50 mL/min; Column Temp: 38° C.; Nozzle Pressure: 100 Bar; Nozzle Temp: 60° C.; Evaporator Temp: 20° C.; Trimmer Temp: 25° C.; Wavelength: 220 nm) to afford compound 41b (15.10 mg, 37.8% yield, purity >99%) and compound 41a (15.00 mg, 37.5% yield, purity >99%).

Compound 41b: LC-MS (ESI) General procedure B, method 2: $R_T$=1.08 min, mass calcd. for $C_{29}H_{29}F_3N_8O$ 562.2, m/z found 563.3 [M+H]$^+$.

$^1$H NMR (400 MHz, CD$_3$OD) General procedure A: δ: 8.68 (d, J=4.8 Hz, 2H), 8.09 (d, J=8.4 Hz, 1H), 7.53-7.49 (m, 2H), 7.33 (d, J=8.0 Hz, 1H), 7.28-7.25 (m, 1H), 7.19-7.15 (m, 2H), 7.04-7.02 (m, 1H), 5.47 (q, J=6.8 Hz, 1H), 3.24-3.22 (m, 4H), 2.72-2.65 (m, 6H), 2.50-2.41 (m, 2H), 1.79 (d, J=6.8 Hz, 3H).

Compound 41a: LC-MS (ESI) General procedure A, method 4: $R_T$=0.59 min, mass calcd. for $C_{29}H_{29}F_3N_8O$ 562.2, m/z found 563.3 [M+H]$^+$.

$^1$H NMR (400 MHz, CD$_3$OD) General procedure A: δ: 8.67 (d, J=4.8 Hz, 2H), 8.09 (d, J=8.4 Hz, 1H), 7.52 (t, J=7.2 Hz, 2H), 7.32 (d, J=7.6 Hz, 1H), 7.27-7.25 (m, 1H), 7.18 (t, J=7.6 Hz, 2H), 7.04-7.01 (m, 1H), 5.47 (q, J=6.8 Hz, 1H), 3.23-3.21 (m, 4H), 2.72-2.66 (m, 6H), 2.53-2.43 (m, 2H), 1.79 (d, J=6.8 Hz, 3H).

Compound 43a (S*)-4-((1-(pyrimidin-2-yl)ethyl)amino)-3-(6-(4-(trifluoromethoxy)piperidin-1-yl)-1H-benzo[d]imidazol-2-yl)quinolin-2(1H)-one The mixture was cooled to room temperature and then concentrated under reduced pressure. The residue was purified by silica gel chromatography (dichloromethane:methanol=30:1) and then further purified by Prep-HPLC (Column:

WatersXBridge 30*150 mm 5 um, Flow rate: 20 mL/min, Mobile Phase A: Water (0.1% $NH_3.H_2O$), Mobile Phase B: Acetonitrile, Gradient: 35-55% (% B)). The desired fraction was collected and the volatile was removed under reduced pressure. The water phase was lyophilized to give compound 43 (mixture of stereoisomers) (40.0 mg, 22.1% yield) as yellow solids. The crude compound was further purified by prep. SFC (separation condition: Column: ChiralPak AD-H Daicel chemical Industries, Ltd, 250*30 mm I.D., 5 u; Mobile phase A: Supercritical $CO_2$, Mobile phase B: Ethanol (0.1% DEA), A:B=60:40 at 50 mL/min; Column Temp: 38° C.; Nozzle Pressure: 100 Bar; Nozzle Temp: 60° C.; Evaporator Temp: 20° C.; Trimmer Temp: 25° C.; Wavelength: 220 nm) to afford the title compound 43a (15.35 mg, 38.4% yield, purity >99%) and compound 43b.

Compound 43a

LC-MS (ESI) General procedure B, method 2: $R_T$=1.48 min, mass calcd. for $C_{28}H_{26}F_3N_7O_2$ 549.2, m/z found 550.3 $[M+H]^+$.

$^1$H NMR (400 MHz, $CD_3OD$) General procedure A: δ: 8.68 (d, J=4.8 Hz, 2H), 8.09 (d, J=8.0 Hz, 1H), 7.53-7.49 (m, 2H), 7.33 (d, J=8.0 Hz, 1H), 7.28 (t, J=8.4 Hz, 1H), 7.19-7.15 (m, 2H), 7.05-7.03 (m, 1H), 5.47 (q, J=6.8 Hz, 1H), 4.55-4.51 (m, 1H), 3.49-3.46 (m, 2H), 3.10-3.04 (m, 2H), 2.15 (m, 2H), 2.02-1.97 (m, 2H), 1.79 (d, J=6.8 Hz, 3H).

Compound 44a 3-(6-(8-oxa-3-azabicyclo[3.2.1]octan-3-yl)-1H-benzo[d]imidazol-2-yl)-4-(((S*)-1-(pyrimidin-2-yl)ethyl)amino)quinolin-2(1H)-one The reaction mixture was purified by silica gel column chromatography (dichloromethane:methanol=30:1) to give compound 44 (mixture of stereoisomers) as yellow solid (50 mg, yield 15.6%). The crude compound was further purified by prep. SFC (Separation condition: Column: ChiralCel OZ-H Daicel chemical Industries, Ltd, 250*30 mm I.D., 5 um. Mobile phase A: Supercritical $CO_2$, Mobile phase B: Ethanol (0.1% DEA) A:B=60:40 at 50 ml/min Column Temp: 38° C. Nozzle Pressure: 100 Bar; Nozzle Temp: 60° C.; Evaporator Temp: 20° C.; Trimmer Temp: 25° C.; Wavelength: 220 nm) to afford compound 44a (2.58 mg, 5.2% yield, purity 98%) and compound 44b.

Compound 44a

LC-MS (ESI) General procedure A, method 2: $R_T$=1.25 min, mass calcd. for $C_2H_{27}N_7O_2$ 493.2, m/z found 494.3 $[M+H]^+$.

$^1$H NMR (400 MHz, DMSO-$d_6$) General procedure A: δ 8.74-8.72 (m, 2H), 8.02 (d, J=8.2 Hz, 1H), 7.51-7.44 (m, 2H), 7.33 (d, J=6.6 Hz, 2H), 7.13-7.09 (m, 1H), 7.05 (s, 0.6H), 7.05 (s, 0.4H), 6.91-6.86 (m, 1H), 5.48 (d, J=6.7 Hz, 1H), 4.43 (s, 2H), 3.37 (d, J=10.7 Hz, 3H), 2.82 (d, J=11.0 Hz, 2H), 1.90-1.81 (m, 4H), 1.74-1.71 (m, 3H).

Compound 45

(S*)-3-(6-morpholino-5-(trifluoromethyl)-1H-benzo[d]imidazol-2-yl)-4-((1-(pyrimidin-2-yl)ethyl)amino)quinolin-2(1H)-one The mixture was cooled to room temperature and purified by Prep-HPLC (Column: WatersXBridge 30*150 mm 5 um, Flow rate: 20 mL/min, Mobile Phase A: Water (0.1% $NH_3.H_2O$), Mobile Phase B: Acetonitrile, Gradient: 35-55% (% B)). The desired fraction was collected and the volatile was removed under reduced pressure. The water phase was lyophilized to give the title compound as a mixture of stereoisomers (50.0 mg, 20.8% yield) as yellow solids. The crude compound was further purified by prep. SFC (separation condition: Column: ChiralPak AD-H Daicel chemical Industries, Ltd, 250*30 mm I.D., 5 u; Mobile phase A: Supercritical $CO_2$, Mobile phase B: Ethanol (0.1% DEA), A:B=60:40 at 50 mL/min; Column Temp: 38° C.; Nozzle Pressure: 100 Bar; Nozzle Temp: 60° C.; Evaporator Temp: 20° C.; Trimmer Temp: 25° C.; Wavelength: 220 nm) to afford compound 45 (9.00 mg, 18.0% yield, purity >99%) and compound 45a.

LC-MS (ESI) General procedure B, method 2: $R_T$=1.92 min, mass calcd. for $C_{27}H_{24}F_3N_7O_2$ 535.1, m/z found 536.2 $[M+H]^+$.

$^1$H NMR (400 MHz, $CD_3OD$) General procedure A: δ: 8.72-8.70 (m, 2H), 8.11 (d, J=8.4 Hz, 1H), 7.93-7.90 (m, 1H), 7.79-7.73 (m, 1H), 7.54-7.51 (m, 1H), 7.33-7.29 (m, 2H), 7.18-7.14 (m, 1H), 5.57 (q, J=6.8 Hz, 1H), 3.84 (m, 4H), 2.98 (m, 4H), 1.83-1.81 (m, 3H).

Compound 46

(S)-3-(4-methyl-6-morpholino-1H-benzo[d]imidazol-2-yl)-4-((1-(pyrimidin-2-yl)ethyl)-amino)quinolin-2(1H)-one The reaction mixture was purified by Prep-HPLC (Column: WatersXBridge 30*150 mm 5 um, Flow rate: 20 mL/min, Mobile Phase A: Water (0.1% $NH_3.H_2O$), Mobile Phase B: Acetonitrile, Gradient: 35-55% (% B)). The desired fraction was collected and the volatile was removed under reduced pressure. The water phase was lyophilized to give compound 46 (50 mg, 20.5% yield) as yellow solids.

LC-MS (ESI) General procedure A, method 3: $R_T$=1.02 min, mass calcd. for $C_{27}H_{27}N_7O_2$ 481.22, m/z found 482.2 $[M+H]^+$.

$^1$H NMR (400 MHz, $CD_3OD$) General procedure A: δ 8.68 (d, J=4.8 Hz, 2H), 8.10 (d, J=8.3 Hz, 1H), 7.49 (t, J=7.4 Hz, 1H), 7.35-7.24 (m, 2H), 722-7.04 (m, 1H), 6.96 (s, 1H), 6.84 (s, 1H), 5.55 (d, J=6.6 Hz, 1H), 3.87 (s, 4H), 3.20-3.02 (m, 4H), 2.64-2.52 (m, 3H), 1.82 (d, J=6.6 Hz, 3H).

Compound 47

(S)-3-(7-methyl-6-morpholino-1H-benzo[d]imidazol-2-yl)-4-((1-(pyrimidin-2-yl)-ethyl)amino)quinolin-2(1H)-one The reaction mixture was purified by Prep-HPLC (Column: WatersXBridge 30*150 mm 5 um, Flow rate: 20 mL/min, Mobile Phase A: Water (0.1% $NH_3.H_2O$), Mobile Phase B: Acetonitrile, Gradient: 35-55% (% B)). The desired fraction was collected and the volatile was removed under reduced pressure. The water phase was lyophilized to give the title compound as a mixture of stereoisomers (80 mg, 32.8% yield) as yellow solids. The crude compound was further purified by prep. SFC (separation condition: Column: ChiralPak AD-H Daicel chemical Industries, Ltd, 250*30 mm I.D., 5 um; Mobile phase A: Supercritical $CO_2$, Mobile phase B: Ethanol (0.1% DEA), A:B=50:50 at 50 mL/min; Column Temp: 38° C.; Nozzle Pressure: 100 Bar; Nozzle Temp: 60° C.; Evaporator Temp: 20° C.; Trimmer Temp: 25° C.; Wavelength: 220 nm) to afford compound 47 (60.36 mg, 75.5% yield, purity >99%).

LC-MS (ESI) General procedure A, method 3: $R_T$=1.13 min, mass calcd. for $C_{27}H_{27}N_7O_2$ 481.22, m/z found 482.3 [M+H]$^+$.

$^1$H NMR (400 MHz, CD$_3$OD) General procedure A: δ 8.68 (d, J=4.8 Hz, 2H), 8.10 (d, J=8.3 Hz, 1H), 7.49 (t, J=7.4 Hz, 1H), 7.35-7.30 (m, 2H), 7.28-7.26 (m, 1H), 7.14 (s, 1H), 7.10-7.07 (s, 1H), 5.55 (d, J=6.6 Hz, 1H), 3.88 (m, 4H), 2.95 (m, 4H), 2.67-2.51 (m, 3H), 1.80 (d, J=6.6 Hz, 3H).

Compound 48a (S*)-4-((1-(4-methoxypyridin-2-yl)ethyl)amino)-3-(6-morpholino-1H-benzo[d]imidazol-2-yl)quinolin-2(1H)-one The reaction mixture was purified by Prep-HPLC (Column: WatersXBridge 30*150 mm 5 um, Flow rate: 20 mL/min, Mobile Phase A: Water (0.1% NH$_3$.H$_2$O), Mobile Phase B: Acetonitrile, Gradient: 35-55% (% B)). The desired fraction was collected and the volatile was removed under reduced pressure. The water phase was lyophilized to give compound 48 (mixture of stereoisomers) (300 mg, 32.9% yield) as brown solids. The crude compound was further purified by prep. SFC (separation condition: Column: ChiralPak AD-H Daicel chemical Industries, Ltd, 250*30 mm I.D., 5 um; Mobile phase A: Supercritical CO$_2$, Mobile phase B: Ethanol (0.1% DEA), A:B=60:40 at 50 mL/min; Column Temp: 38° C.; Nozzle Pressure: 100 Bar; Nozzle Temp: 60° C.; Evaporator Temp: 20° C.; Trimmer Temp: 25° C.; Wavelength: 220 nm) to afford compound 48a (77.41 mg, 25.8% yield, purity >99%) and compound 48b.

Compound 48a: LC-MS (ESI) General procedure B, method 2: $R_T$=1.17 min, mass calcd. for $C_{28}H_{28}N_6O_3$ 496.2, m/z found 497.2 [M+H]$^+$.

$^1$H NMR (400 MHz, CD$_3$OD) General procedure A: δ 8.25 (d, J=5.9, 1H), 7.96 (d, J=8.2, 1H), 7.63-7.45 (m, 2H), 7.35-7.02 (m, 5H), 6.85-6.77 (m, 1H), 5.44-5.34 (m, 1H), 3.93-3.85 (m, 4H), 3.64 (s, 3H), 3.19-3.13 (m, 4H), 1.77 (d, J=6.7, 3H).

Compound 49a (S*)-4-((1-(4-isopropylpyrimidin-2-yl)ethyl)amino)-3-(6-morpholino-1H-benzo[d]-imidazol-2-yl)quinolin-2(1H)-one The reaction mixture was purified by Prep-HPLC (Column: WatersXBridge 30*150 mm 5 um, Flow rate: 20 mL/min, Mobile Phase A: Water (0.1% NH$_3$.H$_2$O), Mobile Phase B: Acetonitrile, Gradient: 35-55% (% B)). The desired fraction was collected and the volatile was removed under reduced pressure. The water phase was lyophilized to give compound 49 (mixture of stereoisomers) (60 mg, 26.1% yield) as brown solids. The crude compound was further purified by prep. SFC (separation condition: Column: ChiralPak AD-H Daicel chemical Industries, Ltd, 250*30 mm I.D., 5 um; Mobile phase A: Supercritical CO$_2$, Mobile phase B: Ethanol (0.1% DEA), A:B=60:40 at 50 mL/min; Column Temp: 38° C.; Nozzle Pressure: 100 Bar; Nozzle Temp: 60° C.; Evaporator Temp: 20° C.; Trimmer Temp: 25° C.; Wavelength: 220 nm) to afford the title compound 49a (8.53 mg, 14.2% yield, purity >99%) and compound 49b.

Compound 49a: LC-MS (ESI) General procedure B, method 2: $R_T$=1.47 min, mass calcd. for $C_{29}H_{31}N_7O_2$ 509.2, m/z found 510.2 [M+H]$^+$.

$^1$H NMR (400 MHz, CD$_3$OD) General procedure A: δ 8.47 (d, J=5.2 Hz, 1H), 8.14 (d, J=8.4 Hz, 1H), 7.63-6.97 (m, 7H), 5.50-5.42 (m, 1H), 3.94-3.83 (m, 4H), 3.21-3.13 (m, 4H), 2.87-2.76 (m, 1H), 1.80 (d, J=6.6 Hz, 3H), 1.10 (dd, J=6.8, 2.7 Hz, 6H).

Compound 50a (S*)-4-((1-(4-cyclopropylpyrimidin-2-yl)ethyl)amino)-3-(6-morpholino-H-benzo[d]-imidazol-2-yl)quinolin-2(1H)-one The reaction mixture was purified by Prep-HPLC (Column: WatersXBridge 30*150 mm 5 um, Flow rate: 20 mL/min, Mobile Phase A: Water (0.1% NH$_3$.H$_2$O), Mobile Phase B: Acetonitrile, Gradient: 35-55% (% B)). The desired fraction was collected and the volatile was removed under reduced pressure. The water phase was lyophilized to give compound 50 (mixture of stereoisomers) (120 mg, 20.8% yield) as brown solids. The crude compound was further purified by prep. SFC (separation condition: Column: ChiralPak AD-H Daicel chemical Industries, Ltd, 250*25 mm I.D., 10 um; Mobile phase A: Supercritical CO$_2$, Mobile phase B: EtOH/ACN/DEA=95/5/0.2; A:B=50:50 at 70 mL/min; Column Temp: 25° C.; Nozzle Pressure: 100 Bar; Nozzle Temp: 60° C.; Evaporator Temp: 20° C.; Trimmer Temp: 25° C.; Wavelength: 220 nm) to afford compound 50a (58.16 mg, 48.5% yield, purity >99%) and compound 50b.

Compound 50a: LC-MS (ESI) General procedure B, method 2: $R_T$=1.41 min, mass calcd. for $C_{29}H_{29}N_7O_2$ 507.2, m/z found 508.2 [M+H]$^+$.

$^1$H NMR (400 MHz, CD$_3$OD) General procedure A: δ 8.34 (d, J=5.3, 1H), 8.16 (d, J=8.1, 1H), 7.59-7.50 (m, 2H), 7.33 (d, J=8.2, 1H), 7.26-7.06 (m, 4H), 5.27-5.13 (m, 1H), 3.93-3.84 (m, 4H), 3.22-3.16 (m, 4H), 1.96-1.88 (m, 1H), 1.69 (d, J=6.4, 3H), 0.98-0.78 (m, 4H).

Compound 51a (S*)-3-(6-morpholino-1H-benzo[d]imidazol-2-yl)-4-((1-(oxazol-4-yl)ethyl)amino)-quinolin-2(1H)-one The reaction mixture was purified by Prep-HPLC (Column: WatersXBridge 30*150 mm 5 um, Flow rate: 20 mL/min, Mobile Phase A: Water (0.1% NH$_3$.H$_2$O), Mobile Phase B: Acetonitrile, Gradient: 35-55% (% B)). The desired fraction was collected and the volatile was removed under reduced pressure. The water phase was lyophilized to give compound 51 (mixture of stereoisomers) (130 mg, 21.7% yield) as yellow solids. The crude compound was further purified by prep. SFC (separation condition: Column: ChiralPak AD-H Daicel chemical Industries, Ltd, 250*30 mm I.D., 5 um; Mobile phase A: Supercritical CO$_2$, Mobile phase B: Ethanol (0.1% DEA), A:B=60:40 at 50 mL/min; Column Temp: 38° C.; Nozzle Pressure: 100 Bar; Nozzle Temp: 60° C.; Evaporator Temp: 20° C.; Trimmer Temp: 25° C.; Wavelength: 220 nm) to afford compound 51a (48.32 mg, 37.2% yield, purity >99%) and compound 51b.

Compound 51a: LC-MS (ESI) General procedure A, method 3: $R_T$=1.10 min, mass calcd. for $C_{25}H_{24}N_6O_3$ 456.19, m/z found 457.2 [M+H]$^+$.

$^1$H NMR (400 MHz, CD$_3$OD) General procedure A: δ 8.13 (s, 1H), 8.09 (d, J=8.3 Hz, 1H), 7.89 (t, J=7.4 Hz, 1H), 7.56-7.53 (m, 2H), 7.36-7.34 (m, 1H), 7.22-7.18 (m, 1H), 7.03-7.01 (s, 1H), 5.27 (d, J=6.6 Hz, 1H), 3.87 (m, 4H), 3.16 (m, 4H), 1.71 (d, J=6.6 Hz, 3H).

Compound 52a (S*)-3-(6-morpholino-1H-benzo[d]imidazol-2-yl)-4-((1-(thiazol-4-yl)ethyl)amino)-quinolin-2(1H)-one The reaction mixture was purified by Prep-HPLC (Column: WatersXBridge 30*150 mm 5 um, Flow rate: 20 mL/min, Mobile Phase A: Water (0.1% $NH_3.H_2O$), Mobile Phase B: Acetonitrile, Gradient: 35-55% (% B)). The desired fraction was collected and the volatile was removed under reduced pressure. The water phase was lyophilized to give compound 52 (mixture of stereoisomers) (110 mg, 17.7% yield) as yellow solids. The crude compound was further purified by prep. SFC (separation condition: Column: ChiralCel OZ-H Daicel chemical Industries, Ltd, 250*30 mm I.D., 5 um; Mobile phase A: Supercritical $CO_2$, Mobile phase B: Ethanol (0.1% DEA), A:B=60:40 at 50 mL/min; Column Temp: 38° C.; Nozzle Pressure: 100 Bar; Nozzle Temp: 60° C.; Evaporator Temp: 20° C.; Trimmer Temp: 25° C.; Wavelength: 220 nm) to afford compound 52a (25.88 mg, 23.5% yield, purity >99%) and compound 52b.

Compound 52a: LC-MS (ESI) General procedure A, method 3: $R_T$=1.12 min, mass calcd. for $C_{25}H_{24}N_6O_2S$ 472.17, m/z found 473.2 [M+H]$^+$.

$^1$H NMR (400 MHz, $CD_3OD$) General procedure A: δ 8.96 (d, J=4.8 Hz, 1H), 8.01 (d, J=8.3 Hz, 1H), 7.52 (t, J=7.4 Hz, 3H), 7.34-7.32 (d, J=8.0 Hz, 1H), 7.16-7.12 (m, 2H), 7.02 (s, 1H), 5.55 (d, J=6.6 Hz, 1H), 3.88 (m, 4H), 3.22 (m, 4H), 1.78 (d, J=6.6 Hz, 3H).

Compound 53b (R*)-3-(6-(1-methyl-1H-pyrazol-4-yl)-1H-benzo[d]imidazol-2-yl)-4-((1-(pyrimidin-2-yl)ethyl)amino) quinolin-2(1H)-one and compound 53a (S*)-3-(6-(1-methyl-1H-pyrazol-4-yl)-1H-benzo[d]imidazol-2-yl)-4-((1-(pyrimidin-2-yl)ethyl)amino) quinolin-2(1H)-one Water (20 mL) was added to the reaction mixture and filtered in reduced pressure. The filter cake was washed with diethyl ether to afford compound 53 (mixture of stereoisomers) (200 mg, 12.4% yield) as yellow solid. The crude compound was further purified by prep. SFC (Separation condition: Column: ChiralCel OJ-H Daicel chemical Industries, Ltd, 250*30 mm I.D., 5 um, Mobile phase A: Supercritical $CO_2$, Mobile phase B: Methanol (0.1% DEA) A:B=60:40 at 50 ml/min Column Temp: 38° C. Nozzle Pressure: 100 Bar; Nozzle Temp: 60° C.; Evaporator Temp: 20° C.; Trimmer Temp: 25° C.; Wavelength: 220 nm) to afford compound 53b (29.27 mg, 14.64% yield, purity >99%) and compound 53a (40.90 mg, 20.45% yield, purity 99%).

Compound 53b: LC-MS (ESI) General procedure A, method 2: $R_T$=1.29 min, mass calcd. for $C_{26}H_{22}N_8O$ 462.2, m/z found 463.4 [M+H]$^+$.

$^1$H NMR (400 MHz, DMSO-$d_6$) General procedure A: δ 13.02 (s, 1H), 12.13 (dd, J=23.8, 8.1 Hz, 1H), 11.60 (s, 1H), 8.79 (dd, J=4.8, 3.6 Hz, 2H), 8.17 (s, 0.5H), 8.09-8.05 (m, 1.5 zH), 7.88 (d, J=17.6 Hz, 1H), 7.79 (d, J=16.2 Hz, 1H), 7.68 (d, J=8.4 Hz, 0.5H), 7.58 (d, J=8.3 Hz, 0.5H), 7.51 (t, J=7.5 Hz, 1H), 7.44-7.33 (m, 3H), 7.11 (t, J=7.6 Hz, 1H), 5.61-5.53 (m, 1H), 3.88 (d, J=4.7 Hz, 3H), 1.78 (t, J=7.0 Hz, 3H).

Compound 53a: LC-MS (ESI) General procedure A, method 2: $R_T$=1.28 min, mass calcd. for $C_{26}H_{22}N_8O$ 462.2, m/z found 463.4 [M+H]$^+$.

$^1$H NMR (400 MHz, DMSO-$d_6$) General procedure A: δ 13.02 (s, 1H), 12.13 (dd, J=23.9, 8.2 Hz, 1H), 11.60 (d, J=3.6 Hz, 1H), 8.79 (dd, J=4.8, 3.5 Hz, 2H), 8.17 (s, 0.5H), 8.09-8.04 (m, 1.5H), 7.88 (d, J=17.5 Hz, 1H), 7.79 (d, J=16.0 Hz, 1H), 7.68 (d, J=8.2 Hz, 0.5H), 7.58 (d, J=8.3 Hz, 0.5H), 7.51 (t, J=7.4 Hz, 1H), 7.44-7.33 (m, 3H), 7.11 (t, J=7.6 Hz, 1H), 5.61-5.52 (m, 1H), 3.88 (d, J=4.7 Hz, 3H), 1.78 (t, J=7.0 Hz, 3H).

Compound 55

(S)-3-(6-Morpholino-1H-benzo[d]imidazol-2-yl)-4-((1-(pyridin-2-yl)ethyl)amino)-quinolin-2(1H)-one After the reaction was finished, the reaction mixture was then poured into 20 mL of water and extracted with DCM (20 mL×3). The combined organic layers were washed with brine (20 mL), dried over $Na_2SO_4$ and filtered. The filtrate was concentrated to dryness which was purified by prep. TLC (DCM:MeOH=10:1) to afford the partially purified materials as brown oil. The product was partitioned between acetonitrile (10 mL) and water (5 mL). The solution was lyophilized to give compound 55 (15.0 mg, 98.8% purity, 13.4% yield) as yellow solids.

LC-MS (ESI) General procedure B-2, method 5: $R_T$=3.360 min, mass calcd. for $C_{27}H_{26}N_6O_2$ 466.21, m/z found 467.0 [M+H]$^+$.

$^1$H NMR (400 MHz, DMSO-$d^6$) General procedure B δ 12.92 (br. s., 0.4H), 12.89 (br. s., 0.6H), 12.31 (d, J=7.9 Hz, 0.4H), 12.18 (d, J=8.2 Hz, 0.6H), 11.61 (br. s., 1H), 8.58-8.52 (m, 1H), 7.97 (d, J=8.4 Hz, 1H), 7.81-7.72 (m, 1H), 7.59 (d, J=8.8 Hz, 0.4H), 7.54-7.45 (m, 2.6H), 7.34 (d, J=8.2 Hz, 1H), 7.29-7.22 (m, 1.6H), 7.13 (s, 0.4H), 7.10-7.03 (m, 1H), 7.02-6.93 (m, 1H), 5.55-5.45 (m, 1H), 3.81-3.73 (m, 4H), 3.18-3.04 (m, 4H), 1.76-1.68 (m, 3H).

Compound 56

(S)-3-(6-(4-isopropylpiperazin-1-yl)-1H-benzo[d]imidazol-2-yl)-4-((1-(pyridin-2-yl)-ethyl)amino) quinolin-2(1H)-one After the reaction was finished, the reaction mixture was poured into 45 mL of water and extracted with DCM (20 mL×3). The combined organic layers were washed with brine (50 mL), dried over $Na_2SO_4$ and filtered. The filtrate was concentrated to dryness which was purified by prep. TLC (DCM:MeOH=10:1) to give the product as brown oil. The product was partitioned between acetonitrile (10 mL) and water (5 mL). The solution was lyophilized to dryness to give compound 56 (20.0 mg, 96.3% purity, 8.90% yield) as yellow solids.

LC-MS (ESI) General procedure B-2, method 4: $R_T$=5.307 min, mass calcd. for $C_{30}H_{33}N_7O$ 507.27, m/z found 508.1 [M+H]$^+$.

$^1$H NMR (400 MHz, DMSO-$d^6$) General procedure B: δ 12.92-12.82 (m, 1H), 12.32-12.27 (m, 0.5H), 12.20-12.12 (m, 0.5H), 11.58 (br s, 1H), 8.54 (d, J=4.0 Hz, 1H), 7.97 (d, J=8.4 Hz, 1H), 7.79-7.72 (m, 1H), 7.58-7.43 (m, 3H), 7.38-7.30 (m, 1H), 7.30-7.19 (m, 1.5H), 7.12-7.02 (m, 1.5H), 7.01-6.90 (m, 1H), 5.48 (br d, J=7.3 Hz, 1H), 3.12 (br s, 4H), 2.72-2.66 (m, 1H), 2.63 (br s, 4H), 1.78-1.65 (m, 3H), 1.03 (d, J=6.4 Hz, 6H).

Compound 7

(S)-Methyl-1-(2-(2-oxo-4-((1-(pyridin-2-yl)ethyl)amino)-1,2-dihydroquinolin-3-yl)-1H-benzo[d]imidazol-6-yl)piperidine-4-carboxylate After the reaction was finished, the mixture was concentrated to dryness which was purified by prep.HPLC(Column: Phenomenex Gemini 150*25 mm*10 um, Mobile Phase A: water (0.05% ammonia hydroxide v/v), Mobile Phase B: acetonitrile, Flow rate: 25 mL/min, gradient condition from 51% B to 81%). The pure fractions were collected and the solvent was evaporated under vacuum, and then lyophilized to give compound 7 (70 mg, 96.62% purity, 37.7 yield) as yellow solids.

LC-MS (ESI) General procedure B-2, method 5: $R_T$=3.706 min, mass calcd. for $C_{30}H_{30}N_6O_3$ 522.24, m/z found 523.0 [M+H]$^+$.

$^1$H NMR (400 MHz, DMSO-d$^6$) General procedure B: δ 12.91 (br. s., 0.4H), 12.86 (br. s., 0.6H), 12.32 (d, J=8.2 Hz, 0.4H), 12.19 (d, J=8.2 Hz, 0.6H), 11.59 (br. s., 1H), 8.58-8.52 (m, 1H), 7.96 (d, J=8.2 Hz, 1H), 7.81-7.72 (m, 1H), 7.57 (d, J=8.8 Hz, 0.4H), 7.53-7.44 (m, 2.6H), 7.34 (d, J=8.2 Hz, 1H), 7.28-7.22 (m, 1.6H), 7.13 (s, 0.4H), 7.09-7.03 (m, 1H), 7.00-6.93 (m, 1H), 5.58-5.42 (m, 1H), 3.64 (s, 3H), 3.61-3.54 (m, 2H), 2.83-2.70 (m, 2H), 2.54-2.53 (m, 1H), 1.96 (d, J=13.0 Hz, 2H), 1.80-1.65 (m, 5H).

Compound 57

(S*)-tert-butyl 1-(2-(2-oxo-4-((1-(pyrimidin-2-yl)ethyl)amino)-1,2-dihydroquinolin-3-yl)-5-(trifluoromethyl)-1H-benzo[d]imidazol-6-yl)piperidine-4-carboxylate The resultant mixture was concentrated to dryness under reduced pressure to afford the crude product.

The crude product was purified by prep. HPLC (Column: Phenomenex Gemini 150×25 mm×10 um, Mobile Phase A: water (0.05% ammonia hydroxide v/v), Mobile Phase B: acetonitrile, Flow rate: 25 mL/min, gradient condition from 75% B to 100%). The pure fractions were collected and the volatiles were removed under vacuum. The residue was suspended in water (10 mL) and the resulting mixture was lyophilized to give the racemic compounds (101 mg, 95% purity, 33.7% yield) as yellow solids. Then theracemic products were separated by Supercritical Fluid Chromatography (separation condition: AD (250 mm×30 mm, 10 um); Mobile phase: A: Supercritical CO$_2$, B: 0.1% NH$_3$H$_2$OEtOH, A:B=55:45 at 80 mL/min; Column Temp: 38; Nozzle Pressure: 100 Bar; Nozzle Temp: 60; Evaporator Temp: 20; Trimmer Temp: 25; Wavelength: 220 nm). The two fractions were collected and the solvent was evaporated under vacuum. The two residues were re-suspended in water (10 mL) and the resulting mixtures were lyophilized to dryness to give compound 57 (39.3 mg, 99.9% purity, 13.2% yield).

LC-MS (ESI) General procedure B-2, method 6: $R_T$=5.242 min, mass calcd. for $C_{33}H_{34}F_3N_7O_3$ 633.27, m/z found 634.0 [M+H]$^+$.

$^1$H NMR (400 MHz, DMSO-d$^6$) General procedure B: δ 13.30 (br. s., 0.5H), 13.28 (br. s., 0.5H), 12.10 (d, J=7.1 Hz, 0.5H), 11.97 (d, J=7.3 Hz, 0.5H), 11.62 (s, 1H), 8.79 (s, 2H), 8.08 (s, 1H), 8.05 (s, 0.5H), 7.86 (d, J=6.0 Hz, 1H), 7.72 (s, 0.5H), 7.52 (t, J=6.8 Hz, 1H), 7.41-7.32 (m, 2H), 7.11 (t, J=7.4 Hz, 1H), 5.64-5.54 (m, 1H), 3.03-2.93 (m, 2H), 2.92-2.84 (m, 1H), 2.81-2.70 (m, 1H), 2.43-2.36 (m, 1H), 2.06-1.94 (m, 1H), 1.93-1.85 (m, 2H), 1.81-1.75 (m, 3H), 1.72-1.66 (m, 1H), 1.44 (s, 9H).

Compound 58

(S*)-1-(2-(2-oxo-4-((1-(pyrimidin-2-yl)ethyl)amino)-1,2-dihydroquinolin-3-yl)-5-(trifluoromethyl)-1H-benzo[d]imidazol-6-yl)piperidine-4-carboxylic acid The resultant mixture was concentrated to dryness under reduced pressure to afford the crude product. The crude mixture product was purified by preparative HPLC (Column: Phenomenex Gemini C18 250×50 10 u, Mobile Phase A: water (0.225% FA); Mobile Phase B: acetonitrile, Flow rate: 22 mL/min, gradient condition from 38% B to 68%). The pure fractions were collected and the volatiles were removed under vacuum. The residue was suspended in water (10 mL) and the resulting mixture was lyophilized to give the racemic compounds (50 mg, 97% purity) as yellow solid. The racemic compounds were separated by Supercritical Fluid Chromatography (separation condition: AD (250 mm×30 mm, 10 um); Mobile phase: A: Supercritical CO$_2$, B: 0.1% NH$_3$H$_2$O EtOH, A:B=55:45 at 80 mL/min; Column Temp: 38; Nozzle Pressure: 100 Bar; Nozzle Temp: 60; Evaporator Temp: 20; Trimmer Temp: 25; Wavelength: 220 nm). The two fractions were collected and the solvent was evaporated under vacuum. The two residues were re-suspended in water (10 mL) and the resulting mixtures were lyophilized to dryness to give compound 58 (6.5 mg, 100% purity, 12.3% yield).

LC-MS (ESI) General procedure B-2, method 5: $R_T$=5.147 min, mass calcd. for $C_{29}H_{26}F_3N_7O_3$ 577.20, m/z found 578.2 [M+H]$^+$.

$^1$H NMR (400 MHz, DMSO-d$^6$) General procedure B: δ 13.28 (s, 0.5H), 13.24 (s, 0.5H), 12.12 (d, J=7.7 Hz, 0.5H), 11.95 (d, J=7.9 Hz, 0.5H), 11.61 (s, 1H), 8.78 (t, J=5.3 Hz, 2H), 8.08 (s, 1H), 8.06 (s, 0.5H), 7.90-7.84 (m, 1H), 7.73 (s, 0.5H), 7.53 (t, J=7.7 Hz, 1H), 7.41-7.32 (m, 2H), 7.11 (t, J=7.6 Hz, 1H), 5.66-5.54 (m, 1H), 3.02-2.94 (m, 2H), 2.93-2.83 (m, 1H), 2.83-2.71 (m, 1.5H), 2.70-2.66 (m, 0.5H), 1.96-1.87 (m, 2H), 1.83-1.76 (m, 3H), 1.75-1.64 (m, 2H).

Compound 59

(Rac)-methyl 4-(2-(2-oxo-4-(((S)-1-(pyridin-2-yl)ethyl)amino)-1,2-dihydroquinolin-3-yl)-1H-benzo[d]imidazol-6-yl)morpholine-2-carboxylate After the reaction was finished, the mixture was basified by saturated sodium bicarbonate solution to pH>7. Then the mixture was extracted by DCM (dichloromethane) (10 mL*3). The combined organic layers were washed with brine, dried over Na$_2$SO$_4$(s) and filtered. The filtrate was evaporated to dryness to give compound 59 (24 mg, 96.0% purity, 89.6% yield) as yellow solids.

LC-MS (ESI) General procedure B, method 5: $R_T$=3.639 min, mass calcd. for $C_{29}H_{28}N_6O_4$ 524.22, m/z found 525.0 [M+H]$^+$.

$^1$H NMR (400 MHz, DMSO-d$^6$) General procedure B: δ12.92 (br. s., 1H), 12.12 (br. s., 1H), 11.58 (br. s., 1H), 8.53 (d, J=3.7 Hz, 1H), 7.99 (d, J=8.2 Hz, 1H), 7.76 (dt, J=1.8, 7.7 Hz, 1H), 7.55 (s, 1H), 7.53-7.45 (m, 2H), 7.34 (d, J=7.5 Hz, 1H), 7.25 (dd, J=5.2, 7.2 Hz, 2H), 7.08 (t, J=7.7 Hz, 1H), 6.98 (d, J=8.6 Hz, 1H), 5.45 (s, 1H), 4.47 (dd, J=3.1, 7.5 Hz, 1H), 4.08-3.98 (m, 1H), 3.82-3.75 (m, 1H), 3.73 (s, 3H), 3.47 (dd, J=2.8, 12.0 Hz, 1H), 3.25 (d, J=13.5 Hz, 1H), 3.14 (dd, J=7.6, 11.8 Hz, 1H), 3.03-2.93 (m, 1H), 1.71 (d, J=6.6 Hz, 3H).

Compound 60

(Rac)-4-(2-(2-oxo-4-(((S)-1-(pyridin-2-yl)ethyl) amino)-1,2-dihydroquinolin-3-yl)-1H-benzo[d]imidazol-6-yl)morpholine-2-carboxylic acid After the reaction was finished, the mixture was extracted by DCM (20 mL*3). Then the combined aqueous layers were adjusted to pH 5-6 with 1 M HCl (aqueous). The mixture was concentrated to dryness under reduced pressure to afford the crude product which was purified by prep. HPLC (Column: Phenomenex Gemini C18 150×25 mm×5 μm, Mobile Phase A: water (0.225% formic acid); Mobile Phase B: acetonitrile, Flow rate: 22 mL/min, gradient condition from 8% B to 38%). The pure fractions were collected and the solvent was evaporated under vacuum, and then lyophilized to give compound 60 (50.0 mg, 96.6% purity, 45.5% yield) as yellow solids.

LC-MS (ESI) General procedure B, method 5: $R_T$=3.75 min, mass calcd. for $C_{28}H_{26}N_6O_4$ 510.2, m/z found 511.0 $[M+H]^+$.

1H NMR (400 MHz, DMSO-$d_6$) General procedure B: δ=12.94 (br. s., 0.4H), 12.91 (br. s., 0.6H), 12.31 (d, J=7.7 Hz, 0.4H), 12.19 (d, J=7.3 Hz, 0.6H), 11.60 (br. s., 1H), 8.54 (d, J=2.4 Hz, 1H), 8.20 (s, 0.2H), 7.96 (d, J=8.4 Hz, 1H), 7.81-7.70 (m, 1H), 7.61 (d, J=8.8 Hz, 0.4H), 7.54-7.44 (m, 2.6H), 7.37-7.28 (m, 1.6H), 7.28-7.21 (m, 1H), 7.14 (s, 0.4H), 7.07 (t, J=7.1 Hz, 1H), 7.01-6.92 (m, 1H), 5.52-5.45 (m, 1H), 4.31-4.19 (m, 1H), 4.15-4.00 (m, 1H), 3.73 (t, J=8.7 Hz, 1H), 3.53-3.49 (m, 2H), 3.07-2.84 (m, 2H), 1.78-1.66 (m, 3H)

Compound 62

(R*)-methyl 4-(2-(2-oxo-4-(((S)-1-(pyridin-2-yl) ethyl)amino)-1,2-dihydroquinolin-3-yl)-1H-benzo[d] imidazol-6-yl)morpholine-2-carboxylate After the reaction was finished, the mixture was basified by saturated sodium bicarbonate solution to pH>7. Then the mixture was extracted by DCM (10 mL*3). The combined organic layers were washed with brine, dried over $Na_2SO_4$ (s) and filtered. The filtrate was evaporated to dryness to give compound 62 (6.50 mg, 95.7% purity, 60.6% yield) as yellow solids.

LC-MS (ESI) General procedure B, method 5: $R_T$=3.544 min, mass calcd. for $C_{29}H_{28}N_6O_4$ 524.22, m/z found 525.0 $[M+H]^+$.

$^1$H NMR (400 MHz, DMSO-$d^6$) General procedure B: δ12.96 (br. s., 0.4H), 12.93 (br. s., 0.6H), 12.29 (d, J=8.2 Hz, 0.4H), 12.17 (d, J=8.4 Hz, 0.6H), 11.59 (br. s., 1H), 8.57-8.52 (m, 1H), 7.96 (d, J=8.4 Hz, 1H), 7.79-7.72 (m, 1H), 7.61 (d, J=8.6 Hz, 0.4H), 7.54-7.48 (m, 2.6H), 7.35-7.30 (m, 1.6H), 7.28-7.23 (m, 1H), 7.15 (s, 0.4H), 7.06 (t, J=7.7 Hz, 1H), 6.97 (ddd, J=2.1, 9.0, 11.2 Hz, 1H), 5.55-5.44 (m, 1H), 4.47 (dt, J=3.1, 7.6 Hz, 1H), 4.10-3.97 (m, 1H), 3.82-3.75 (m, 1H), 3.75-3.70 (m, 3H), 3.50-3.43 (m, 1H), 3.25 (dd, J=3.6, 12.5 Hz, 1H), 3.13 (dd, J=7.9, 11.7 Hz, 1H), 3.03-2.94 (m, 1H), 1.75-1.70 (m, 3H).

Compound 63

(S)-7-Fluoro-3-(6-(4-methylpiperazin-1-yl)-1H-benzo[d]imidazol-2-yl)-4-((1-(pyridin-2-yl)ethyl) amino)quinolin-2(1H)-one After the reaction was finished, the resulting mixture was concentrated in vacuum to give the crude product which was purified by prep. HPLC (Column: Phenomenex Gemini 150×25 mm×5 μm, Mobile Phase A: water (0.05% ammoniahydroxide v/v; Mobile Phase B: acetonitrile, Flow rate: 22 mL/min, gradient condition from 42% B to 72%). The pure fractions were collected and the solvent was evaporated under vacuum, and then lyophilized to give compound 63 (33.3 mg, 95.3% purity, 26.3% yield) as yellow solids.

LC-MS (ESI) General procedure B-2, method 6: $R_T$=1.986 min, mass calcd. for $C_2H_{28}FN_7O$ 497.23, m/z found 498.0 $[M+H]^+$.

$^1$H NMR (400 MHz, DMSO-$d^6$) General procedure B: δ=12.81 (br. s., 0.4H), 12.77 (br. s., 0.6H), 12.39 (d, J=8.2 Hz, 0.4H), 12.26 (d, J=7.9 Hz, 0.6H), 11.65 (br. s., 1H), 8.57-8.52 (m, 1H), 8.07-8.01 (m, 1H), 7.80-7.71 (m, 1H), 7.56 (d, J=8.8 Hz, 0.4H), 7.51-7.44 (m, 1.6H), 7.28-7.22 (m, 1.6H), 7.12-7.04 (m, 1.4H), 7.00-6.90 (m, 2H), 5.53-5.42 (m, 1H), 3.17-3.10 (m, 4H), 2.54-2.52 (m, 4H), 2.25 (s, 3H), 1.75-1.68 (m, 3H).

Compound 64

(S)-3-(6-((1-Methylpiperidin-4-yl)oxy)-1H-benzo[d] imidazol-2-yl)-4-((1-(pyridin-2-yl)-ethyl)amino) quinolin-2(1H)-one After the reaction was finished, the reaction mixture was evaporated to dryness which was purified by flash column chromatography (DCM/MeOH from 100/0 to 70/30). The pure fractions were collected and the solvent was evaporated under vacuum to dryness which was further purified by prep. HPLC Column: Phenomenex Gemini 150×25 mm×10 um, Mobile Phase A: water (0.05% ammonia hydroxide v/v; Mobile Phase B: acetonitrile, Flow rate: 25 mL/min, gradient condition from 40% B to 70%). The pure fractions were collected and the solvent was evaporated under vacuum, and then lyophilized to give compound 64 (19.2 mg, 98.3% purity, 5.20% yield) as yellow solids.

LC-MS (ESI) General procedure B-2, method 5: $R_T$=3.107 min, mass calcd. for $C_{29}H_{30}N_6O_2$ 494.24, m/z found 495.1 $[M+H]^+$.

$^1$H NMR (400 MHz, DMSO-$d^6$) General procedure B: δ 12.98 (br. s., 0.4H), 12.95 (br. s., 0.6H), 12.24 (d, J=8.3 Hz, 0.4H), 12.17 (d, J=8.3 Hz, 0.6H), 11.60 (br. s., 1H), 8.58-8.51 (m, 1H), 7.97 (dd, J=2.9, 8.4 Hz, 1H), 7.82-7.71 (m, 1H), 7.60 (d, J=8.8 Hz, 0.4H), 7.50 (m, 2.6H), 7.37-7.31 (m, 1.6H), 7.25 (dd, J=4.8, 6.5 Hz, 1H), 7.20 (d, J=2.3 Hz, 0.4H), 7.07 (t, J=7.7 Hz, 1H), 6.90-6.78 (m, 1H), 5.50 (t, J=7.3 Hz, 1H), 4.44-4.24 (m, 1H), 2.73-2.58 (m, 2H), 2.26-2.09 (m, 5H), 1.97 (m, 2H), 1.77-1.70 (m, 3H), 1.67 (m, 2H).

Compound 65

(S)-3-(6-(4-methylpiperazin-1-yl)-1H-benzo[d]imidazol-2-yl)-4-((1-(pyridin-2-yl)-ethyl)amino)quinolin-2(1H)-one After the reaction was finished, the reaction mixture was poured into 45 mL of water and extracted with DCM (20 mL×3). The combined organic layers were washed with brine (50 mL), dried over $Na_2SO_4$ and filtered. The filtrate was concentrated to dryness which was purified by prep. TLC (DCM/MeOH=10/1). The product was partitioned between acetonitrile (10 mL) and water (5 mL). The solution was lyophilized to dryness to give compound 65 (26.5 mg, 97.5% purity, 14.2% yield) as yellow solid.

LC-MS (ESI) General procedure B-2, method 5: $R_T$=2.857 min, mass calcd. for $C_2H_{29}N_7O$ 479.24, m/z found 480.2 $[M+H]^+$.

$^1$H NMR (400 MHz, DMSO-d$^6$) General procedure B: δ 12.91 (s, 0.4H), 12.87 (s, 0.6H), 12.31 (d, J=7.9 Hz, 0.4H), 12.18 (d, J=8.2 Hz, 0.6H), 11.59 (s, 1H), 8.54 (d, J=2.9 Hz, 1H), 7.97 (d, J=8.6 Hz, 1H), 7.80-7.70 (m, 1H), 7.58 (d, J=8.6 Hz, 0.4H), 7.54-7.45 (m, 2.6H), 7.34 (d, J=7.3 Hz, 1H), 7.29-7.21 (m, 1.6H), 7.12 (s, 0.4H), 7.07 (br t, J=7.7 Hz, 1H), 7.01-6.91 (m, 1H), 5.49 (br t, J=7.2 Hz, 1H), 3.19-3.07 (m, 4H), 2.60-2.52 (m, 4H), 2.27 (s, 3H), 1.79-1.66 (m, 3H).

Compound 38b (S)-5-chloro-3-(6-morpholino-1H-benzo[d]imidazol-2-yl)-4-((1-(pyridin-2-yl)ethyl)-amino)quinolin-2(1H)-one LC-MS (ESI) General procedure B, method 2: $R_T$=1.22 min, mass calcd. for $C_{27}H_{25}ClN_6O_2$ 500.1, m/z found 501.1 $[M+H]^+$.

$^1$H NMR (400 MHz, CD$_3$OD) General procedure A δ 8.28 (d, J=4.0 Hz, 1H), 7.59 (t, J=6.8 Hz, 2H), 7.46 (t, J=8.0 Hz, 1H), 7.32-7.30 (m, 1H), 7.24-7.05 (m, 5H), 4.97 (q, J=6.8 Hz, 1H), 3.89-3.87 (m, 4H), 3.19-3.17 (m, 4H), 1.57 (d, J=6.8 Hz, 3H).

Compound 38a (R*)-5-chloro-3-(6-morpholino-1H-benzo[d]imidazol-2-yl)-4-((1-(pyridin-2-yl)ethyl)-amino)quinolin-2(1H)-one LC-MS (ESI) General procedure B, method 2: $R_T$=1.22 min, mass calcd. for $C_{27}H_{25}ClN_6O_2$ 500.1, m/z found 501.1 $[M+H]^+$.

$^1$H NMR (400 MHz, CD$_3$OD) General procedure A δ 8.28 (d, J=4.4 Hz, 1H), 7.60 (t, J=6.8 Hz, 2H), 7.46 (t, J=8.0 Hz, 1H), 7.32-7.30 (m, 1H), 7.24-7.06 (m, 5H), 4.97 (q, J=6.8 Hz, 1H), 3.89-3.87 (m, 4H), 3.20-3.17 (m, 4H), 1.57 (d, J=6.8 Hz, 3H).

Compound 42

(S)-5-fluoro-3-(6-(4-methylpiperazin-1-yl)-1H-benzo[d]imidazol-2-yl)-4-((1-(oxazol-4-yl)-ethyl)amino)quinolin-2(1H)-one The reaction mixture was purified by Prep-HPLC (Column: WatersXBridge 30*150 mm 5 um, Flow rate: 20 mL/min, Mobile Phase A: Water (0.1% NH$_3$.H$_2$O), Mobile Phase B: Acetonitrile, Gradient: 35-55% (% B)). The desired fraction was collected and the volatile was removed under reduced pressure. The water phase was lyophilized to afford compound 42 (10 mg, 9% yield, purity >99%) as yellow solids.

LC-MS (ESI) General procedure A, method 2: $R_T$=1.0 min, mass calcd. for $C_{26}H_{26}FN_7O_2$ 487.21, m/z found 488.3 $[M+H]^+$.

$^1$H NMR (400 MHz, DMSO-d$_6$) General procedure A δ 12.71 (d, J=22.5 Hz, 1H), 11.81 (s, 1H), 11.47 (dd, J=43.6, 9.9 Hz, 1H), 8.17 (d, J=5.4 Hz, 1H), 7.80 (d, J=8.8 Hz, 1H), 7.51 (m, J=44.7, 8.7 Hz, 2H), 7.32-7.15 (m, 2H), 7.14-6.92 (m, 2H), 4.75 (s, 1H), 3.17 (s, 4H), 2.67 (m, 2H), 2.51 (m, 2H), 2.36 (s, 3H), 1.58 (t, J=6.8 Hz, 3H).

Analytical Part

LC-MS

General procedure A for LC-MS

The LCMS measurement was performed using a Waters UPLC-QDa system comprising a quaternary pump, an autosampler, a column oven (set at 50° C., unless otherwise indicated), a photo-diode array (PDA) detector and a column as specified in the respective methods below. Flow from the column was split to a MS spectrometer. The MS detector was QDa detector and configured with an electrospray ionization source. Mass spectra were acquired by scanning from 100 to 1000. The capillary needle voltage was 0.8 kV and the source temperature was maintained at 120° C. Nitrogen was used as the nebulizer gas. Data acquisition was performed with a Waters-Micromass MassLynx-Openlynx data system.

Method 1 (95:5)

In addition to the general procedure A: Reversed phase HPLC was carried out on an ACQUITY UPLC BEH C18 column (1.7 μm 2.1×50 mm) with a flow rate of 0.6 ml/min. Two mobile phases (mobile phase C: 0.1% formic acid in water; mobile phase D: 0.1% formic acid in acetonitrile) were employed to hold 95% C and 5% D for 1.2 minutes, then hold 5% C and 95% D for 0.8 minutes. An injection volume between 0.3-5 μl was depended on the concentration of sample. Cone voltage was 15 V for positive ionization mode.

Method 2 (90:10)

In addition to the general procedure A: Reversed phase HPLC was carried out on an ACQUITY UPLC BEH C18 column (1.7 μm 2.1×50 mm) with a flow rate of 0.6 ml/min. Two mobile phases (mobile phase C: 0.1% formic acid in water; mobile phase D: 0.1% formic acid in acetonitrile) were employed to hold 90% C and 10% D for 1.2 minutes, then hold 5% C and 95% D for 0.8 minutes. An injection volume between 0.3-5 μl was depended on the concentration of sample. Cone voltage was 15 V for positive ionization mode.

Method 3 (80:20)

In addition to the general procedure A: Reversed phase HPLC was carried out on an ACQUITY UPLC BEH C18 column (1.7 μm 2.1×50 mm) with a flow rate of 0.6 ml/min. Two mobile phases (mobile phase C: 0.1% formic acid in water; mobile phase D: 0.1% formic acid in acetonitrile) were employed to hold 80% C and 20% D for 1.2 minutes, then hold 5% C and 95% D for 0.8 minutes. An injection volume between 0.3-5 μl was depended on the concentration of sample. Cone voltage was 15 V for positive ionization mode.

Method 4 (70:30)

In addition to the general procedure A: Reversed phase HPLC was carried out on an ACQUITY UPLC BEH C18 column (1.7 μm 2.1×50 mm) with a flow rate of 0.6 ml/min. Two mobile phases (mobile phase C: 0.1% formic acid in water; mobile phase D: 0.1% formic acid in acetonitrile) were employed to hold 70% C and 30% D for 1.2 minutes, then hold 5% C and 95% D for 0.8 minutes. An injection volume between 0.3-5 μl was depended on the concentration of sample. Cone voltage was 15 V for positive ionization mode.

General Procedure B for LC-MS

The LCMS measurement was performed using a Shimadzu LC-MS2020 system comprising a pump (LC-20AD) with degasser (DGU-20A$_3$), an autosampler (SIL-20AHT), a column oven (CTO-20A) (set at 40° C., unless otherwise indicated), a photo-diode array (PDA) (SPD-M20A) detector, an evaporative light-scattering (ELSD)(Alltech 3300ELSD) detector and a column as specified in the respective methods below. Flow from the column was split to a MS spectrometer. The MS detector was configured with an electrospray ionization source. Mass spectra were acquired by scanning from 80 to 1000. Nitrogen was used as the nebulizer gas. Data acquisition was performed with a Labsolution data system.

Method 1 (95:5)

In addition to the general procedure B: Reversed phase UPLC was carried out on a Shimadzu SunFire C18 (5 μm 50*4.6 mm) with a flow rate of 2.0 ml/min. Two mobile phases (mobile phase A: 0.1% formic acid in water; mobile phase B: 0.1% formic acid in acetonitrile) were employed to hold 95% A and 5% B for 1.6 minutes, then hold 5% A and 95% B for 1.0 minute. An injection volume between 0.3-5 μl was depended on the concentration of sample. Cone voltage was 20 V for positive and negative ionization mode. Mass spectra were acquired by scanning from 100 to 1000 in 0.2 seconds using an interscan delay of 0.1 seconds.

Method 2 (90:10)

In addition to the general procedure B: Reversed phase UPLC was carried out on a Shimadzu SunFire C18 (5 μm 50*4.6 mm) with a flow rate of 2.0 ml/min. Two mobile phases (mobile phase A: 0.1% formic acid in water; mobile phase B: 0.1% formic acid in acetonitrile) were employed to hold 90% A and 10% B for 1.6 minutes, then hold 5% A and 95% B for 1.0 minute. An injection volume between 0.3-5 μl was depended on the concentration of sample. Cone voltage was 20 V for positive and negative ionization mode. Mass spectra were acquired by scanning from 100 to 1000 in 0.2 seconds using an interscan delay of 0.1 seconds.

Method 3 (80:20)

In addition to the general procedure B: Reversed phase UPLC was carried out on a Shimadzu SunFire C18 (5 μm 50*4.6 mm) with a flow rate of 2.0 ml/min. Two mobile phases (mobile phase A: 0.1% formic acid in water; mobile phase B: 0.1% formic acid in acetonitrile) were employed to hold 80% A and 20% B for 1.6 minutes, then hold 5% A and 95% B for 1.0 minute. An injection volume between 0.3-5 μl was depended on the concentration of sample. Cone voltage was 20 V for positive and negative ionization mode. Mass spectra were acquired by scanning from 100 to 1000 in 0.2 seconds using an interscan delay of 0.1 seconds.

Method 4 (30:70)

In addition to the general procedure B: Reversed phase UPLC was carried out on a Shimadzu SunFire C18 (5 μm 50*4.6 mm) with a flow rate of 2.0 ml/min. Two mobile phases (mobile phase A: 0.1% formic acid in water; mobile phase B: 0.1% formic acid in acetonitrile) were employed to hold 30% A and 70% B for 1.6 minutes, then hold 5% A and 95% B for 1.0 minute. An injection volume between 0.3-5 μl was depended on the concentration of sample. Cone voltage was 20 V for positive and negative ionization mode. Mass spectra were acquired by scanning from 100 to 1000 in 0.2 seconds using an interscan delay of 0.1 seconds.

Method 5 (70:30)

In addition to the general procedure B: Reversed phase UPLC was carried out on a Shimadzu SunFire C18 (5 μm 50*4.6 mm) with a flow rate of 2.0 ml/min. Two mobile phases (mobile phase A: 0.1% formic acid in water; mobile phase B: 0.1% formic acid in acetonitrile) were employed to hold 70% A and 30% B for 1.6 minutes, then hold 5% A and 95% B for 1.0 minute. An injection volume between 0.3-5 μl was depended on the concentration of sample. Cone voltage was 20 V for positive and negative ionization mode. Mass spectra were acquired by scanning from 100 to 1000 in 0.2 seconds using an interscan delay of 0.1 seconds General Procedure B-2

The LC measurement was performed using an Agilent 1200 HPLC system comprising a degasser, a binary pump, an auto-sampler, a column heater, a diode-array detector (DAD) and a column as specified in the respective methods below. Flow from the DAD was split to a MS spectrometer (Agilent 6110 or 6140) and an ELSD. The MS detector was configured with an electrospray ionization source. Nitrogen was used as the nebulizer gas. The drying gas temperature was maintained at 350° C. Capillary voltage was 2.5 V for positive ionization mode and 3.0 V for negative ionization mode. Mass spectra were acquired by scanning from 100 to 1000 in step size 0.1. The cycle time is 0.89 sec/cycle. Data acquisition was performed with a Chemstation B.04.03

Method 4

In addition to the general procedure B: Reversed phase HPLC was carried out on a Waters XBridge Shield RP18 column (50*2.1 mm 5 μm) with a flow rate of 0.8 mL/min. Two mobile phases (mobile phase A: water with 0.05% NH$_3$.H$_2$O; mobile phase B: acetonitrile) were used. First, 100% A was hold for 1 minute. Then a gradient was applied to 40% A and 60% B in 4 minutes and then to 5% A and 95% B in 2.5 minutes. Finally return to 100% A in 2 minutes and hold for 0.5 minute. Post Time was 0.5 minute. Oven temperature was 40° C. The injection volume was 2 uL. (MS polarity: positive)

Method 5

In addition to the general procedure B: Reversed phase HPLC was carried out on a Phenomenex Luna-C18 column (5 μm, 2.0×50 mm) with a flow rate of 0.8 m/min. Two mobile phases (mobile phase A: water with 0.1% TFA; mobile phase B: acetonitrile with 0.05% TFA) were used. 100% A was hold for 1 minute, A gradient from 100% A to 40% A is applied in 4 minutes, and 40% A down to 15% A in 2.5 minutes. And then return to 100% A in 2 minutes and hold for 0.5 minutes. The post time was 0.5 min. Oven temperature was 50° C. The injection volume was 2 uL. (MS polarity: positive)

Method 6

In addition to the general procedure B: Reversed phase HPLC was carried out on a Phenomenex Luna-C18 column (5 μm, 2.0×50 mm) with a flow rate of 0.8 mL/min. Two mobile phases (mobile phase A: water with 0.1% TFA; mobile phase B: acetonitrile with 0.05% TFA) were used. First, 90% A was hold for 0.8 minute. Then a gradient was applied to 20% A and 80% B in 3.7 minutes and hold for 3 minutes. And then return to 90% A in 2 minutes and hold for 0.5 minutes. The post time was 0.5 min. Oven temperature was 50° C. The injection volume was 2 uL. (MS polarity: positive)

NMR

General Procedure A for NMR Data

The below NMR experiments were carried out using a Bruker Avance 111400 spectrometers at ambient temperature, using internal deuterium lock and equipped with 5 mm PABBO ($^1$H, $^{13}$C, $^{15}$N, $^{31}$P, $^{19}$F) probe head. Chemical shifts (δ) are reported in parts per million (ppm).

General Procedure B for NMR Data

The below NMR experiments were carried out using a Bruker Avance III 400 and a Varian 400 spectrometers at ambient temperature, using internal deuterium lock and equipped with BBO 400 MHz probe head for the Bruker Avance III 400 and with Varian 400 ASW PFG 4nuc($^1$H, $^{13}$C, $^{19}$F, $^{31}$P) probe head for the Varian 400. Chemical shifts (δ) are reported in parts per million (ppm).

Pharmacological Part

Biological Assays

FGFR3 Wild Type Mobility Shift Assay (Enzymatic Assay)

In a final reaction volume of 25 μL, 0.04 ng/μL human FGFR3 wild type enzyme (cytoplasmic domain, from Carna Biosciences) was incubated with 75 μM ATP, 1 μM FL-peptide 30 substrate and 250 nL of testing compound (1% DMSO final) in assay buffer (100 mM HEPES pH 7.4, 10 mM MgCl$_2$, 0.003% Brij35, 1 mM DTT). After incubation for 50 minutes at 30° C. the reaction was stopped with 10 μL of 0.5M EDTA pH 8.0, and then 25 μL of reaction mixture was transferred to reading plate and measured on Caliper EZ reader II. The substrate-product conversion rate was used as raw data for normalization and concentration-response curve (10 dose points with 4× serial dilution, starting with 10 μM) was plotted using Prism to calculate IC$_{50}$ (M), pIC$_{50}$ (−log IC$_{50}$) and HillSlope value.

FGFR3 V555M Mobility Shift Assay (Enzymatic Assay)

In a final reaction volume of 25 μL, 0.04 ng/μL human FGFR3 V555M enzyme (cytoplasmic domain carrying V555M mutation, from Carna Biosciences) was incubated with 30 μM ATP, 1 μM FL-peptide 30 substrate and 250 nL of testing compound (1% DMSO final) in assay buffer (100 mM HEPES pH 7.4, 10 mM MgCl$_2$, 0.003% Brij35, 1 mM DTT). After incubation for 45 minutes at 30° C. the reaction was stopped with 10 μL of 0.5M EDTA pH 8.0, and then 25 μL of reaction mixture was transferred to reading plate and measured on Caliper EZ reader II. The substrate-product conversion rate was used as raw data for normalization and concentration-response curve (10 dose points with 4× serial dilution, starting with 10 μM) was plotted using Prism to calculate IC$_{50}$ (M), pIC$_{50}$ (−log IC$_{50}$) and HillSlope value.

FGFR3 V555L Mobility Shift Assay (Enzymatic Assay)

In a final reaction volume of 25 μL, 0.04 ng/μL human FGFR3 V555L enzyme (cytoplasmic domain carrying V555L mutation, from Carna Biosciences) was incubated with 40 μM ATP, 1 μM FL-peptide 30 substrate and 250 nL of testing compound (1% DMSO final) in assay buffer (100 mM HEPES pH 7.4, 10 mM MgCl$_2$, 0.003% Brij35, 1 mM DTT). After incubation for 50 minutes at 30° C. the reaction was stopped with 10 μL of 0.5M EDTA pH 8.0, and then 25 μL of reaction mixture was transferred to reading plate and measured on Caliper EZ reader II. The substrate-product conversion rate was used as raw data for normalization and concentration-response curve (10 dose points with 4× serial dilution, starting with 10 μM) was plotted using Prism to calculate IC$_{50}$ (M), pIC$_{50}$ (−log IC$_{50}$) and HillSlope value.

NIH/3T3 FGFR3 WT-TACC3 Cell Proliferation Assay

In day 1, 90 μL of cell suspension (NIH/3T3 cells over-expressing FGFR3 WT-TACC3 fusion protein) (total 30,000 cells per well in growth medium (DMEM containing 1% Glutamax, 10% FBS and 1% Pen/Strep)) was seeded in a 96-well plate and then incubated overnight at 37° C. and 5% CO$_2$. In day 2, 10 μL of growth medium containing 10-fold stock solution of testing compound was added into cell cultures (9 dose points with 4× serial dilution, starting with 10 μM, 0.1% DMSO final). After 72-hr incubation at 37° C. and 5% CO$_2$, in day 5 a volume of 50 μL CellTiter Glo (CTG) reagent was added into cell-containing 96-well plate and the plate was incubated at room temperature for 10 minutes before RLUs (relative light unit) were measured on a microplate reader with luminescence detection module. The RLU value was normalized to survival % and concentration-response curve was plotted using Prism to calculate IC$_{50}$ (M), pIC$_{50}$ (−log IC$_{50}$) and HillSlope value.

NIH/3T3 FGFR3 V555M-TACC3 Cell Proliferation Assay

In day 1, 90 μL of cell suspension (NIH/3T3 cells overexpressing FGFR3 V555M-TACC3 fusion protein) (total 30,000 cells per well in growth medium (DMEM containing 1% Glutamax, 10% FBS and 1% Pen/Strep)) was seeded in a 96-well plate and then incubated overnight at 37° C. and 5% CO$_2$. In day 2, 10 μL of growth medium containing 10-fold stock solution of testing compound was added into cell cultures (9 dose points with 4× serial dilution, starting with 10 μM, 0.1% DMSO final). After 72-hr incubation at 37° C. and 5% CO$_2$, in day 5 a volume of 50 μL CellTiter Glo (CTG) reagent was added into cell-containing 96-well plate and the plate was incubated at room temperature for 10 minutes before RLUs (relative light unit) were measured on a microplate reader with luminescence detection module. The RLU value was normalized to survival % and concentration-response curve was plotted using Prism to calculate IC$_{50}$ (M), pIC$_{50}$ (−log IC$_{50}$) and HillSlope value.

NIH/3T3 Mock Cell Proliferation Assay

In day 1, 90 μL of cell suspension (NIH/3T3 cells transfected with the same control vector as in the above two proliferation assays) (total 30,000 cells per well in growth medium (DMEM containing 1% Glutamax, 10% FBS and 1% Pen/Strep)) was seeded in a 96-well plate and then incubated overnight at 37° C. and 5% CO$_2$. In day 2, 10 μL of growth medium containing 10-fold stock solution of testing compound was added into cell cultures (9 dose points with 3× serial dilution, starting with 30 μM, 0.3% DMSO final). After 72-hr incubation at 37° C. and 5% CO$_2$, in day 5 a volume of 50 μL CellTiter Glo (CTG) reagent was added into cell-containing 96-well plate and the plate was incubated at room temperature for 10 minutes before RLUs (relative light unit) were measured on a microplate reader with luminescence detection module. The RLU value was normalized to survival % and concentration-response curve was plotted using Prism to calculate IC$_{50}$ (M), pIC$_{50}$ (−log IC$_{50}$) and HillSlope value. This assay served as a counter assay for NIH/3T3 FGFR WT/VM-TACC3 cell proliferation assays to indicate general toxicity of testing compounds caused by off-target effect.

NIH/3T3 FGFR3 WT-TACC3 Cellular Phospho-ERK Assay (In Vitro PD Assay)

50 μL of cell suspension (NIH/3T3 cells overexpressing FGFR3 WT-TACC3 fusion protein) (total 10,000 cells per well in growth medium (DMEM containing 1% Glutamax, 10% FBS and 1% Pen/Strep)) was seeded in a 384-well plate. After overnight incubation at 37° C. and 5% CO$_2$, 5.5 μL of growth medium containing 10× testing compound was added into cell cultures (10 dose points with 4× serial dilution, starting with 10 μM, 0.1% DMSO final). After 1-hr incubation at 37° C. and 5% CO$_2$, the medium was depleted and AlphaLISA SureFire Ultra p-ERK1/2 (Thr202/Tyr204) Assay Kit (from PerkinElmer) was applied for phospho-ERK level detection according to the kit instructions. The RFUs (relative fluorescence units were measured on EnVision microplate reader (ex. 680 nm, em. 615 nm) and concentration-response curve was plotted using Prism to calculate IC$_{50}$ (M), pIC$_{50}$ (−log IC$_{50}$) and HillSlope value.

NIH/3T3 FGFR3 V555M-TACC3 Cellular Phospho-ERK Assay (In Vitro PD Assay)

50 μL of cell suspension (NIH/3T3 cells overexpressing FGFR3 V555M-TACC3 fusion protein) (total 10,000 cells per well in growth medium (DMEM containing 1% Glutamax, 10% FBS and 1% Pen/Strep)) was seeded in a 384-well plate. After overnight incubation at 37° C. and 5% $CO_2$, 5.5 μL of growth medium containing 10× testing compound was added into cell cultures (10 dose points with 4× serial dilution, starting with 10 μM, 0.1% DMSO final). After 1-hr incubation at 37° C. and 5% $CO_2$, the medium was depleted and AlphaLISA SureFire Ultra p-ERK1/2 (Thr202/Tyr204) Assay Kit (from PerkinElmer) was applied for phospho-ERK level detection according to the kit instructions. The RFUs (relative fluorescence units) were measured on EnVision microplate reader (ex. 680 nm, em. 615 nm) and concentration-response curve was plotted using Prism to calculate $IC_{50}$ (M), $pIC_{50}$ ($-\log IC_{50}$) and HillSlope value.

TABLE 2

Pharmacological data ($IC_{50}$; unit nM)

| Compound Number | FGFR3 wild type Caliper | FGFR3 V555M Caliper | FGFR3 V555L Caliper | NIH/3T3 MOCK CTG | NIH/3T3 FGFR3 WT-TACC3 CTG | NIH/3T3 FGFR3 V555M-TACC3 CTG | NIH/3T3 FGFR3 WT-TACC3 pERK | NIH/3T3 FGFR3 V555M-TACC3 pERK |
|---|---|---|---|---|---|---|---|---|
| Compound 11a | 32.57 | 11.98 | | | | | | |
| Compound 13b | 1.051 | 0.4493 | | 1743 | 3.458 | 4.342 | | |
| Compound 14 | 3.376 | 2.146 | | 3013 | 52.16 | 140.9 | | |
| Compound 15 | 0.8513 | 0.3509 | | 1191 | 12.42 | 24.93 | | |
| Compound 2 | 0.3371 | 0.2134 | | 15272 | 3.611 | 4.892 | 1.243 | 0.9457 |
| Compound 3 | 585.1 | 204.3 | | 11022 | 58.47 | 41.82 | | |
| Compound 16 | 16.63 | 2.659 | | 2604 | 253 | 274.2 | | |
| Compound 17 | 4.895 | 0.9972 | | 660.9 | 58.75 | 114.3 | | |
| Compound 18 | 1.347 | 1.348 | | 732.7 | 56.85 | 87.8 | | |
| Compound 19 | 0.3666 | 0.3579 | | 2446 | 46.07 | 66.45 | | |
| Compound 20 | 0.8258 | 0.49 | | 951.7 | 23.54 | 17.08 | | |
| Compound 4 | 2.593 | 1.343 | | 7691 | 24.75 | 42.7 | 3.87 | 1.093 |
| Compound 21 | 5.037 | 2.748 | | 13627 | 25.03 | 48.8 | 8.411 | 2.345 |
| Compound 22a | 0.4454 | 0.4209 | | 6393 | 13.3 | 6.478 | | |
| Compound 23a | 0.5907 | 0.2446 | | 15336 | 8.339 | 13.39 | | |
| Compound 24 | 2.181 | 0.9286 | | 13111 | 20.17 | 39.44 | 13.27 | 0.9593 |
| Compound 25a | 1.222 | 1.035 | | 2257 | 5.164 | 4.815 | | |
| Compound 26a | 0.3165 | 0.1779 | | 2583 | 2.22 | 4.305 | | |
| Compound 27a | 0.4445 | 0.2553 | | 3879 | 6.928 | 5.8 | | |
| Compound 28a | 0.5523 | 0.3017 | | 7219 | 5.491 | 8.353 | | |
| Compound 29a | 0.2424 | 0.1499 | | 4686 | 8.463 | 10.78 | | |
| Compound 30a | 0.2815 | 0.1766 | 0.6172 | 2912 | 7.194 | 5.339 | | |
| Compound 31a | 0.8426 | 0.181 | | 2921 | 25.71 | 14.29 | | |
| Compound 32a | 0.368 | 0.1705 | 0.3639 | 2607 | 16.46 | 5.753 | | |
| Compound 33a | 0.5945 | 0.2375 | 0.6298 | 1080 | 9.245 | 6.412 | | |
| Compound 34a | 8.996 | 1.587 | | 1320 | 43.09 | 70.42 | | |
| Compound 35b | 11.08 | 2.86 | | 1679 | 127.1 | 197.5 | | |
| Compound 36b | 7.317 | 2.348 | | 1516 | 314.6 | 170.1 | | |
| Compound 37b | 29.26 | 20.16 | | | | | | |

TABLE 2-continued

| | Pharmacological data (IC$_{50}$; unit nM) | | | | | | | |
|---|---|---|---|---|---|---|---|---|
| Compound Number | FGFR3 wild type Caliper | FGFR3 V555M Caliper | FGFR3 V555L Caliper | NIH/ 3T3 MOCK CTG | NIH/3T3 FGFR3 WT-TACC3 CTG | NIH/3T3 FGFR3 V555M-TACC3 CTG | NIH/3T3 FGFR3 WT-TACC3 pERK | NIH/3T3 FGFR3 V555M-TACC3 pERK |
| Compound 37a | 0.478 | 0.3255 | | 898 | 11.66 | 4.181 | | |
| Compound 39a | 0.1745 | 0.1357 | | 1602 | 6.581 | 6.468 | | |
| Compound 40a | 0.3127 | 0.1675 | | 2478 | 3.145 | 1.855 | | |
| Compound 41b | 39.41 | 19.45 | | | | | | |
| Compound 41a | 0.6681 | 0.4853 | | 6972 | 7.077 | 5.01 | | |
| Compound 43a | 1.005 | 0.6426 | | 8271 | 20.26 | 9.932 | | |
| Compound 44a | 0.2439 | 0.1471 | | 3037 | 9.458 | 3.98 | | |
| Compound 45 | 1.173 | 0.4835 | | 12721 | 25.27 | 12.17 | | |
| Compound 46 | 1.174 | 0.7421 | | 3908 | 19.95 | 15.93 | | |
| Compound 47 | 0.6702 | 0.2697 | | 547.2 | 15.95 | 12.29 | | |
| Compound 48a | 19.9 | 5.407 | | 5668 | 453.7 | 547.2 | | |
| Compound 49a | 27.04 | 7.067 | | | | | | |
| Compound 50a | 48.92 | 8.749 | | | | | | |
| Compound 51a | 1.31 | 0.2367 | | 1175 | 30.06 | 30.17 | | |
| Compound 52a | 0.8581 | 0.2085 | | 1433 | 23.06 | 6.691 | | |
| Compound 53b | 35.17 | 15.31 | | | | | | |
| Compound 53a | 0.4698 | 0.1858 | | 1691 | 9.905 | 8.641 | | |
| Compound 55 | 1.759 | 0.5377 | 1.246 | 460.1 | | 34.31 | | |
| Compound 56 | 0.1281 | 0.0676 | 0.1349 | 770.5 | | 10.7 | | |
| Compound 7 | 1.833 | 1.299 | | 858.3 | 19.84 | 99.69 | | |
| Compound 6 | 0.8092 | 0.4839 | | 795.3 | 32.3 | 61.68 | | |
| Compound 57 | 61.87 | 19.17 | | | | | | |
| Compound 58 | 0.545 | 0.382 | | 8236 | 4.189 | 28.89 | | |
| Compound 59 | 0.7882 | 0.3595 | | 7287 | 31.86 | 61.73 | | |
| Compound 60 | 1.18 | 0.6034 | | >30 000 | 1278 | 1623 | | |
| Compound 61 | 2.149 | 1.133 | | 1837 | 113.5 | 111.1 | | |
| Compound 62 | 2.914 | 1.214 | | 12671 | 388.7 | 451.4 | | |
| Compound 63 | 0.7089 | 1.647 | 1.388 | 636.7 | | 51.44 | | |
| Compound 64 | 0.3695 | 0.2629 | 0.5043 | | | | | |
| Compound 65 | 0.3773 | 0.1933 | 0.246 | 164.8 | 5.93 | 8.189 | | |

The invention claimed is:
1. A compound of formula (I)

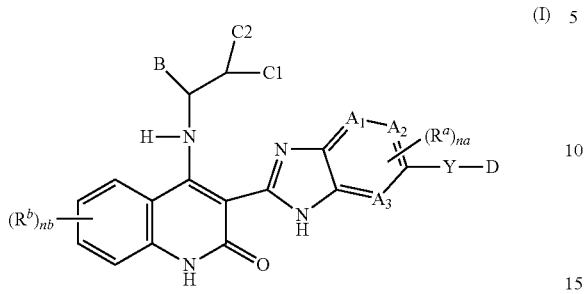

including any tautomeric and stereochemically isomeric form thereof, wherein
$A_1$, $A_2$ and $A_3$ each independently represent a carbon atom or a nitrogen atom;
C1 is hydrogen or $C_{1-4}$alkyl;
C2 is hydrogen, $C_{1-4}$alkyl, hydroxyl or $C_{1-4}$alkoxy;
or C1 and C2 are taken together to form a $C_{3-6}$cycloalkyl together with the carbon atom to which they are attached;
Y is a direct bond, —O—, C(=O), $NR^y$, S(=O)$_2$, or $C_{1-4}$alkyl;
$R^y$ is hydrogen or $C_{1-4}$alkyl;
each $R^a$ independently is hydrogen, $C_{1-6}$alkyl, halo$C_{1-6}$alkyl, halo, $C_{1-6}$alkoxy, carboxyl, $C_{1-6}$alkyloxycarbonyl, $C_{2-6}$alkenyl, $C_{2-6}$alkynyl, cyano, cyano$C_{1-6}$alkyl, hydroxy$C_{1-6}$alkyl, —C(=O)—NH$_2$, —C(=O)—NH($C_{1-4}$alkyl), —C(=O)—N($C_{1-4}$alkyl)$_2$, or a 3 to 6 membered monocyclic saturated heterocyclyl containing at least one heteroatom selected from N, O or S;
na is an integer equal to 1 or 2;
each $R^b$ independently is hydrogen, $C_{1-6}$alkyl, halo$C_{1-6}$alkyl, halo, $C_{1-6}$alkoxy, $C_{1-6}$alkyloxycarbonyl, $C_{2-6}$alkenyl, $C_{2-6}$alkynyl, cyano, cyano$C_{1-6}$alkyl, hydroxy$C_{1-6}$alkyl, —C(=O)—NH$_2$, —C(=O)—NH($C_{1-4}$alkyl), —C(=O)—N($C_{1-4}$alkyl)$_2$, $C_{3-6}$cycloalkyl, phenyl, a 3 to 6 membered monocyclic heterocyclyl containing at least one heteroatom selected from N, O or S, or $C_{1-6}$alkyl substituted with $C_{3-6}$cycloalkyl or with phenyl or with a 3 to 6 membered monocyclic heterocyclyl containing at least one heteroatom selected from N, O or S;
nb is an integer equal to 1 or 2;
D is a 3 to 12 membered heterocyclyl containing at least one heteroatom selected from N, O or S, wherein said heterocyclyl is optionally being substituted with 1 to 5 $R^c$ substituents;
each $R^c$ independently is oxo, halo, $C_{1-6}$alkyl, $C_{1-6}$alkyloxy, hydroxy$C_{1-6}$alkyl, halo $C_{1-6}$alkyl, halo$C_{1-6}$alkyloxy, carboxyl, HOOC—$C_{1-6}$alkyl-, $C_{1-6}$alkyl substituted with —C(=O)—O—$C_{1-6}$alkyl, $C_{1-6}$alkyl-O—C(=O)—, cyano, cyano$C_{1-6}$alkyl, $C_{1-6}$alkyl-C(=O)—, —SO$_2$—$C_{1-6}$alkyl, $C_{3-6}$cycloalkyl, phenyl, a 3 to 6 membered monocyclic saturated heterocyclyl containing at least one heteroatom selected from N, O or S, or a 5 or 6 membered monocyclic aromatic heterocyclyl containing at least one heteroatom selected from N, O or S;
B is a 3 to 12 membered carbocyclyl or a 3 to 12 membered heterocyclyl containing at least one heteroatom selected from N, O or S, wherein said carbocyclyl and heterocyclyl are each optionally being substituted with 1 to 5 R substituents;
each R independently is $C_{1-6}$alkyl, cyano, halo, $C_{1-6}$alkoxy, halo$C_{1-6}$alkoxy, hydroxyl, hydroxy$C_{1-6}$alkyl, halo$C_{1-6}$alkyl, oxo, —SO$_2$—NH$_2$, —SO$_2$—NH($C_{1-4}$alkyl), —SO$_2$—N($C_{1-4}$alkyl)$_2$, —NH—C(=O)—$C_{2-6}$alkenyl, —C(=O)—$C_{1-6}$alkyl, —C(=O)—$C_{2-6}$alkenyl, $C_{1-6}$alkyl-O—C(=O)—, $C_{3-6}$cycloalkyl, phenyl, or a 3 to 6 membered monocyclic heterocyclyl containing at least one heteroatom selected from N, O or S;
or a pharmaceutically acceptable salt thereof or a solvate thereof.

2. A compound according to claim 1 having the formula (I)

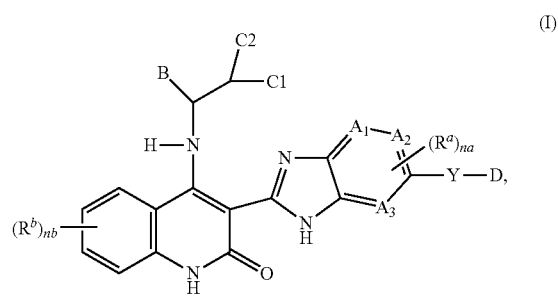

including any tautomeric and stereochemically isomeric form thereof, wherein
$A_1$, $A_2$ and $A_3$ each independently represent a carbon atom or a nitrogen atom;
$C_1$ is hydrogen or $C_{1-4}$alkyl;
$C_2$ is hydrogen or $C_{1-4}$alkyl or hydroxyl;
or $C_1$ and $C_2$ are taken together to form a $C_{3-6}$cycloalkyl together with the carbon atom to which they are attached;
Y is a direct bond, —O—, C(=O), $NR^y$, S(=O)$_2$, or $C_{1-4}$alkyl;
$R^y$ is hydrogen or $C_{1-4}$alkyl;
each $R^a$ independently is hydrogen, $C_{1-6}$alkyl, halo$C_{1-6}$alkyl, halo, $C_{1-6}$alkoxy, carboxyl, $C_{1-6}$alkyloxycarbonyl, $C_{2-6}$alkenyl, $C_{2-6}$alkynyl, cyano, cyano$C_{1-6}$alkyl, hydroxy-$C_{1-6}$alkyl, —C(=O)—NH$_2$, —C(=O)—NH($C_{1-4}$alkyl), —C(=O)—N($C_{1-4}$alkyl)$_2$, or a 3 to 6 membered monocyclic saturated heterocyclyl containing at least one heteroatom selected from N, O or S;
na is an integer equal to 1 or 2;
each $R^b$ independently is hydrogen, $C_{1-6}$alkyl, halo$C_{1-6}$alkyl, halo, $C_{1-6}$alkoxy, $C_1$-6alkyloxycarbonyl, $C_{2-6}$alkenyl, $C_{2-6}$alkynyl, cyano, cyano$C_{1-6}$alkyl, hydroxyl$C_{1-6}$alkyl, —C(=O)—NH$_2$, —C(=O)—NH($C_{1-4}$alkyl), —C(=O)—N($C_{1-4}$alkyl)$_2$, $C_{3-6}$cycloalkyl, phenyl, a 3 to 6 membered monocyclic heterocyclyl containing at least one heteroatom selected from N, O or S, or $C_{1-6}$alkyl substituted with $C_{3-6}$cycloalkyl or with phenyl or with a 3 to 6 membered monocyclic heterocyclyl containing at least one heteroatom selected from N, O or S;
nb is an integer equal to 1 or 2;
D is a 3 to 12 membered heterocyclyl containing at least one heteroatom selected from N, O or S, wherein said heterocyclyl is optionally being substituted with 1 to 5 $R^c$ substituents;

each $R^c$ independently is oxo, $C_{1-6}$alkyl, hydroxy$C_{1-6}$alkyl, halo$C_{1-6}$alkyl, halo$C_{1-6}$alkyloxy, carboxyl, HOOC—$C_{1-6}$alkyl-, $C_{1-6}$alkyl substituted with —C(=O)—O—$C_{1-6}$alkyl, $C_{1-6}$alkyl-O—C(=O)—, cyano, cyano$C_{1-6}$alkyl, $C_{1-6}$alkyl-C(=O)—, —SO$_2$—$C_{1-6}$alkyl, $C_{3-6}$cycloalkyl, phenyl, a 3 to 6 membered monocyclic saturated heterocyclyl containing at least one heteroatom selected from N, O or S, or a 5 or 6 membered monocyclic aromatic heterocyclyl containing at least one heteroatom selected from N, O or S;

B is a 3 to 12 membered carbocyclyl or a 3 to 12 membered heterocyclyl containing at least one heteroatom selected from N, O or S, wherein said carbocyclyl and heterocyclyl are each optionally being substituted with 1 to 5 R substituents;

each R independently is $C_{1-6}$alkyl, cyano, halo, $C_{1-6}$alkoxy, halo$C_{1-6}$alkoxy, hydroxyl, hydroxy$C_{1-6}$alkyl, halo$C_{1-6}$alkyl, oxo, —SO$_2$—NH$_2$, —SO$_2$—NH($C_{1-4}$alkyl), —SO$_2$—N($C_{1-4}$alkyl)$_2$, —NH—C(=O)—$C_{2-6}$alkenyl, —C(=O)—$C_{1-6}$alkyl, —C(=O)—$C_{2-6}$alkenyl, $C_{1-6}$alkyl-O—C(=O)—, $C_{3-6}$cycloalkyl, phenyl, or a 3 to 6 membered monocyclic heterocyclyl containing at least one heteroatom selected from N, O or S;

or a pharmaceutically acceptable salt thereof or a solvate thereof.

3. The compound according to claim 1 having the following formula (I-a)

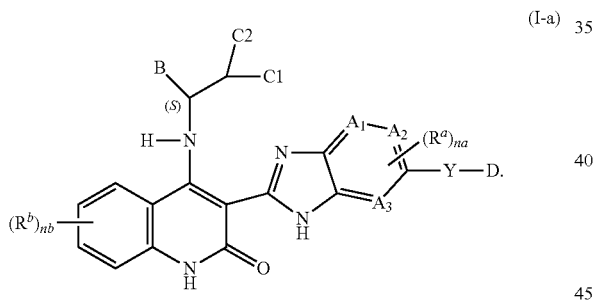

(I-a)

4. The compound according to claim 1 wherein D is piperazin-1-yl, wherein said piperazin-1-yl is optionally being substituted with 1 to 5 $R^c$ substituents.

5. The compound according to claim 1 wherein D is morpholin-1-yl, wherein said morpholin-1-yl is optionally being substituted with 1 to 5 $R^c$ substituents.

6. The compound according to claim 1 wherein D is a 4, 5, 6, or 7 membered monocyclic heterocyclyl, wherein said heterocyclyl is optionally being substituted with 1 to 5 $R^c$ substituents.

7. The compound according to claim 1 wherein $A_1$, $A_2$ and $A_3$ each represent a carbon atom.

8. The compound according to claim 1 wherein one of $A_1$, $A_2$ and $A_3$ is a nitrogen atom and the remaining A substituents are carbon atoms.

9. The compound according to claim 1 wherein Y is a direct bond.

10. The compound according to claim 1 wherein Y is —O—, C(=O), NR$^y$, S(=O)$_2$, or $C_{1-4}$alkyl.

11. The compound according to claim 1 wherein $C_1$ is hydrogen and $C_2$ is $C_{1-4}$alkyl.

12. The compound according to claim 1 wherein $C_1$ and $C_2$ are taken together to form $C_{3-6}$cycloalkyl together with the carbon atom to which they are attached.

13. The compound according to claim 1 wherein $R^a$ is hydrogen.

14. The compound according to claim 1 wherein $R^b$ is hydrogen.

15. The compound according to claim 1 wherein D is optionally substituted with 1 or 2 $R_c$ substituents and each $R_c$ is independently selected from oxo, $C_{1-6}$alkyl, halo$C_{1-6}$alkyl, halo$C_{1-6}$alkyloxy, HOOC—$C_{1-6}$alkyl-, carboxyl, $C_{1-6}$alkyl substituted with —C(=O)—O—$C_{1-6}$alkyl, and $C_{1-6}$alkyl-O—C(=O)—.

16. The compound according to claim 1 wherein B is a 5 or 6 membered carbocyclyl or heterocyclyl containing at least one heteroatom selected from N, O or S, wherein said carbocyclyl and heterocyclyl are each optionally being substituted with 1 to 5 R substituents.

17. The compound according to claim 16 wherein B is an aromatic carbocyclyl or heterocyclyl.

18. The compound according to claim 1 wherein
$A_1$, $A_2$ and $A_3$ each independently represent a carbon;
C1 is hydrogen or $C_{1-4}$alkyl;
C2 is hydrogen or $C_{1-4}$alkyl;
or C1 and C2 are taken together to form a $C_{3-6}$cycloalkyl together with the carbon atom to which they are attached;
Y is a direct bond, C(=O) or NR$^y$;
R$^y$ is hydrogen or $C_{1-4}$alkyl;
each R$^a$ independently is hydrogen, $C_{1-6}$alkyl, halo$C_{1-6}$alkyl, or halo;
$n_a$ is an integer equal to 1;
each R$^b$ independently is hydrogen or halo;
$n_b$ is an integer equal to 1;
D is a 5 or 6 membered monocyclic saturated or aromatic heterocyclyl containing at least one heteroatom selected from N, O or S, wherein said heterocyclyl is optionally being substituted with 1 or 2 $R^c$ substituents; or D is a bridged heterocyclyl containing at least one heteroatom selected from N, O or S, wherein said heterocyclyl is optionally being substituted with 1 or 2 $R^c$ substituents;
each $R^c$ independently is oxo, $C_{1-6}$alkyl, halo$C_{1-6}$alkyl, halo$C_{1-6}$alkyloxy, carboxyl, HOOC—$C_{1-6}$alkyl-, $C_{1-6}$alkyl substituted with —C(=O)—O—$C_{1-6}$alkyl, or $C_{1-6}$alkyl-O—C(=O)—; B is a 5 or 6 membered aromatic monocyclic heterocyclyl containing at least one heteroatom selected from N, O or S, wherein said heterocyclyl is optionally being substituted with 1 R substituent;
R is $C_{1-6}$alkyl, $C_{1-6}$alkoxy, or $C_{3-6}$cycloalkyl.

19. The compound according to claim 1 wherein the compound is selected from

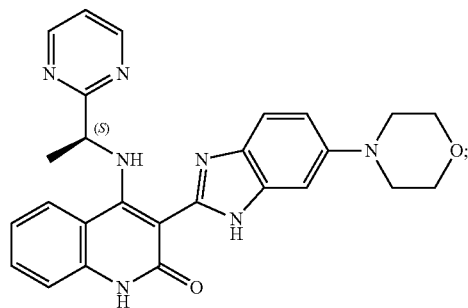

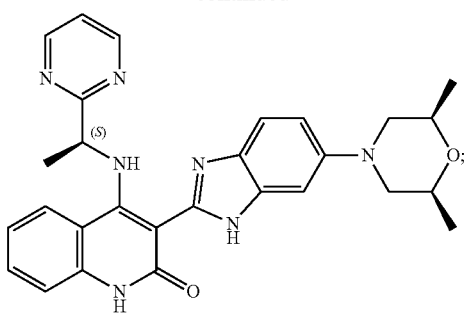

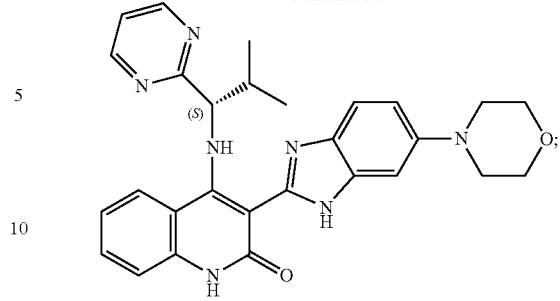

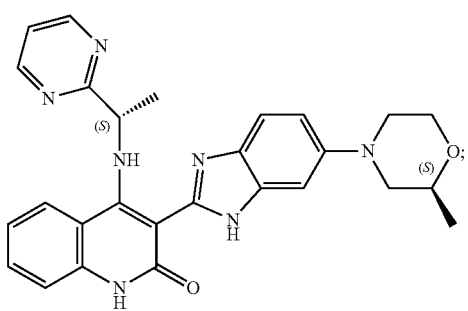

or a pharmaceutically acceptable salt thereof or a solvate thereof.

20. A pharmaceutical composition comprising a compound according to claim 1 and a pharmaceutically acceptable carrier.

21. A method of treating a disease state or condition mediated by a FGFR kinase, which method comprises administering to a subject in need thereof a compound as defined in claim 1; wherein the disease state or condition mediated by the FGFR kinase is cancer.

22. A method of treating a disease state or condition mediated by a FGFR kinase, which method comprises administering to a subject in need thereof a compound as defined in claim 19: wherein the disease state or condition mediated by the FGFR kinase is cancer.

23. The compound according to claim 15, wherein each Re is independently selected from methyl, trifluoromethoxy, —CH₂—COOH, —CH₂—C(=O)—O—CH₂—CH₃, and —C(=O)—O—CH₃.

* * * * *